(12) United States Patent
Jala et al.

(10) Patent No.: US 12,377,069 B2
(45) Date of Patent: Aug. 5, 2025

(54) COMPOUNDS, COMPOSITIONS, METHODS OF USING, AND METHODS FOR PREPARING COMPOUNDS

(71) Applicants: UNIVERSITY OF LOUISVILLE RESEARCH FOUNDATION, INC., Louisville, KY (US); THE INSTITUTE FOR STEM CELL BIOLOGY AND REGENERATIVE MEDICINE (INSTEM), Bangalore (IN)

(72) Inventors: Venkatakrishna Rao Jala, Louisville, KY (US); Haribabu Bodduluri, Louisville, KY (US); Rajbir Singh, Louisville, KY (US); Praveen Kumar Vemula, Bangalore (IN); Sandeep Chandrashekharappa, Bangalore (IN); Ankita Arun Hiwale, Bangalore (IN)

(73) Assignees: UNIVERSITY OF LOUISVILLE RESEARCH FOUNDATION, INC., Louisville, KY (US); THE INSTITUTE FOR STEM CELL BIOLOGY AND REGENERATIVE MEDICINE (INSTEM), Bangalore (IN)

( * ) Notice: Subject to any disclaimer, the term of this patent is extended or adjusted under 35 U.S.C. 154(b) by 0 days.

(21) Appl. No.: 18/494,818

(22) Filed: Oct. 26, 2023

(65) Prior Publication Data

US 2024/0173288 A1    May 30, 2024

Related U.S. Application Data

(63) Continuation of application No. 17/053,811, filed as application No. PCT/US2019/032117 on May 14, 2019, now abandoned.

(Continued)

(51) Int. Cl.
*A61K 31/352* (2006.01)
*A61P 1/00* (2006.01)
(Continued)

(52) U.S. Cl.
CPC .............. *A61K 31/352* (2013.01); *A61P 1/00* (2018.01); *A61P 1/16* (2018.01); *A61P 35/00* (2018.01); *A61P 37/06* (2018.01); *C07D 311/80* (2013.01)

(58) Field of Classification Search
CPC ..... C07C 50/34; C07C 65/105; C07C 251/22; C07C 2603/26; C07C 2603/50;
(Continued)

(56) References Cited

U.S. PATENT DOCUMENTS 8,183,282 B2   5/2012  Seeram et al.
9,096,795 B2   8/2015  Taugerbeck et al.
(Continued)

FOREIGN PATENT DOCUMENTS

CN   103319695 B    9/2013
WO   2004/073612 A2  9/2004
(Continued)

OTHER PUBLICATIONS

Castiel et al. (2011) "A phenanthrene derived PARP inhibitor is an extra-centrosomes de-clustering agent exclusively eradicating human cancer cells" BMC Cancer, vol. 11, Article 412, (14 pages).
(Continued)

*Primary Examiner* — Taylor V Oh
(74) *Attorney, Agent, or Firm* — ALGM LLP; Harry J. Guttman

(57) ABSTRACT

In some embodiments of the invention, inventive compounds (e.g., Formula (I), (IA), (II), and (III), and urolithin derivatives) are disclosed. Other embodiments include compositions (e.g., pharmaceutical compositions) comprising
(Continued)

the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases). Further embodiments include methods for making the inventive compounds. Additional embodiments of the invention are also discussed herein.

19 Claims, 161 Drawing Sheets

Related U.S. Application Data

(60) Provisional application No. 62/671,737, filed on May 15, 2018.

(51) Int. Cl.
  *A61P 1/16* (2006.01)
  *A61P 35/00* (2006.01)
  *A61P 37/06* (2006.01)
  *C07D 311/80* (2006.01)

(58) Field of Classification Search
  CPC ..... C07C 2603/74; C07C 39/12; C07C 39/17; C07C 45/455; C07C 46/00; C07C 46/04; C07C 251/84; C07C 39/23; C07C 229/54; C07C 251/20; C07C 2603/22; C07C 2603/40; A61K 31/15; A61K 31/352; A61K 31/122; A61K 31/37; A61K 31/433; A61K 31/513; C07D 311/80; C07D 241/42; C07D 285/14; C07D 285/10; A61P 9/00; A61P 21/00; A61P 25/00; A61P 29/00; A61P 1/00; A61P 1/16; A61P 35/00; A61P 37/06; A61P 25/28
  USPC .......................................................... 514/454
  See application file for complete search history.

(56) References Cited

U.S. PATENT DOCUMENTS

| | | |
|---|---|---|
| 2010/0310512 A1 | 12/2010 | Guo et al. |
| 2012/0069289 A1 | 3/2012 | Taugerbeck et al. |
| 2012/0164243 A1 | 6/2012 | Rinsch et al. |
| 2014/0018415 A1 | 1/2014 | Rinsch et al. |
| 2016/0045472 A1 | 2/2016 | Priem et al. |
| 2016/0279097 A1 | 9/2016 | Cros et al. |
| 2016/0332982 A1 | 11/2016 | Rinsch et al. |

FOREIGN PATENT DOCUMENTS

| | | |
|---|---|---|
| WO | 2008/016554 A1 | 2/2008 |
| WO | 2010/132601 A1 | 11/2010 |
| WO | 2011/160764 A1 | 12/2011 |
| WO | 2012/068234 A2 | 5/2012 |
| WO | 2014/004902 A2 | 1/2014 |
| WO | 2015/097231 A1 | 7/2015 |
| WO | 2017/036992 A1 | 3/2017 |
| WO | 2017/036993 A1 | 3/2017 |
| WO | 2017/109195 A1 | 6/2017 |

OTHER PUBLICATIONS

Groschwitz et al. (2009) "Intestinal barrier function: molecular regulation and disease pathogenesis" J Allergy Clin Immunol, vol. 124, No. 1, pp. 3-20.
Gulcan et al (2014) "Design, synthesis and biological evaluation of novel 6H-benzo[c]chromen-6-one, and 7,8,9,10-tetrahydrobenzo[c]chromen-6-one derivatives as potential cholinesterase inhibitors" Bioorg Medicinal Chem, vol. 22, No. 19, pp. 5141-5154.
Gunzel et al. (2013) "Claudins and the modulation of tight junction permeability" Physiol Rev, vol. 93, No. 2, pp. 525-569.
Habauzit et al. (2012) "Evidence for a protective effect of polyphenols-containing foods on cardiovascular health: an update for clinicians" Ther Adv Chronic Dis vol. 3, No. 2, pp. 87-106.
Harhaj et al. (2004) "Regulation of tight junctions and loss of barrier function in pathophysiology" Int J Biochem Cell Biol, vol. 36, No. 7, pp. 1206-1237.
Hayes et al. (2009) "Cross-talk between transcription factors AhR and Nrf2: lessons for cancer chemoprevention from dioxin" Toxicol Sci, vol. 111, No. 2, pp. 199-201.
Heber (2008) "Multitargeted therapy of cancer by ellagitannins" Cancer Lett, vol. 269, pp. 262-268.
Heilman et al. (2017) "Safety assessment of Urolithin A, a metabolite produced by the human gut microbiota upon dietary intake of plant derived ellagitannins and ellagic acid" Food Chem Toxicol, vol. 108(Pt A), pp. 289-297.
Ismail, et al. (2016) "Ellagitannins in Cancer Chemoprevention and Therapy" Toxins (Basel), vol. 8, No. 5, Article 151 (22 pages).
Ito et al. (2008) "Identification of urinary and intestinal bacterial metabolites of ellagitannin geraniin in rats" J Agric Food Chem, vol. 56, No. 2, pp. 393-400.
Kallio et al. (2013) "Urolithins display both antioxidant and pro-oxidant activities depending on assay system and conditions" J Agric Food Chem, vol. 61, No. 45, pp. 10720-10729.
Kannan et al. (2013) "Ellagic acid inhibits cardiac arrhythmias, hypertrophy and hyperlipidaemia during myocardial infarction in rats" Metabolism, vol. 62, No. 1, pp. 52-61.
Kanojia et al. (1995) "Synthesis of the Diaza Analogue of Ellagic Acid" Tetrahedron Letters, vol. 36, No. 47, pp. 8553-8556.
Kensler et al. (2007) "Cell survival responses to environmental stresses via the Keap1-Nrf2-ARE pathway" Annu Rev Pharmacol Toxicol, vol. 47, pp. 89-116.
Khor et al. (2006) "Nrf2-deficient mice have an increased susceptibility to dextran sulfate sodium-induced colitis" Cancer Res, vol. 66, No. 24, pp. 11580-11584.
Kim et al (2012) "Investigating intestinal inflammation in DSS-induced model of IBD" J Vis Exp, vol. 60, Article, 3678, (6 pages).
Kim et al (2013) "TopHat2: accurate alignment of transcriptomes in the presence of insertions, deletions and gene fusions" Genome Biol, vol. 14, No. 4, pp. R36. (13 pages).
Kobayashi et al. (2016) "Nrf2 suppresses macrophage inflammatory response by blocking proinflammatory cytokine transcription" Nat Commun, vol. 7, Article 11624, (14 pages).
Konig et al. (2016) "Human Intestinal Barrier Function in Health and Disease" Clin Transl Gastroenterol, vol. 7, No. 10, e196. (13 pages).
Konturek et al. (2018) "Gut(-)Liver Axis: How Do Gut Bacteria Influence the Liver?" Med Sci (Basel), vol. 6, No. 3, Article 79, (9 pages).
Kowapradit et al. (2010) "In vitro permeability enhancement in intestinal epithelial cells (Caco-2) monolayer of water soluble quaternary ammonium chitosan derivatives" AAPS PharmSciTech, vol. 11, No. 2, pp. 497-508.
Krzeszewski et al. (2013), "Color-Tunable Fluorescent Dyes Based on Benzo[c]coumarin" Eur J Org Chem, vol. 2013, No. 25, pp. 5631-5644.
Kurowska-Stolarska et al. (2009) "IL-33 amplifies the polarization of alternatively activated macrophages that contribute to airway inflammation" J Immunol, vol. 183, No. 10, pp. 6469-6477.
Landy et al. (2016) "Tight junctions in inflammatory bowel diseases and inflammatory bowel disease associated colorectal cancer" World J Gastroenterol, vol. 22, No. 11, pp. 3117-3126.
Larrosa et al. (2010) "Anti-inflammatory properties of a pomegranate extract and its metabolite urolithin-A in a colitis rat model and the effect of colon inflammation on phenolic metabolism" The J Nutr Biochem, vol. 21, No. 8, pp. 717-725.
Larrosa et al. (2010) "Ellagitannins, ellagic acid and vascular health" Mol Aspects Med, vol. 31, No. 6, pp. 513-539.

(56) References Cited

OTHER PUBLICATIONS

Laso et al. (2007), "Production of inflammatory cytokines by peripheral blood monocytes in chronic alcoholism: relationship with ethanol intake and liver disease" Cytometry B Clin Cytom, vol. 72, No. 5, pp. 408-415.

Leclercq et al. (2014) "Intestinal permeability, gut-bacterial dysbiosis, and behavioral markers of alcohol-dependence severity" Proc Natl Acad Sci U S A, vol. 111, No. 42, pp. E4485-E4493.

Leclercq et al. (2014) "Role of inflammatory pathways, blood mononuclear cells, and gut-derived bacterial products in alcohol dependence" Biol Psychiatry, vol. 76, No. 9, pp. 725-733.

Levy et al. (2017) "Dysbiosis and the immune system" Nat Rev Immunol vol. 17, No. 4, pp. 219-232.

Levy et al. (2017) "Microbiome, metabolites and host immunity" Curr Opin Microbiol vol. 35, pp. 8-15.

Llopis et al. (2016) "Intestinal microbiota contributes to individual susceptibility to alcoholic liver disease" Gut, vol. 65, No. 5, pp. 830-839.

Loboda et al. (2016) "Role of Nrf2/HO-1 system in development, oxidative stress response and diseases: an evolutionarily conserved mechanism" Cell Mol Life Sci, vol. 73, No. 17, pp. 3221-3247.

Lucas et al. (2009) "A concise synthesis of glucuronide metabolites of urolithin-B, resveratrol, and hydroxytyrosol" Carbohydr Res, vol. 344, No. 11, pp. 1340-1346.

Lynch et al. (2016). "The Human Intestinal Microbiome in Health and Disease" N Engl J Med, vol. 375, No. 24, pp. 2369-2379.

Masillamani et al. (2012) "Multiscale charge injection and transport properties in self-assembled monolayers of biphenyl thiols with varying torsion angles" Chemistry, vol. 18, No. 33, pp. 10335-10347.

Metidji et al. (2018) "The Environmental Sensor AHR Protects from Inflammatory Damage by Maintaining Intestinal Stem Cell Homeostasis and Barrier Integrity" Immunity, vol. 49, pp. 353-362 e355.

Miao et al. (2005) "Transcriptional regulation of NF-E2 p45-related factor (NRF2) expression by the aryl hydrocarbon receptor-xenobiotic response element signaling pathway: direct cross-talk between phase I and II drug-metabolizing enzymes" J Biol Chem, vol. 280, No. 21, pp. 20340-20348.

Mir et al. (2016) "Occludin deficiency promotes ethanol-induced disruption of colonic epithelial junctions, gut barrier dysfunction and liver damage in mice" Biochim Biophys Acta, vol. 1860, No. 4, pp. 765-774.

Mitsuishi et al. (2012) "The Keap1-Nrf2 system in cancers: stress response and anabolic metabolism" Front Oncol, vol. 2, Article 200, (13 pages).

Monteleone et al. (2011) "Aryl hydrocarbon receptor-induced signals up-regulate IL-22 production and inhibit inflammation in the gastrointestinal tract" Gastroenterology, vol. 141, No. 1, pp. 237-248.

Murthy et al. (1993) "Treatment of dextran sulfate sodium-induced murine colitis by intracolonic cyclosporin" Dig Dis Sci, vol. 38, No. 9, pp. 1722-1734.

Nealmongkol et al. (2013) "Cu(I)-mediated lactone formation in subcritical water: a benign synthesis of benzopyranones and urolithins A-C" Tetrahedron, vol. 69, No. 44, pp. 9277-9283.

Novak et al. (2015) "Mitochondrial dysfunction in inflammatory bowel disease" Front Cell Dev Biol, vol. 3, Article 62, (18 pages).

Nunez-Sanchez MA, et al. (2014) "Targeted metabolic profiling of pomegranate polyphenols and urolithins in plasma, urine and colon tissues from colorectal cancer patients" Mol Nutr Food Res, vol. 58, No. 6, pp. 1199-1211.

Okey (2007) "An aryl hydrocarbon receptor odyssey to the shores of toxicology: the Deichmann Lecture, International Congress of Toxicology—XI" Toxicol Sci, vol. 98, No. 1, pp. 5-38.

Organization, World Health. Global status Reports on Alcohol and Health 2014. 2014. Available from: http://www.who.int/substance_abuse/publications/global_alcohol_report/en/, (392 pages).

Pandey et al. (2004) "Synthesis and biological activities of some new dibenzopyranones and dibenzopyrans: search for potential oestrogen receptor agonists and antagonists" Bioorg Med Chem, vol. 12, No. 9, pp. 2239-2249.

Parlesak et al. (2000) "Increased intestinal permeability to macromolecules and endotoxemia in patients with chronic alcohol abuse in different stages of alcohol-induced liver disease" J Hepatol, vol. 32, No. 5, pp. 742-747.

Quigley et al. (2013) "The gut microbiota and the liver. Pathophysiological and clinical implications" J Hepatol, vol. 58, No. 5, pp. 1020-1027.

Rao (2009) "Endotoxemia and gut barrier dysfunction in alcoholic liver disease" Hepatology, vol. 50, No. 2, pp. 638-644.

Rao et al. (2004) "Recent Advances in Alcoholic Liver Disease I. Role of intestinal permeability and endotoxemia in alcoholic liver disease" Am J Physiol Gastrointest Liver Physiol, vol. 286, No. 6, pp. G881-G884.

Razani et al. (2017) "Cardioprotective Effects of Pomegranate (*Punica granatum*) Juice in Patients with Ischemic Heart Disease" Phytother Res, vol. 31, No. 11, pp. 1731-1738.

Rodenburg et al. (2008) "Impaired barrier function by dietary fructo-oligosaccharides (FOS) in rats is accompanied by increased colonic mitochondrial gene expression" BMC Genomics vol. 9, Article 144, (15 pages).

Ryu et al. (2016) "Urolithin A induces mitophagy and prolongs lifespan in C. elegans and increases muscle function in rodents" Nat Med, vol. 22, No. 8, pp. 879-888.

Saha et al. (2016) "Gut Microbiota Conversion of Dietary Ellagic Acid into Bioactive Phytoceutical Urolithin A Inhibits Heme Peroxidases" PLOS One, vol. 11, No. 6, Article e0156811, (21 pages).

Sak (2014) "Cytotoxicity of dietary flavonoids on different human cancer types" Pharmacogn Rev, vol. 8, No. 16, pp. 122-146.

Sarkar et al. (2015) "Ellagic Acid, a Dietary Polyphenol, Inhibits Tautomerase Activity of Human Macrophage Migration Inhibitory Factor and Its Pro-inflammatory Responses in Human Peripheral Blood Mononuclear Cells" J Agric Food Chem, vol. 63, No. 20, pp. 4988-4998.

Schiering et al. (2017) "Feedback control of AHR signalling regulates intestinal immunity" Nature, vol. 542, No. 7640, pp. 242-245.

Schulzke et al. (2009) "Epithelial tight junctions in intestinal inflammation" Ann N Y Acad Sci, vol. 1165, pp. 294-300.

Schwabe et al. (2013). "The microbiome and cancer" Nature reviews Cancer, vol. 13, pp. 800-812.

Seeram et al. (2006) "Pomegranate juice ellagitannin metabolites are present in human plasma and some persist in urine for up to 48 hours" J Nutr, vol. 136, No. 10, pp. 2481-2485.

Seeram et al. (2007) "Pomegranate ellagitannin-derived metabolites inhibit prostate cancer growth and localize to the mouse prostate gland" J Agric Food Chem, vol. 55, No. 19, pp. 7732-7737.

Seeram et al. (2008) "Pomegranate juice and extracts provide similar levels of plasma and urinary ellagitannin metabolites in human subjects" J Med Food, vol. 11, No. 2, pp. 390-394.

Sekine et al. (2009) "Hypersensitivity of aryl hydrocarbon receptor-deficient mice to lipopolysaccharide-induced septic shock" Mol Cell Biol, vol. 29, pp. 6391-6400.

Selma et al. (2014) "Description of urolithin production capacity from ellagic acid of two human intestinal *Gordonibacter* species" Food Funct, vol. 5, No. 8, pp. 1779-1784.

Selma et al. (2017) "Isolation of Human Intestinal Bacteria Capable of Producing the Bioactive Metabolite Isourolithin A from Ellagic Acid" Front Microbiol, vol. 8, Article 1521 (8 pages).

Shin et al. (2007) "NRF2 modulates aryl hydrocarbon receptor signaling: influence on adipogenesis" Mol Cell Biol, vol. 27, pp. 7188-7197.

Singh et al. (2013) "Evaluation of memory enhancing clinically available standardized extract of Bacopa monniera on p. glycoprotein and cytochrome P450 3A in Sprague-Dawley rats" PloS One, vol. 8, No. 8, Article e72517, (9 pages).

Singh et al. (2019) "Enhancement of the gut barrier integrity by a microbial metabolite through the Nrf2 pathway" Nat Commun, vol. 10, No. 1, Article 89, (18 pages).

(56) References Cited

OTHER PUBLICATIONS

Smith et al. (2011) "Intestinal macrophages and response to microbial encroachment" Mucosal Immunol, vol. 4, No. 1, pp. 31-42.
Sobhani et al. (2011) "Microbial dysbiosis in colorectal cancer (CRC) patients" PloS One, vol. 6, No. 1, Article e16393, (7 pages).
Sonnenburg et al. (2016) "Diet-microbiota interactions as moderators of human metabolism" Nature, vol. 535, No. 7610, pp. 56-64.
Stockinger et al. (2014) "The aryl hydrocarbon receptor: multitasking in the immune system" Annu Rev Immunol, vol. 32, pp. 403-432.
Stockton et al. (2017) "Effect of pomegranate extract on blood pressure and anthropometry in adults: a double-blind placebo-controlled randomised clinical trial" J Nutr Sci, vol. 6, Article e39 (8 pages).
Sun et al. (2006) "6H-Benzo[c]chromen-6-one derivatives as selective ERbeta agonists" Bioorg Med Chem Lett, vol. 16, No. 6, pp. 1468-1472.
Tamboli et al. (2004) "Dysbiosis in inflammatory bowel disease" Gut, vol. 53, No. 1, pp. 1-4.
Tomas-Barberan et al. (2014) "Ellagic acid metabolism by human gut microbiota: consistent observation of three urolithin phenotypes in intervention trials, independent of food source, age, and health status" J Agric Food Chem, vol. 62, No. 28, pp. 6535-6538.
Tomas-Barberan et al. (2017) "Urolithins, the rescue of "old" metabolites to understand a "new" concept: Metabotypes as a nexus among phenolic metabolism, microbiota dysbiosis, and host health status" Mol Nutr Food Res, vol. 61, No. 1, Article 1500901, (35 pages).
Trapnell et al. (2012) "Differential gene and transcript expression analysis of RNAseq experiments with TopHat and Cufflinks" Nat Protoc, vol. 7, No. 3, pp. 562-578.
Trapnell et al. (2013) "Differential analysis of gene regulation at transcript resolution with RNA-seq" Nat Biotechnol, vol. 31, No. 1, pp. 46-53.
Tremlett et al. (2017) "The gut microbiome in human neurological disease: A review" Ann Neurol, vol. 81, No. 3, pp. 369-382.
Trosien et al. (2012) "Synthesis of highly functionalized 9,10-phenanthrenequinones by oxidative coupling using MoCl5" Org Lett, vol. 14, No. 12, pp. 2976-2979.
Tsukita et al. (2002) "Claudin-based barrier in simple and stratified cellular sheets" Curr Opin Cell Biol, vol. 14, No. 5, pp. 531-536.
Vindigni et al. (2016) "The intestinal microbiome, barrier function, and immune system in inflammatory bowel disease: a tripartite pathophysiological circuit with implications for new therapeutic directions" Therap Adv Gastroenterol, vol. 9, No. 4, pp. 606-625.
Wang et al. (2014) "Effects of alcohol on intestinal epithelial barrier permeability and expression of tight junction-associated proteins" Mol Med Rep; vol. 9, No. 6, pp. 2352-2356.
Wang et al. (2014) "Synthesis and Photovoltaic Properties of Conjugated D-A Coplymers based on thienyl substituted pyrene and diketopyrrolopyrrole for polymer solar cells" J Polymer Science Part A: Polymer Chemistry, vol. 52, No. 22, pp. 3198-3204.
Wardyn et al. (2015) "Dissecting molecular cross-talk between Nrf2 and NF-kappaB response pathways" Biochem Soc Trans, vol. 43, No. 4, pp. 621-626.
Yeager et al. (2009) Introducing the "TCDD-inducible AhR-Nrf2 gene battery" Toxicol Sci, vol. 111, No. 2, pp. 238-246.
Zhou et al. (2017) "Targeting the gut barrier for the treatment of alcoholic liver disease" Liver Res, vol. 1, No. 4, pp. 197-207.
CN 103319695 A (Sep. 25, 2013)—English-language abstract from Espacenet, 1 page.
International Search Report from PCT/US2019/032117, mailed Jul. 25, 2019, 4 pages.
Written Opinion from PCTAJS2019/032117, mailed Jul. 25, 2019, 8 pages.
Aijaz et al. (2006) "Tight junctions: molecular architecture and function" Int Rev Cytol, vol. 248, pp. 261-298.
Al-Sawaf et al. (2015) "Nrf2 in health and disease: current and future clinical implications" Clin Sci (Lond), vol. 129, No. 12, pp. 989-999.

Antoniou et al. (2016) "The TNBS-induced colitis animal model: An overview" Ann Med Surg (Lond), vol. 11, pp. 9-15.
Arrieta et al. (2006) "Alterations in intestinal permeability" Gut, vol. 55, No. 10, pp. 1512-1520.
Bain et al. (2014) "Macrophages in intestinal homeostasis and inflammation" Immunol Rev, vol. 260, No. 1, pp. 102-117.
Bajaj (2019) "Alcohol, liver disease and the gut microbiota" Nat Rev Gastroenterol Hepatol, vol. 16, No. 4, pp. 235-246.
Beischlag et al. (2008) "The aryl hydrocarbon receptor complex and the control of gene expression" Crit Rev Eukaryot Gene Expr, vol. 18, No. 3, pp. 207-250.
Belkaid et al. (2014) "Role of the microbiota in immunity and inflammation" Cell, vol. 157, No. 1, pp. 121-141.
Benson et al. (2011) "Aryl hydrocarbon receptor activation by TCDD reduces inflammation associated with Crohn's disease" Toxicol Sci, vol. 120, No. 1, pp. 68-78.
Bertola et al. (2013) "Mouse model of chronic and binge ethanol feeding (the NIAAA model)" Nat Protoc, vol. 8, No. 3, pp. 627-637.
Bialonska et al. (2009) "Urolithins, intestinal microbial metabolites of Pomegranate ellagitannins, exhibit potent antioxidant activity in a cell-based assay" J Agric Food Chem, vol. 57, No. 21, pp. 10181-10186.
Bischoff et al. (2014) "Intestinal permeability—a new target for disease prevention and therapy" BMC Gastroenterol, vol. 14, Article 189, (25 pages).
Capaldo et al. (2009) "Cytokine regulation of tight junctions" Biochim Biophys Acta, vol. 1788, No. 4, pp. 864-871.
Cerda et al. (2004) "The potent in vitro antioxidant ellagitannins from pomegranate juice are metabolised into bioavailable but poor antioxidant hydroxy-6H-dibenzopyran-6-one derivatives by the colonic microflora of healthy humans" Eur J Nutr vol. 43, No. 4, pp. 205-220.
Cerda et al. (2005) "Identification of urolithin a as a metabolite produced by human colon microflora from ellagic acid and related compounds" J Agric Food Chem vol. 53, No. 14, pp. 5571-5576.
Cerda et al. (2005) "Metabolism of antioxidant and chemopreventive ellagitannins from strawberries, raspberries, walnuts, and oak-aged wine in humans: identification of biomarkers and individual variability" J Agric Food Chem vol. 53, No. 2, pp. 227-235.
Chen et al. (2010) "Regiocontrolled synthesis of ethene-bridged para-phenylene oligomers based on Pt(II)- and Ru(II)-catalyzed aromatization" Chemistry, vol. 16, No. 6, pp. 1826-1833.
Cozza et al. (2011) "Urolithin as a converging scaffold linking ellagic acid and coumarin analogues: design of potent protein kinase CK2 inhibitors" ChemMedChem, vol. 6, No. 12, pp. 2273-2286.
Delpre et al. (1989) "Ultrastructural abnormalities in endoscopically and histologically normal and involved colon in ulcerative colitis" Am J Gastroenterol, vol. 84, No. 9, pp. 1038-1046.
Derosa et al. (2016) "Ellagic Acid and Its Role in Chronic Diseases" Adv Exp Med Biol, vol. 928, pp. 473-479.
Devlin (1975) "6H-Dibenzo[b,d]pyrans. I. Synthesis" Can J Chem, vol. 53, No. 3, pp. 343-349.
Di Meglio et al. (2014) "Activation of the aryl hydrocarbon receptor dampens the severity of inflammatory skin conditions" Immunity, vol. 40, No. 6, pp. 989-1001.
Dubost, et al. (2010) "General method for the synthesis of substituted phenanthridin-6(5H)-ones using a KOH-mediated anionic ring closure as the key step" Tetrahedron, vol. 66, No. 27-28, pp. 5008-5016.
Dzutsev et al. (2017) "Microbes and Cancer" Annu Rev Immunol, vol. 35, pp. 199-228.
Engen et al. (2015) "The Gastrointestinal Microbiome: Alcohol Effects on the Composition of Intestinal Microbiota" Alcohol Res, vol. 37, No. 2, pp. 223-236.
Erben et al. (2014) "A guide to histomorphological evaluation of intestinal inflammation in mouse models" Int J Clin Exp Pathol, vol. 7, No. 8, pp. 4557-4576.
Espin et al. (2007) "Iberian pig as a model to clarify obscure points in the bioavailability and metabolism of ellagitannins in humans" J Agric Food Chem, vol. 55, No. 25, pp. 10476-10485.

(56) References Cited

OTHER PUBLICATIONS

Espin et al. (2013). "Biological significance of urolithins, the gut microbial ellagic Acid-derived metabolites: the evidence so far" Evid Based Complement Alternat Med, vol. 2013, Article 270418 (15 pages).

Esser et al. (2015) "The aryl hydrocarbon receptor in barrier organ physiology, immunology, and toxicology" Pharmacol Rev, vol. 67, No. 2, pp. 259-279.

Fieser (1929) "The Sulfonation of Phenanthrene. II. Disulfonation" J Am Chem Soc, vol. 51, No. 8, pp. 2471-2486.

Flicek et al. (2014) "Ensembl 2014" Nucleic Acids Res, vol. 42 (database issue), pp. D749-D755.

Forster, C. (2008) "Tight junctions and the modulation of barrier function in disease" Histochem Cell Biol, vol. 130 130, No. 1, pp. 55-70.

Fukui et al. (1991) "Plasma endotoxin concentrations in patients with alcoholic and non-alcoholic liver disease: reevaluation with an improved chromogenic assay" J Hepatol, vol. 12, No. 2, pp. 162-169.

Fukumoto et al. (2014) "Identification of a probiotic bacteria-derived activator of the aryl hydrocarbon receptor that inhibits colitis" Immunol Cell Biol, vol. 92, No. 5, pp. 460-465.

Furumatsu et al. (2011) "A role of the aryl hydrocarbon receptor in attenuation of colitis" Dig Dis Sci, vol. 56, No. 9, pp. 2532-2544.

Furuta et al. (2001) "Hypoxia-inducible factor 1-dependent induction of intestinal trefoil factor protects barrier function during hypoxia" J Exp Med, vol. 193, No. 9, pp. 1027-1034.

Fusco et al. (2016) "N-Rich Fused Heterocyclic Systems: Synthesis, Structure, Optical and Electrochemical Characterization" Eur J Org Chem, pp. 1772-1780.

Garcia-Muñoz et al. (2014) "Metabolic fate of ellagitannins: implications for health, and research perspectives for innovative functional foods" Crit Rev Food Sci Nutr, vol. 54, No. 12, pp. 1584-1598.

Garcia-Villalba et al. (2013) "Time course production of urolithins from ellagic acid by human gut microbiota" J Agric Food Chem, vol. 61, No. 37, pp. 8797-8806.

Gaya et al. (2018) "Bifidobacterium pseudocatenulatum INIA P815: The first bacterium able to produce urolithins A and B from ellagic acid" J. Funct Foods, vol. 45, pp. 95-99.

Gbinigie et al. (2017) "Evidence for the effectiveness of pomegranate supplementation for blood pressure management is weak: A systematic review of randomized clinical trials" Nutr Res, vol. 46, pp. 38-48.

Ge et al. (2014) "High mobility group box-1 (HMGB1) participates in the pathogenesis of alcoholic liver disease (ALD)" J Biol Chem, vol. 289, No. 33, pp. 22672-22691.

Gimenez-Bastida et al. (2012) "Ellagitannin metabolites, urolithin A glucuronide and its aglycone urolithin A, ameliorate TNF-alpha-induced inflammation and associated molecular markers in human aortic endothelial cells" Mol Nutr Food Res, vol. 56, No. 5, pp. 784-796.

Goettel et al. (2016) "AHR Activation Is Protective against Colitis Driven by T Cells in Humanized Mice" Cell Rep, vol. 17, No. 5, pp. 1318-1329.

Gonzalez-Sarrias et al. (2010) "Occurrence of urolithins, gut microbiota ellagic acid metabolites and proliferation markers expression response in the human prostate gland upon consumption of walnuts and pomegranate juice" Mol Nutr Food Res, vol. 54, No. 3, pp. 311-322.

Gopalakrishnan et al. (2018) "The Influence of the Gut Microbiome on Cancer, Immunity, and Cancer Immunotherapy" Cancer Cell, vol. 33, No. 4, pp. 570-580.

A

B

BMDM

C

Serum

B

D

E

F

7-ethoxyresorufin-O-deethylase (EROD) assay

G

P450-Glo Cyp1A1 assay

Q

C

D

H

I

J

K

K

*Nrf2*

*HO1*

L

O

Q

Basal levels (colon tissue)

R

Replicate # 3

A

E

F

G

H

J

K

L

M

N

P

A

B

F

G

L

M

No DSS

DSS+Veh

DSS+UroA

DSS+UAS03

G

H

A

B

A

B

C

G

A

E

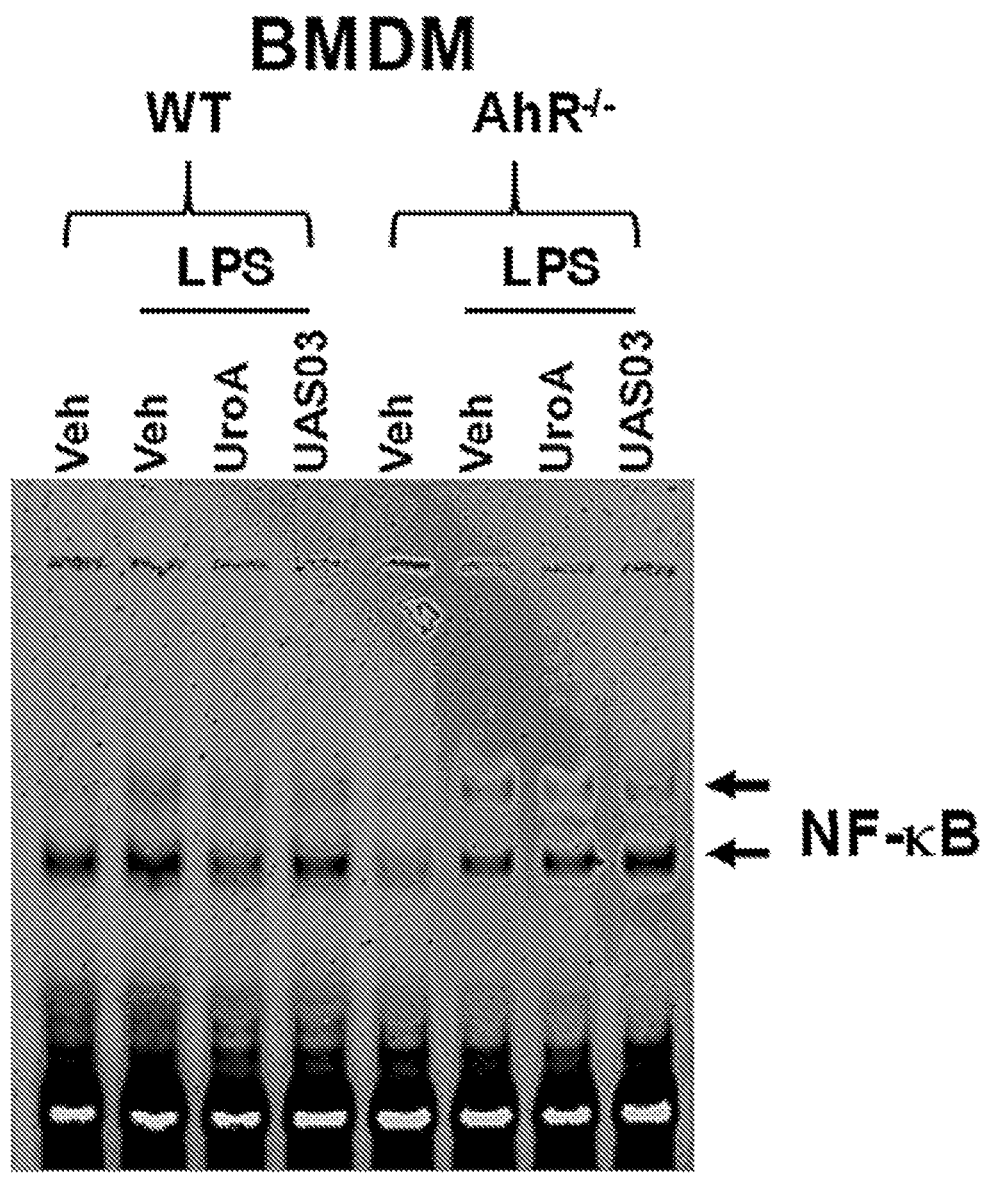

A

B

A

B

Comparison with EA, UroB and UroC

D

Protects against HMGB1 induced barrier dysfunction

A

B

H

Ileum - Ocln

EtOH Diet

Veh    UAS03

Ocln

β-actin

Primary screening was done at 100 µM concentration

MAO A

Primary screening was done at 100 µM concentration

MAO B

Compounds that exhibited maximum inhibition of both MAO activities were selected for dose dependence inhibition study (0.1, 1, and 10 µM)

D

All compounds screened at 100 µM, except positive controls

MAO-A

FIG. 35 (Cont.)

| Compound | IC50 (µM) | | Ki (µM) | |
|---|---|---|---|---|
| | MAO A | MAO B | MAO A | MAO B |
| UroA | 5.88 ± 1.45 | >100 | 9.9 | ND |
| UroB | 0.88 ± 0.17 | >100 | 2.29 | ND |
| UroC | 29.6 ± 9.82 | >100 | 44.3 | ND |
| PKL02/UAS03 | 48.43 ± 5.8 | 37 | ND | 48.08 |
| PKL03 | 0.69 ± 0.07 | 0.52 ± 0.1 | 0.23 | 0.139 |
| PKL04 | 0.75 ± 0.03 | 0.36 ± 0.002 | 0.018 | 0.102 |
| PKL05 | 9.99 ± 0.65 | >20 | 8.6 | ND |
| PKL15 | 1.57 ± 0.11 | 2.39 ± 0.05 | 0.75 | 0.15 |
| PKL16 | 6.24 ± 0.49 | 17.73 ± 2.9 | 4.25 | ND |

D
HUVECs VE-Cadherin (CDH5)

Vehicle UroA UAS03

E

F

A

A

MRP2

B

A

COMPOUNDS, COMPOSITIONS, METHODS OF USING, AND METHODS FOR PREPARING COMPOUNDS

CROSS-REFERENCE TO RELATED APPLICATIONS

This application is a continuation application of U.S. application Ser. No. 17/053,811 filed Nov. 9, 2020, entitled "COMPOUNDS, COMPOSITIONS, METHODS OF USING, AND METHODS FOR PREPARING COMPOUNDS" which is herein incorporated by reference in its entirety, which is a National Stage Entry of International Application No. PCT/US2019/032117 filed May 14, 2019, entitled "COMPOUNDS, COMPOSITIONS, METHODS OF USING, AND METHODS FOR PREPARING COMPOUNDS" which is herein incorporated by reference in its entirety, which claims the benefit of U.S. Provisional Application No. 62/671,737, filed May 15, 2018, entitled "Synthetic Analogs of Gut Microbial Metabolites for Protection of Endothelial and Epithelial Barriers and Applications Thereof" which is herein incorporated by reference in its entirety.

GOVERNMENT RIGHTS

This invention was made with government support under R21 CA216090 and P20 GM125504 awarded by National Institutes of Health. The government has certain rights in the invention.

BACKGROUND

Numerous diseases (e.g., inflammatory bowel diseases, alcoholic liver disease, cancer and many other diseases) plague humankind. In some instances, controlling or reducing inflammation can assist in the treatment of these diseases. Several compounds are known to treat certain diseases (e.g., by reducing inflammation), but do so inadequately.

Certain embodiments of the invention address one or more of the deficiencies described above. For example, in some embodiments of the invention, inventive compounds inventive compounds (e.g., Formula (I), (IA), (II), and (III), and urolithin derivatives) are disclosed. Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases). Further embodiments include methods for making the inventive compounds. Additional embodiments of the invention are also discussed herein.

This invention was made with the Government of India support under BT/PR12490/AAQ/3/716/2015 awarded by Department of Biotechnology

SUMMARY

Some embodiments of the invention include a compound selected from

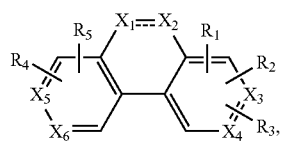
(I)

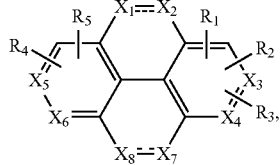
(II)

-continued

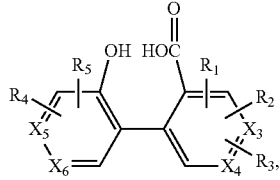
(III)

salts, optical isomers, geometric isomers, salts of isomers, and derivatives thereof. In other embodiments, the bond between $X_1$ and $X_2$ is a single bond or a double bond. In other embodiments, the bond between $X_7$ and $X_8$ is a single bond or a double bond. In still other embodiments, $X_1$, $X_2$, $X_7$, and $X_8$ are the same or different and each can be independently selected from CH, $CH_2$, O, S, C—$NH_2$, C—N=$CH_2$, C(H)($NH_2$), C=O, C=N—$NH_2$, C=NH, C=N-cycloalkyl, C=N—S(O)H, C=NC(EtOH)$_3$, C=NCH(EtOH)$_2$, C=NEtOH, C($CH_3$)(OH), N, NH, C-halogen, C(H)(halogen), C-(halogen)$_2$, C-cycloalkyl, C-heterocyclyl, C-aryl, C-heteroaryl, C(H)(cycloalkyl), C(H)(heterocyclyl), C(H)(aryl), or C(H)(heteroaryl), which CH, $CH_2$, C—$NH_2$, C—N=$CH_2$, C(H)($NH_2$), C=N—$NH_2$, C=NH, C=N-cycloalkyl, C=N—S(O)H, C=NC(EtOH)$_3$, C=NCH(EtOH)$_2$, C=NEtOH, C($CH_3$)(OH), NH, C(H)(halogen), C-cycloalkyl, C-heterocyclyl, C-aryl, C-heteroaryl, C(H)(cycloalkyl), C(H)(heterocyclyl), C(H)(aryl), or C(H)(heteroaryl), are optionally substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In some embodiments, $X_1$ and $X_2$ are optionally further cyclized to form a 5 or 6 membered cycloalkyl, 5 or 6 membered heterocyclyl, 5 or 6 membered aryl, or 5 or 6 membered heteroaryl, which 5 or 6 membered cycloalkyl, 5 or 6 membered heterocyclyl, 5 or 6 membered aryl, or 5 or 6 membered heteroaryl are optionally substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In still other embodiments, $X_7$ and $X_8$ are optionally further cyclized to form a 5 or 6 membered cycloalkyl, 5 or 6 membered heterocyclyl, 5 or 6 membered aryl, or 5 or 6 membered heteroaryl, which 5 or 6 membered cycloalkyl, 5 or 6 membered heterocyclyl, 5 or 6 membered aryl, or 5 or 6 membered heteroaryl are optionally substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In certain embodiments, $R_1$, $R_2$, $R_3$, $R_4$, and $R_5$ are the same or different and each is independently selected from H, OH, halogen, methanoyl (—COH), —OCF$_3$, —COCH$_3$, carbonyl, carboxy (—CO$_2$H), ethynyl (—CCH), cyano (—CN), amine, —NO$_2$, sulfo (—SO$_3$H), $C_1$-$C_4$ alkyl, $C_2$-$C_4$ alkenyl, $C_2$-$C_4$ alkynyl, $C_1$-$C_3$ alkoxy, methyl, ethyl, perfluorinated methyl, perfluorinated ethyl, cycloalkyl, or heterocyclyl, which H, OH, methanoyl (—COH), —COCH$_3$, carbonyl, carboxy (—CO$_2$H), ethynyl (—CCH), sulfo (—SO$_3$H), C$_1$-C$_4$ alkyl, C$_2$-C$_4$ alkenyl, C$_2$-C$_4$ alkynyl, C$_1$-C$_3$ alkoxy, methyl, ethyl, cycloalkyl, or heterocyclyl are optionally substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In some embodiments, $X_3$, $X_4$, $X_5$, and $X_6$ are the same or different and each is independently selected from CH or N, which CH is optionally substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl.

In some embodiments $X_1$, $X_2$, $X_7$, and $X_8$ are the same or different and each can be independently selected from CH$_2$, O, C(H)(NH$_2$), C=O, C=N—NH$_2$, C=NH, C=N-cycloalkyl, C=N-adamantane, C=NC(EtOH)$_3$, C=NCH(EtOH)$_2$, C=NEtOH, C(CH$_3$)(OH), or C(H)(cycloalkyl). In other embodiments, $X_1$ and $X_2$ are the same, $X_7$ and $X_8$ is the same, $X_1$ and $X_7$ is the same, $X_2$ and $X_8$ is the same, or a combination thereof. In still other embodiments, $X_3$, $X_4$, $X_5$, and $X_6$ are the same or different and each is independently selected from CH or N. In yet other embodiments, R$_1$, R$_2$, R$_3$, R$_4$, and R$_5$ are the same or different and each is independently selected from H, OH, halogen, methanoyl (—COH), —OCF$_3$, —COCH$_3$, carbonyl, carboxy (—CO$_2$H), cyano (—CN), amine, —NO$_2$, methoxy, ethoxy, methyl, ethyl, perfluorinated methyl, perfluorinated ethyl, cycloalkyl, bicycloalkyl, heterocyclyl, or imidazolyl. In some embodiments, the compound is selected from Formula (IA)

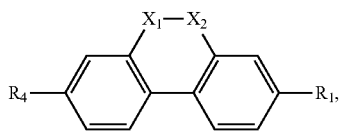

(IA)

salts, optical isomers, geometric isomers, salts of isomers, and derivatives thereof. In certain embodiments, $X_1$ and $X_2$ are the same or different and each is independently selected from CH$_2$, O, C(H)(NH$_2$), C=O, C=N—NH$_2$, C=NH, C=N-cycloalkyl, C=NC(EtOH)$_3$, C=NCH(EtOH)$_2$, C=NEtOH, C(CH$_3$)(OH), or C(H)(cycloalkyl), which CH$_2$, C(H)(NH$_2$), C=N—NH$_2$, C=NH, C=N-cycloalkyl, C=NC(EtOH)$_3$, C=NCH(EtOH)$_2$, C=NEtOH, C(CH$_3$)(OH), or C(H)(cycloalkyl), are optionally substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In other embodiments, $X_1$ and $X_2$ are the same or different and each is independently selected from CH$_2$, O, C=O, C=NH, C=N-cycloalkyl, C=NC(EtOH)$_3$, C=NCH(EtOH)$_2$, C=NEtOH, C(CH$_3$)(OH), or C(H)(cycloalkyl). In yet other embodiments, R$_1$ and R$_2$ are the same or different and each is independently selected from H, OH, halogen, methanoyl (—COH), —OCF$_3$, —COCH$_3$, carbonyl, carboxy (—CO$_2$H), ethynyl (—CCH), cyano (—CN), amine, —NO$_2$, sulfo (—SO$_3$H), C$_1$-C$_4$ alkyl, C$_2$-C$_4$ alkenyl, C$_2$-C$_4$ alkynyl, C$_1$-C$_3$ alkoxy, methyl, ethyl, perfluorinated methyl, perfluorinated ethyl, which H, OH, methanoyl (—COH), —COCH$_3$, carbonyl, carboxy (—CO$_2$H), ethynyl (—CCH), sulfo (—SO$_3$H), C$_1$-C$_4$ alkyl, C$_2$-C$_4$ alkenyl, C$_2$-C$_4$ alkynyl, C$_1$-C$_3$ alkoxy, methyl, or ethyl, are optionally substituted with one or more of halogen, hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In still other embodiments, R$_1$ and R$_2$ are the same or different and each is independently selected from H, OH, halogen, methanoyl (—COH), —OCF$_3$, —COCH$_3$, carbonyl, carboxy (—CO$_2$H), cyano (—CN), amine, —NO$_2$, methoxy, ethoxy, methyl, ethyl, perfluorinated methyl, or perfluorinated ethyl. In certain embodiments, the compound (a) is not I-1, I-2, I-3, I-5, I-7, I-20, I-26, I-27, I-28, I-33, I-53, I-54, I-55, I-56, I-57, I-59, I-94, I-98, II-99, II-100, II-101, II-102, II-103, II-118, II-119, II-120, II-121, and II-122, (b) is a compound selected from Table 1, or (c) both. In certain embodiments, the compound (a) is not I-1, I-3, I-5, I-7, I-20, I-26, I-27, I-28, I-33, I-53, I-54, I-55, I-56, I-57, I-59, I-94, I-98, II-99, II-100, II-101, II-102, II-103, II-118, II-119, II-120, II-121, and II-122, (b) is a compound selected from Table 1, or (c) both.

Some embodiments of the invention include a urolithin derivative having a chemical group substitution of the urolithin cyclic ester resulting in improved potency of the derivative as compared to urolithin A, or improved stability of the derivative at acidic pH and/or in presence of esterase and/or protease as compared to urolithin A. In other embodiments, the urolithin cyclic ester is replaced with a cyclic ether. In yet other embodiments, the urolithin cyclic ether comprises one or more substituents. In still other embodiments, the cyclic ether substituents are independently selected from halo, amine, substituted amine, hydroxyl, and a C5 or C6 heterocycle having one or two heteroatoms independently selected from O, N, or S. In certain embodiments, the urolithin cyclic ester is replaced with a carbocycle having adjacent carbonyl groups. In some embodiments, the urolithin cyclic ester is replaced with a cyclic alkenyl group, which is optionally aromatic, and optionally substituted. In other embodiments, the cyclic alkenyl group has one or more substituents. In still other embodiments, the cyclic alkenyl group substituents are independently selected from ketone, optionally substituted imine, optionally substituted amine, halo, and hydroxyl. In yet other embodiments, the urolithin cyclic ester is replaced with a cyclic amide. In some embodiments, the urolithin cyclic ester is replaced with a non-cyclic bridge. In some embodiments, the urolithin aromatic groups have one or more substituents. In other embodiments, the aromatic groups are phenyl groups which are optionally substituted. In certain embodiments, the one or more aromatic substituents are independently selected from hydroxyl, alkoxy, halo, amine, a 5 or 6 membered carbocyclic or heterocyclic ring, nitro, nitrile, alkyl, alkyl ether, and haloalkyl. In other embodiments, one or more urolithin aromatic rings are heterocyclic. In still other embodiments, the heteroatoms of the heterocyclic ring are independently selected from N, O, and S. In yet other embodiments, substituents of each aromatic ring together form a second bridging ring. In certain embodiments. the second bridging ring is identical in structure to a first bridging ring. In other embodiments, the second bridging ring is different in structure to the first bridging ring.

Some embodiments of the invention include a composition comprising a compound of any compound disclosed herein (e.g., Formula (I), (II), (III), (IA), I-1, or I-2, or a urolithin derivative). In other embodiments, the amount of the compound in the composition is from about 0.0001% (by weight total composition) to about 99%. In still other embodiments, the composition further comprises a formulary ingredient, an adjuvant, or a carrier. In yet other embodiments, the composition further comprises 5-florouracil.

Some embodiments of the invention include a pharmaceutical composition comprising a compound of any compound disclosed herein (e.g., Formula (I), (II), (III), (IA), I-1, or I-2, or a urolithin derivative). In other embodiments, the amount of the compound in the pharmaceutical composition is from about 0.0001% (by weight total composition) to about 50%. In still other embodiments, the pharmaceutical composition further comprises a formulary ingredient, an adjuvant, or a carrier. In yet other embodiments, the pharmaceutical composition further comprises 5-florouracil.

Some embodiments of the invention include methods for providing an animal with a compound comprising one or more administrations of one or more compositions comprising any compound disclosed herein (e.g., Formula (I), (II), (III), (IA), I-1, or I-2, a urolithin derivative), wherein the compositions may be the same or different if there is more than one administration. In certain embodiments, at least one of the one or more compositions further comprises a formulary ingredient. In other embodiments, at least one of the one or more compositions comprises any composition as disclosed herein or any pharmaceutical as disclosed herein. In still other embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In still other embodiments, if there is more than one administration at least one composition used for at least one administration is different from the composition of at least one other administration. In yet other embodiments, the compound of at least one of the one or more compositions is administered to the animal in an amount of from about 0.01 mg/kg animal body weight to about 50 mg/kg animal body weight. In certain embodiments, the animal is a human, a rodent, or a primate.

Some embodiments of the invention include a method for treating an animal for a disease, comprising one or more administrations of one or more compositions comprising any compound disclosed herein (e.g., Formula (I), (II), (III), (IA), I-1, or I-2, a urolithin derivative), wherein the compositions may be the same or different if there is more than one administration. In other embodiments, at least one of the one or more compositions further comprises a formulary ingredient. In other embodiments, at least one of the one or more of any of the compositions disclosed herein or the pharmaceutical composition any of the compositions disclosed herein. In still other embodiments, at least one of the one or more administrations comprises parenteral administration, a mucosal administration, intravenous administration, subcutaneous administration, topical administration, intradermal administration, oral administration, sublingual administration, intranasal administration, or intramuscular administration. In yet other embodiments, if there is more than one administration at least one composition used for at least one administration is different from the composition of at least one other administration. In certain embodiments, the compound of at least one of the one or more compositions is administered to the animal in an amount of from about 0.005 mg/kg animal body weight to about 50 mg/kg animal body weight. In other embodiments, the animal is a human, a rodent, or a primate. In still other embodiments, the animal is in need of the treatment. In other embodiments, the method is for treating alcoholic liver disease (ALD), non-alcoholic steatohepatitis (NASH), intestinal permeability, leaky gut, metal induced gut leakiness, stress induced gut leakiness, radiation induced gut permeability, colitis, local inflammation, inflammation in the brain, inflammation in the mouth, inflammation in the esophagus, inflammation in the stomach, inflammation in the small intestine, systemic inflammation, inflammatory bowel disease, ulcerative colitis, Crohn's disease, infection-induced inflammatory disease, sepsis, sepsis-induced kidney injury, sepsis-induced lung injury, scleroderma, vasculitis, drug-induced vasculitis, neuroinflammatory disorders, Alzheimer's Disease, Parkinson's Disease, anxiety, depression, metabolic stress, cardiovascular disease, sarcopenia, muscle degenerative disease, Duchenne muscular dystrophy, nonalcoholic fatty liver disease, drug-induced liver injury, alpha-antitrypsin deficiency, ischemia/reperfusion injury, obesity, metabolic syndrome, type II diabetes mellitus, hyperlipidemia, osteoarthritis, neurodegenerative disease, amyotrophic lateral sclerosis (ALS), cancer, cancerous tumors, breast cancer, colon cancer, cognitive disorder, stress, mood disorder, or fibrosis. In still other embodiments, the method is for treating alcoholic liver disease (ALD), non-alcoholic steatohepatitis (NASH), colitis, intestinal permeability, leaky gut, metal induced gut leakiness, stress induced gut leakiness, radiation induced gut permeability, local inflammation, systemic inflammation, inflammatory bowel disease, ulcerative colitis, Crohn's disease, infection-induced inflammatory disease, sepsis, sepsis-induced kidney injury, sepsis-induced lung injury, scleroderma, vasculitis, drug-induced vasculitis, neuroinflammatory disorders, Alzheimer's Disease, Parkinson's Disease, cancer, cancerous tumors, breast cancer, colon cancer, or fibrosis. In yet other embodiments, the method is for treating alcoholic liver disease (ALD), non-alcoholic steatohepatitis (NASH), intestinal permeability, leaky gut, metal induced gut leakiness, stress induced gut leakiness, radiation induced gut permeability, local inflammation, systemic inflammation, inflammatory bowel disease, ulcerative colitis, Crohn's disease, sepsis, Alzheimer's Disease, Parkinson's Disease, cancer, cancerous tumors, breast cancer colon cancer, or fibrosis. In still other embodiments, the method is for treating vasculitis, drug-induced vasculitis, scleroderma, internal vascular bleeding, drug-induced internal bleeding, atopic dermatitis, perfusion-related injury, perfusion related inflammation, diabetic retinopathy, celiac disease, Non-Alcoholic SteatoHepatitis (NASH), Alcoholic SteatoHepatitis (ASH), metabolic stress, cardiovascular disease, sarcopenia, muscle degenerative disease, Duchenne muscular dystrophy, alcoholic liver disease, nonalcoholic fatty liver disease, drug-induced liver injury, chronic kidney disease, alpha-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, neuroinflammatory disorder, Alzheimer's disease, Parkinson's disease, multiple sclerosis, myotrophic lateral sclerosis (ALS), pulmonary fibrosis, chronic obstructive pulmonary disease (COPD), acute lung injury, blood transfusion related acute lung injury, acute respiratory distress syndrome, asthma, cancer, cognitive disorder, stress, or mood disorder. In some embodiments, the method is for treating cancer and the cancer is pancreatic cancer, pancreatic ductal adenocarcinoma, lung cancer, liver cancer, colorectal cancer, colon cancer, rectal cancer, melanoma, cutaneous malignant melanoma, melanoma tumorigenesis, bladder cancer, prostate cancer, malignant nerve sheath tumors, multiple myeloma, breast cancer, squamous cell carcinoma, head and neck squamous cell carcinoma, lymphoma, leukemia, bone marrow cancer, non-Hodgkin lymphoma, diffuse large B-cell lymphoma, glioblastoma multiforme, endometrial cancer, kidney cancer, basal cell carcinoma, thyroid cancer, neuroblastoma, ovarian cancer, renal cell carcinoma, hepatocellular carcinoma, chronic lymphocytic leukemia (CLL), acute lymphoblastic leukemia, rhabdomyosarcoma, meningioma, gastric cancer, Glioma, oral cancer, nasopharyngeal carcinoma, stomach cancer, uterine cancer, medulloblastoma, cancers that can result in metastasis, cancers resulting from metastasis, or cancerous tumors thereof.

Some embodiments of the invention include a method of inducing the expression of tight junction proteins in a tissue, comprising administering an effective amount of a pharmaceutical composition comprising a urolithin structural analogue to a subject in need. In other embodiments, there is a method of inducing the expression of tight junction proteins in a tissue, comprising administering an effective amount of the composition of any compound disclosed herein (e.g., Formula (I), (II), (III), (IA), I-1, or I-2, a urolithin derivative) to a subject in need. In some embodiments, the subject exhibits symptoms of gastrointestinal permeability or inflammation, and the composition is administered to the small and/or large intestine. In other embodiments, the subject has an inflammatory bowel disease. In still other embodiments, the inflammatory bowel disease is Crohn's disease or ulcerative colitis. In yet other embodiments, the subject has celiac disease. In certain embodiments, the inflammatory bowel disease comprises colonic inflammation. In some embodiments, the composition is administered systemically in an amount effect to improve endothelial or vascular barrier integrity in organs. In still other embodiments, the organs are one or more selected from liver, kidneys, pancreas, heart, lungs, skin, muscle, fat, brain, eyes, bone, and intestine. In yet other embodiments, the subject has a condition selected from vasculitis, drug-induced vasculitis, scleroderma, internal vascular bleeding, drug-induced internal bleeding, atopic dermatitis, perfusion-related injury, perfusion related inflammation, and diabetic retinopathy.

Some embodiments of the invention include a method of treating systemic inflammation comprising administering to a patient in need thereof an effective amount of a composition comprising any compound disclosed herein (e.g., Formula (I), (II), (III), (IA), I-1, or I-2, a urolithin derivative). In other embodiments, the composition is administered enterally or parenterally. In still other embodiments, the subject has or is at risk of sepsis or an infection-induced inflammatory disease. In yet other embodiments, the subject has or is at risk of alcoholic liver disease (ALD). In certain embodiments, the subject has or is at risk of Non-Alcoholic SteatoHepatitis (NASH) or Alcoholic SteatoHepatitis (ASH). In some embodiments, the subject has inflammation of one or more organs or tissues selected from liver, kidneys, pancreas, heart, lungs, skin, muscle, fat, brain, eyes, bone, marrow, intestine, and cartilage.

Some embodiments of the invention include a method for treating neuroinflammatory disorder comprising administering to a patient in need thereof an effective amount of a composition comprising any compound disclosed herein (e.g., Formula (I), (II), (III), (IA), I-1, or I-2, a urolithin derivative). In other embodiments, the neuroinflammatory disorder is Alzheimer's Disease. In still other embodiments, the neuroinflammatory disorder is Parkinson's Disease. In yet other embodiments, the neuroinflammatory disorder is a neurodegenerative disease, which is optionally multiple sclerosis. In certain embodiments, Some embodiments of the invention include a method for treating anxiety or depression, comprising administering an effective amount of the composition comprising any compound disclosed herein (e.g., Formula (I), (II), (III), (IA), I-1, or I-2, a urolithin derivative) to a subject in need, in an amount effective to inhibit monoamine oxidase enzymes in the subject. In other embodiments, the composition is administered systemically or locally to the brain. In still other embodiments, the composition is administered enterally, parenterally, or intranasally.

Some embodiments of the invention include a method of enhancing airway barrier integrity in lungs comprising administering to a subject in need thereof an effective amount of a composition comprising any compound disclosed herein (e.g., Formula (I), (II), (III), (IA), I-1, or I-2, a urolithin derivative). In certain embodiments, the subject has pulmonary fibrosis, chronic obstructive pulmonary disease (COPD), acute lung injury, blood transfusion related acute lung injury, acute respiratory distress syndrome, or asthma.

Some embodiments of the invention include a method of improving or increasing autophagy in a subject, comprising administering to a subject in need thereof an effective amount of the composition comprising any compound disclosed herein (e.g., Formula (I), (II), (III), (IA), I-1, or I-2, a urolithin derivative). In other embodiments, autophagy is improved or increased in a tissue or organ of the subject selected from brain, eye, skin, bone, marrow, cartilage, heart, lung, stomach, intestine, liver, pancreas, kidney, muscle, and fat. In certain embodiments, autophagy is improved or increased in cells of the subject selected from adult stem cells, differentiated cells, blood cells, hematopoietic cells, endothelial cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells. In still other embodiments, the subject has a disease or condition selected from metabolic stress, cardiovascular disease, sarcopenia, muscle degenerative disease, Duchenne muscular dystrophy, alcoholic liver disease, nonalcoholic fatty liver disease, drug-induced liver injury, chronic kidney disease, alpha-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, amyotrophic lateral sclerosis (ALS), cancer, cognitive disorder, stress, and mood disorder, whereby the administering treats or ameliorates the disease or condition.

Some embodiments of the invention include a method of increasing longevity in a subject, comprising administering to a subject a regimen of the composition comprising any compound disclosed herein (e.g., Formula (I), (II), (III), (IA), I-1, or I-2, a urolithin derivative) effective to increase longevity in an animal. In other embodiments, the subject is a vertebrate animal. In still other embodiments, the subject is a mammal, which is optionally a primate. In yet other embodiments, the subject is a human. In certain embodiments, the subject is a veterinary patient.

Some embodiments of the invention include a method of increasing autophagy in a cell, comprising contacting a cell with an effective amount of any compound disclosed herein (e.g., Formula (I), (II), (III), (IA), I-1, or I-2, a urolithin derivative). In other embodiments, the autophagy is mitophagy. In still other embodiments, the cell is selected from: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

Some embodiments of the invention include a method of increasing longevity of eukaryotic cells in vitro, comprising contacting the cells with any compound disclosed herein (e.g., Formula (I), (II), (III), (IA), I-1, or I-2, a urolithin derivative) to increase longevity of the cells. In other embodiments, the eukaryotic cells are eukaryotic cells in primary culture. In yet other embodiments, the eukaryotic cells are part of a cell line. In certain embodiments, the eukaryotic cells are cells selected from: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells. In some embodiments, the eukaryotic cells are cells selected from: embryonic stem cells, induced pluripotent stem cells, and adult stem cells.

Some embodiments of the invention include a method for preparing a compound of Formula (I) comprising (a) reacting a compound of Formula (V) with a compound of Formula (VI) to result in a mixture comprising a compound of Formula (VII); (b) reacting the compound of Formula (VII) with a suitable compound to result in a mixture comprising a compound of Formula (I); (c) optionally further reacting the compound of Formula (I) to result in a different compound of Formula (I) so that the identity of one or more of $R_1$, $R_2$, $R_3$, $R_4$, $R_5$, $X_1$ or $X_2$ is changed by the further reacting; and (d) recovering Formula (I). In other embodiments, Formula (V) is

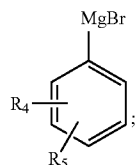

(V)

Formula (VI) is

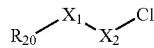

(VI)

where $R_{20}$ is a halogen or

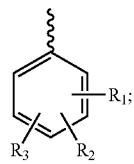

and Formula (VII) is

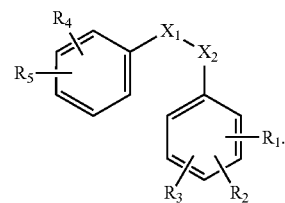

(VII)

In certain embodiments, the suitable compound in step b comprises Ti(IV)chloride, molybdenum(V)chloride, or a combination thereof. In other embodiments, Formula (I) is Formula (IA), I-1, or I-2. In yet other embodiments, $R_{20}$ is Cl or

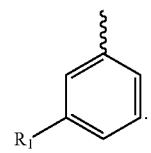

In other embodiments, Formula (V) is

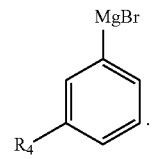

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

Figure 10:
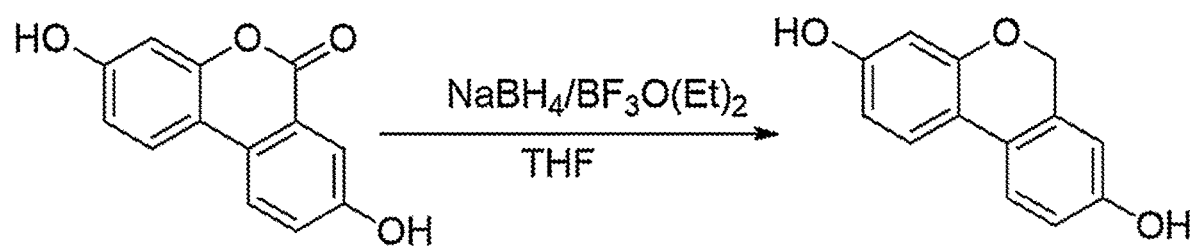

FIG. 10: Synthesis of UAS03. The compound UAS03 has been synthesized by reducing the lactone to cyclic ether as described herein.

Figure 11:
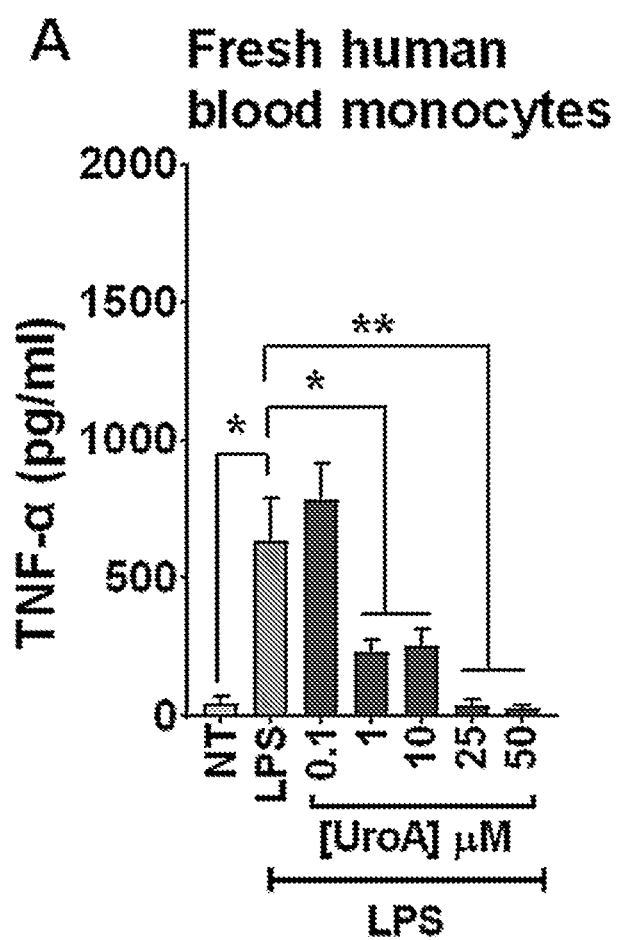
Figure 11:
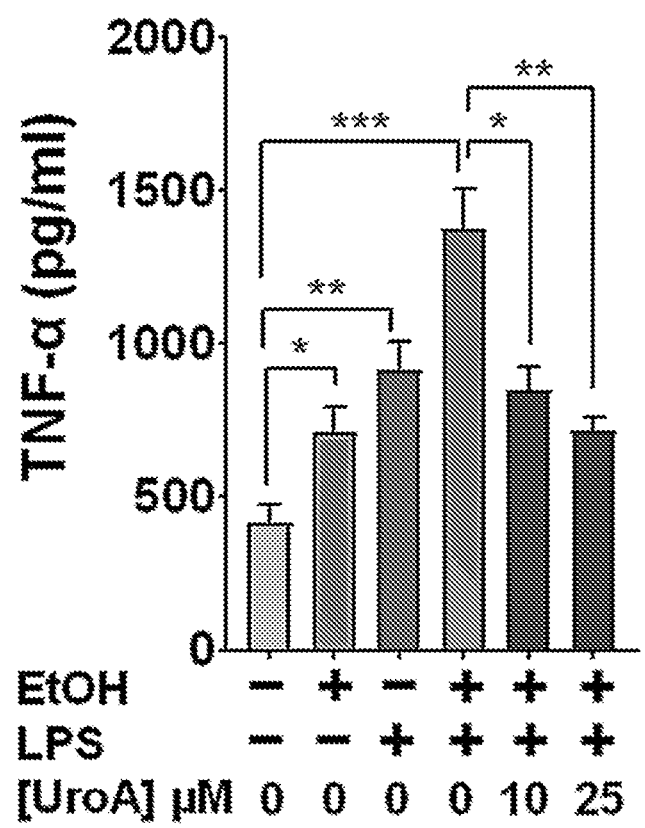

FIG. 11: UroA reduces the LPS and EtOH induced TNF-α in human primary monocytes. (A) Human primary monocytes treated with UroA and LPS (50 ng/ml) for 6 h. The TNF-α in supernatant was measured. (B) Human primary monocytes were exposed to EtOH (25 mM) for 7 days. LPS (50 ng/ml) and UroA were added at day 6 and incubated for 24 h. The TNF-α levels in supernatant were measured using standard ELISA methods. Statistics performed using unpaired t-test using Graphpad Prism software. Error bars, ±SEM; *p<0.001; p<0.01

Figure 12:
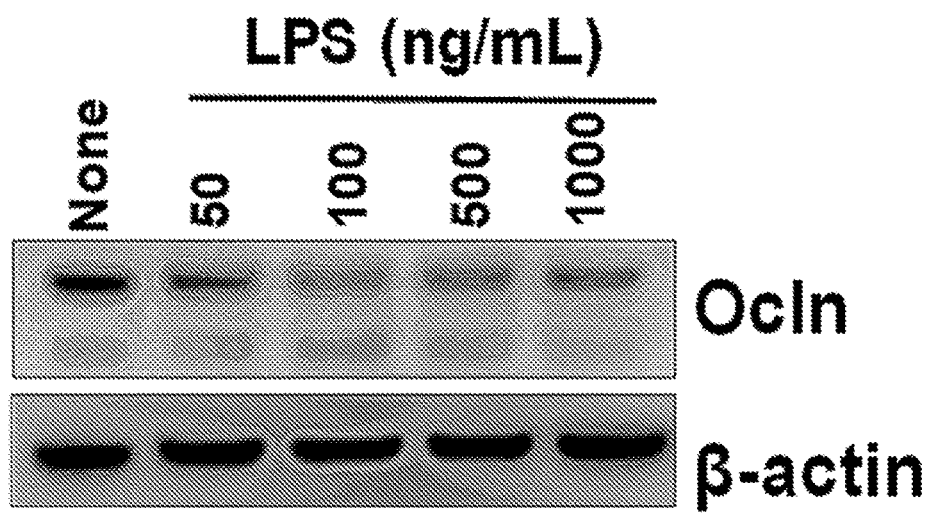
Figure 12:
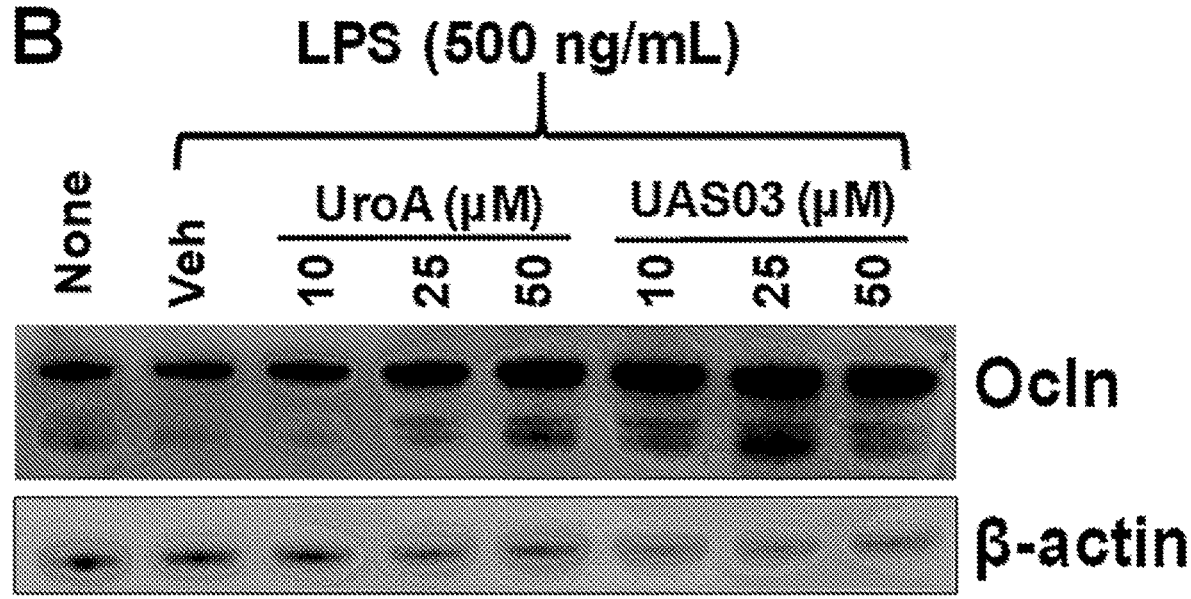

FIG. 12: UroA/UAS03 protect from LPS or alcohol induced depletion of Ocln and protected permeability. (A) Caco 2 cells were treated with LPS for 24 h at indicated doses and Western blots performed to determine expression of Ocln. (B) Caco2 cells were treated with LPS in combination with UroA or UAS03 (10, 25, 50 μM) for 24 h and determined Ocln expression.

Figure 13:
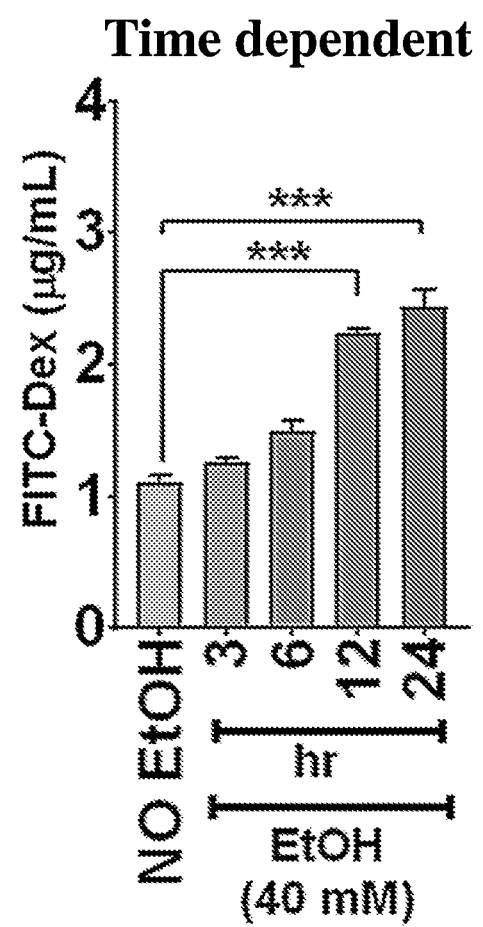
Figure 13:
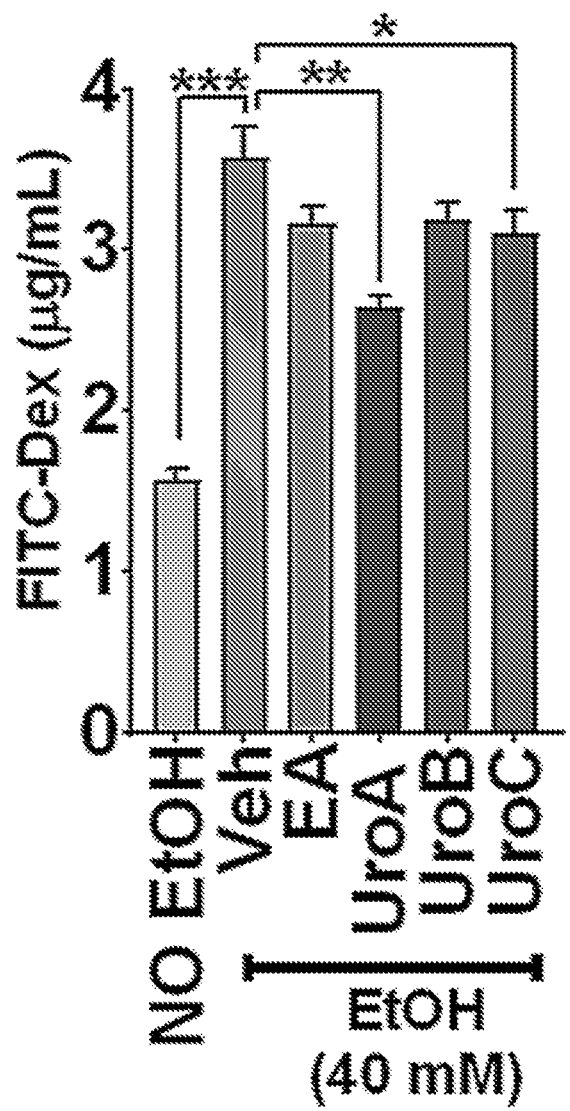
Figure 13:
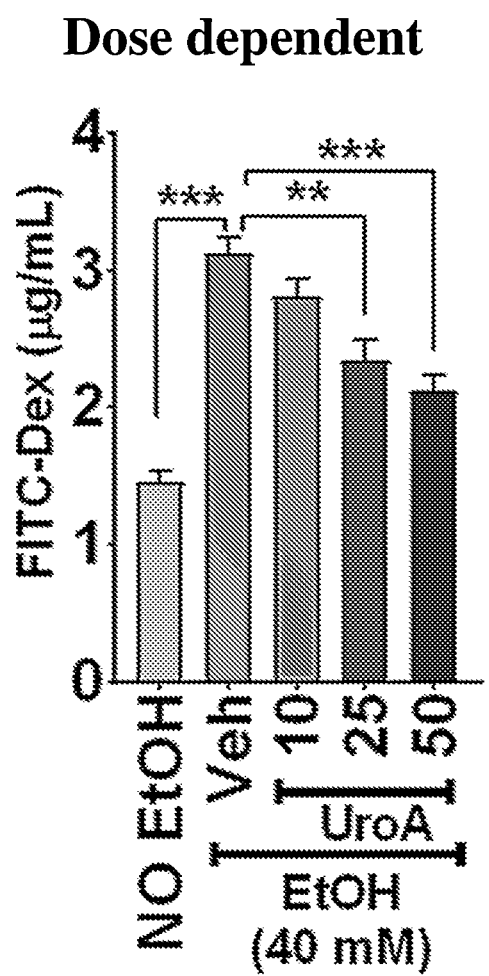
Figure 13:
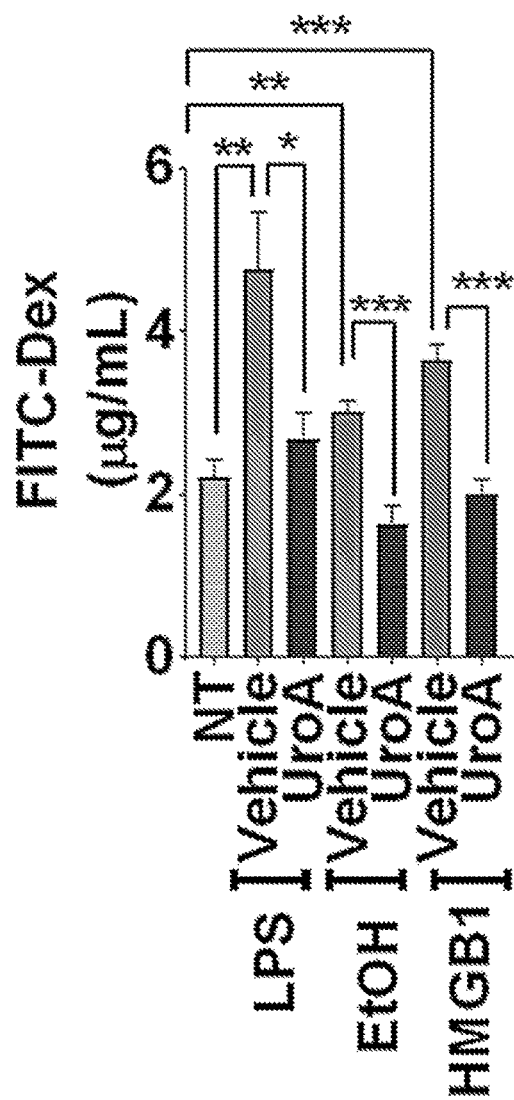
Figure 13:
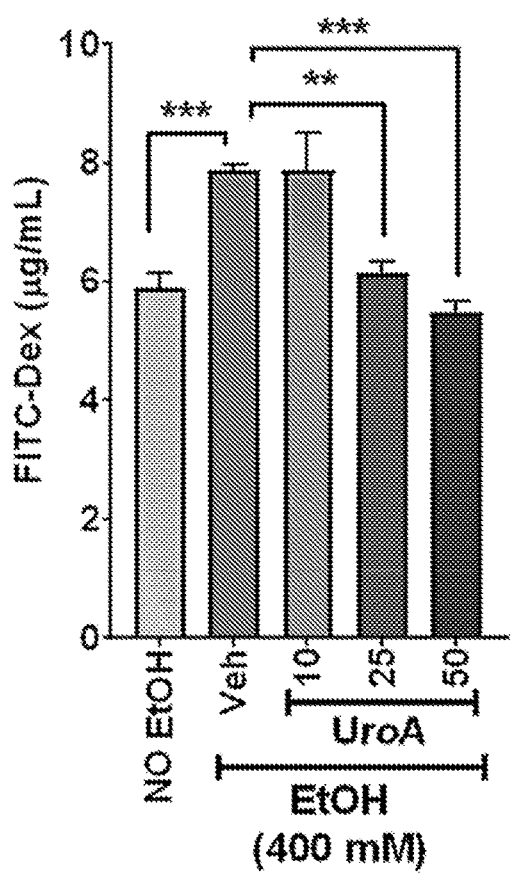
Figure 13:
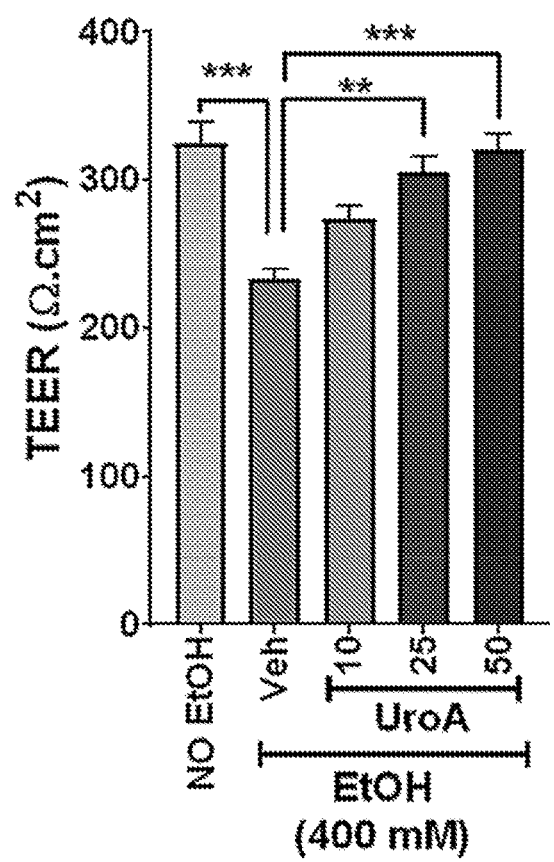
Figure 13:
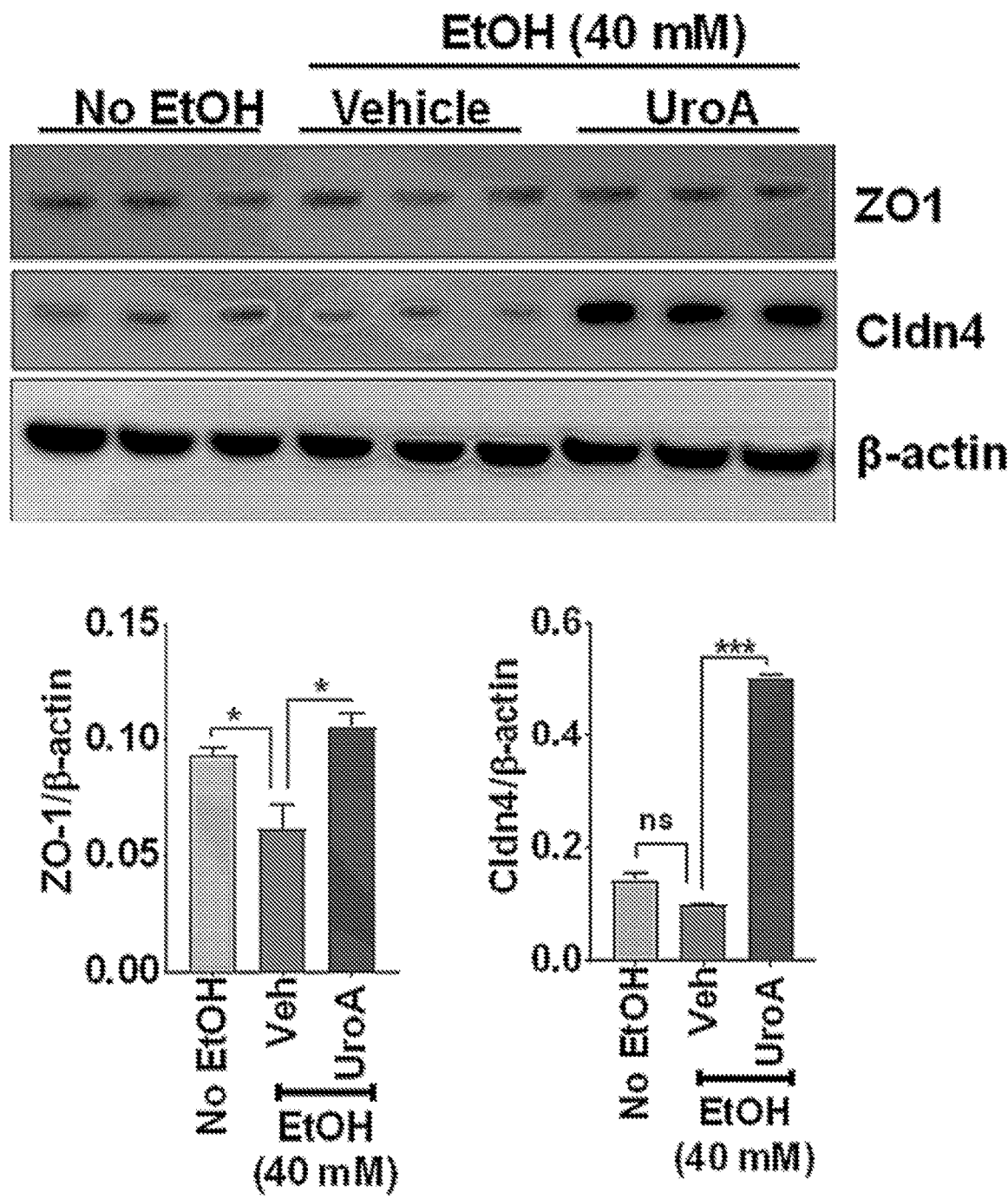
Figure 13:
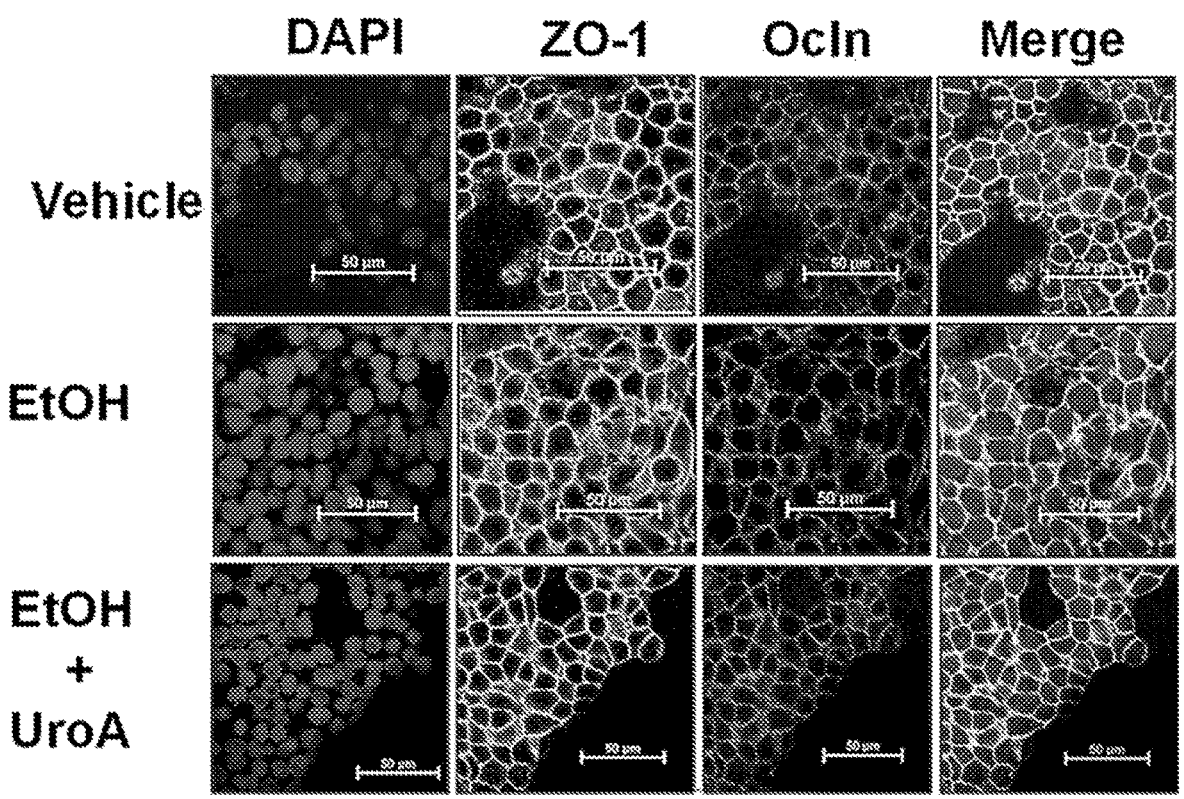

FIG. 13: Caco2 cells were grown as monolayer on transwell membrane filters. (A) Cells were treated with 40 mM EtOH and FITC-dextran permeability was performed in time dependent manner. (B-F) Cells were treated with respective Urolithins (50 μM) and Ellagic acid (50 μM) or different doses of UroA (B) for 24 hrs. After treatments, cells were treated with ethanol (40 mM) (B, D) or 400 mM (E, F), LPS (100 ng/mL), HMGB1 (500 ng/mL) for 2 hrs and washed with PBS. FITC-Dex (1 mg/mL) solution was added (100 μl) on apical side. Permeability of FITC-Dex across the monolayer as well as TEER values were measured after 2 hr. (G-H) UroA protects against EtOH induced TJ disruption in Caco-2 cells. Confocal images of TJ proteins staining. Statistics performed using unpaired t-test. *p<0.05, p<0.01, * p<0.001, Error bars, ±SEM.

Figure 14:
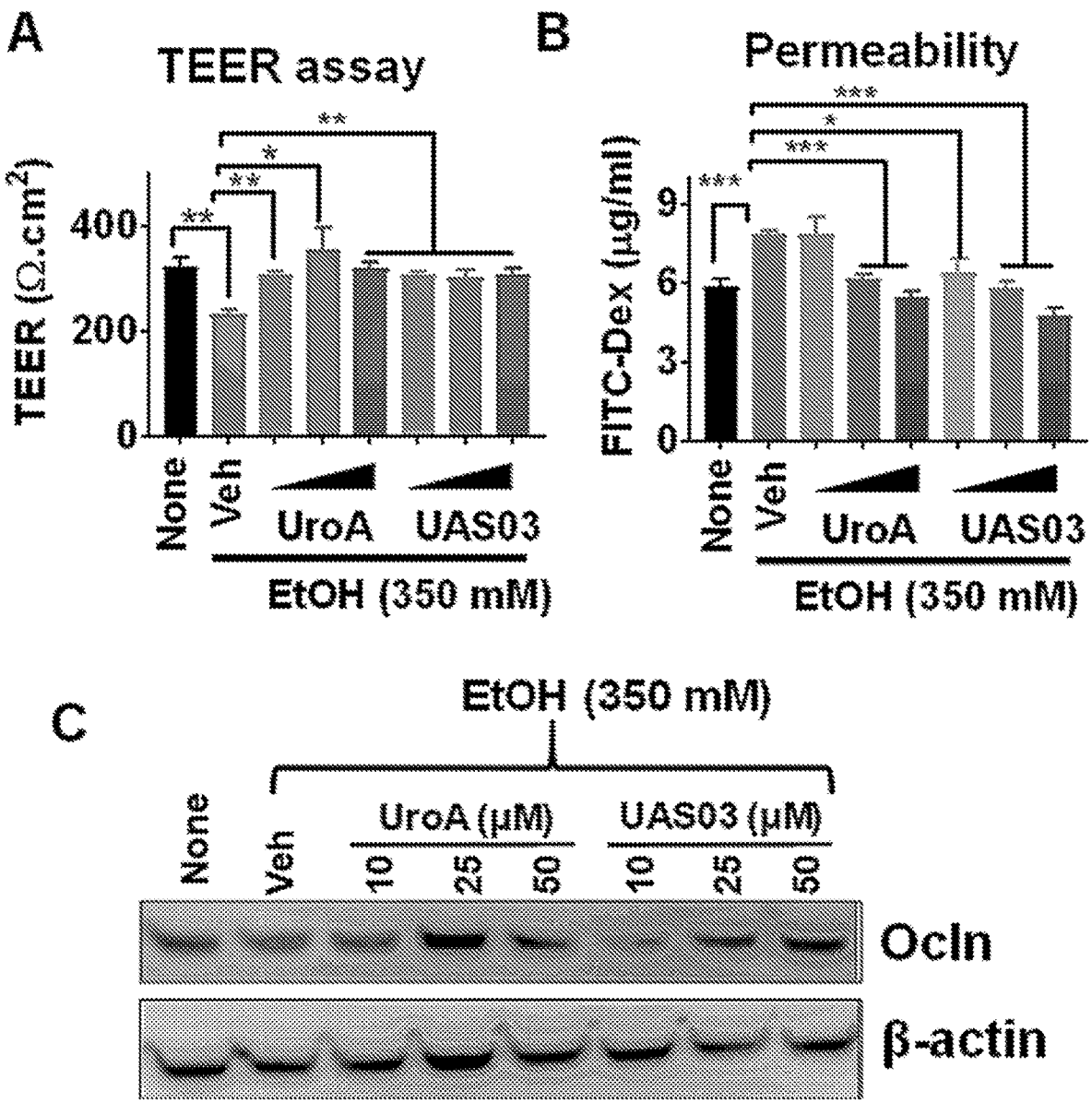

FIG. 14: UAS03 protects against EtOH induced barrier dysfunction. Caco2 cells on transwell membrane were pre-treated with vehicle or UroA or UAS03 (10, 25, 50 μM) for 24 h followed by addition of alcohol (2%) for 24 h. TEER values (A) and the FITC-dextran permeability assay (B) was performed as described in FIG. 2. Statistics performed using unpaired t-test using Graphpad Prism software. Error bars, ±SEM; *p<0.001; p<0.01. (C) Caco2 cells were treated with alcohol (EtOH) (350 mM or 2%) in the presence or with UroA or UAS03 (10, 25, 50 μM) for 24 h and determined expression of Ocln by Western blots. Representative of 3 independent blots was shown.

Figure 15:
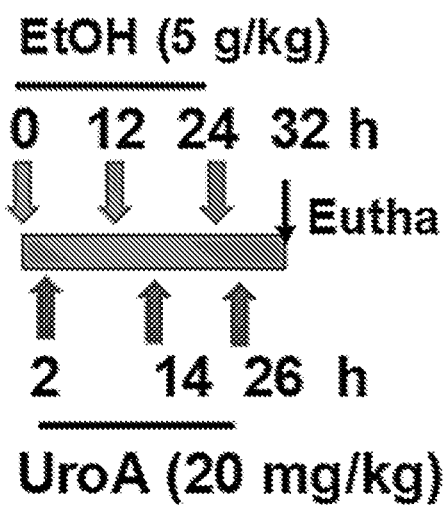
Figure 15:
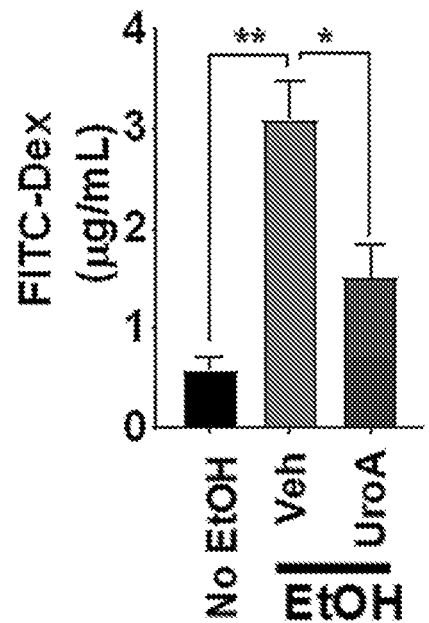
Figure 15:
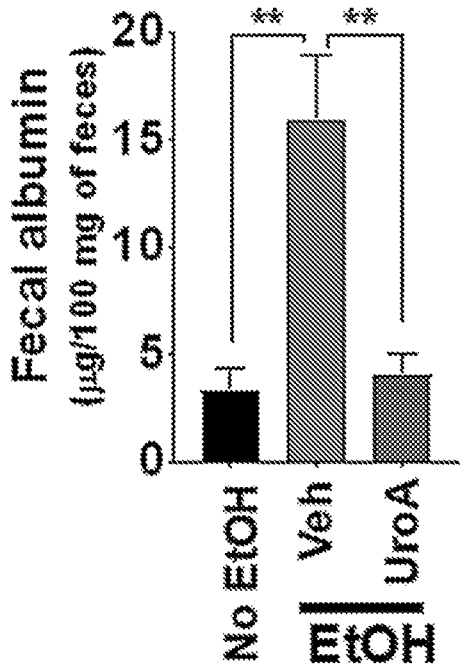
Figure 15:
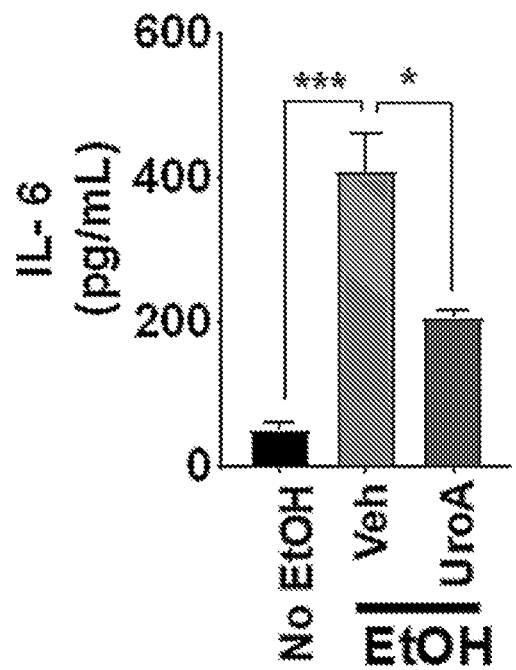
Figure 15:
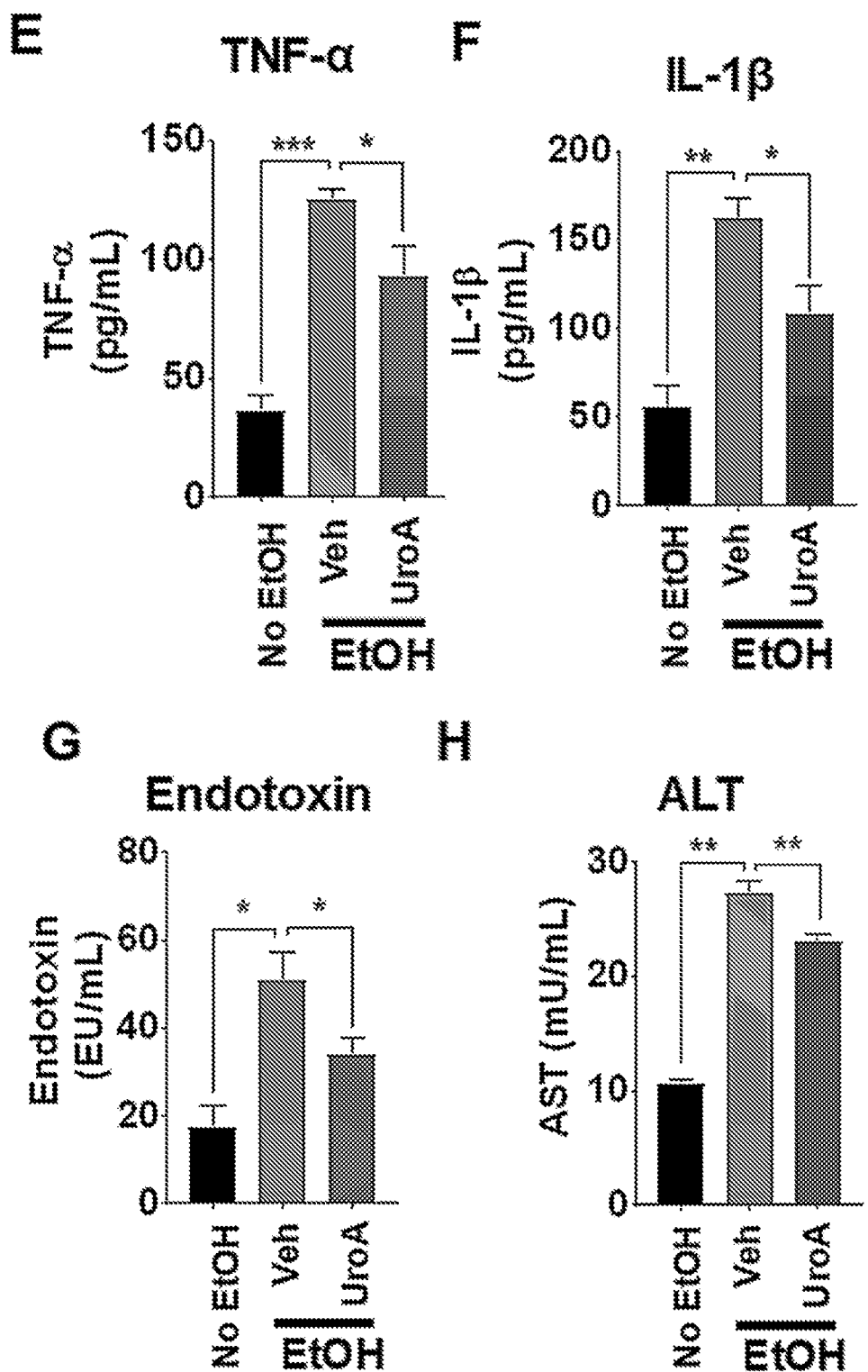
Figure 15:
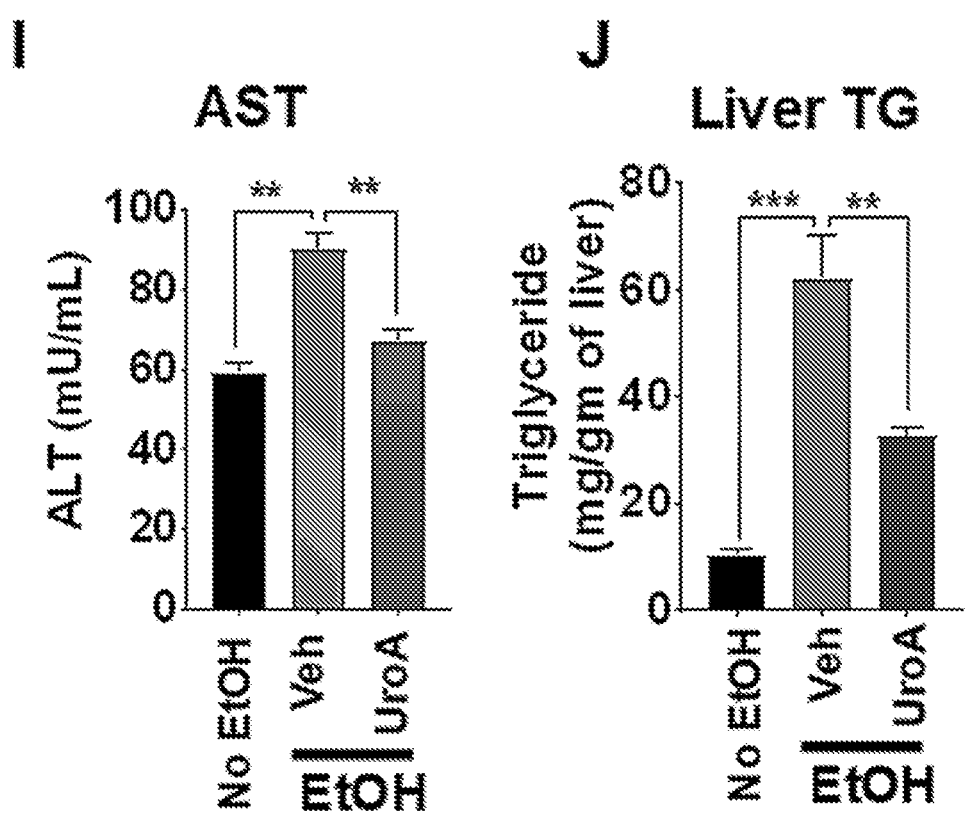

FIG. 15: UroA treatment reduces binge EtOH-induced ALD. (A) Acute alcohol model: Female wild type (C547BL/6) mice (n=6/group) were oral gavaged with alcohol (5 g/kg) at 0, 12 and 24 h. Mice were treated with Veh (0.25% CMC) or UroA (20 mg/kg) at 2, 14 and 26 h. Mice were euthanized at 32 h. (B) In vivo permeability was measured by determining serum levels of FITC-Dextran post 4 h oral gavage of FITC-dextran (C) Fecal albumin was measured using standard ELISA. (D-I) Indicated serum cytokines/markers levels were measured in serum using standard ELISA. (J) The levels of triglycerides (TGs) in liver were measured using ELISA methods. Error bars, ±SEM. Statistics were performed using 2 way ANOVA multiple comparisons. * p<0.05,  p<0.01, * p<0.001.

Figure 16:
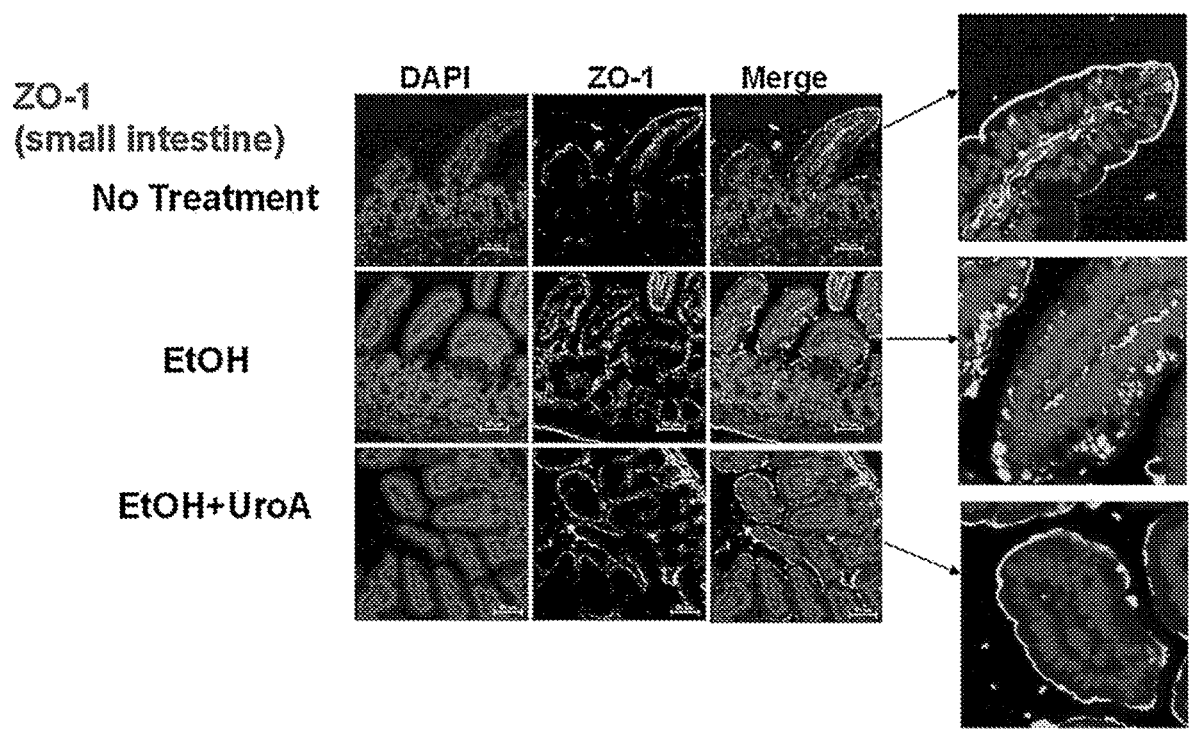

FIG. 16: UroA treatment protects against EtOH induced ZO-1 disruption in small intestines. Confocal images of ZO-1 (green) and nucleus (DAPI staining). EtOH damaged ZO-1 proteins (middle panel) and UroA treatment protected from damage induced by EtOH (bottom panel).

Figure 17:
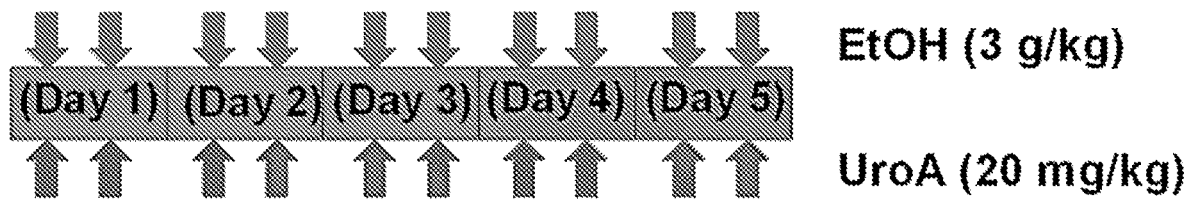
Figure 17:
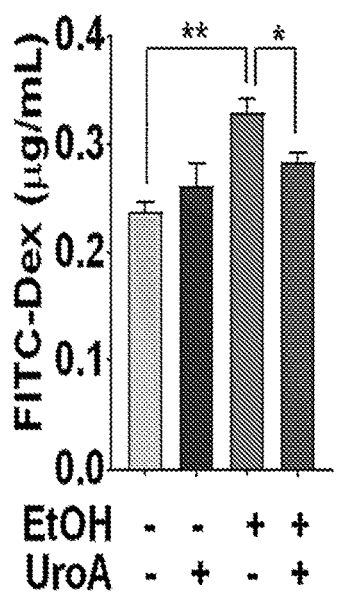
Figure 17:
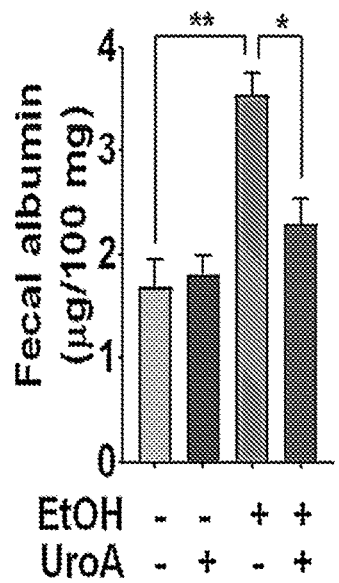
Figure 17:
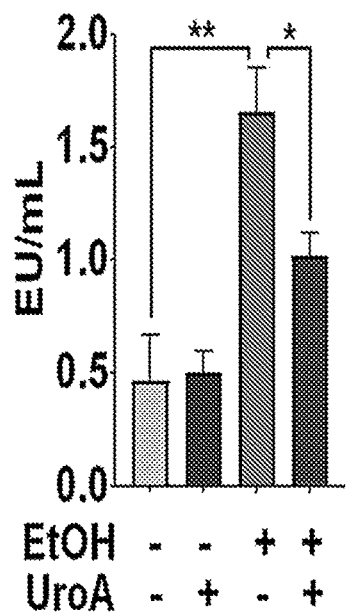
Figure 17:
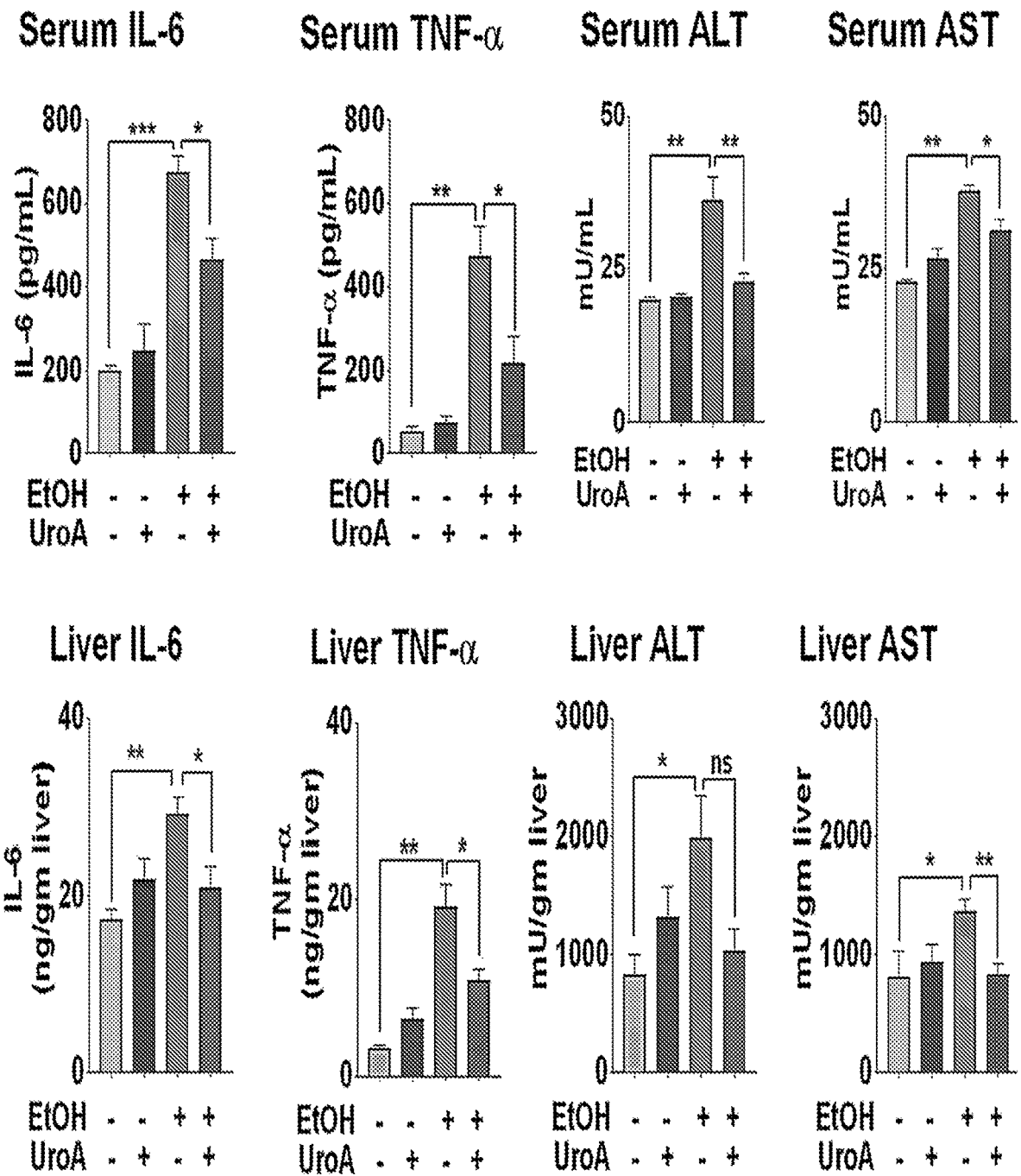

FIG. 17: UroA protects against chronic low dose alcohol induced gut barrier dysfunction and inflammation. C57BL/6 mice (10 wk old age) were used in low dose chronic ALD models. Mice were treated with EtOH (3 g/kg) daily twice orally for 5 days at 3 g/kg, UroA (20 mg/kg) was given orally 2 h prior to EtOH treatment. Mice were euthanized on day 6 and analyzed the indicated parameters. Error bars, ±SEM. Statistics were performed using 2 way ANOVA multiple comparisons. * p<0.05,  p<0.01, * p<0.001.

Figure 18:
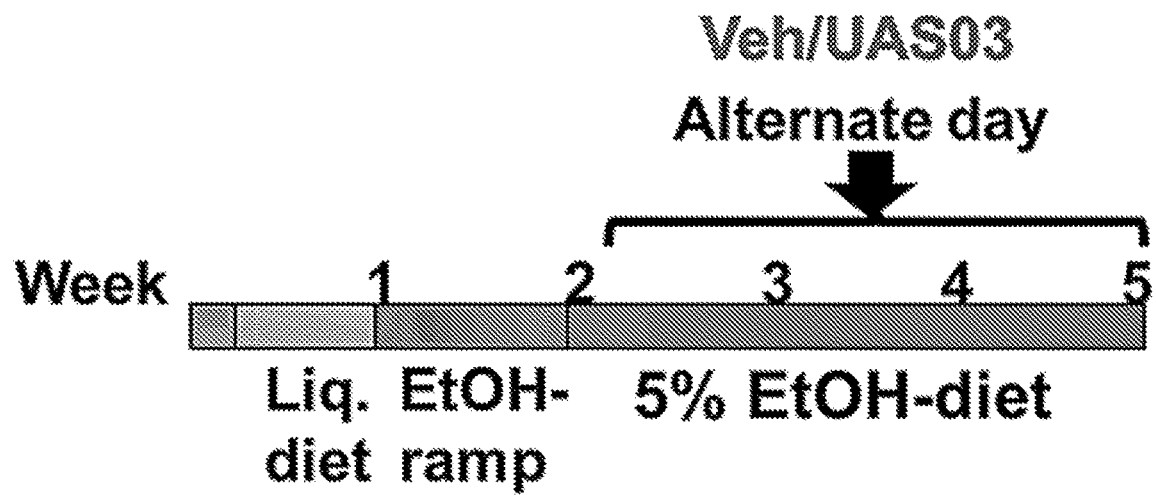
Figure 18:
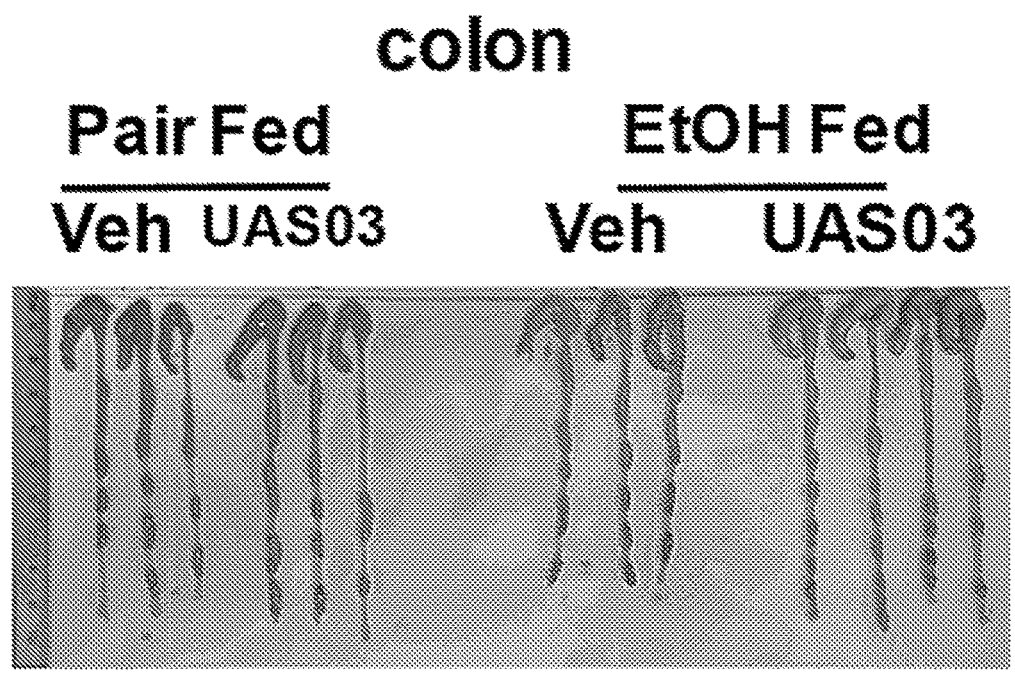
Figure 18:
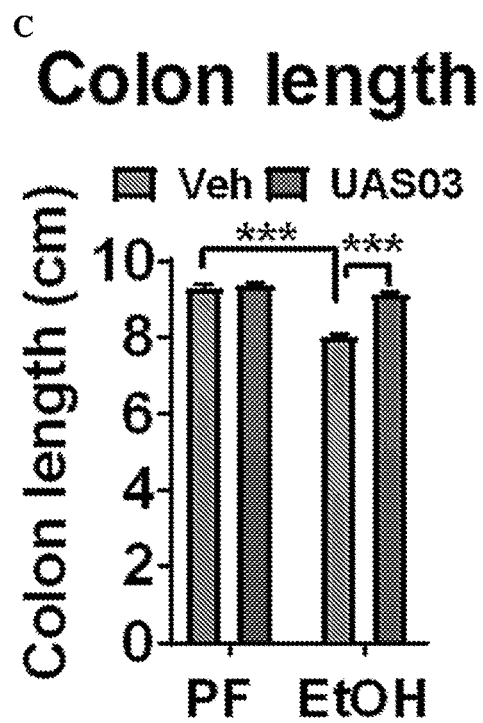
Figure 18:
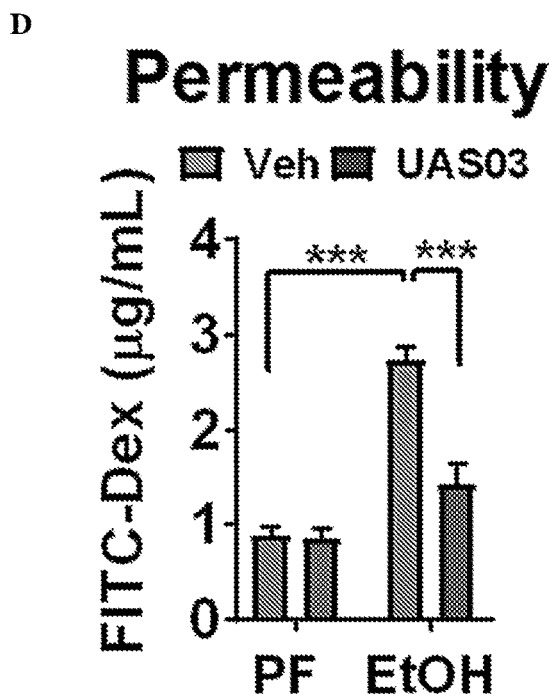
Figure 18:
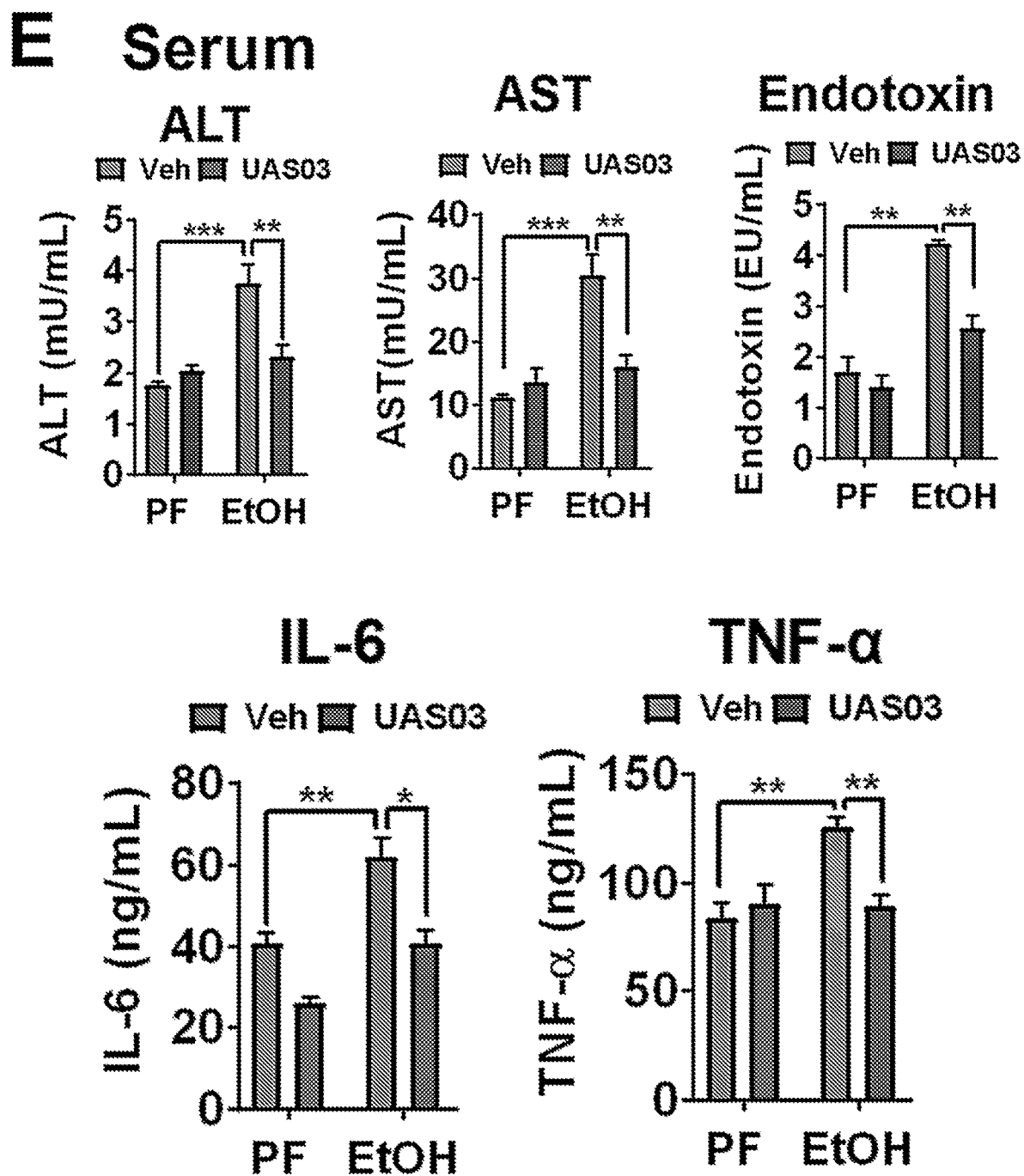
Figure 18:
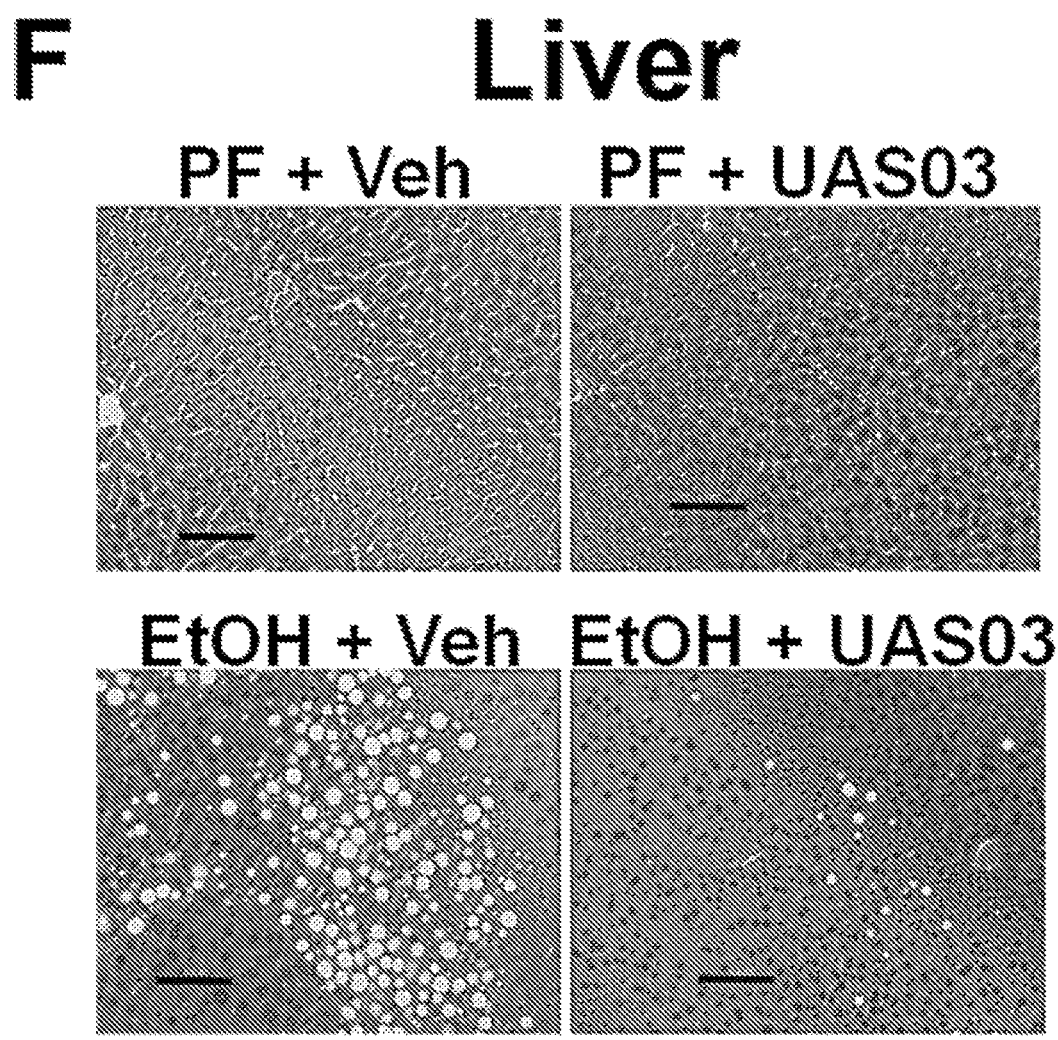
Figure 18:
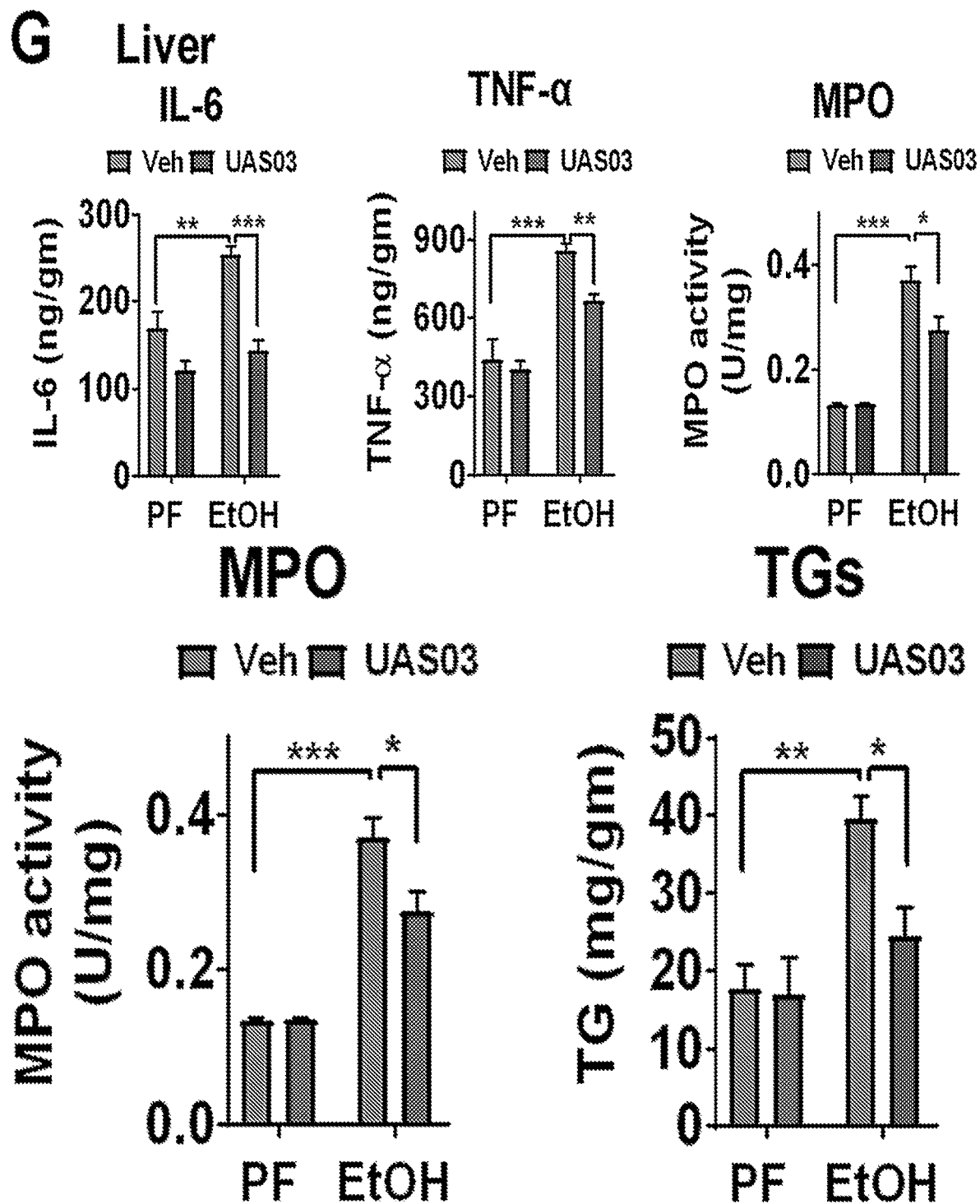
Figure 18:
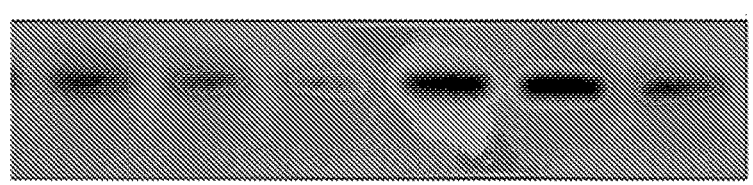
Figure 18:
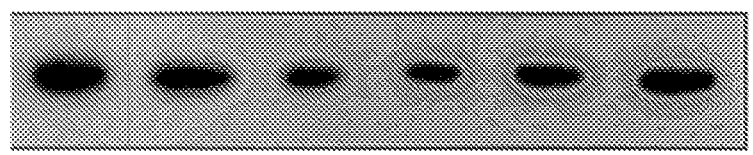

FIG. 18: UAS03 mitigates chronic ALD. (A) C57BL/6 mice (10 wk old age) were used in chronic ALD models and analyzed after 4 weeks as described. Pair fed (n=5/group) and EtOH fed (n=10/group) mice were treated with Veh (0.25% CMC) and UAS03 (20 mg/kg) alternate day for 4 weeks. (B) Gross images of colons (C) colon lengths (D) In vivo permeability using FITC-Dextran was measured. (E) Serum ALT, AST, endotoxin, IL-6, TNF-α were measured using ELISA methods. (F) H&E sections (20×) of liver are shown. Scale bar is 100 μm. Fat droplets (white) are visible in EtOH group. (G) The levels of triglycerides (TGs), IL-6, TNF-α and myeloperoxidase (MPO) were measured in liver tissues. (H) Immunoblot of Ocln expression in ileum tissues (n=3) from mice fed with EtOH treated with Veh or UAS03. Error bars, ±SEM. Statistics were performed using 2way ANOVA multiple comparisons. * p<0.05,  p<0.01, * p<0.001.

Figure 19:
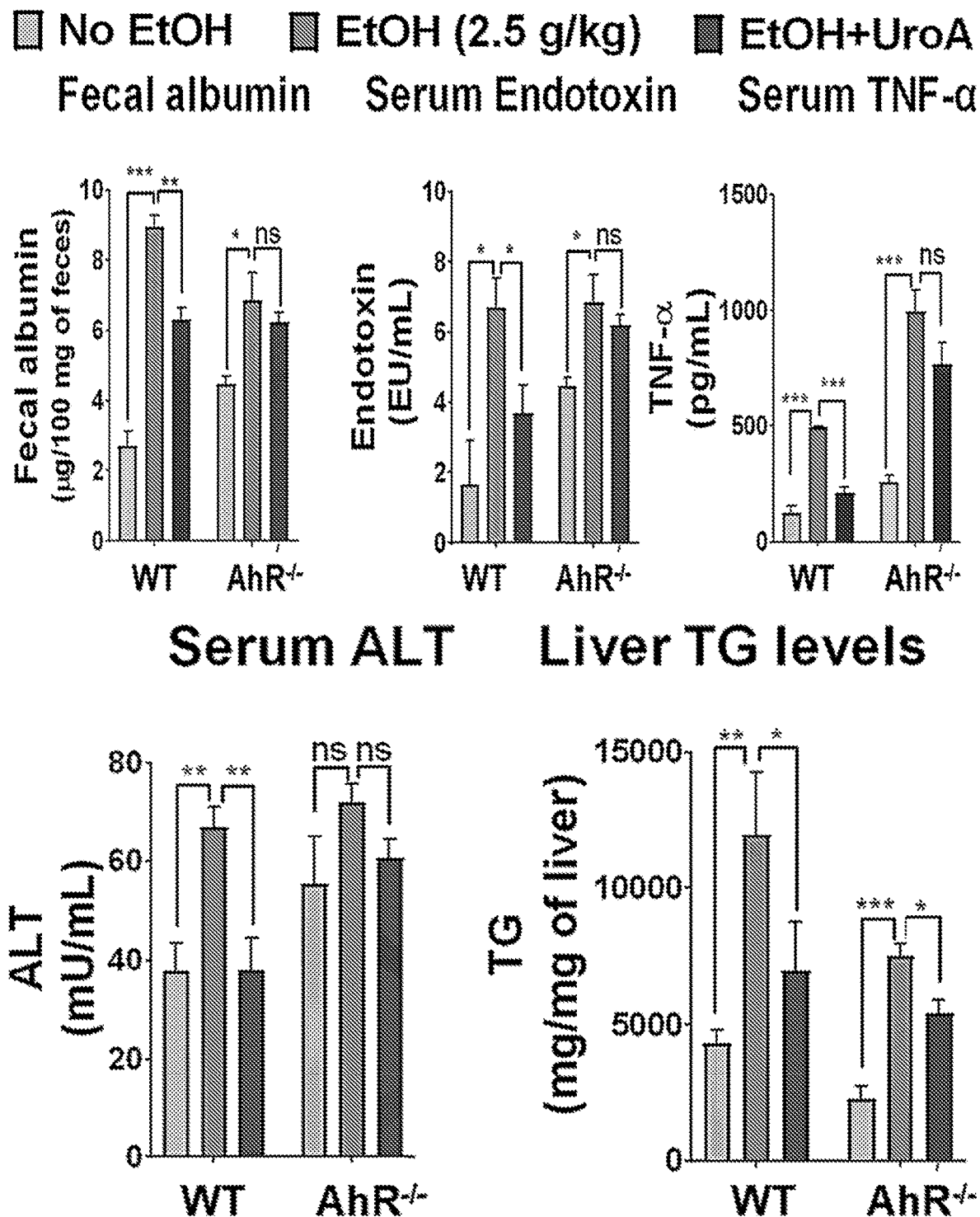

FIG. 19: UroA treatment failed in AhR$^{-/-}$ mice to protect against binge EtOH-induced ALD. C547BL/6 and AhR$^{-/-}$ mice (n=4/group) were oral gavaged with alcohol (2.5 g/kg) at 0, 12 and 24 h. Mice were treated with Veh (0.25% CMC) or UroA (20 mg/kg) at 2, 14 and 26 h. Mice were euthanized at 32 h. The Fecal albumin was measured using standard ELISA. Serum endotoxin, TNF-α, ALT as well as liver ALT and TG levels using ELISA methods. Error bars, ±SEM. Statistics were performed using 2way ANOVA multiple comparisons. * p<0.05,  p<0.01, * p<0.001.

Figure 20:
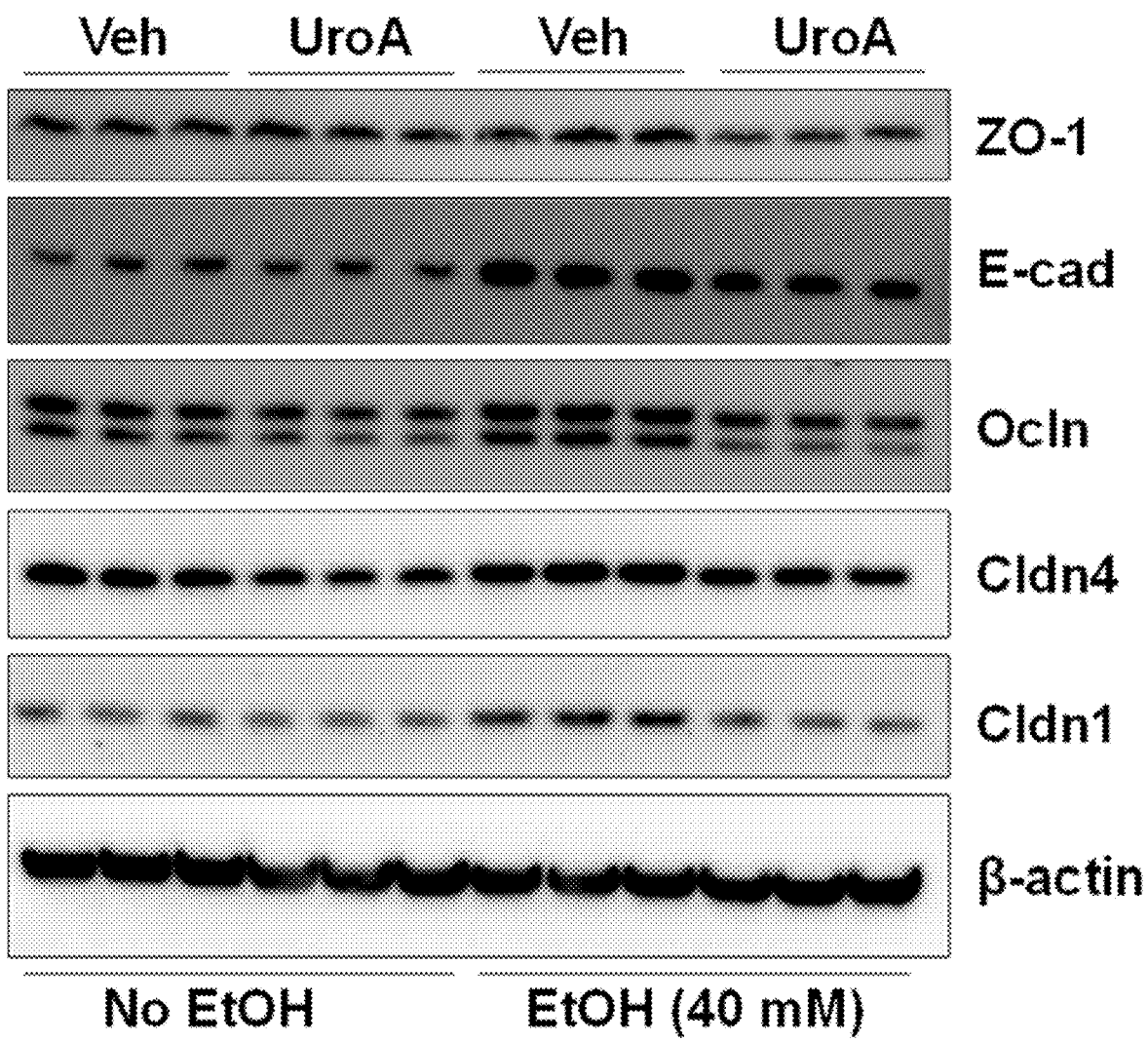
Figure 20:
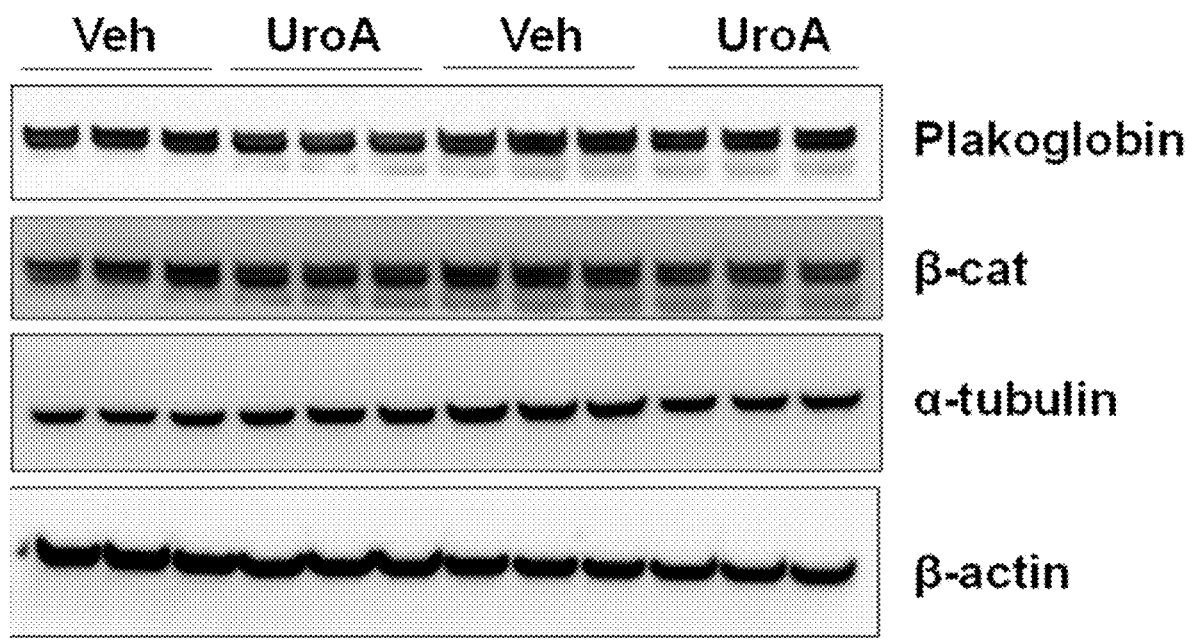
Figure 20:
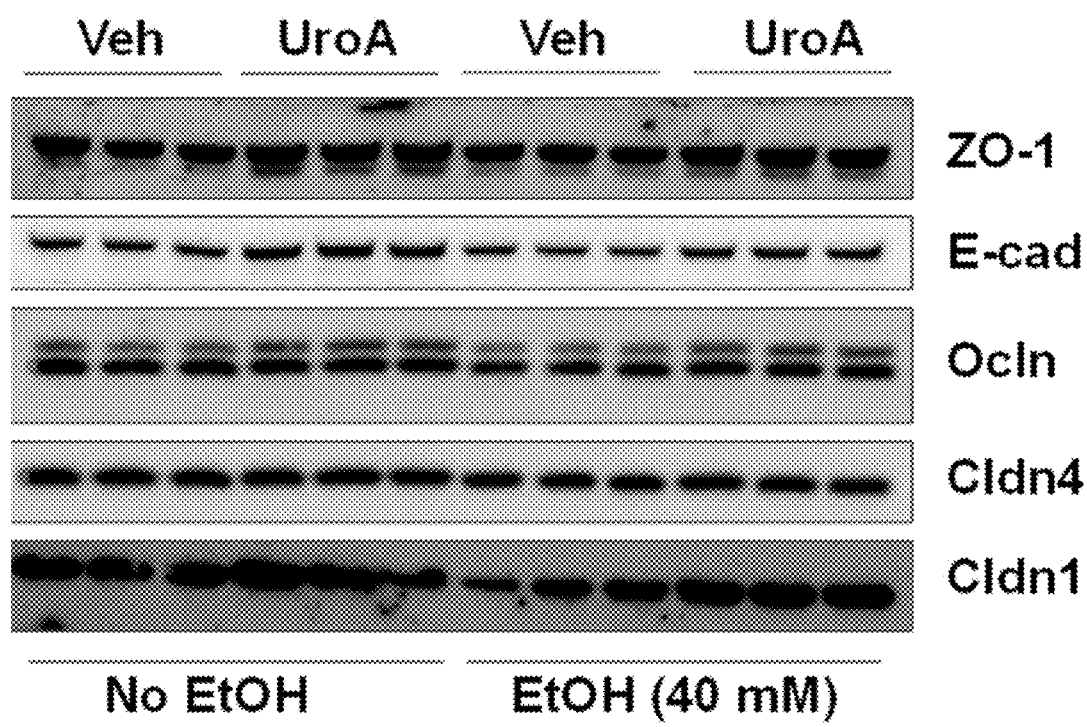
Figure 20:
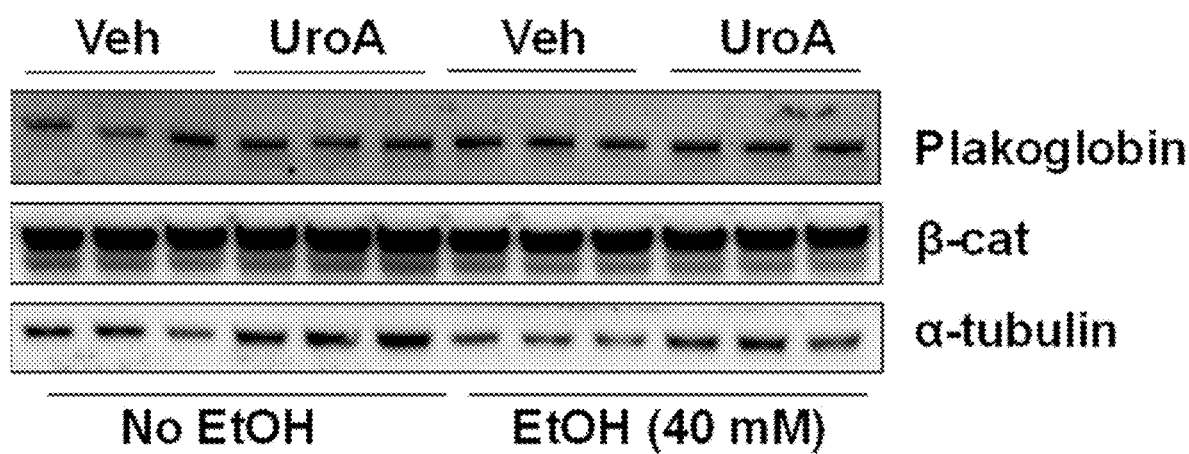

FIG. 20: UroA treatment protects against EtOH-induced internalization of junctional proteins in colon epithelial cells. ZO1: Zonula occludens; E-Cad: E-cadherin; Ocln: Occludin; Cldn4: Claudin 4; Cldn1: Claudin 1.

Figure 21:
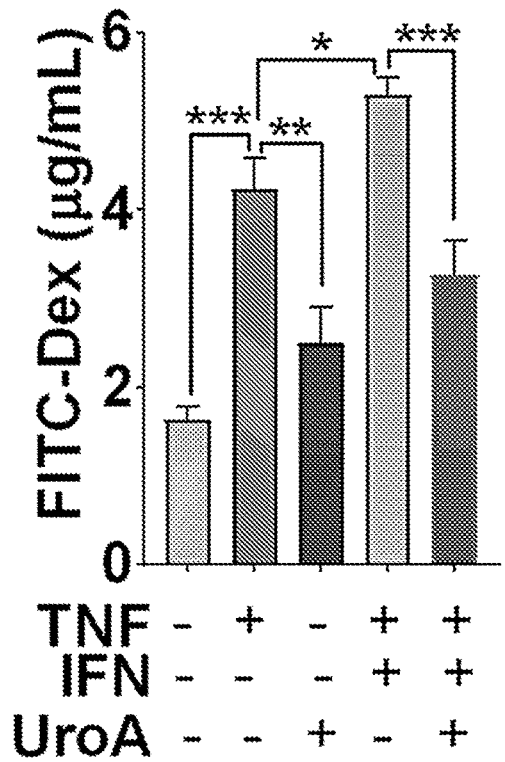
Figure 21:
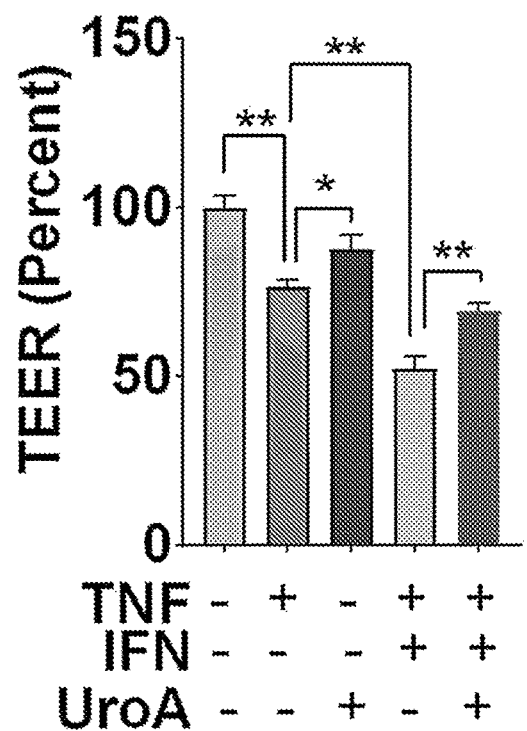

FIG. 21: UroA treatment protects against TNF-α and IFN-γ induced permeability in Caco2 cells. Error bars, ±SEM. Statistics were performed using 2way ANOVA multiple comparisons. * p<0.05,  p<0.01, * p<0.001.

Figure 22:
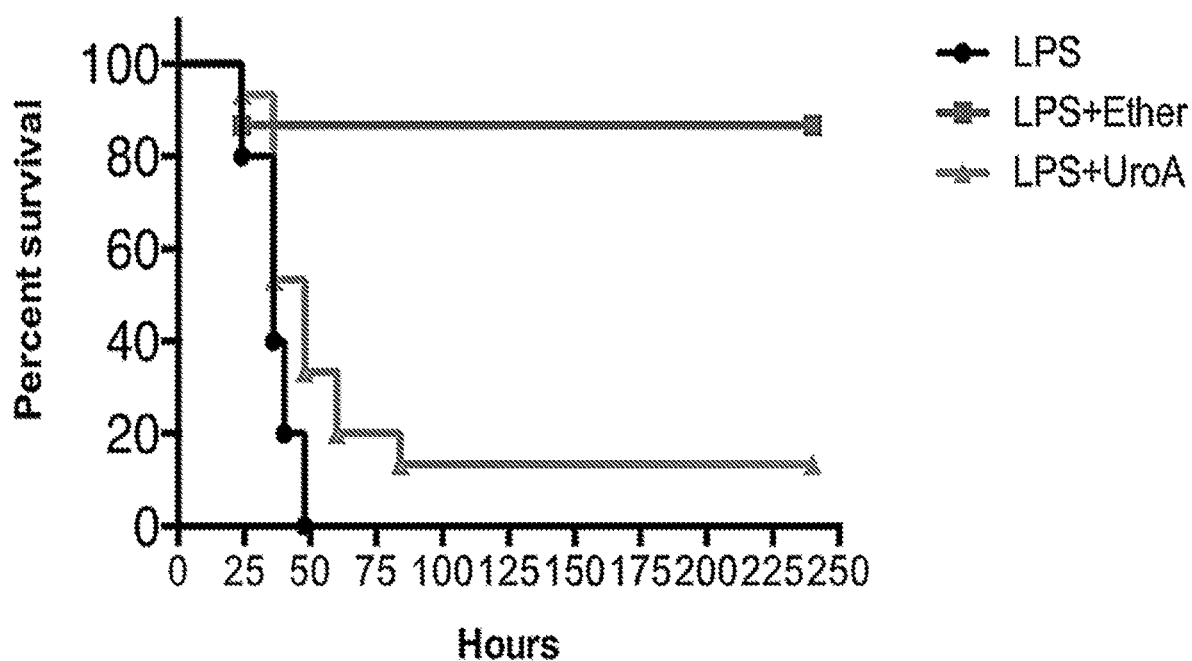

FIG. 22: UAS03 (Ether) attenuates septic mortality. Kaplan-Meir survival analysis for septic mice.

Figure 23:
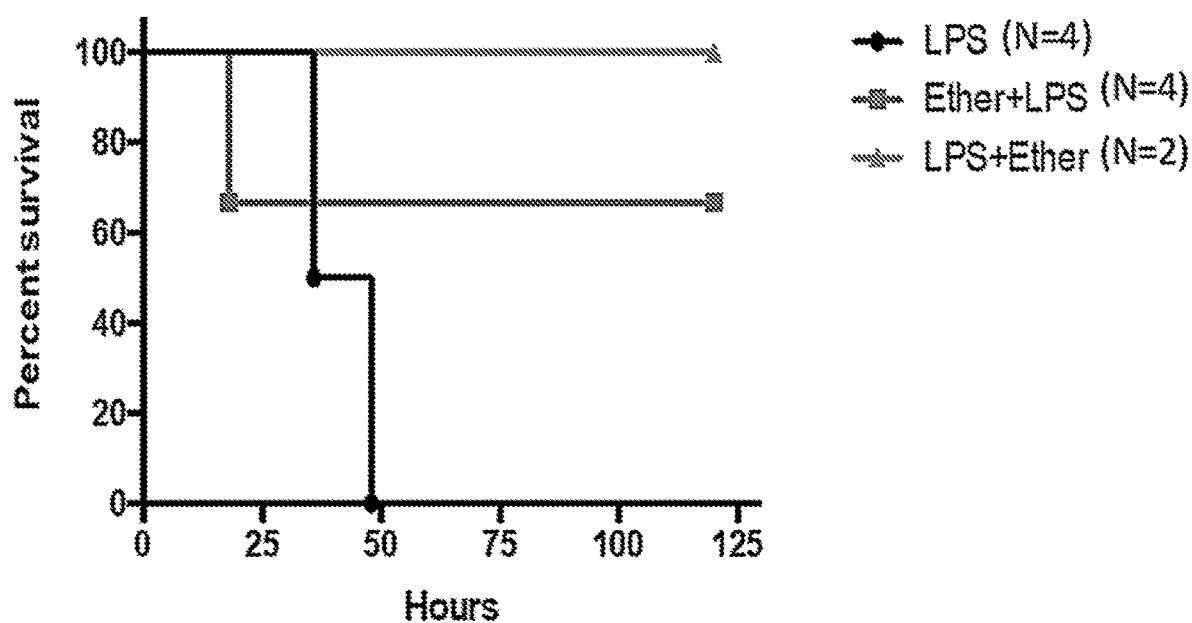

FIG. 23: Preventive and therapeutic effect of UAS03 (Ether) in septic animals. Kaplan-Meir survival analysis for UAS03 in preventive and therapeutic setting.

Figure 24:
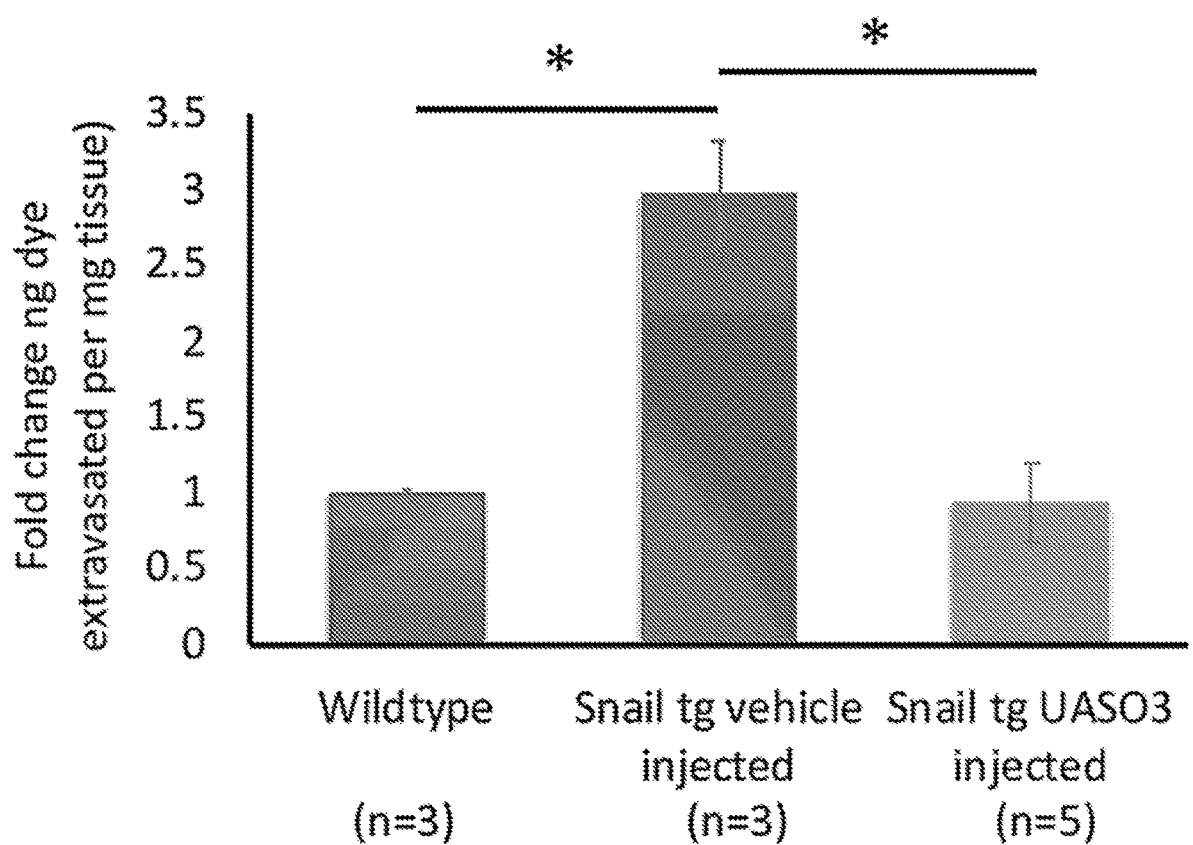

FIG. 24: UAS03 to attenuate Scleroderma associated vascular permeability in Snail transgenic mice. Evan's blue dye leakage assessment in back skin of mice.

Figure 25:
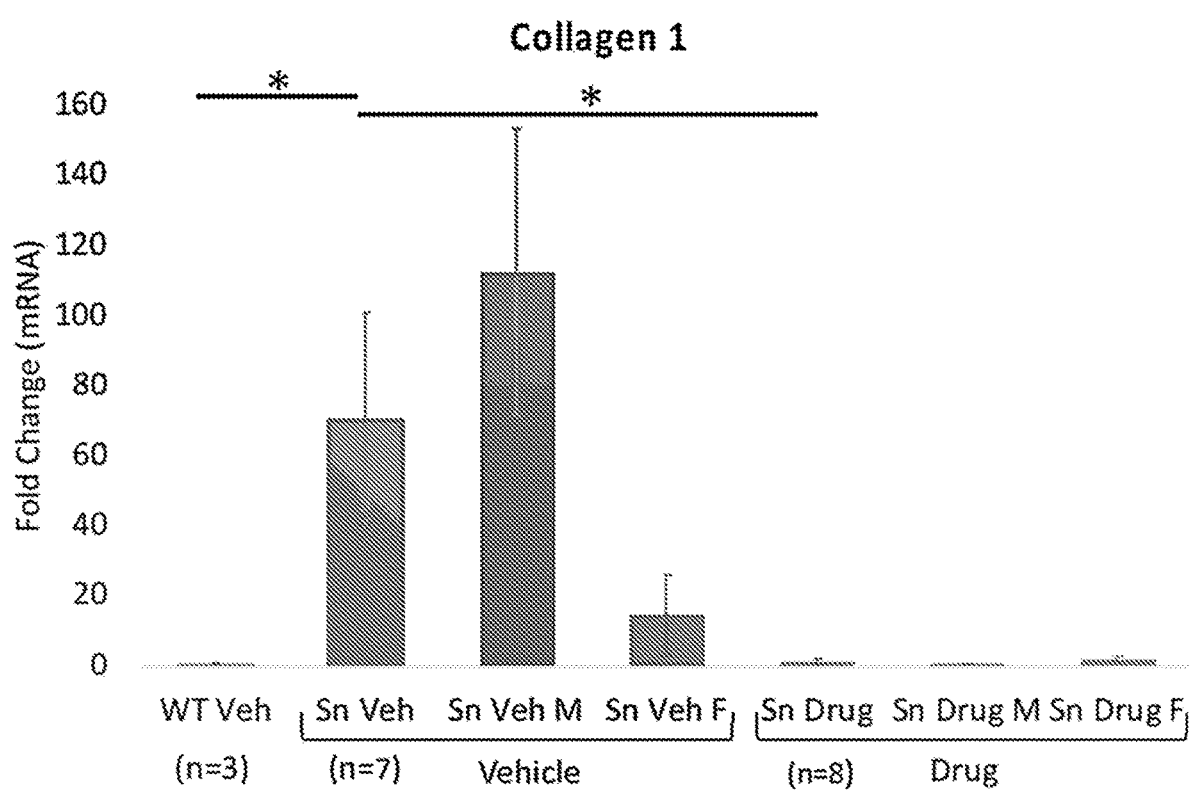

FIG. 25: Expression for fibrosis associated genes in the back skin of the Snail transgenic mice. mRNA expression of Collagen in back skin of mice.

Figure 26:
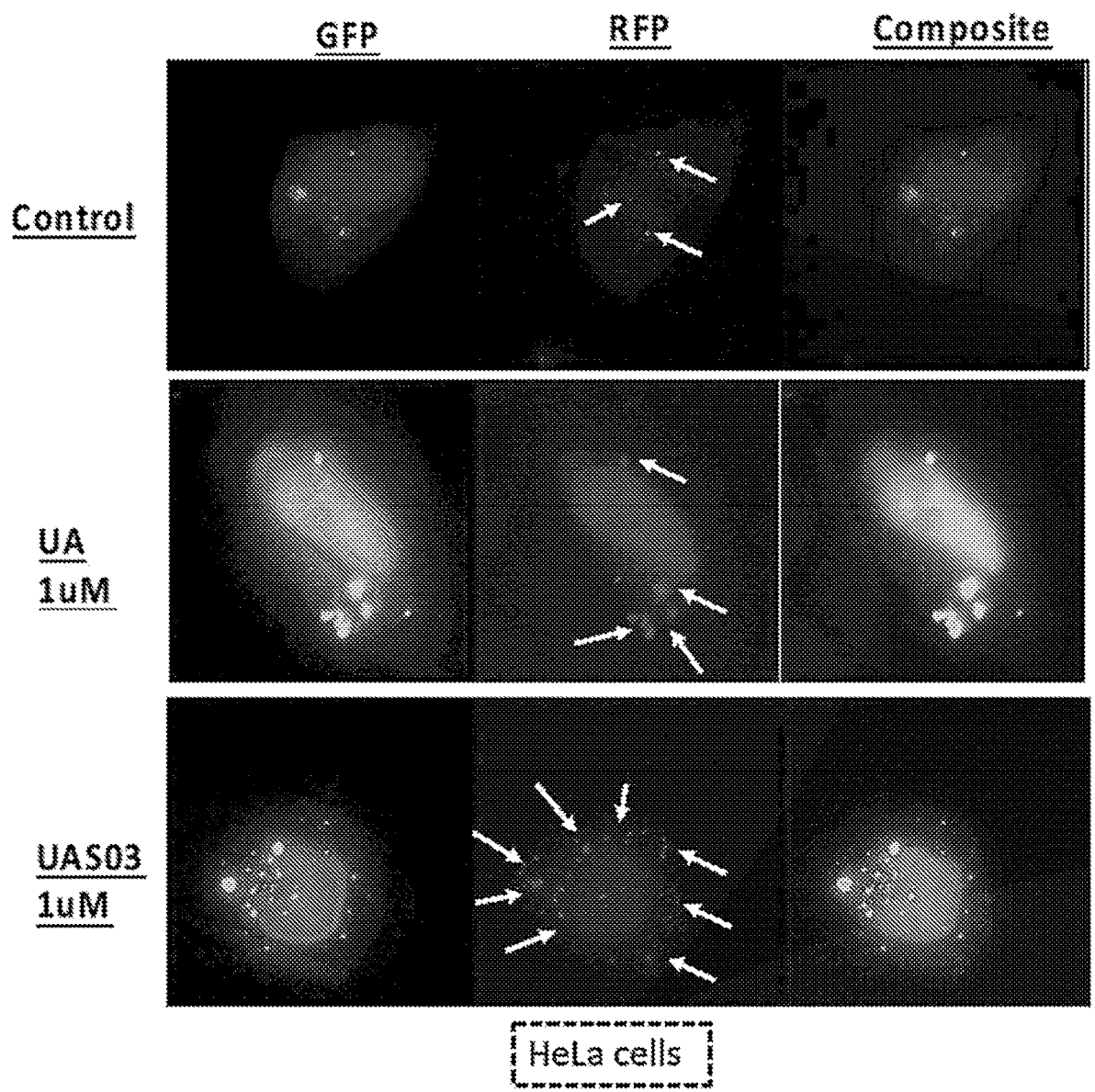

FIG. 26: UAS03 for Autophagy induction. Autophagosomes and autolysosomes formation seen under fluorescence microscope.

Figure 27:
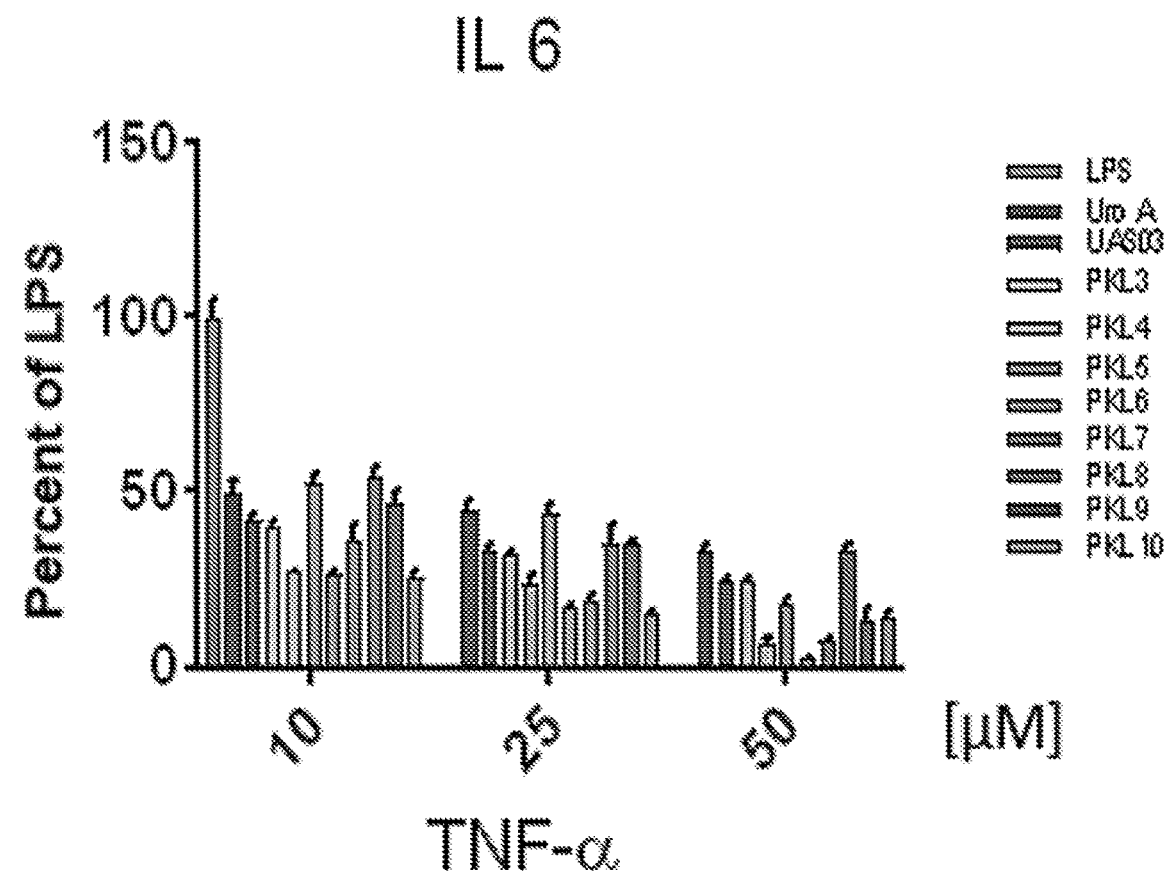
Figure 27:
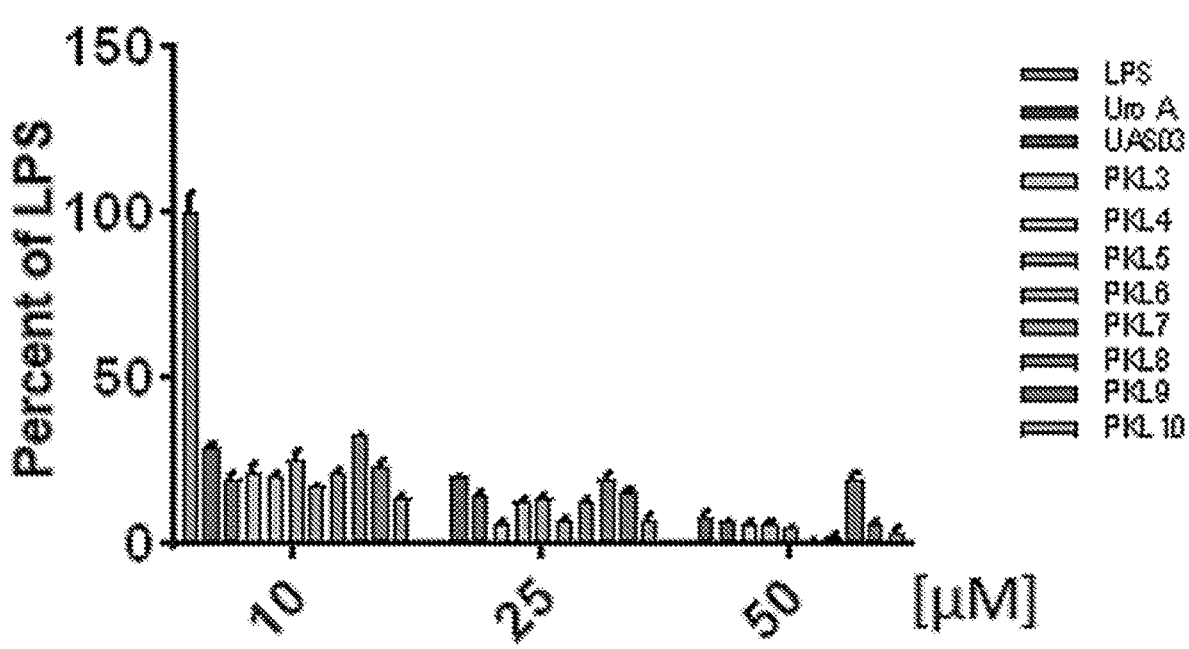

FIG. 27: Screening of UroA, UAS03 along with different analogues (PKL 3-10) for IL-6 and TNF-α in mice BMDMS at 10, 25 and 50 μM conc. (6 hrs).

Figure 28:
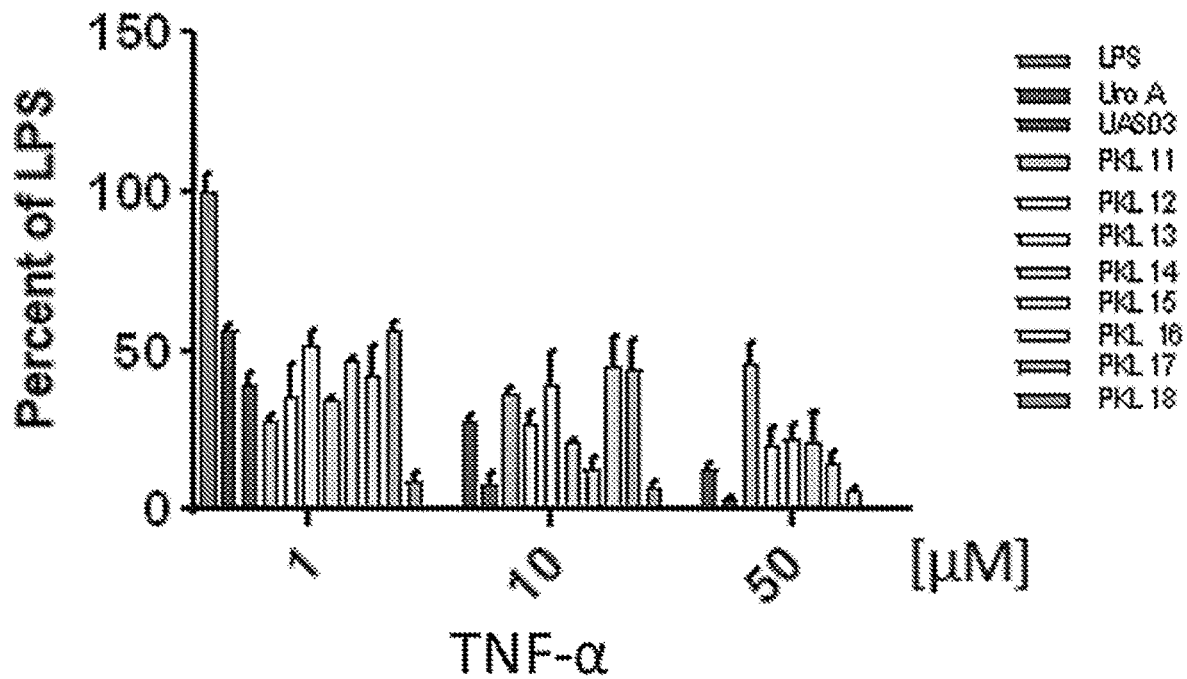
Figure 28:
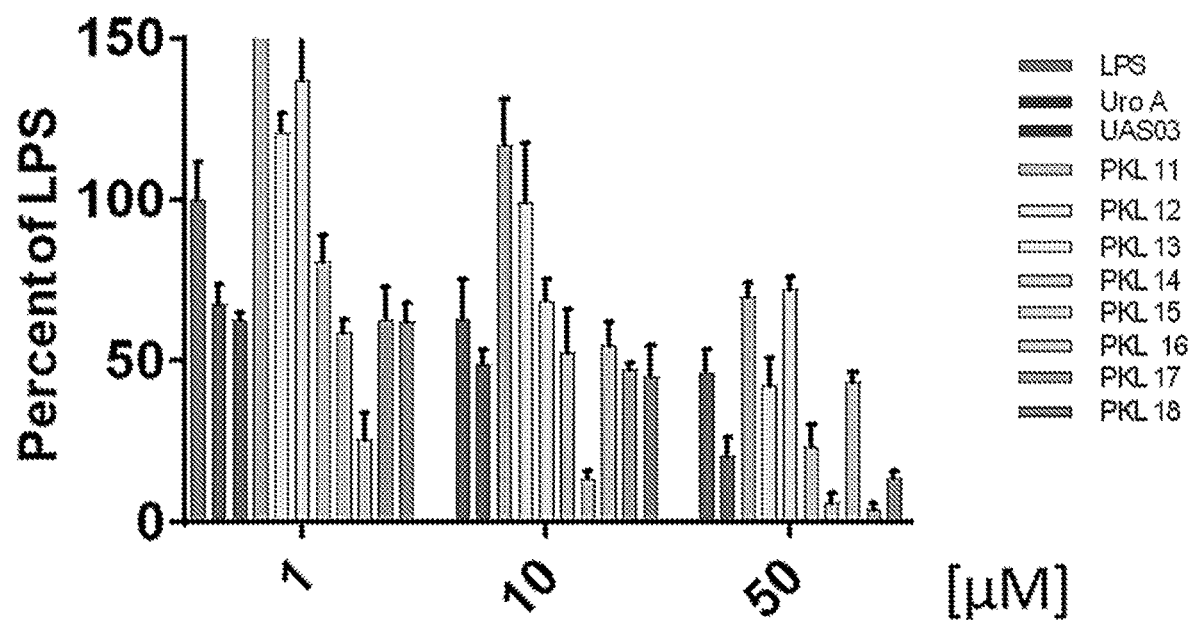

FIG. 28: Screening of UroA, UAS03 along with different analogues (PKL 11-18) for IL-6 and TNF-α in mice BMDMS at 1, 10 and 50 μM conc. (6 hrs).

Figure 29:
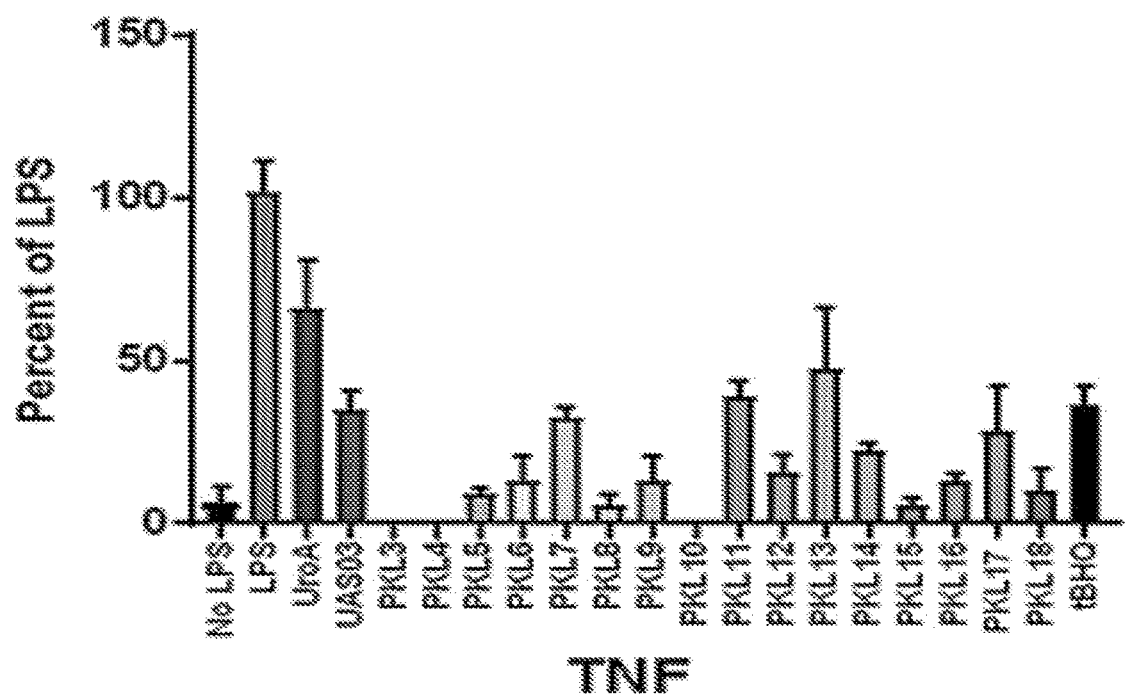
Figure 29:
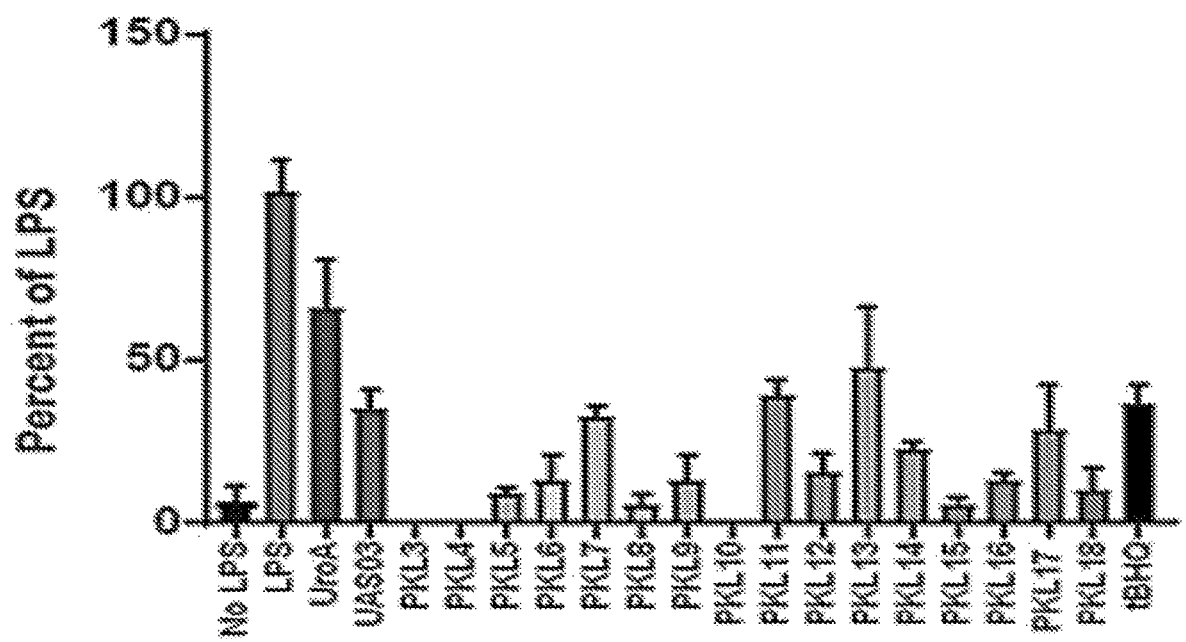

FIG. 29: Screening of UroA, UAS03 along with different analogues (PKL 3-18) for IL-6 and TNF-α in mice BMDMS at 10 μM conc. (6 hrs).

Figure 30:
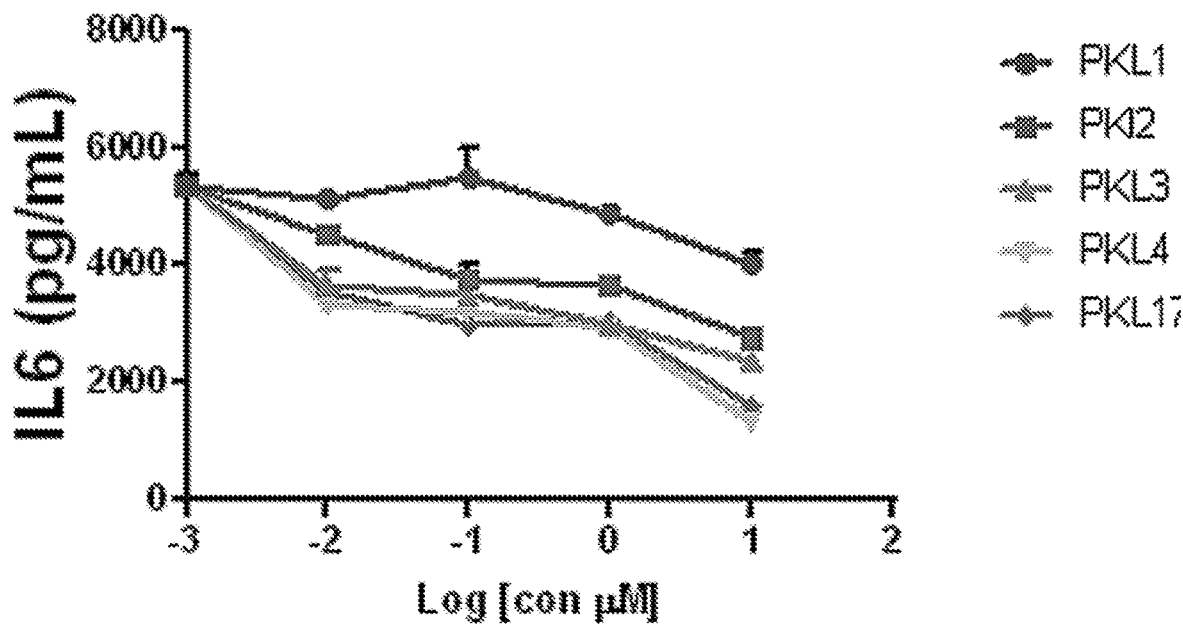
Figure 30:
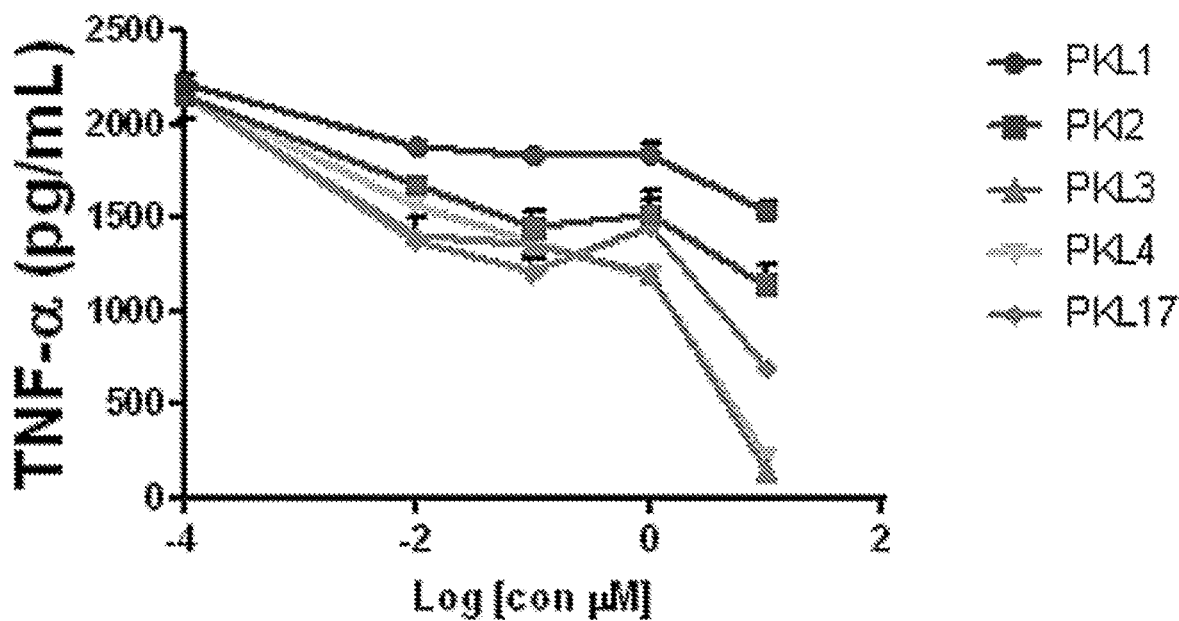

FIG. 30: Screening of UroA, UAS03, PKL 3, PKL4 and PKL 17 at 0.01, 0.1, 1 and 10 μM conc. (6 hrs).

Figure 31:
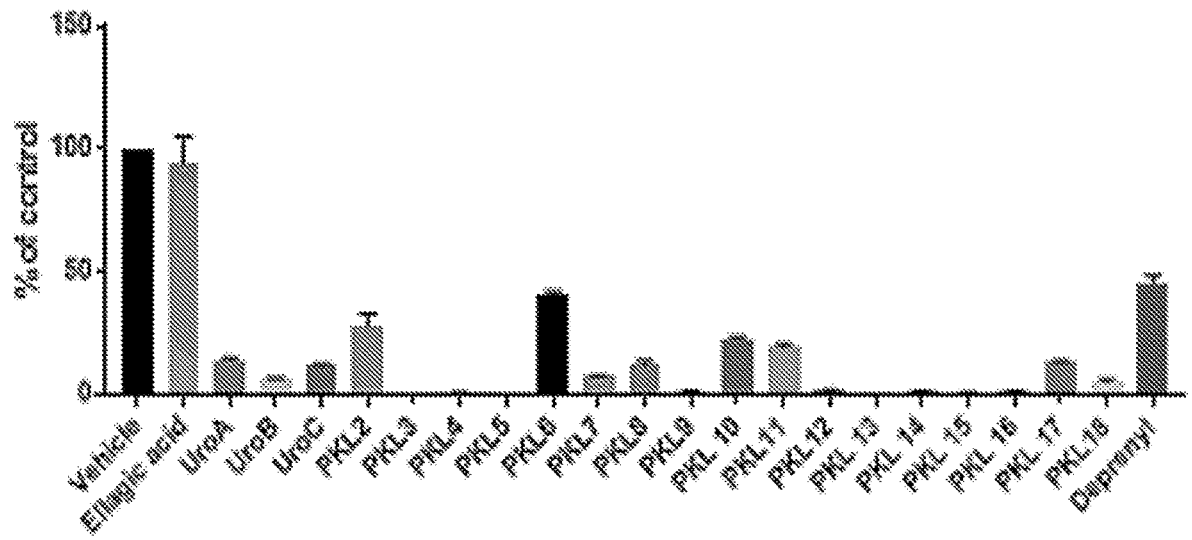
Figure 31:
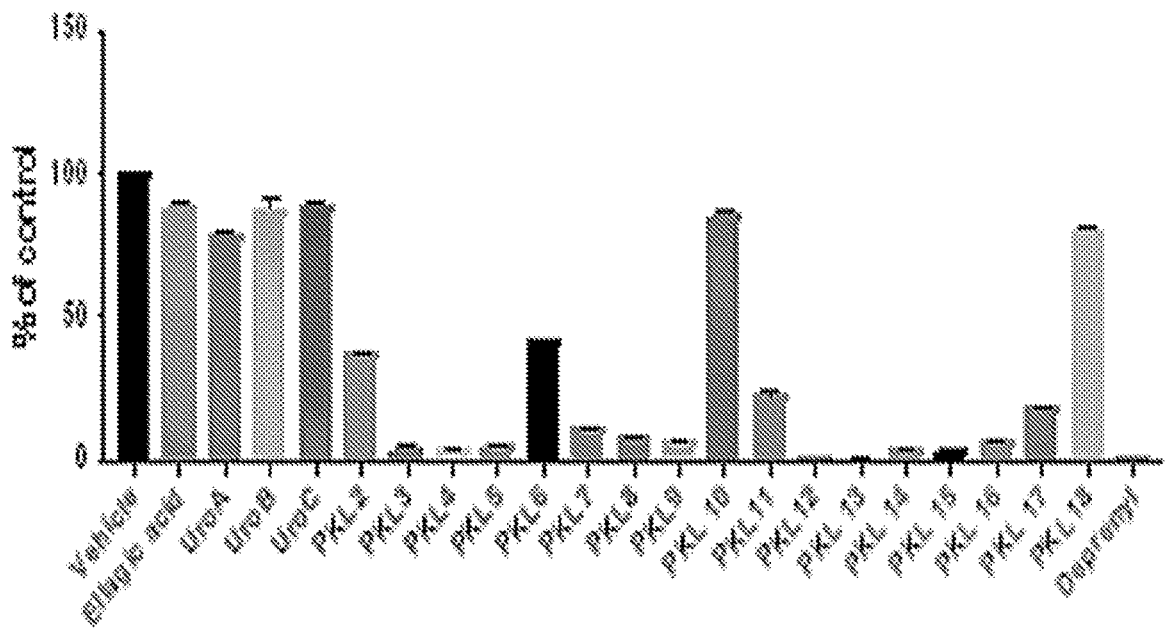

FIG. 31: Primary screening (100 μM concentration) of UroA, UAS03 along with different analogues for MAO A and MAO B inhibition.

Figure 32:
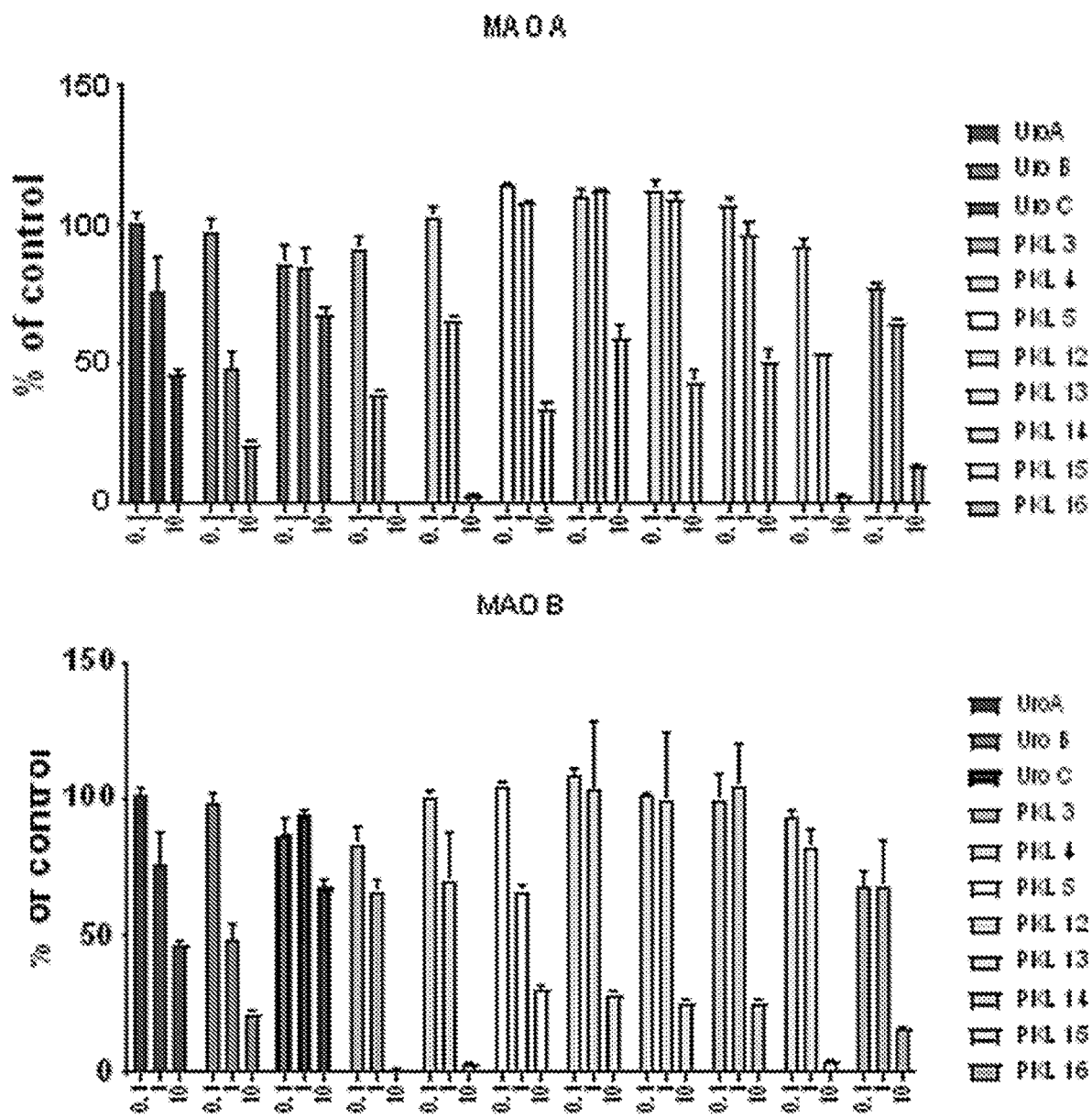

FIG. 32: Dose dependence (100 μM concentration) of UroA, UAS03 along with different analogues for MAO A and MAO B inhibition.

Figure 33:
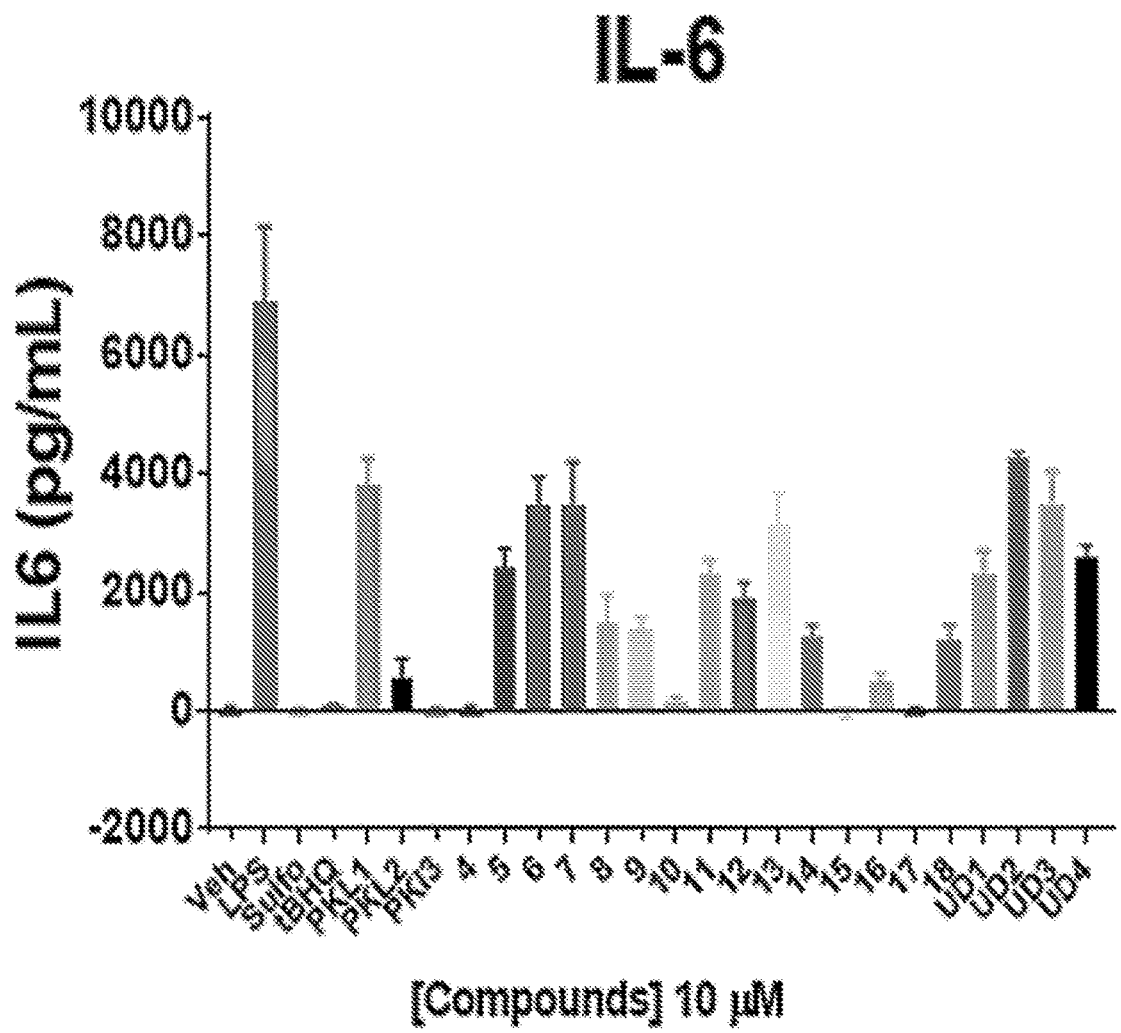
Figure 33:
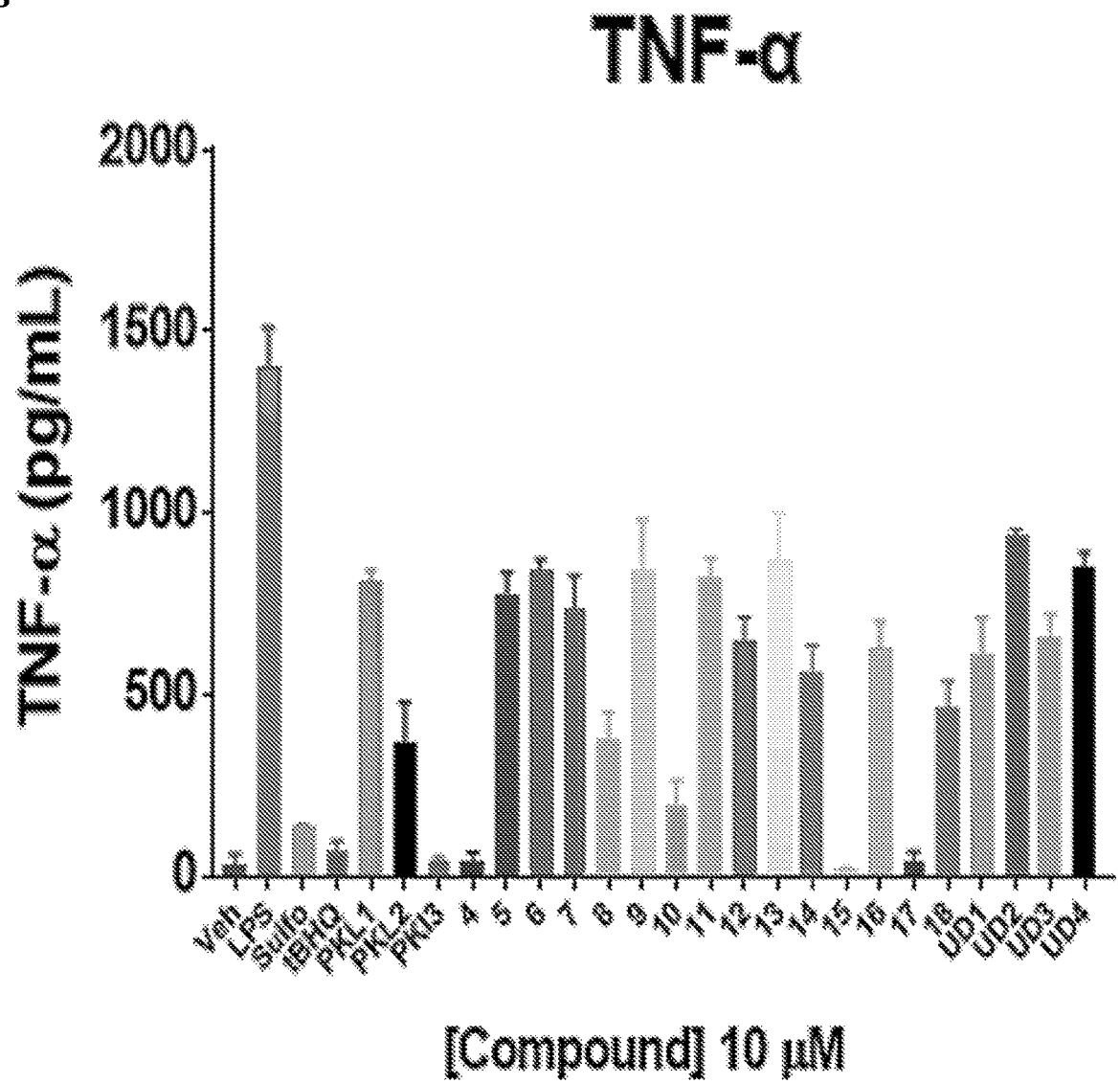
Figure 33:
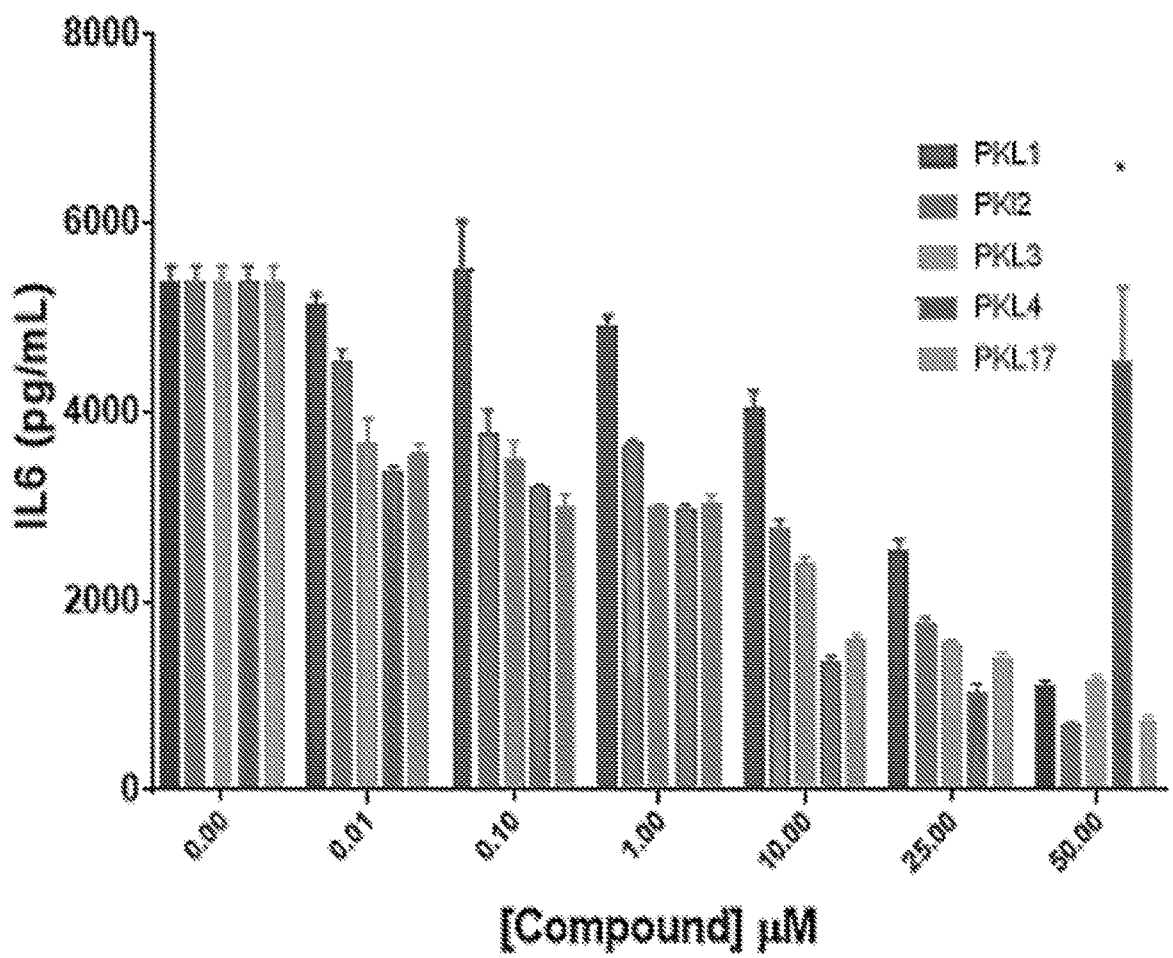
Figure 33:
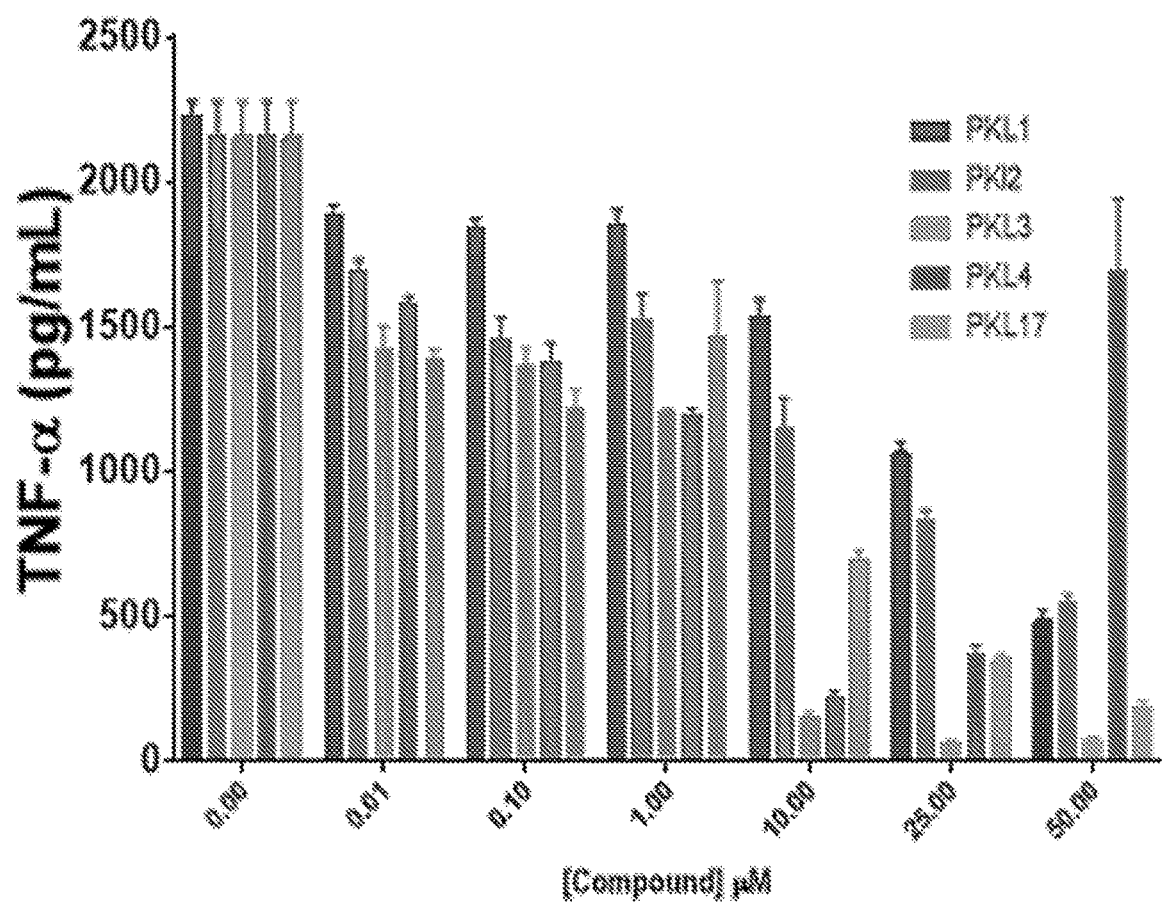

FIG. 33: Screening anti-inflammatory activities. Mouse Bone marrow derived macrophages (BMDMs) were stimulated with LPS (50 ng/ml) with or without compounds for 6 hours. IL-6 and TNF-α levels in supernatants were measured using standard ELISA methods. Results are representative of three independent experiments with triplicates for each concentration.

Figure 34:
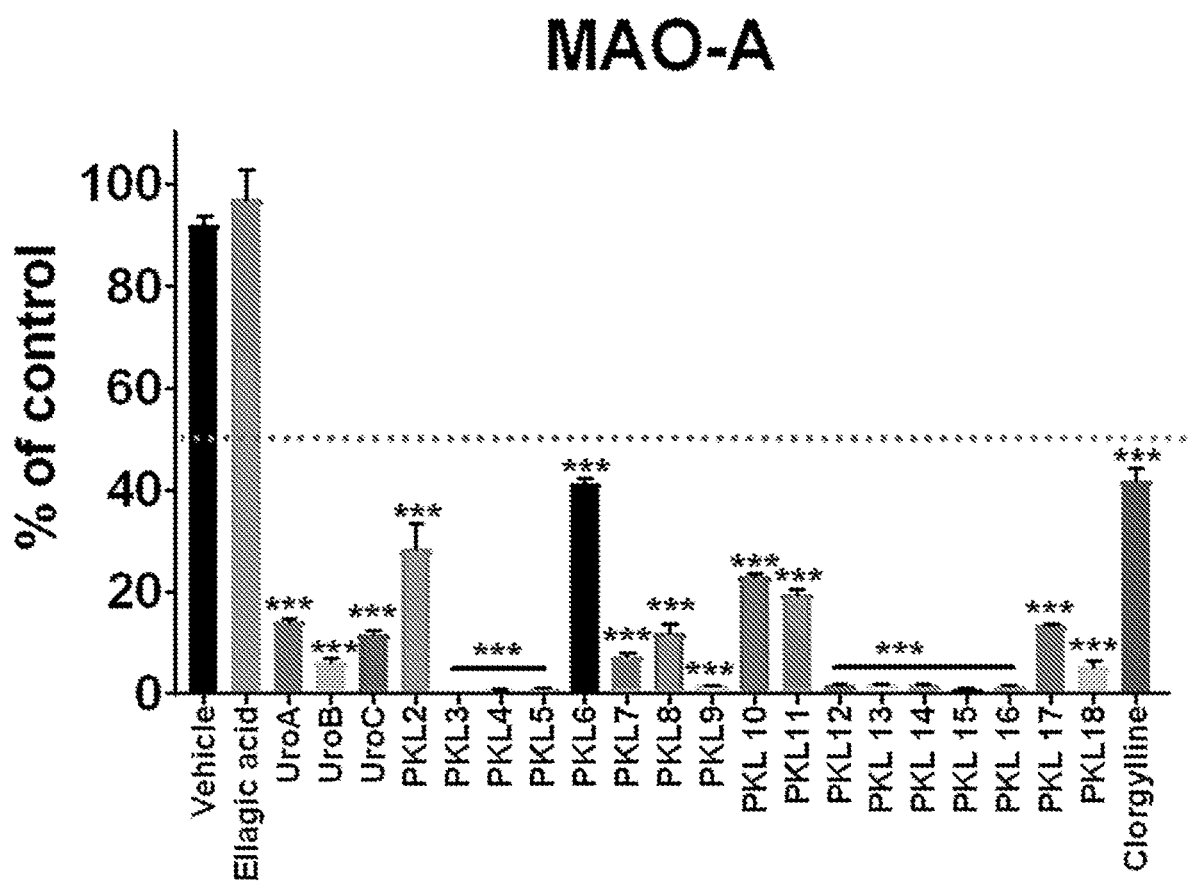
Figure 34:
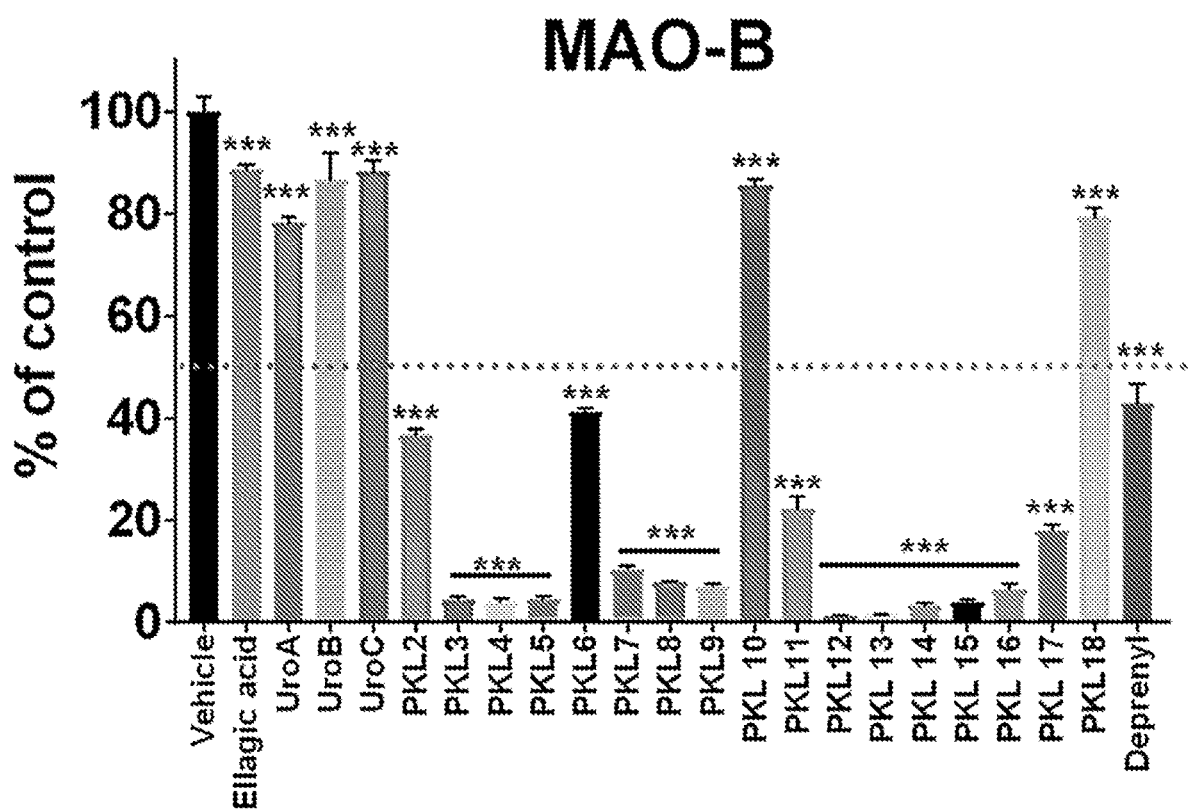

FIG. 34: Activity of MAO enzymes in the presence of various compounds.

Figure 35:
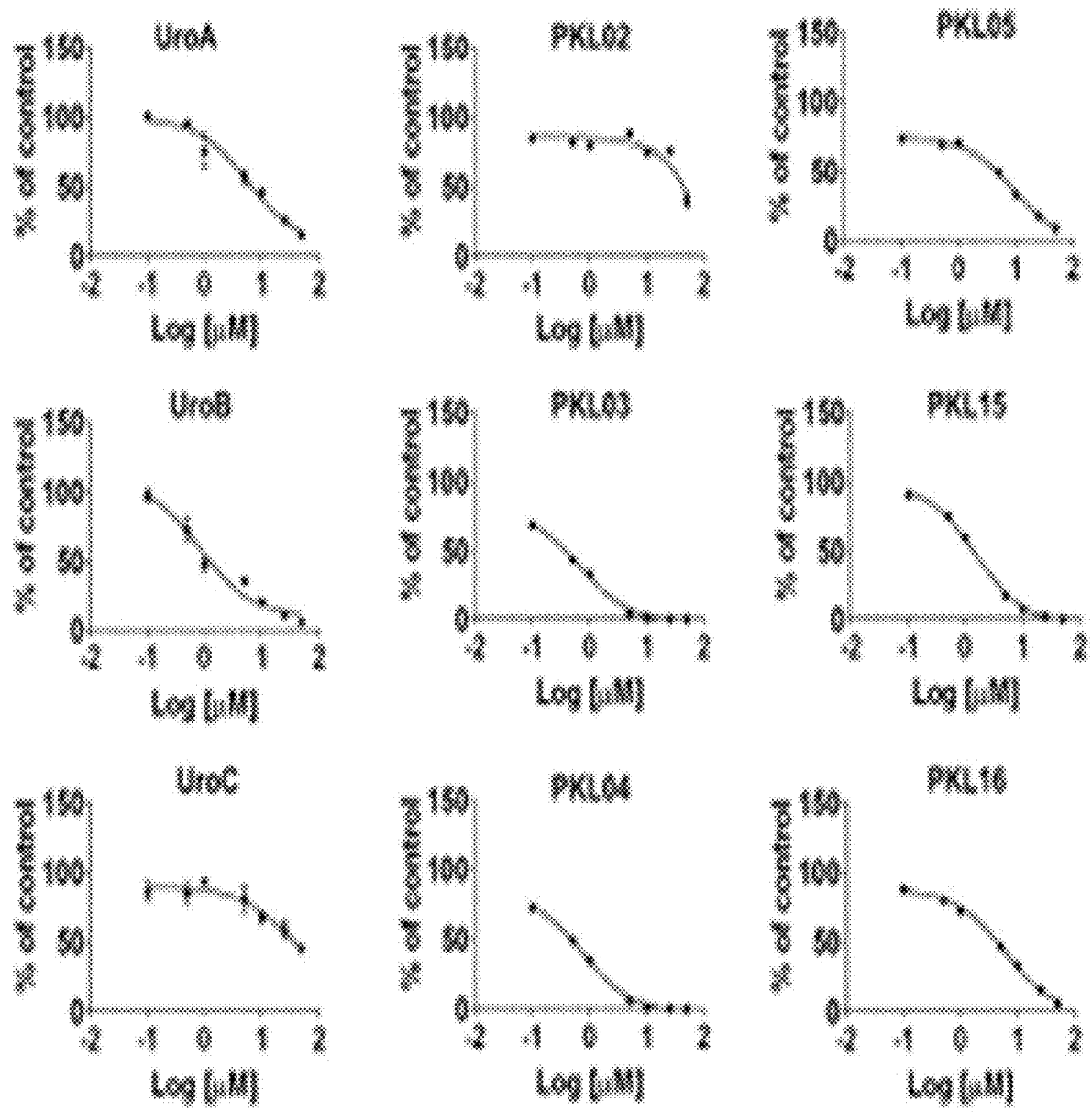
Figure 35:
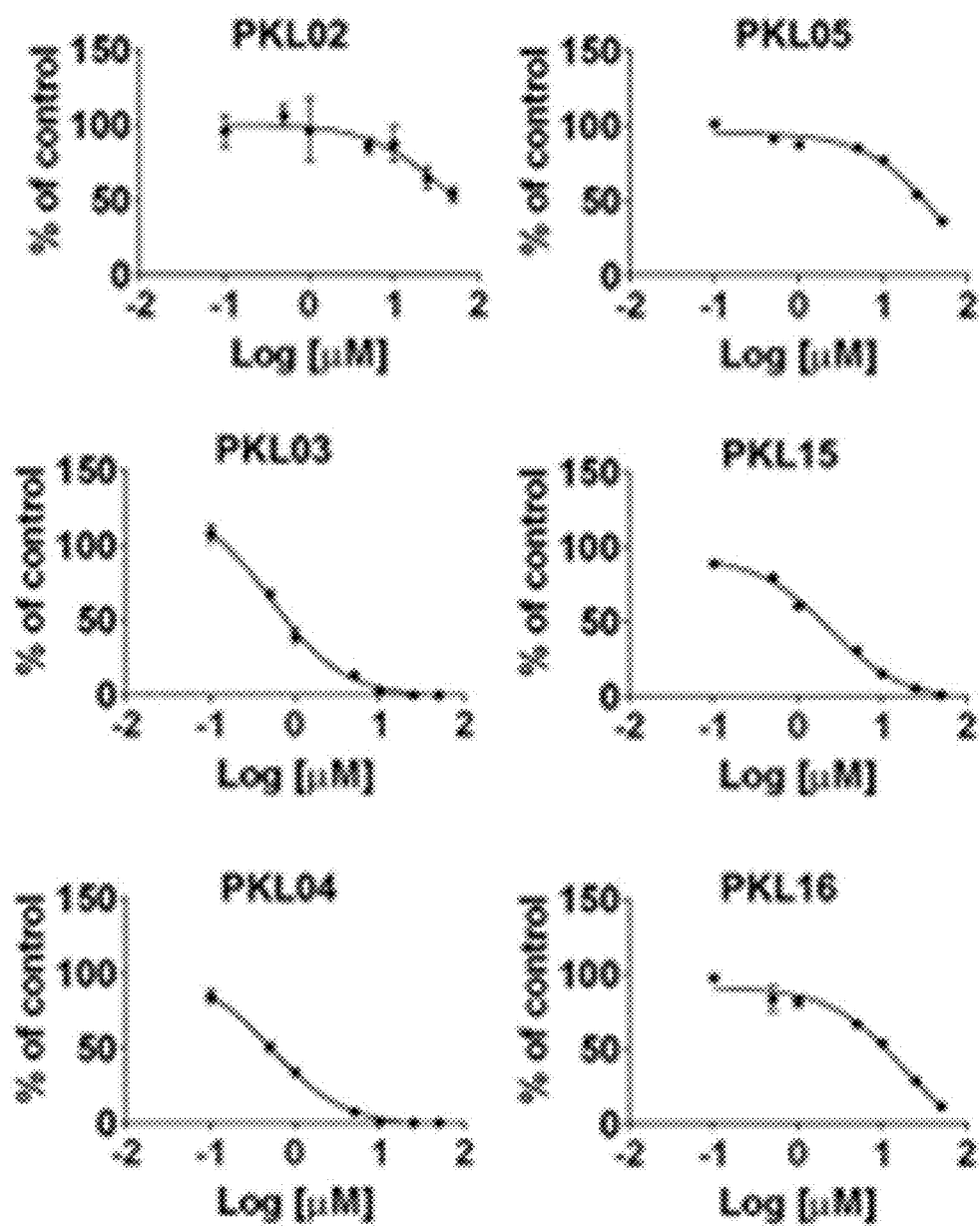

FIG. 35: Compounds tested against MAO-A and MAO-B activities and identified IC50 and Ki values.

Figure 36:
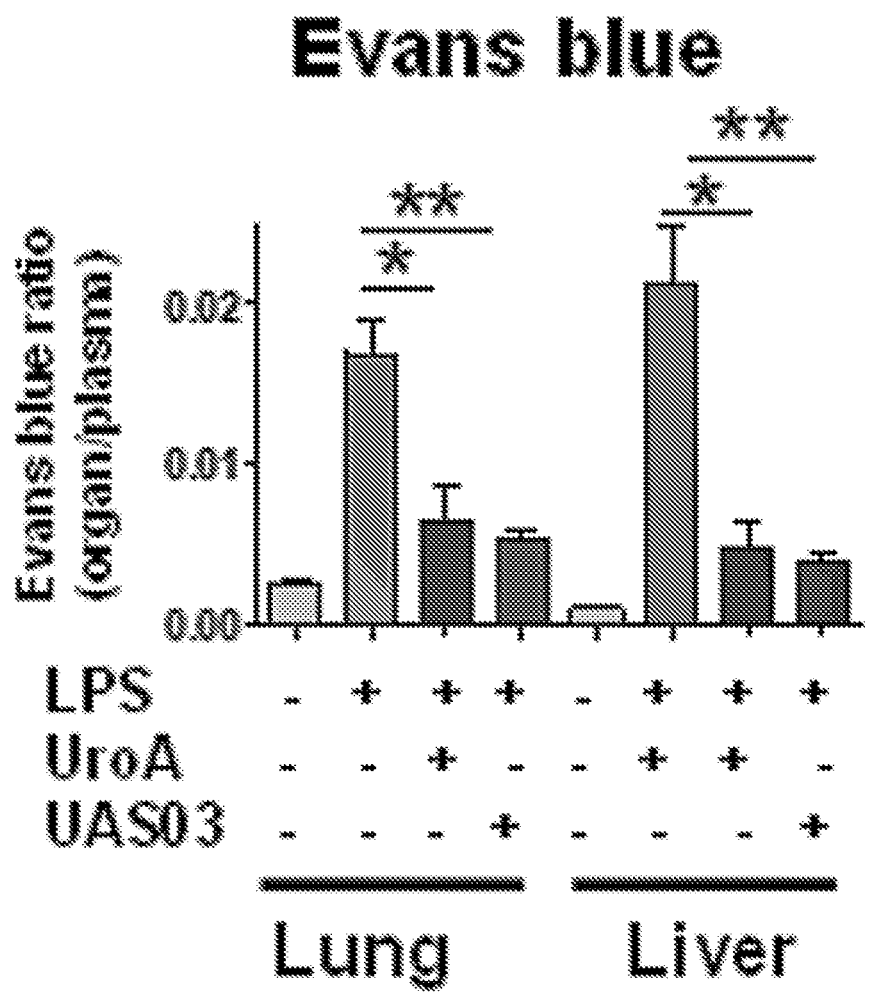
Figure 36:
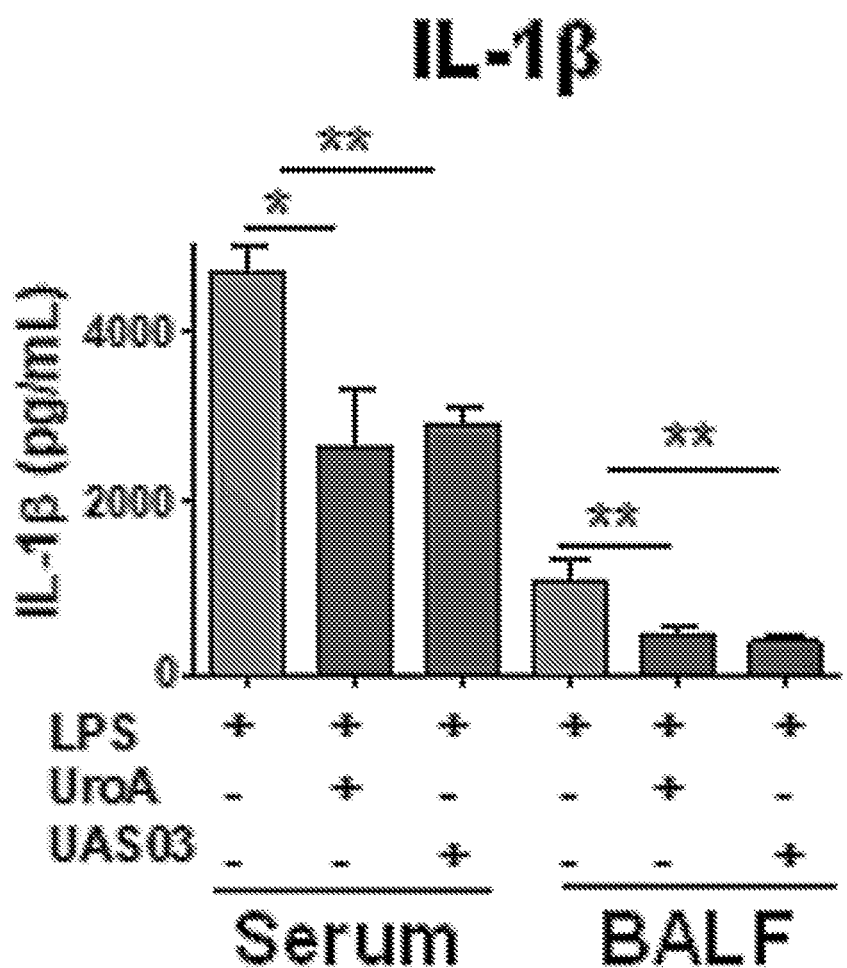
Figure 36:
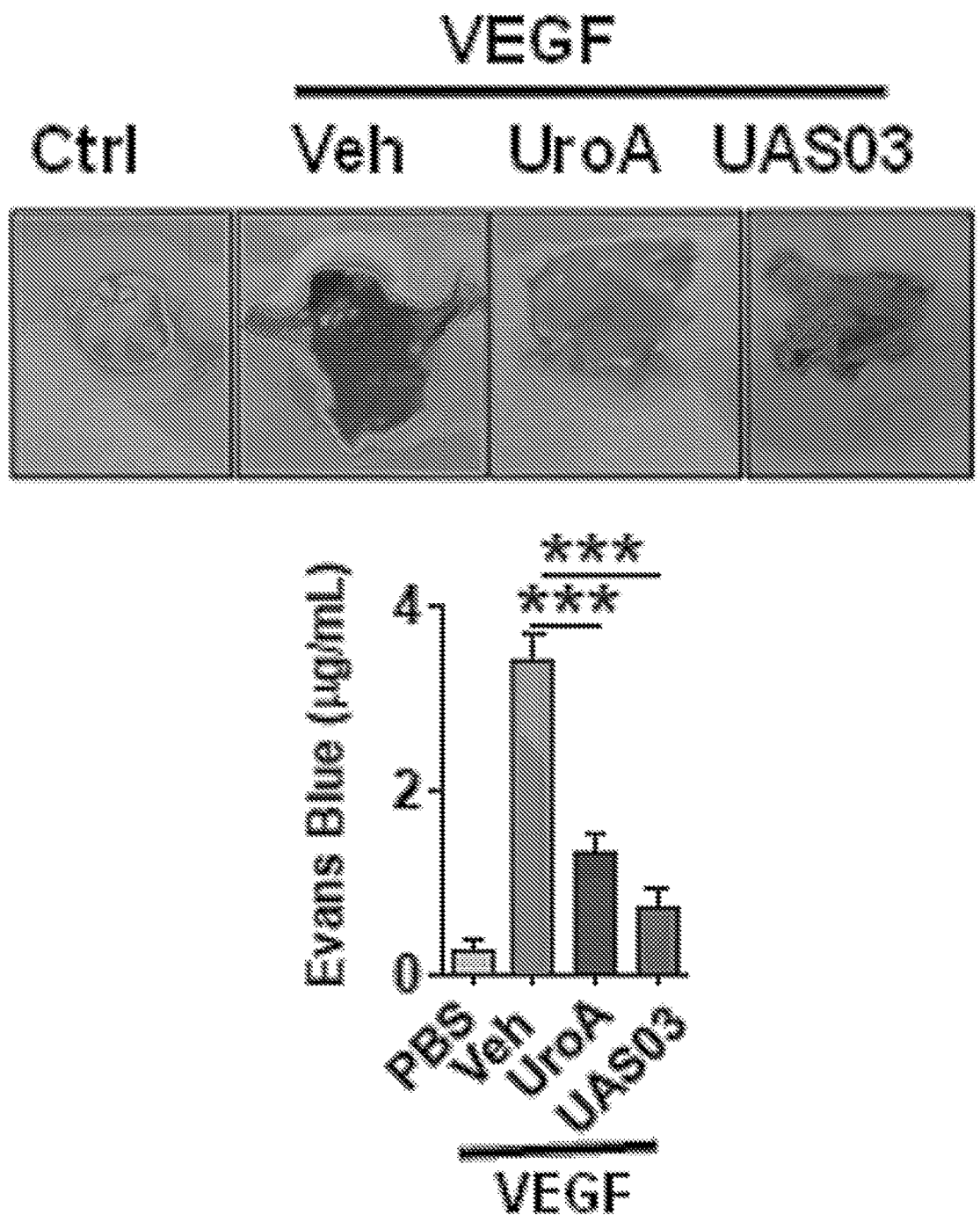
Figure 36:
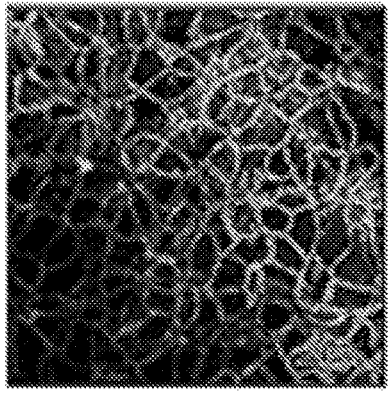
Figure 36:
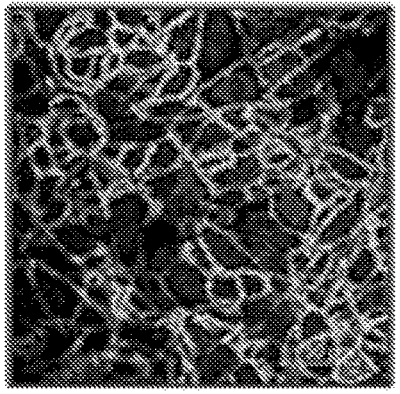
Figure 36:
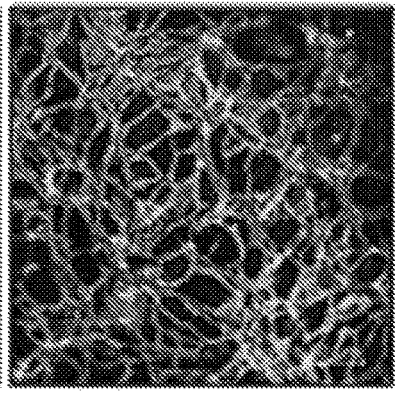
Figure 36:
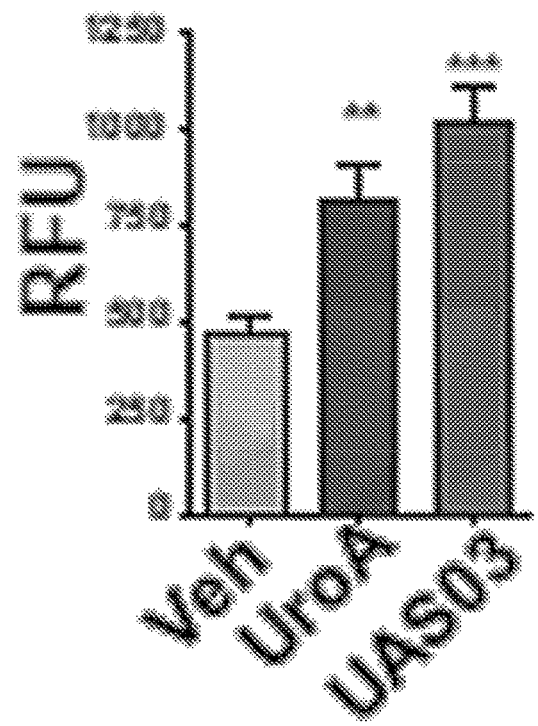
Figure 36:
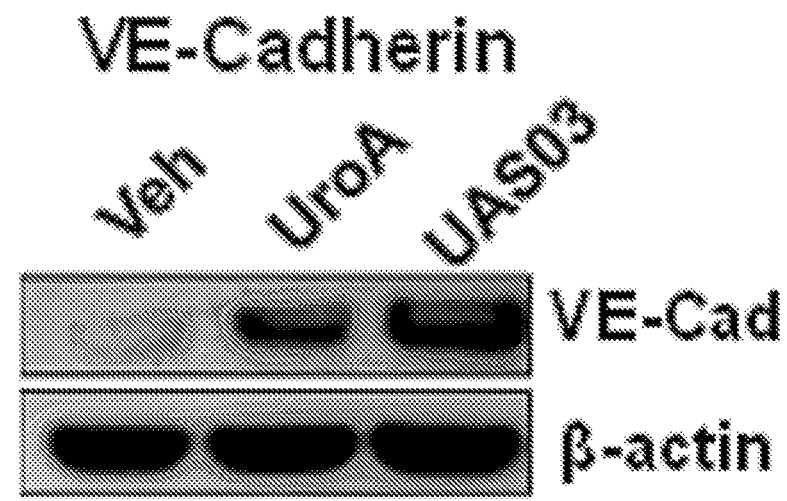
Figure 36:
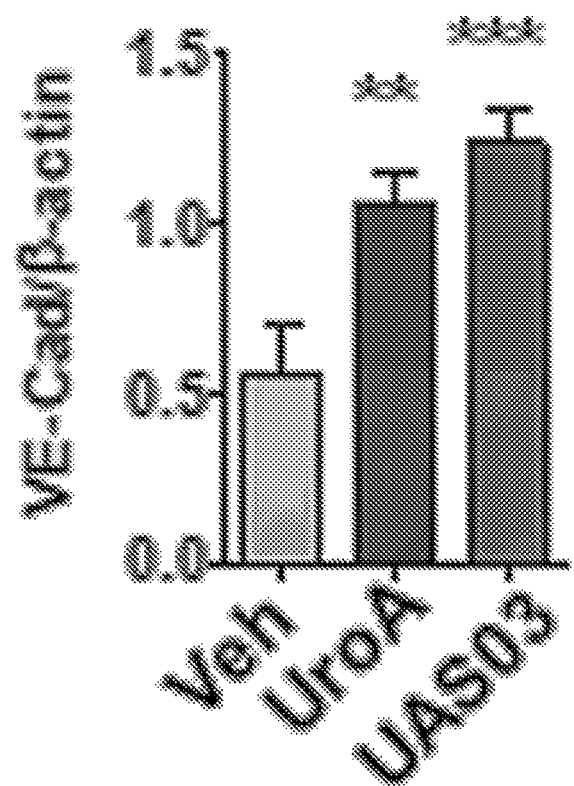
Figure 36:
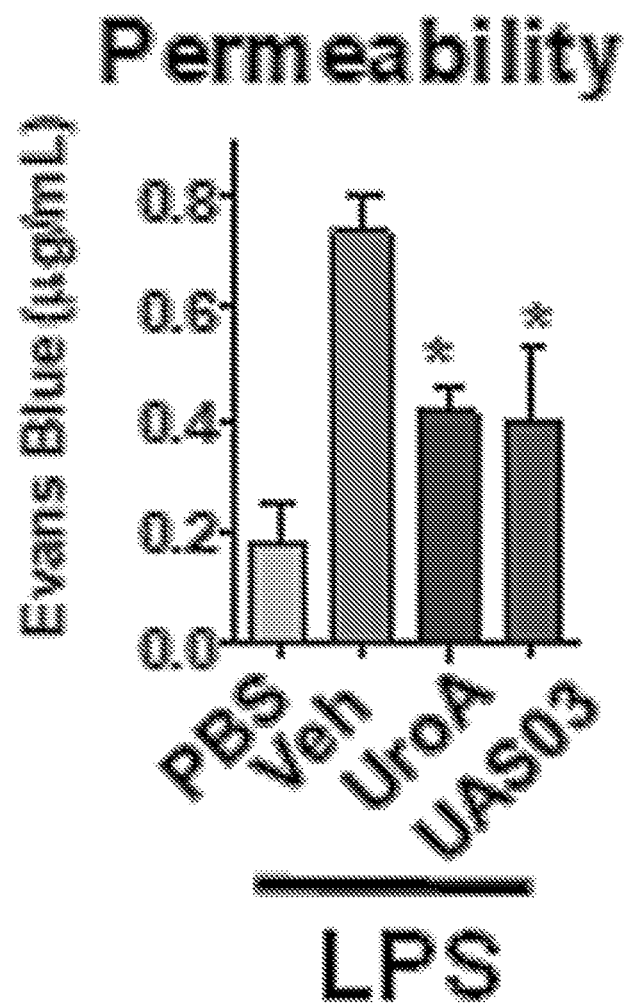

FIG. 36: Compounds enhance endothelial barrier function and protect from endothelial barrier dysfunction.

Figure 37:
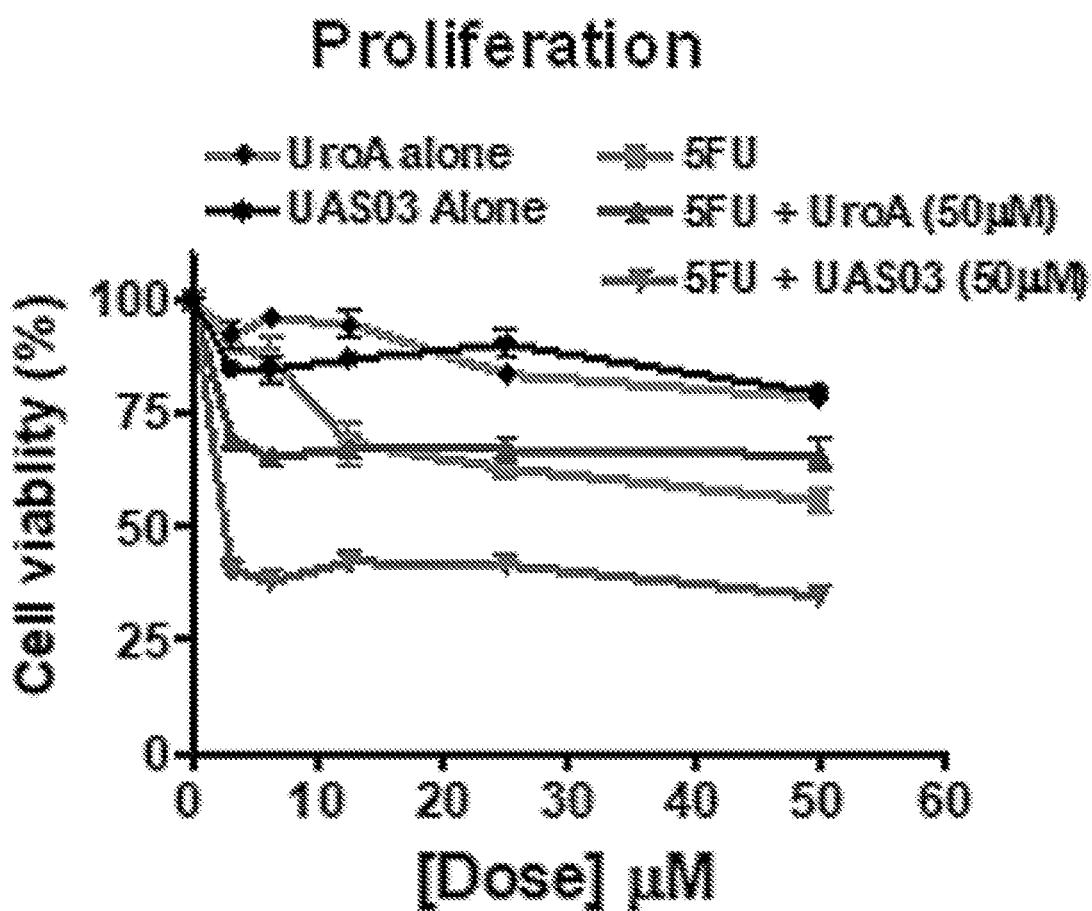
Figure 37:
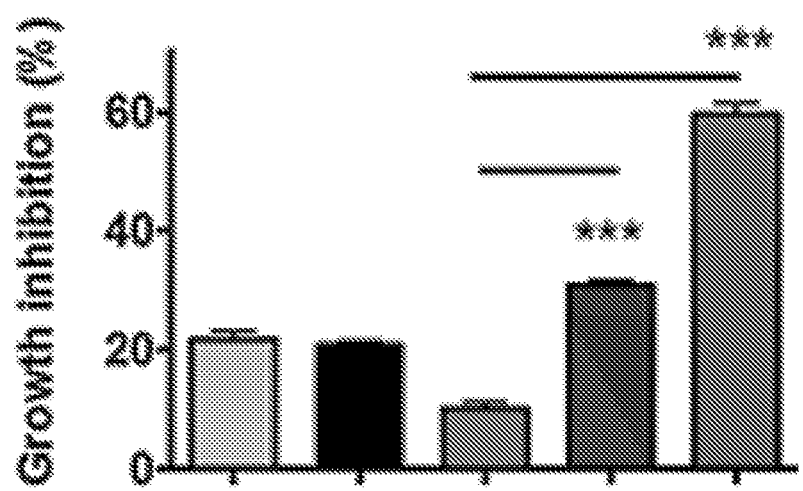
Figure 37:
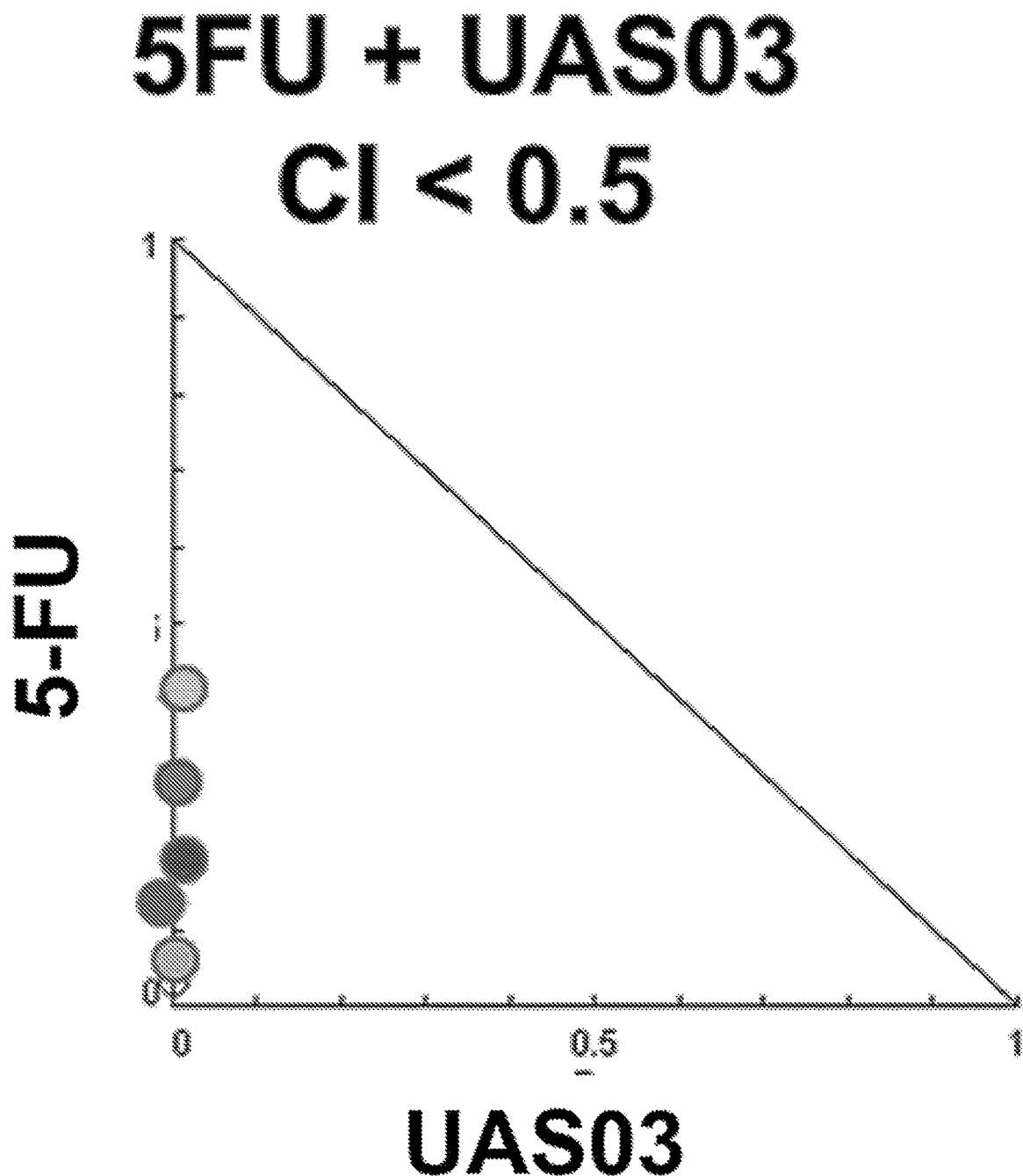
Figure 37:
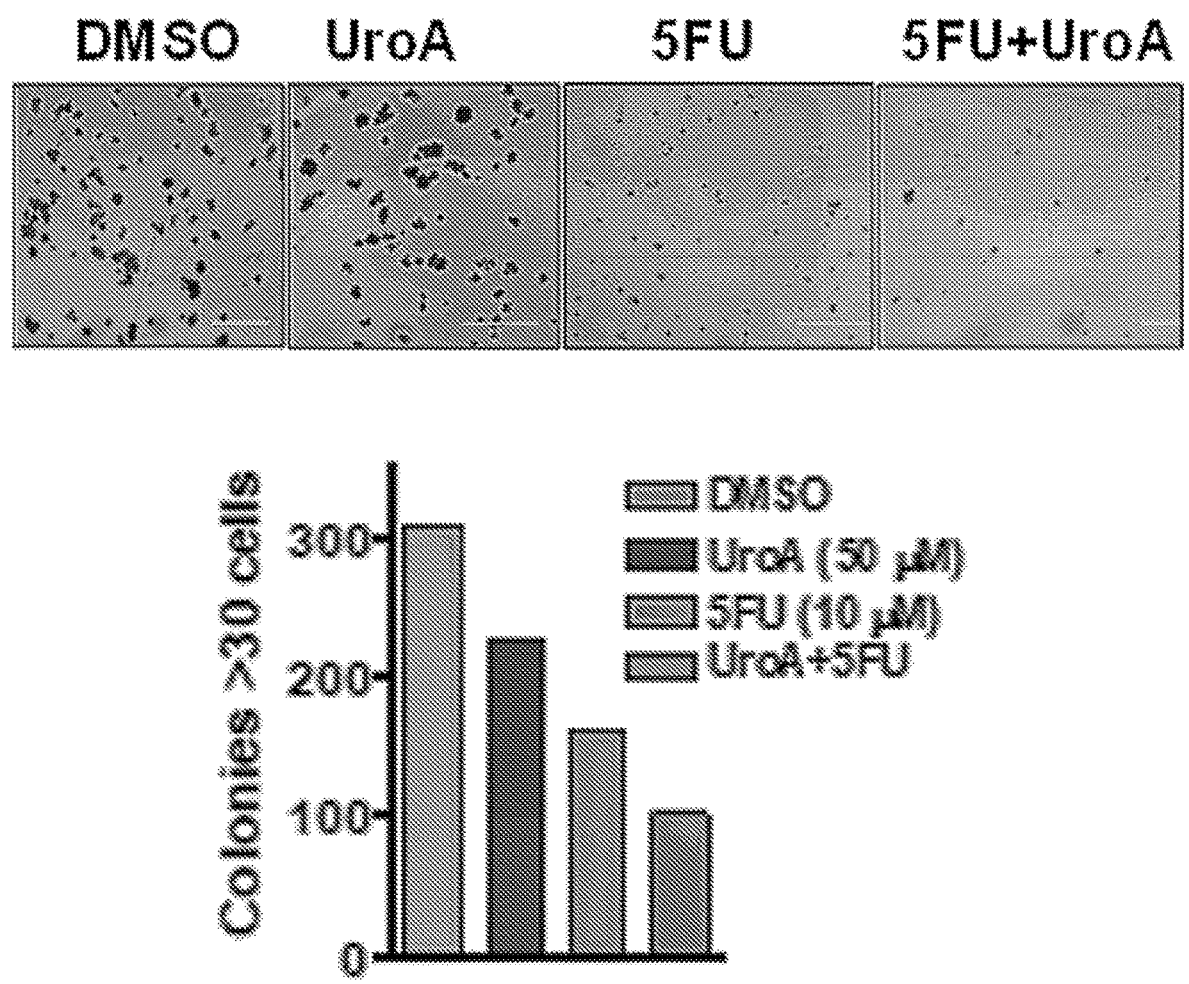

FIG. 37: Compounds chemosensitize the chemoresistance cancers.

Figure 38:
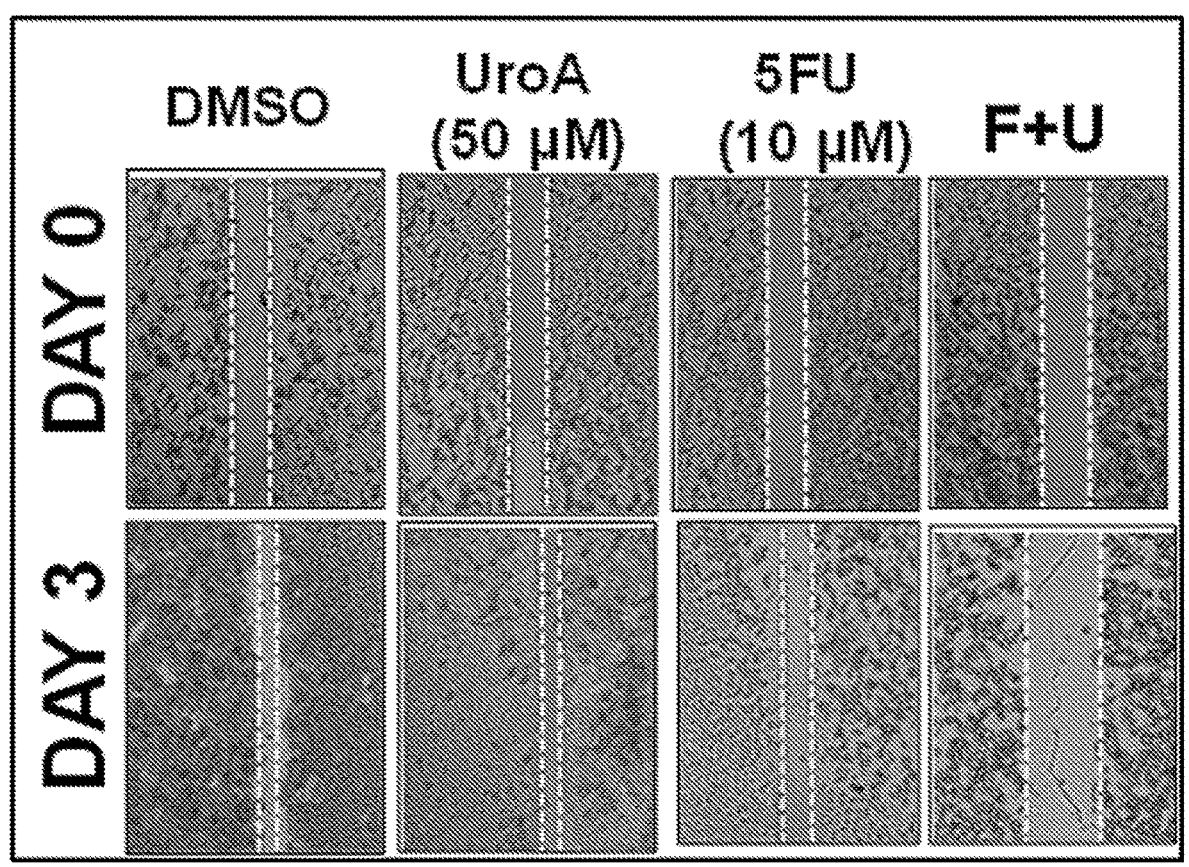

FIG. 38: Compounds show wound healing.

Figure 39:
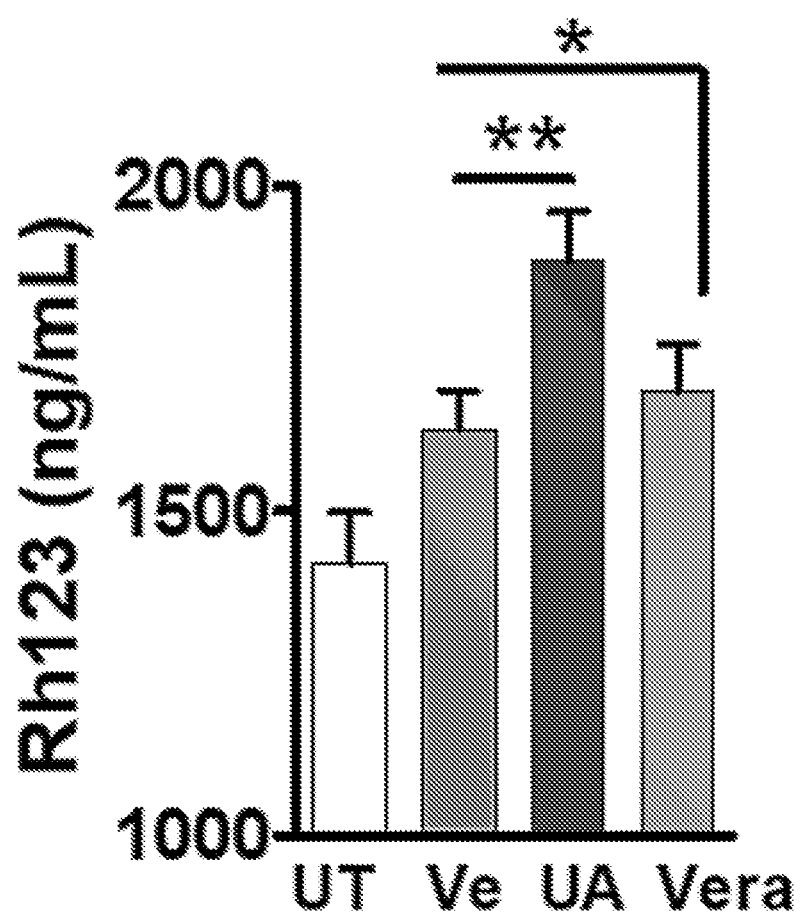

FIG. 39: UroA on the activity of P-glycoprotein (P-gp).

Figure 40:
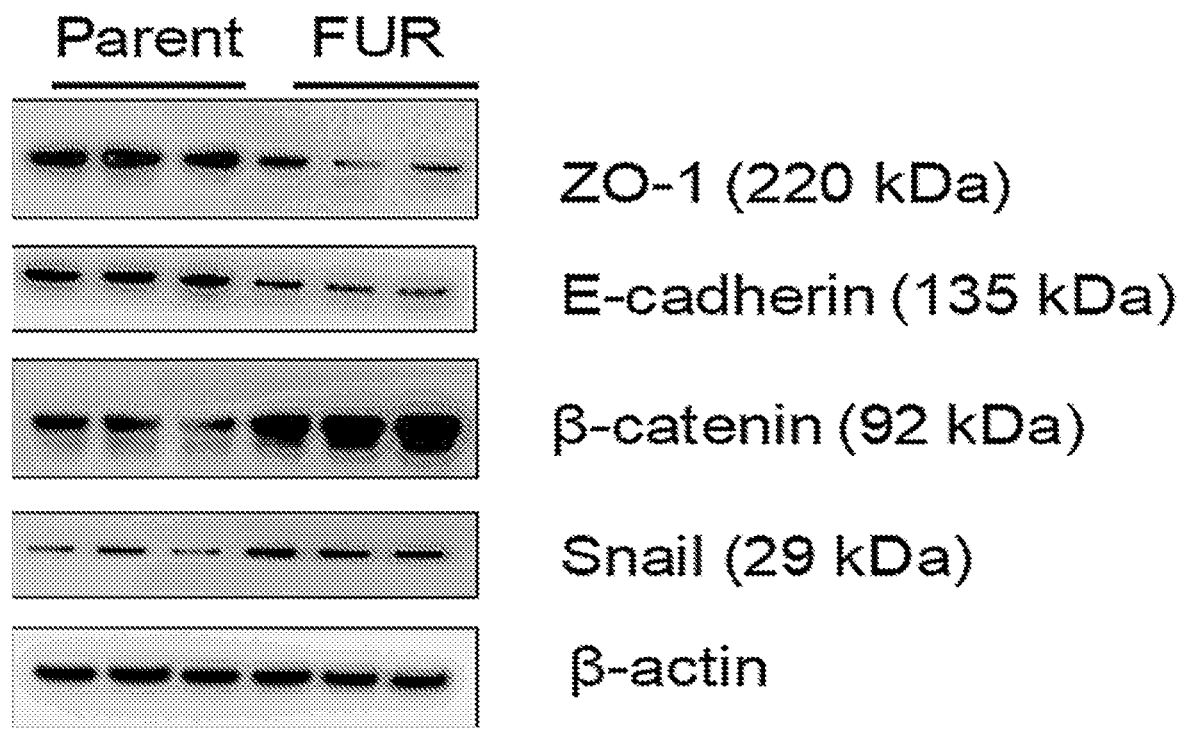

FIG. 40: Western blot analysis of EMT markers in parental and 5FUR HCT116 cells.

Figure 41:
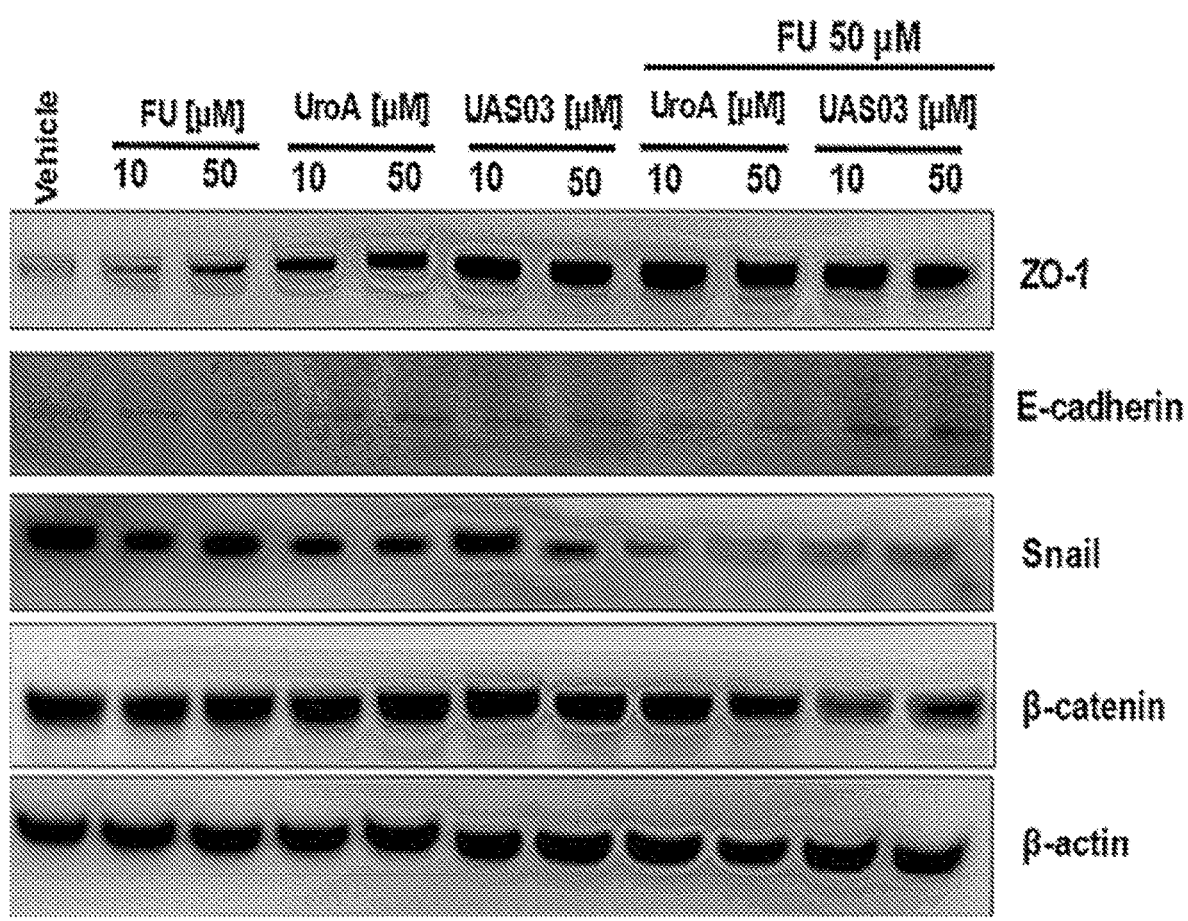

FIG. 41: Western blot analysis of EMT markers in 5FUR HCT116 cells in treated (72 h) with 5FU in the presence or absence of UroA/UAS03.

Figure 42:
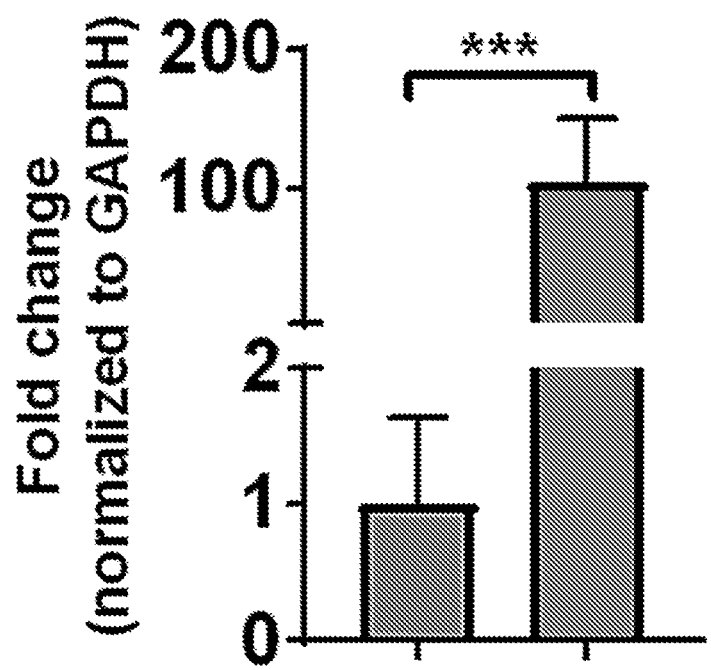
Figure 42:
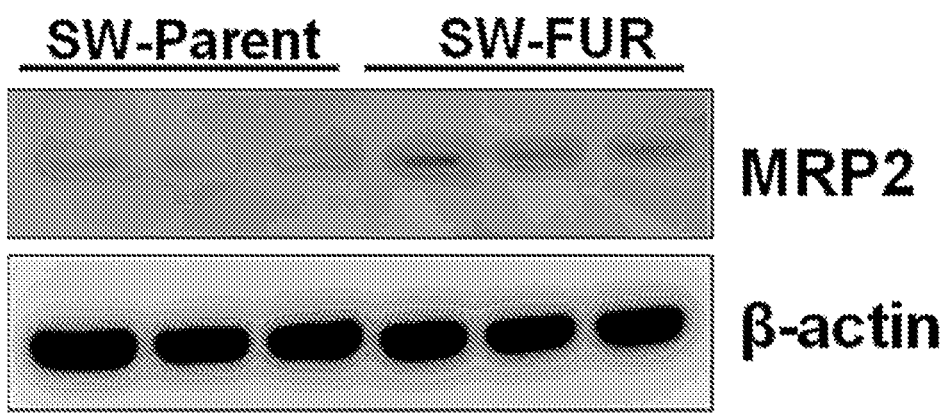
Figure 42:
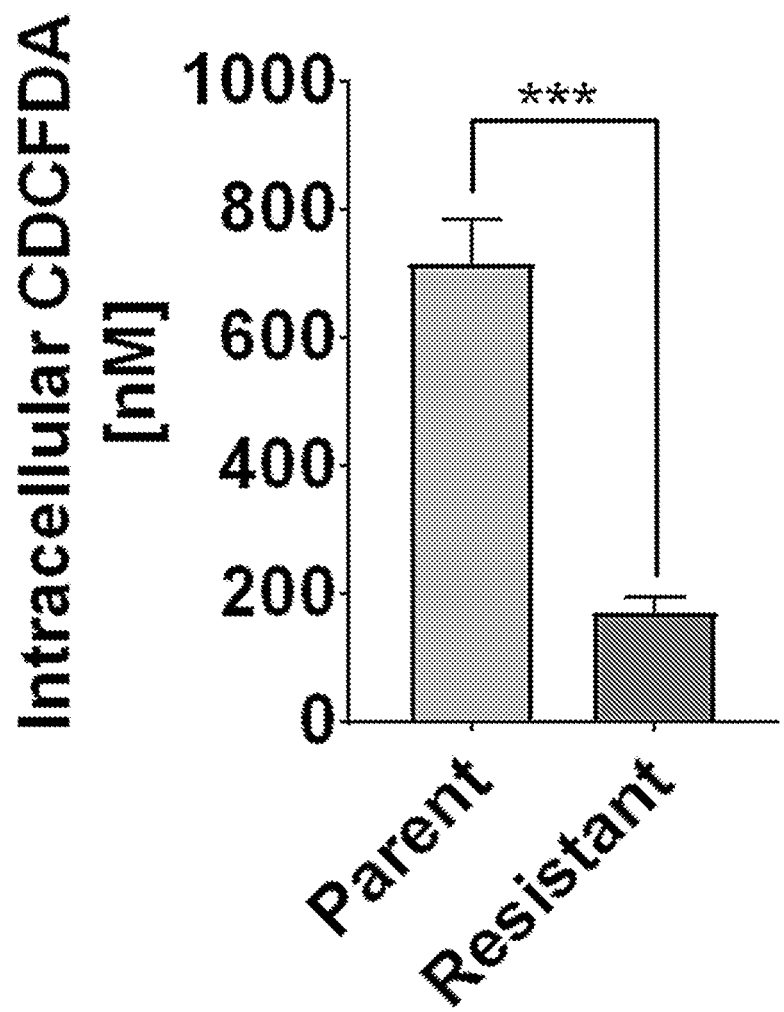

FIG. 42: Expression of MRP2 measured by real time PCR (A) and Western blots (B) in SW-5FUR colon cancer cell lines. (C) MRP2 activity is measured using CDCFDA (diacetate ester of 5(6)-carboxy-2',7'-dichlorofluorescein) transporter assay in SW-FUR colon cancer cell lines.

Figure 43:
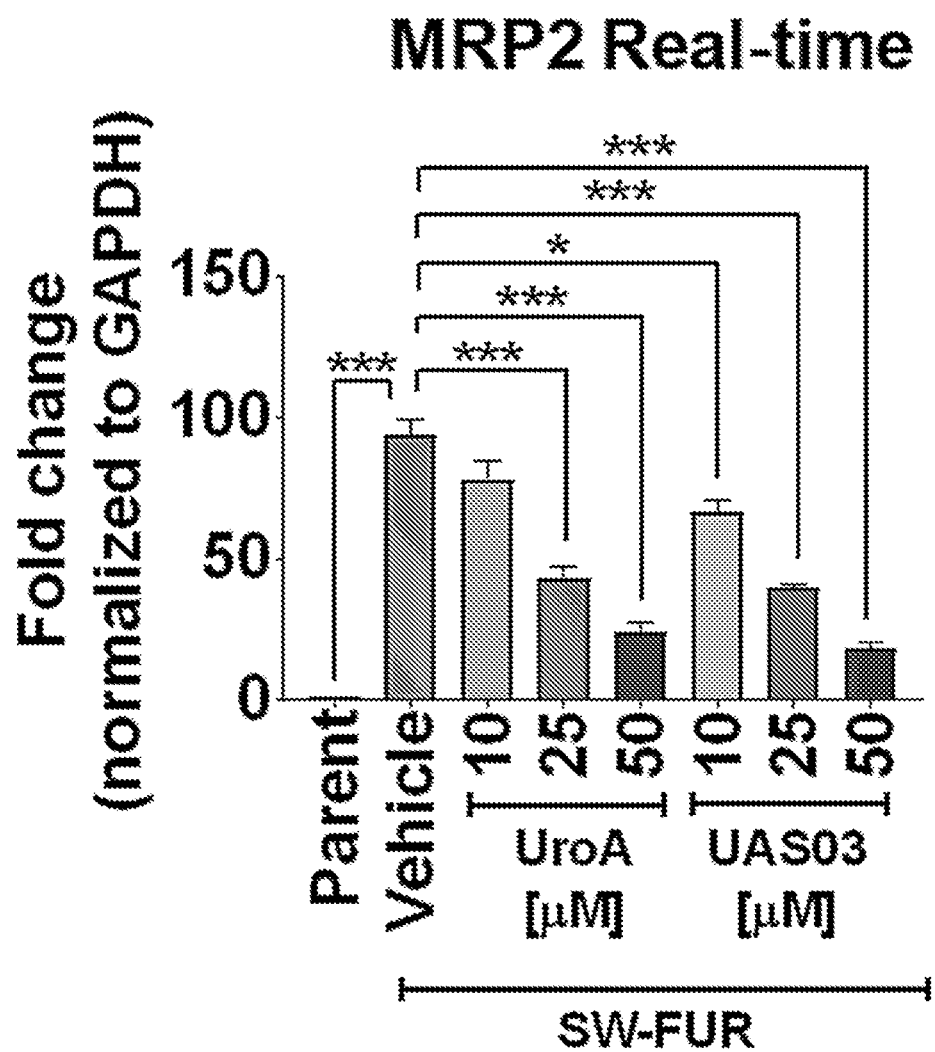
Figure 43:
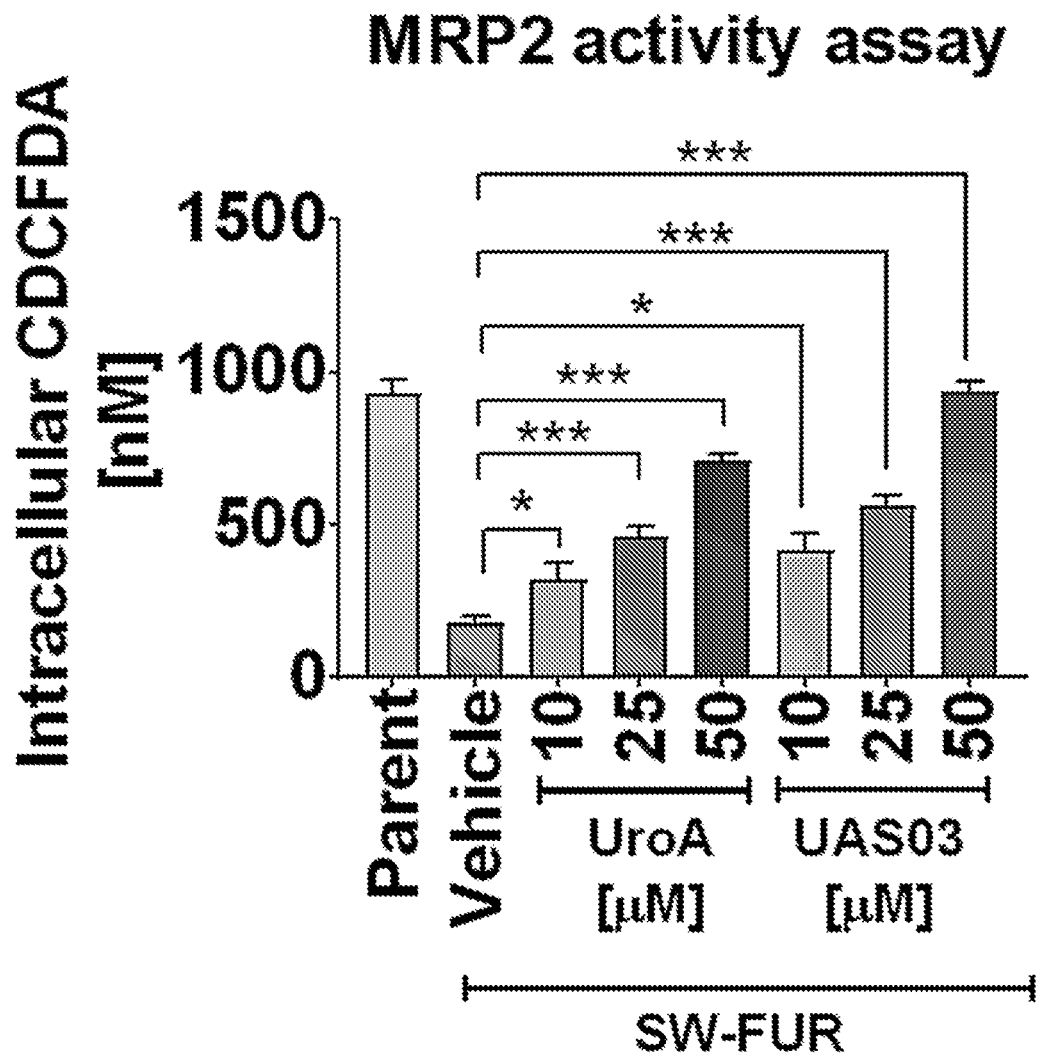

FIG. 43: UroA/UAS03 down regulate drug transporters. (A) Expression of MRP2 is measured by real time PCR upon treating with indicated doses of UroA or UAS03 in SW-5FUR colon cancer cell lines. (B) MRP2 activity is measured using CDCFDA (diacetate ester of 5(6)-carboxy-2',7'-dichlorofluorescein) transporter assay in SW-FUR colon cancer cell lines upon treating with UroA/USA03.

DETAILED DESCRIPTION

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

In some embodiments of the invention, inventive compounds (e.g., Formula (I), (IA), (II), and (III), and urolithin derivatives) are disclosed. Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases). Further embodiments include methods for making the inventive compounds. Additional embodiments of the invention are also discussed herein.

As used herein (unless otherwise specified), the term "alkyl" means a monovalent, straight or branched hydrocarbon chain (e.g., $C_1$-$C_{24}$). For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds (e.g., $C_2$-$C_{24}$). Examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—) (e.g., $C_1$-$C_{23}$). Examples of alkoxy groups include, but are not limited to, methoxy (sometimes shown as MeO—), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain (e.g., $C_2$-$C_{24}$). Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "aryl" means a monovalent, monocyclic or bicyclic, 5, 6, 7, 8, 9, 10, 11, or 12 member aromatic hydrocarbon group which, when unsubstituted. Examples of aryl groups include, but are not limited to, phenyl, naphthyl, tolyl, and xylyl. For a bicyclic aryl that is designated as substituted, one or both rings can be substituted.

As used herein (unless otherwise specified), the term "cycloalkyl" means a monovalent, monocyclic or bicyclic, 3, 4, 5, 6, 7, 8, 9, 10, 11, or 12 membered hydrocarbon group.

The rings can be saturated or partially unsaturated. Examples of cycloalkyl groups include, but are not limited to, cyclopropyl, cyclobutyl, cyclopentyl, cyclohexyl, cycloheptyl, cyclooctyl, and bicycloalkyls (e.g., bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds), and adamantane. For a monocyclic cycloalkyl, the ring is not aromatic. For a bicyclic cycloalkyl, if one ring is aromatic, then the other is not aromatic. For a bicyclic cycloalkyl that is designated as substituted, one or both rings can be substituted.

As used herein (unless otherwise specified), the term "halogen" means monovalent Cl, F, Br, or I.

As used herein (unless otherwise specified), the term "heteroaryl" means a monovalent, monocyclic or bicyclic, 5, 6, 7, 8, 9, 10, 11, or 12 membered, hydrocarbon group, where 1, 2, 3, 4, 5, or 6 carbon atoms are replaced by a hetero atom independently selected from nitrogen, oxygen, or sulfur atom, and the monocyclic or bicyclic ring system is aromatic. Examples of heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, triazolyl, tetrazolyl, 1H-pyrazol-4-yl, 1-Me-pyrazol-4-yl, pyridin-3-yl, pyridin-4-yl, 3,5-dimethyl-isoxazolyl, 1H-pyrrol-3-yl, 3,5-di-Me-pyrazolyl, and 1H-pyrazol-4-yl. For a bicyclic heteroaryl, if one ring is aryl, then the other is heteroaryl. For a bicyclic heteroaryl, one or both rings can have one or more hetero atoms. For a bicyclic heteroaryl that is designated as substituted, one or both rings can be substituted.

As used herein (unless otherwise specified), the term "heterocyclyl" means a monovalent, monocyclic or bicyclic, 5, 6, 7, 8, 9, 10, 11, or 12 membered, hydrocarbon, where 1, 2, 3, 4, 5, or 6 carbon atoms are replaced by a hetero atom independently selected from nitrogen atom, oxygen atom, or sulfur atom, and the monocyclic or bicyclic ring system is not aromatic. Examples of heterocyclyl groups include, but are not limited to, tetrahydropyran, pyrrolidinyl (e.g., pyrrolidin-1-yl, pyrrolidin-2-yl, pyrrolidin-3-yl, or pyrrolidin-4-yl), piperazinyl (e.g., piperazin-1-yl, piperazin-2-yl, piperazin-3-yl, or piperazin-4-yl), piperidinyl (e.g., piperadin-1-yl, piperadin-2-yl, piperadin-3-yl, or piperadin-4-yl), and morpholinyl (e.g., morpholin-1-yl, morpholin-2-yl, morpholin-3-yl, or morpholin-4-yl,). For a bicyclic heterocyclyl, if one ring is aromatic (e.g., monocyclic aryl or heteroaryl), then the other ring is not aromatic. For a bicyclic heterocyclyl, one or both rings can have one or more hetero atoms. For a bicyclic heterocyclyl that is designated as substituted, one or both rings can be substituted.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be substituted.

Some compounds of the invention can have one or more chiral centers and can exist in and be isolated in optically active and racemic forms, for any of the one or more chiral centers. Some compounds can exhibit polymorphism. The compounds of the present invention (e.g., Formula I) encompass any optically active, racemate, stereoisomer form, polymorphism, or mixtures thereof. If a chiral center does not provide an indication of its configuration (i.e., R or S) in a chemical structure, it should be considered to represent R, S or a racemate.

Some Compound Embodiments

Some embodiments of the invention include compounds of Formula (I), (II), or (III):

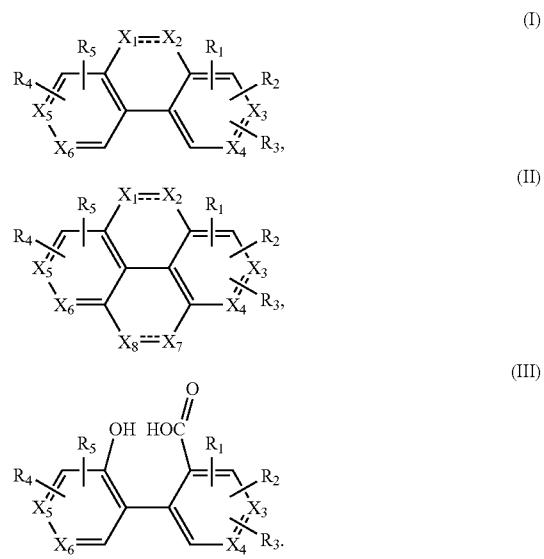

In other embodiments, the bond between $X_1$ and $X_2$ is a single bond or a double bond. In certain embodiments, the bond between $X_7$ and $X_8$ is a single bond or a double bond. In yet other embodiments, $X_1$, $X_2$, $X_7$, and $X_8$ can be the same or different and each can be independently selected from CH, $CH_2$, O, S, C—$NH_2$, C—N=$CH_2$, C(H)($NH_2$), C=O, C=N—$NH_2$, C=NH, C=N-cycloalkyl (e.g., C=N-adamantane), C=N—S(O)H, C=NC(EtOH)$_3$, C=NCH(EtOH)$_2$, C=NEtOH, C($CH_3$)(OH), N, NH, C-halogen, C(H)(halogen), C-(halogen)$_2$, C-cycloalkyl, C-heterocyclyl, C-aryl, C-heteroaryl, C(H)(cycloalkyl), C(H)(heterocyclyl), C(H)(aryl), or C(H)(heteroaryl), which CH, $CH_2$, C—$NH_2$, C—N=$CH_2$, C(H)($NH_2$), C=N—$NH_2$, C=NH, C=N-cycloalkyl, C=N—S(O)H, C=NC(EtOH)$_3$, C=NCH(EtOH)$_2$, C=NEtOH, C($CH_3$)(OH), NH, C(H)(halogen), C-cycloalkyl, C-heterocyclyl, C-aryl, C-heteroaryl, C(H)(cycloalkyl), C(H)(heterocyclyl), C(H)(aryl), or C(H)(heteroaryl), can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In certain embodiments, $X_1$ and $X_2$ can optionally be further cyclized to form a 5 or 6 membered cycloalkyl, 5 or 6 membered heterocyclyl, 5 or 6 membered aryl, or 5 or 6 membered heteroaryl, which 5 or 6 membered cycloalkyl, 5 or 6 membered heterocyclyl, 5 or 6 membered aryl, or 5 or 6 membered heteroaryl can be optionally substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In certain embodiments, X$_7$ and X$_8$ can optionally be further cyclized to form a 5 or 6 membered cycloalkyl, 5 or 6 membered heterocyclyl, 5 or 6 membered aryl, or 5 or 6 membered heteroaryl, which 5 or 6 membered cycloalkyl, 5 or 6 membered heterocyclyl, 5 or 6 membered aryl, or 5 or 6 membered heteroaryl can be optionally substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. Of course, the choice of X$_1$ and X$_2$ will depend on whether there is a single or double bond between X$_1$ and X$_2$; the choice of X$_7$ and X$_8$ will depend on whether there is a single or double bond between X$_7$ and X$_8$.

In some embodiments, X$_1$, X$_2$, X$_7$, and X$_8$ can be the same or different and each can be independently selected from CH$_2$, O, C—NH$_2$, C—N=CH$_2$, C(H)(NH$_2$), C=O, C=N—NH$_2$, C=NH, C=N-cycloalkyl (e.g., adamantane), C=N—S(O)H, C=NC(EtOH)$_3$, C=NCH(EtOH)$_2$, C=NEtOH, C(CH$_3$)(OH), C-halogen, C(H)(halogen), C-(halogen)$_2$, C-cycloalkyl, or C(H)(cycloalkyl), which CH$_2$, C—NH$_2$, C—N=CH$_2$, C(H)(NH$_2$), C=N—NH$_2$, C=NH, C=N-cycloalkyl (e.g., adamantane), C=N—S(O)H, C=NC(EtOH)$_3$, C=NCH(EtOH)$_2$, C=NEtOH, C(CH$_3$)(OH), C(H)(halogen), C-cycloalkyl, or C(H)(cycloalkyl), can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In some embodiments, X$_1$ and X$_2$ can further cyclize to form a pyrazinyl, 1,2,5-thiadiazole 1-oxide, or 2H-imidazol-2-one. In some embodiments, X$_7$ and X$_8$ can further cyclize to form a pyrazinyl, 1,2,5-thiadiazole 1-oxide, 2H-imidazol-2-one.

In other embodiments, X$_1$, X$_2$, X$_7$, and X$_8$ can be the same or different and each can be independently selected from CH$_2$, O, C(H)(NH$_2$), C=O, C=N—NH$_2$, C=NH, C=N-cycloalkyl (e.g., adamantane), C=NC(EtOH)$_3$, C=NCH(EtOH)$_2$, C=NEtOH, C(CH$_3$)(OH), or C(H)(cycloalkyl). In still other embodiments, X$_1$, X$_2$, X$_7$, and X$_8$ can be the same or different and each can be independently selected from CH$_2$, 0, C=O, C=NH, C=N-cycloalkyl (e.g., adamantane), C=NC(EtOH)$_3$, C=NCH(EtOH)$_2$, C=NEtOH, C(CH$_3$)(OH), or C(H)(cycloalkyl). In still other embodiments, X$_1$, X$_2$, X$_7$, and X$_8$ can be the same or different and each can be independently selected from CH$_2$, O, C=O, C=N-cycloalkyl (e.g., adamantane), or C=NEtOH.

In some embodiments, X$_1$, X$_2$, X$_7$, and X$_8$ can be the same. In some embodiments, X$_1$ and X$_2$ can be the same. In some embodiments, X$_1$ and X$_2$ can be different. In some embodiments, X$_7$ and X$_8$ can be the same. In some embodiments, X$_7$ and X$_8$ can be different. In some embodiments, X$_1$ and X$_7$ can be the same. In some embodiments, X$_1$ and X$_7$ can be different. In some embodiments, X$_2$ and X$_8$ can be the same. In some embodiments, X$_2$ and X$_8$ can be different.

In some embodiments, X$_3$, X$_4$, X$_5$, and X$_6$ can be the same or different and each can be independently selected from CH or N, which CH can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In some embodiments, X$_3$, X$_4$, X$_5$, and X$_6$ can be the same or different and each can be independently selected from CH or N. In some embodiments, X$_3$, X$_4$, X$_5$, and X$_6$ can be each CH.

In some embodiments, R$_1$, R$_2$, R$_3$, R$_4$, and R$_5$ can be the same or different and each can be independently selected from H, OH, halogen (e.g., F, Cl, Br, or I), methanoyl (—COH), —OCF$_3$, —COCH$_3$, carbonyl, carboxy (—CO$_2$H), ethynyl (—CCH), cyano (—CN), amine, —NO$_2$, sulfo (—SO$_3$H), C$_1$-C$_4$ alkyl (e.g., C$_1$, C$_2$, C$_3$, or C$_4$ alkyl), C$_2$-C$_4$ alkenyl (e.g., C$_2$, C$_3$, or C$_4$ alkenyl), C$_2$-C$_4$ alkynyl (e.g., C$_2$, C$_3$, or C$_4$ alkynyl), C$_1$-C$_3$ alkoxy (e.g., C$_1$, C$_2$, or C$_3$ alkoxy), methyl, ethyl, perfluorinated methyl, perfluorinated ethyl, cycloalkyl (e.g., bicycloalkyl), or heterocyclyl (e.g., imidazolyl), which H, OH, methanoyl (—COH), —COCH$_3$, carbonyl, carboxy (—CO$_2$H), ethynyl (—CCH), sulfo (—SO$_3$H), C$_1$-C$_4$ alkyl (e.g., C$_1$, C$_2$, C$_3$, or C$_4$ alkyl), C$_2$-C$_4$ alkenyl (e.g., C$_2$, C$_3$, or C$_4$ alkenyl), C$_2$-C$_4$ alkynyl (e.g., C$_2$, C$_3$, or C$_4$ alkynyl), C$_1$-C$_3$ alkoxy (e.g., C$_1$, C$_2$, or C$_3$ alkoxy), methyl, ethyl, cycloalkyl, or heterocyclyl (e.g., imidazolyl) can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In certain embodiments, R$_1$, R$_2$, R$_3$, R$_4$, and R$_5$ can be the same or different and each can be independently selected from H, OH, halogen (e.g., F, Cl, Br, or I), methanoyl (—COH), —OCF$_3$, —COCH$_3$, carbonyl, carboxy (—CO$_2$H), cyano (—CN), amine, —NO$_2$, methoxy, ethoxy, methyl, ethyl, perfluorinated methyl, perfluorinated ethyl, cycloalkyl (e.g., bicycloalkyl), or heterocyclyl (e.g., imidazolyl).

In other embodiments, a compound is selected from Formula (IA):

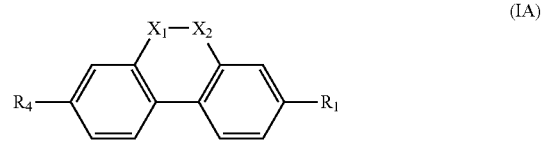

(IA)

In some embodiments, X$_1$, X$_2$, R$_1$, and R$_2$ are defined as above for Formula (I). In other embodiments (e.g., in Formula (I), (II), (III), or (IA)), X$_1$ and X$_2$ are the same. In yet other embodiments (e.g., in Formula (I), (II), (III), or (IA)), X$_1$ and X$_2$ are different. In other embodiments (e.g., in Formula (I), (II), (III), or (IA)), R$_1$ and R$_2$ are the same. In yet other embodiments (e.g., in Formula (I), (II), (III), or (IA)), R$_1$ and R$_2$ are different. In some embodiments (e.g., in Formula (I), (II), (III), or (IA)), X$_1$ and X$_2$ can be the same or different and each can be independently selected from CH$_2$, O, C(H)(NH$_2$), C=O, C=N—NH$_2$, C=NH, C=N-cycloalkyl (e.g., adamantane), C=NC(EtOH)$_3$, C=NCH(EtOH)$_2$, C=NEtOH, C(CH$_3$)(OH), or C(H)(cycloalkyl), which CH$_2$, C(H)(NH$_2$), C=N—NH$_2$, C=NH, C=N-cycloalkyl (e.g., adamantane), C=NC(EtOH)$_3$, C=NCH(EtOH)$_2$, C=NEtOH, C(CH$_3$)(OH), or C(H)(cycloalkyl), can optionally be substituted with one or more (e.g., 0, 1, 2, 3, 4, 5, or 6) of halogen (e.g., F, Cl, Br, or I), hydroxy (—OH), methanoyl (—COH), —COCH$_3$, carboxy (—CO$_2$H), ethynyl (—CCH), cyano (—CN), sulfo (—SO$_3$H), methyl, ethyl, perfluorinated methyl, or perfluorinated ethyl. In other embodiments (e.g., in Formula (I), (II), (III), or (IA)), X$_1$ and X$_2$ can be the same or different and each can be independently selected from $CH_2$, O, $C(H)(NH_2)$, C=O, C=N—$NH_2$, C=NH, C=N— cycloalkyl (e.g., adamantane), C=$NC(EtOH)_3$, C=$NCH(EtOH)_2$, C=NEtOH, $C(CH_3)(OH)$, or C(H)(cycloalkyl). In still other embodiments (e.g., in Formula (I), (II), (III), or (IA)), $X_1$ and $X_2$ can be the same or different and each can be independently selected from $CH_2$, O, C=O, C=NH, C=N-cycloalkyl (e.g., adamantane), C=$NC(EtOH)_3$, C=$NCH(EtOH)_2$, C=NEtOH, $C(CH_3)(OH)$, or C(H)(cycloalkyl). In still other embodiments (e.g., in Formula (I), (II), (III), or (IA)), $X_1$ and $X_2$ can be the same or different and each can be independently selected from $CH_2$, O, C=O, C=N-cycloalkyl (e.g., adamantane), or C=NEtOH.

In some embodiments (e.g., in Formula (I), (II), (III), or (IA)), $R_1$ and $R_2$ can be the same or different and each can be independently selected from H, OH, halogen (e.g., F, Cl, Br, or I), methanoyl (—COH), —$OCF_3$, —$COCH_3$, carbonyl, carboxy (—$CO_2H$), ethynyl (—CCH), cyano (—CN), amine, —$NO_2$, sulfo (—$SO_3H$), $C_1$-$C_4$ alkyl (e.g., $C_1$, $C_2$, $C_3$, or $C_4$ alkyl), $C_2$-$C_4$ alkenyl (e.g., $C_2$, $C_3$, or $C_4$ alkenyl), $C_2$-$C_4$ alkynyl (e.g., $C_2$, $C_3$, or $C_4$ alkynyl), $C_1$-$C_3$ alkoxy (e.g., $C_1$, $C_2$, or $C_3$ alkoxy), methyl, ethyl, perfluorinated methyl, perfluorinated ethyl, which H, OH, methanoyl (—COH), —$COCH_3$, carbonyl, carboxy (—$CO_2H$), ethynyl (—CCH), sulfo (—$SO_3H$), $C_1$-$C_4$ alkyl (e.g., $C_1$, $C_2$, $C_3$, or $C_4$ alkyl), $C_2$-$C_4$ alkenyl (e.g., $C_2$, $C_3$, or $C_4$ alkenyl), $C_2$-$C_4$ alkynyl (e.g., $C_2$, $C_3$, or $C_4$ alkynyl), $C_1$-$C_3$ alkoxy (e.g., $C_1$, $C_2$, or $C_3$ alkoxy), methyl, or ethyl can optionally be substituted with one or more (e.g., 0, 1, 2, 3, 4, 5, or 6) of halogen (e.g., F, Cl, Br, or I), hydroxy (—OH), methanoyl (—COH), —$COCH_3$, carboxy (—$CO_2H$), ethynyl (—CCH), cyano (—CN), sulfo (—$SO_3H$), methyl, ethyl, perfluorinated methyl, or perfluorinated ethyl. In certain embodiments (e.g., in Formula (I), (II), (III), or (IA)), $R_1$ and $R_2$ can be the same or different and each can be independently selected from H, OH, halogen (e.g., F, Cl, Br, or I), methanoyl (—COH), —$OCF_3$, —$COCH_3$, carbonyl, carboxy (—$CO_2H$), cyano (—CN), amine, —$NO_2$, methoxy, ethoxy, methyl, ethyl, perfluorinated methyl, or perfluorinated ethyl. In certain embodiments (e.g., in Formula (I), (II), (III), or (IA)), $R_1$ and $R_2$ can be the same or different and each can be independently selected from H, OH, or methoxy.

In some embodiments, the compounds of Formulas (I), (IA), (II), or (III) can be selected from those specified in Table 1. The table include compound numbers with leading zeros (e.g., I-001 or I-015). These compound numbers are sometimes identified without the leading zeros; the compound is the same with or without the leading zeros (e.g., compound I-001 is the same as compound I-1; compound I-015 is the same as compound I-15).

TABLE 1

| Formula # (other identifiers) | Structure |
| --- | --- |
| I-001 (PLK-01 or Uro-A) | |

TABLE 1-continued

| Formula # (other identifiers) | Structure |
| --- | --- |
| I-002 (PKL-02 or UAS03) | 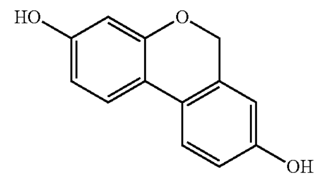 [SMILES: Oc1ccc2c(c1)COc1cc(O)ccc1-2] |
| I-003 (PKL-03) | 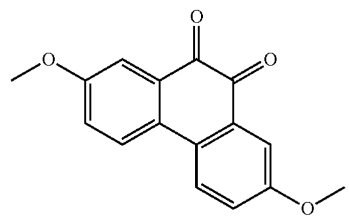 |
| I-004 (PKL-04) | 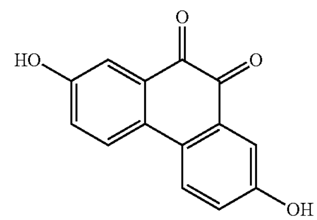 [SMILES: O=C1C(=O)c2cc(O)ccc2-c2ccc(O)cc21] |
| I-005 (PKL-05) | 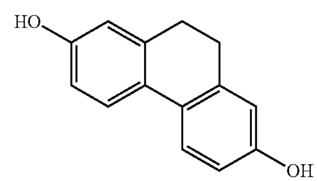 [SMILES: Oc1ccc2c(c1)CCc1cc(O)ccc1-2] |
| I-006 (PKL-06) | 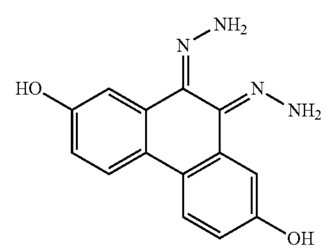 [SMILES: N/N=C1\C(=N\N)c2cc(O)ccc2-c2ccc(O)cc21] |
| I-007 (PKL-07) | 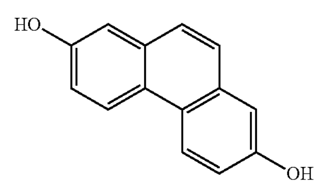 [SMILES: Oc1ccc2c(ccc3cc(O)ccc32)c1] |
| I-008 (PKL-08) | 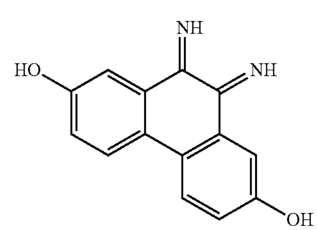 [SMILES: N=C1C(=N)c2cc(O)ccc2-c2ccc(O)cc21] |

TABLE 1-continued

| Formula # (other identifiers) | Structure |
|---|---|
| I-009 (PKL-09) | 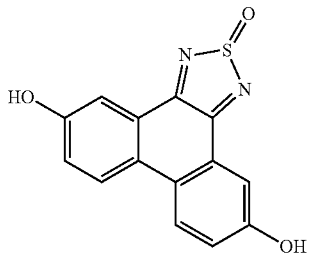 [SMILES: O=S1N=c2c(c3cc(O)ccc3c3ccc(O)cc23)=N1] |
| I-010 (PKL-10) | 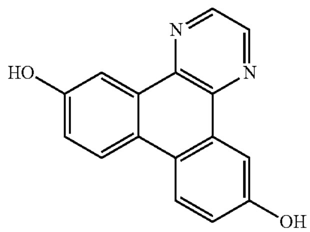 [SMILES: Oc1ccc2c3ccc(O)cc3c3nccnc3c2c1] |
| I-011 (PKL-11) | 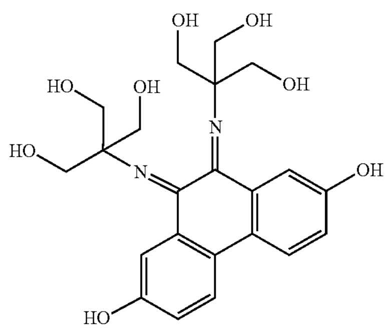 [SMILES: OCC(CO)(CO)N=C1/C(=N\C(CO)(CO)CO)c2cc(O)ccc2-c2ccc(O)cc21] |
| I-012 (PKL-12) | 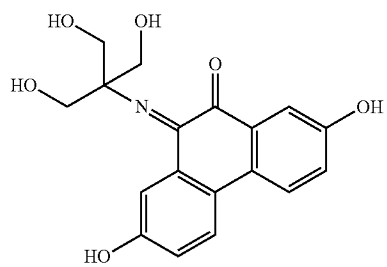 [SMILES: O=C1C(=NC(CO)(CO)CO)c2cc(O)ccc2-c2ccc(O)cc21] |
| I-013 (PKL-13) | 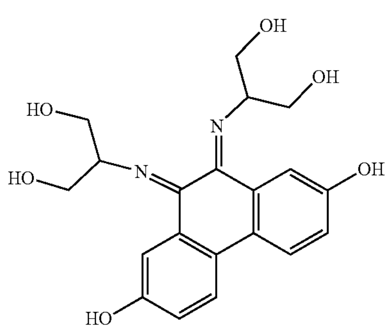 [SMILES: OCC(CO)/N=C1/C(=N/C(CO)CO)c2cc(O)ccc2-c2ccc(O)cc21] |
| I-014 (PKL-014) | |
| I-015 (PKL-15) | |
| I-016 (PKL-16) | |
| I-017 (PKL-17) | |
| I-018 (PKL-18A and PKL-18B) | |

TABLE 1-continued
| Formula # (other identifiers) | Structure |
|---|---|
| I-019 (PKL-18A) | 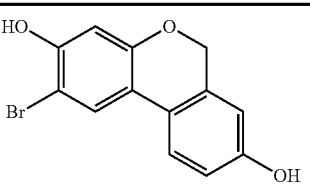 |
| I-020 (PKL-20) | 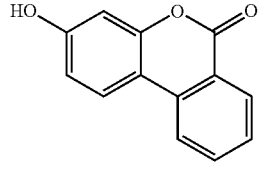 [SMILES: O=c1oc2cc(O)ccc2c2ccccc12] |
| I-021 (PKL-21) | 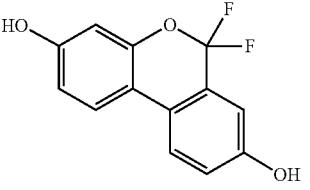 [SMILES: Oc1ccc2c(c1)OC(F)(F)c1cc(O)ccc1-2] |
| I-022 (PKL-22) | 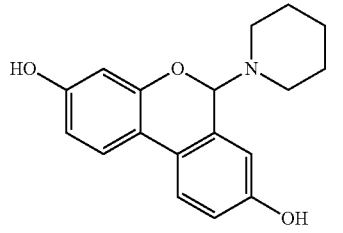 [SMILES: Oc1ccc2c(c1)OC(N1CCCCC1)c1cc(O)ccc1-2] |
| I-023 (PKL-23) | 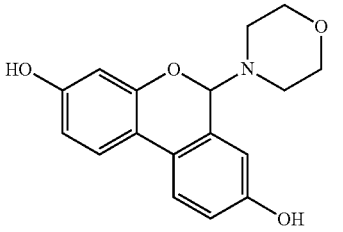 [SMILES: Oc1ccc2c(c1)OC(N1CCOCC1)c1cc(O)ccc1-2] |
| I-024 (PKL-24) | 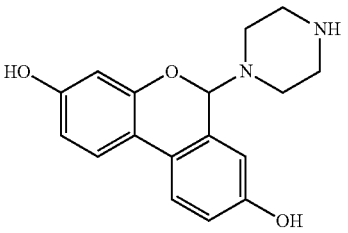 [SMILES: Oc1ccc2c(c1)OC(N1CCNCC1)c1cc(O)ccc1-2] |
| I-025 (PKL-25) | 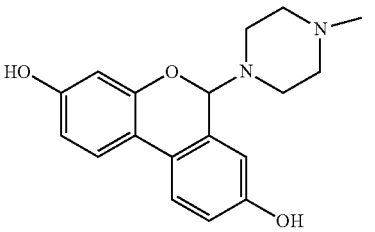 [SMILES: CN1CCN(C2Oc3cc(O)ccc3-c3ccc(O)cc32)CC1] |
TABLE 1-continued
| Formula # (other identifiers) | Structure |
|---|---|
| I-026 (PKL-26) | 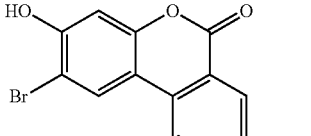 |
| I-027 (PKL-27) | 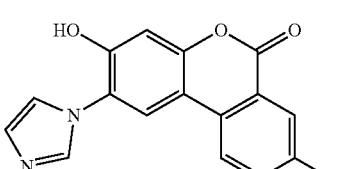 |
| I-028 (PKL-28) | 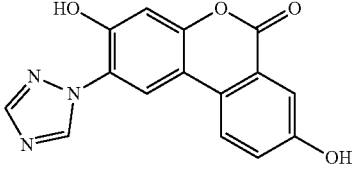 [SMILES: O=c1oc2cc(O)c(-n3cncn3)cc2c2ccc(O)cc12] |
| I-029 (PKL-29) | 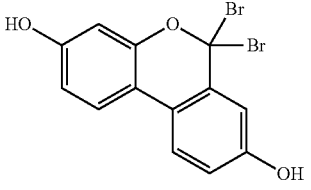 |
| I-030 (PKL-30) | 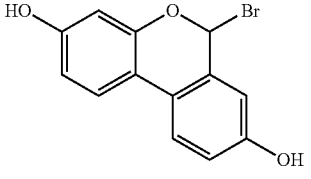 [SMILES: Oc1ccc2c(c1)OC(Br)c1cc(O)ccc1-2] |
| I-032 (PKL-32) | 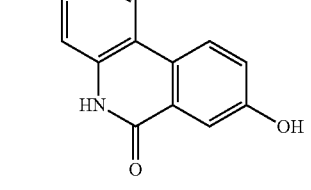 |
| I-033 (PKL-33) | 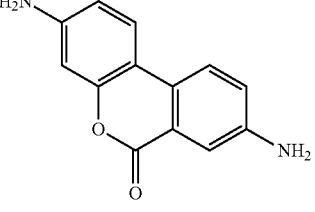 |

TABLE 1-continued

| Formula # (other identifiers) | Structure |
|---|---|
| I-034 (PKL-34) | (structure) |
| I-036 (PKL-36) | (structure) |
| I-037 (PKL-37) | (structure) |
| I-038 (PKL-38) | (structure) |
| I-039 (PKL-39) | (structure) |
| I-040 (PKL-40) | (structure) |
| I-041 (PKL-41) | (structure) |
| I-042 (PKL-42) | (structure) |
| I-043 (PKL-43) | (structure) |
| I-044 (PKL-44) | (structure) |
| I-045 (PKL-45) | (structure) |
| I-046 (PKL-46) | (structure) |
| I-047 (PKL-47) | (structure) |

TABLE 1-continued
| Formula # (other identifiers) | Structure |
|---|---|
| I-048 (PKL-48) | 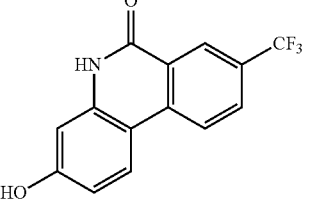 |
| I-049 (PKL-49) | 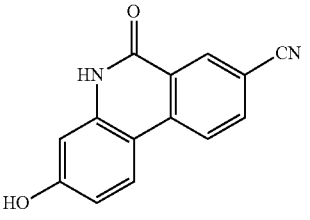 [SMILES: N#Cc1ccc2c(c1)c(=O)[nH]c1cc(O)ccc12] |
| I-050 (PKL-50) | 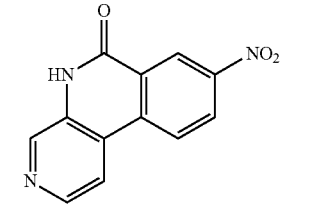 [SMILES: O=c1[nH]c2cnccc2c2ccc([N+](=O)[O-])cc12] |
| I-051 (PKL-51) | 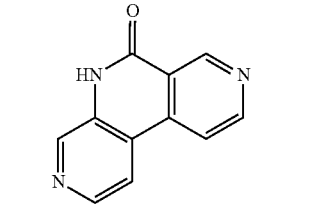 [SMILES: O=c1[nH]c2cnccc2c2ccncc12] |
| I-052 (PKL-52) | 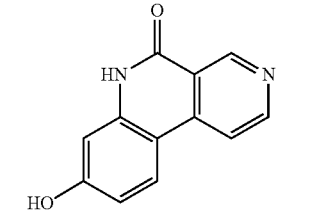 [SMILES: O=c1[nH]c2cc(O)ccc2c2ccncc12] |
| I-053 (PKL-53) | 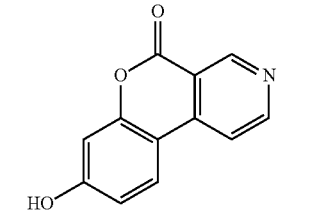 |
| I-054 (PKL-54) | 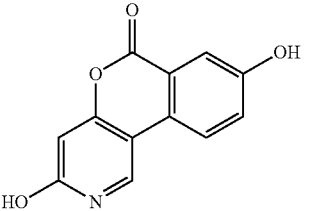 [SMILES: O=c1oc2cc(O)ncc2c2ccc(O)cc12] |
| I-055 (PKL-55) | 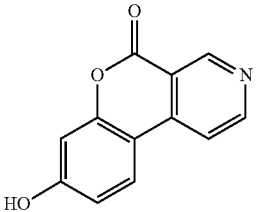 [SMILES: O=c1oc2cc(O)ccc2c2ccncc12] |
| I-056 (PKL-56) | 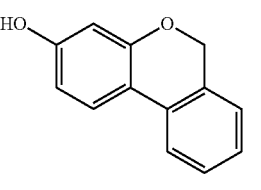 |
| I-057 (PKL-57) | 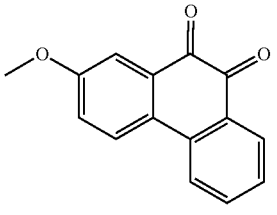 [SMILES: COc1ccc2c(c1)C(=O)C(=O)c1ccccc1-2] |
| I-058 (PKL-58) | 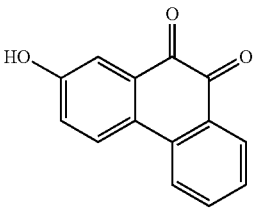 [SMILES: O=C1C(=O)c2cc(O)ccc2-c2ccccc21] |
| I-059 (PKL-59) | 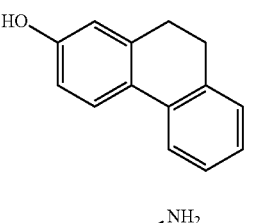 |
| I-060 (PKL-60) | 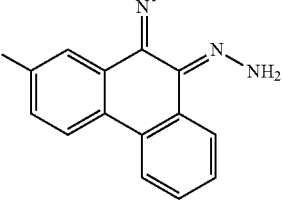 |
| I-061 (PKL-61) | 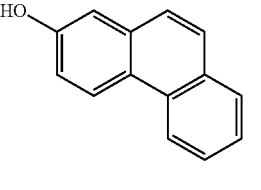 [SMILES: Oc1ccc2c(ccc3ccccc32)c1] |

TABLE 1-continued

| Formula # (other identifiers) | Structure |
|---|---|
| I-062 (PKL-62) | (structure) |
| I-063 (PKL-63) | (structure) |
| I-064 (PKL-64) | (structure) |
| I-065 (PKL-65) | (structure) |
| I-066 (PKL-66) | (structure) |
| I-067 (PKL-67) | (structure) |
| I-068 (PKL-68) | (structure) |
| I-069 (PKL-69) | (structure) |
| I-070 (PKL-70) | (structure) |
| I-071 (PKL-71) | (structure) |
| I-072 (PKL-72) | (structure) |

TABLE 1-continued
| Formula # (other identifiers) | Structure |
|---|---|
| I-073 (PKL-73) | 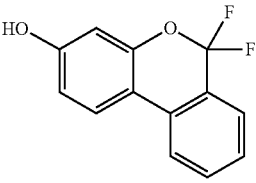 [SMILES: Oc1ccc2c(c1)OC(F)(F)c1ccccc1-2] |
| I-074 (PKL-74) | 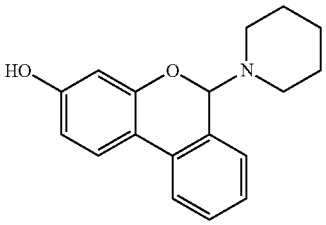 [SMILES: Oc1ccc2c(c1)OC(N1CCCCC1)c1ccccc1-2] |
| I-075 (PKL-75) | 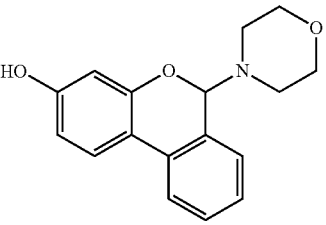 [SMILES: Oc1ccc2c(c1)OC(N1CCOCC1)c1ccccc1-2] |
| I-076 (PKL-76) | 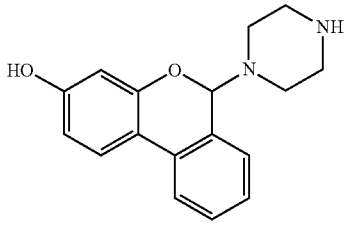 [SMILES: Oc1ccc2c(c1)OC(N1CCNCC1)c1ccccc1-2] |
| I-077 (PKL-77) | 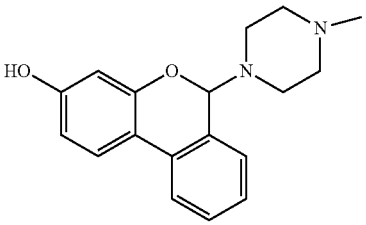 [SMILES: CN1CCN(C2Oc3cc(O)ccc3-c3ccccc32)CC1] |
| I-078 (PKL-78) | 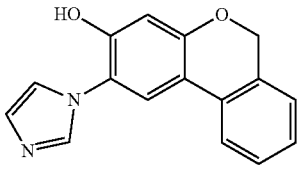 [SMILES: Oc1cc2c(cc1-n1ccnc1)-c1ccccc1CO2] |
| I-079 (PKL-79) | 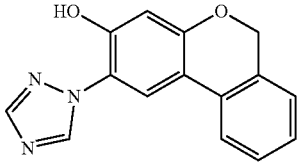 [SMILES: Oc1cc2c(cc1-n1cncn1)-c1ccccc1CO2] |
TABLE 1-continued
| Formula # (other identifiers) | Structure |
|---|---|
| I-080 (PKL-80) | 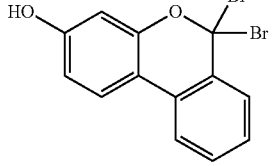 |
| I-081 (PKL-81) | 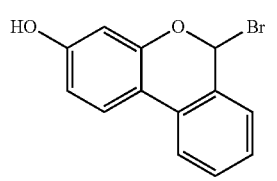 [SMILES: Oc1ccc2c(c1)OC(Br)c1ccccc1-2] |
| I-083 (PKL-83) | 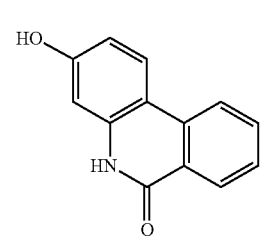 [SMILES: O=c1[nH]c2cc(O)ccc2c2ccccc12] |
| I-084 (PKL-84) | 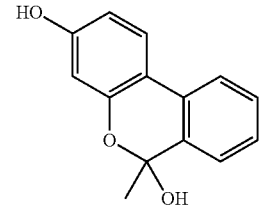 [SMILES: CC1(O)Oc2cc(O)ccc2-c2ccccc21] |
| I-085 (PKL-85) | 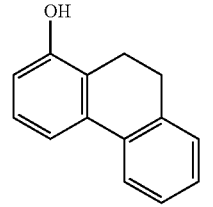 [SMILES: Oc1cccc2c1CCc1ccccc1-2] |
| I-086 (PKL-86) | 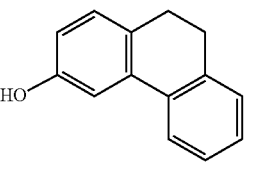 [SMILES: Oc1ccc2c(c1)-c1ccccc1CC2] |
| I-087 (PKL-87) | 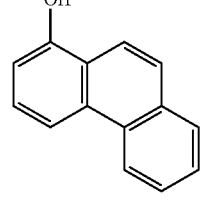 |

TABLE 1-continued

| Formula # (other identifiers) | Structure |
|---|---|
| I-088 (PKL-88) | 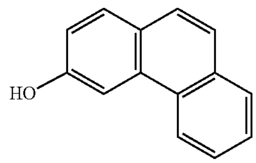 [SMILES: Oc1ccc2ccc3ccccc3c2c1] |
| I-089 (PKL-89) | 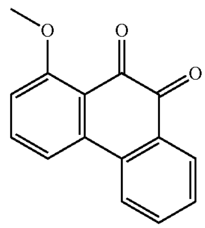 [SMILES: COc1cccc2c1C(=O)C(=O)c1ccccc1-2] |
| I-090 (PKL-90) | 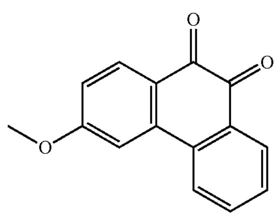 [SMILES: COc1ccc2c(c1)-c1ccccc1C(=O)C2=O] |
| I-091 (PKL-91) | 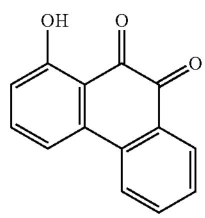 [SMILES: O=C1C(=O)c2c(O)cccc2-c2ccccc21] |
| I-092 (PKL-92) | 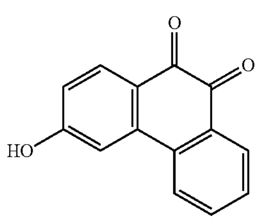 [SMILES: O=C1C(=O)c2ccc(O)cc2-c2ccccc21] |
| I-093 (PKL-93) | 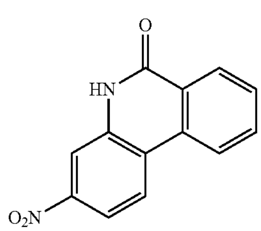 [SMILES: O=c1[nH]c2cc([N+](=O)[O-])ccc2c2ccccc12] |
| I-094 (PKL-94) | 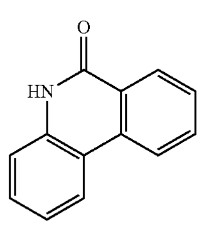 [SMILES: O=c1[nH]c2ccccc2c2ccccc12] |
| I-095 (PKL-95) | |
| I-096 (PKL-96) | |
| I-097 (PKL-97) | |
| I-098 (PKL-98) | |
| II-099 (PKL-99) | |
| II-100 (PKL-100) | |

TABLE 1-continued

| Formula # (other identifiers) | Structure |
|---|---|
| II-101 (PKL-101) | (structure) |
| II-102 (PKL-102) | (structure) |
| II-103 (IPKL-103) | (structure) |
| II-104 (PKL-104) | (structure) |
| II-105 (PKL-105) | (structure) |
| II-106 (PKL-106) | (structure) |
| II-107 (PKL-107) | (structure) |
| II-108 (PKL-108) | (structure) |
| II-109 (PKL-109) | (structure) |
| II-110 (PKL-110) | (structure) |
| II-111 (PKL-111) | (structure) |
| II-112 (PKL-112) | (structure) |

TABLE 1-continued

| Formula # (other identifiers) | Structure |
|---|---|
| II-113 (PKL-113) | 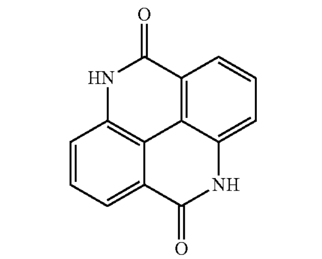 [SMILES: O=c1[nH]c2cccc3c(=O)[nH]c4cccc1c4c23] |
| II-114 (PKL-114) | 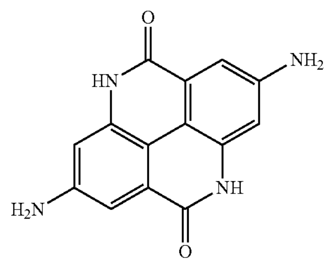 [SMILES: Nc1cc2[nH]c(=O)c3cc(N)cc4[nH]c(=O)c(c1)c2c43] |
| II-115 (PKL-115) | 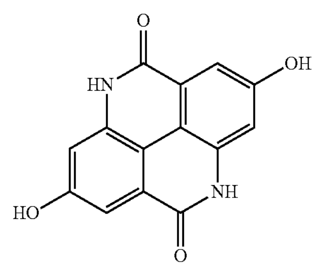 [SMILES: O=c1[nH]c2cc(O)cc3c(=O)[nH]c4cc(O)cc1c4c23] |
| II-116 (PKL-116) | 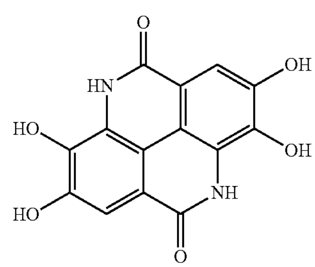 [SMILES: O=c1[nH]c2c(O)c(O)cc3c(=O)[nH]c4c(O)c(O)cc1c4c23] |
| II-117 (PKL-117) | 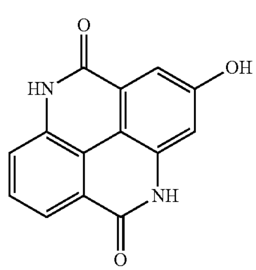 [SMILES: O=c1[nH]c2cc(O)cc3c(=O)[nH]c4cccc1c4c23] |
| II-118 (PKL-118) | |
| II-119 (PKL-119) | |
| II-120 (PKL-120) | |
| II-121 (PKL-121) | |
| II-122 (PKL-122) | |

TABLE 1-continued
| Formula # (other identifiers) | Structure |
|---|---|
| II-123 (PKL-123) | 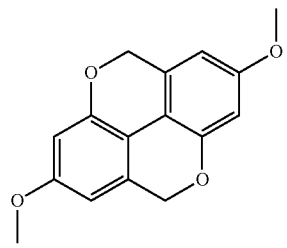 [SMILES: COc1cc2c3c(c1)OCc1cc(OC)cc(c1-3)OC2] |
| II-124 (PKL-124) | 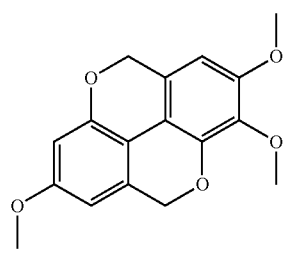 [SMILES: COc1cc2c3c(c1)OCc1cc(OC)c(OC)c(c1-3)OC2] |
| II-125 (PKL-125) | 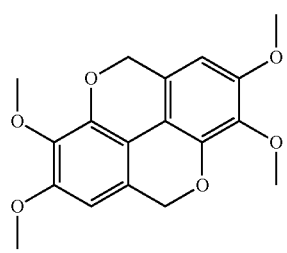 [SMILES: COc1cc2c3c(c1OC)OCc1cc(OC)c(OC)c(c1-3)OC2] |
| II-126 (PKL-126) | 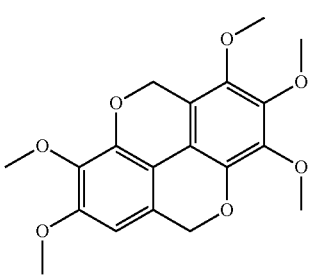 |
| II-127 (PKL-127) | 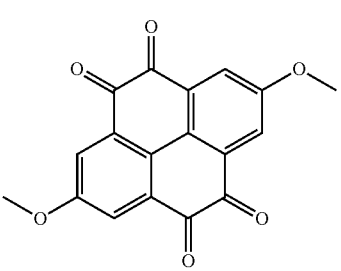 |
| II-128 (PKL-128) | 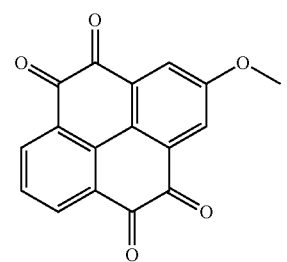 [SMILES: COc1cc2c3c(c1)c(=O)c(=O)c1cccc(c1-3)c(=O)c2=O] |
| II-129 (PKL-129) | 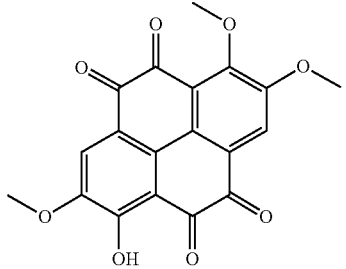 |
| II-130 (PKL-130) | 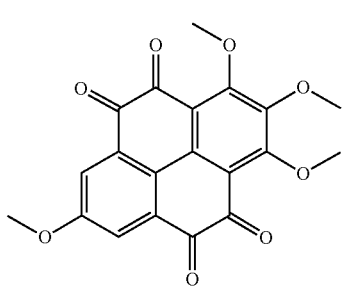 |
| II-131 (PKL-131) | 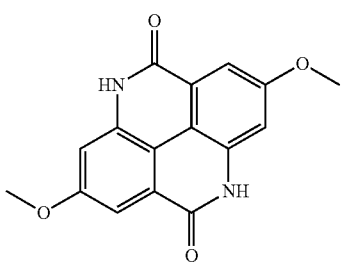 |
| II-132 (PKL-132) | 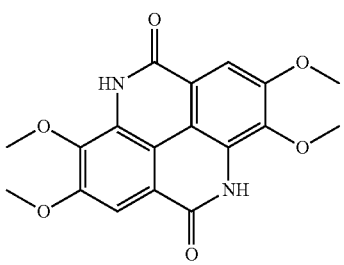 |
| II-133 (PKL-133) | 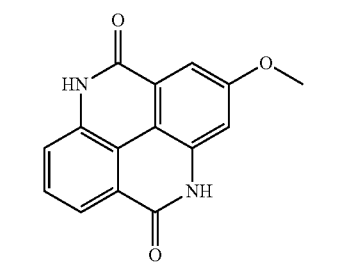 [SMILES: COc1cc2[nH]c(=O)c3cccc4[nH]c(=O)c(c1)c2c43] |
| II-134 (PKL-134) | 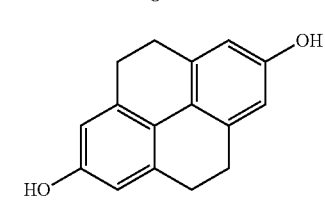 |

TABLE 1-continued
| Formula # (other identifiers) | Structure |
|---|---|
| II-135 (PKL-135) | 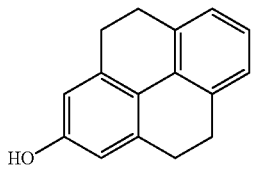 [SMILES: Oc1cc2c3c(c1)CCc1cccc(c1-3)CC2] |
| II-136 (PKL-136) | 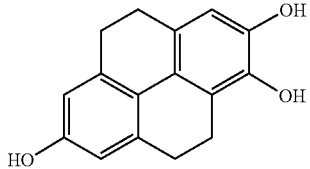 [SMILES: Oc1cc2c3c(c1)CCc1c(O)c(O)cc(c1-3)CC2] |
| II-137 (PKL-137) | 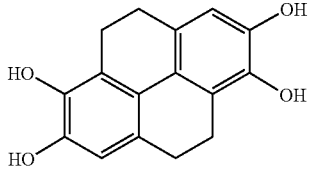 [SMILES: Oc1cc2c3c(c1O)CCc1cc(O)c(O)c(c1-3)CC2] |
| II-138 (PKL-138) | 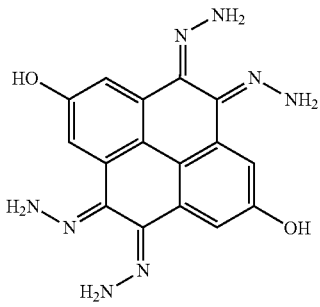 [SMILES: N/N=c1\c(=N\N)c2cc(O)cc3c2-c2c1cc(O)cc2c(=N\N)/c3=N\N] |
| II-139 (PKL-139) | 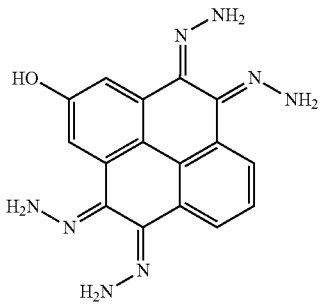 [SMILES: N/N=c1\c(=N\N)c2cccc3c2-c2c1cc(O)cc2c(=N\N)/c3=N\N] |
| II-140 (PKL-140) | 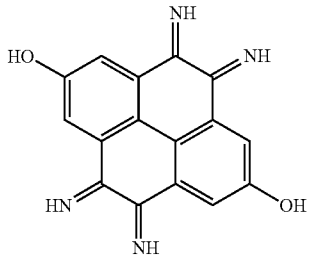 [SMILES: N=c1c(=N)c2cc(O)cc3c2-c2c1cc(O)cc2c(=N)c3=N] |
| II-141 (PKL-141) | 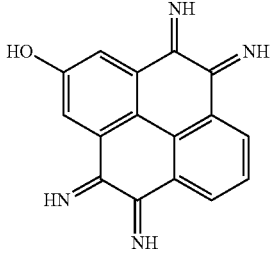 [SMILES: N=c1c(=N)c2cc(O)cc3c2-c2c1cccc2c(=N)c3=N] |
| II-142 (PKL-142) | 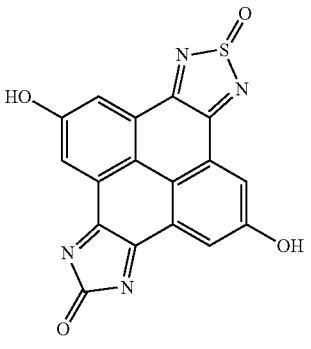 [SMILES: O=c1nc2c3cc(O)cc4c5c(c6cc(O)cc(c2n1)c6c43)=NS(=O)N=5] |
| II-143 (PKL-143) | 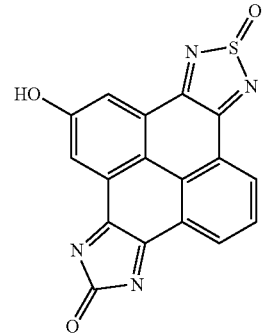 [SMILES: O=c1nc2c3cccc4c5c(c6cc(O)cc(c2n1)c6c43)=NS(=O)N=5] |
| II-144 (PKL-144) | 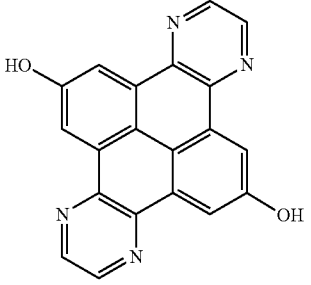 [SMILES: Oc1cc2c3nccnc3c3cc(O)cc4c5nccnc5c(c1)c2c34] |
| II-145 (PKL-145) | 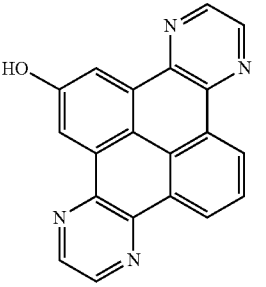 [SMILES: Oc1cc2c3nccnc3c3cccc4c5nccnc5c(c1)c2c34] |

TABLE 1-continued
| Formula # (other identifiers) | Structure |
|---|---|
| II-146 (PKL-146) | 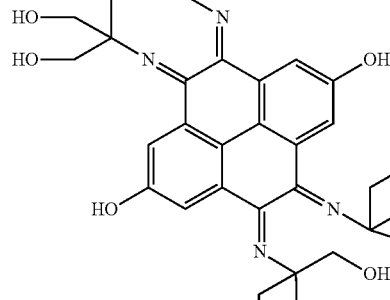 |
| II-147 (PKL-147) | 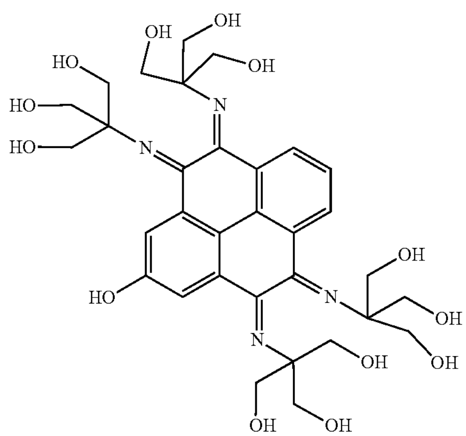 [SMILES: OCC(CO)(CO)N=c1/c(=N\C(CO)(CO)CO)c2cccc3c2-c2c1cc(O)cc2/c(=N/C(CO)(CO)CO)c3=NC(CO)(CO)CO] |
| II-148 (PKL-148) | 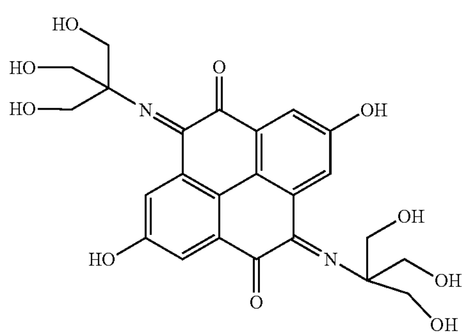 [SMILES: O=c1c(=NC(CO)(CO)CO)c2cc(O)cc3c2-c2c1cc(O)cc2c(=NC(CO)(CO)CO)c3=O] |
| II-149 (PKL-149) | 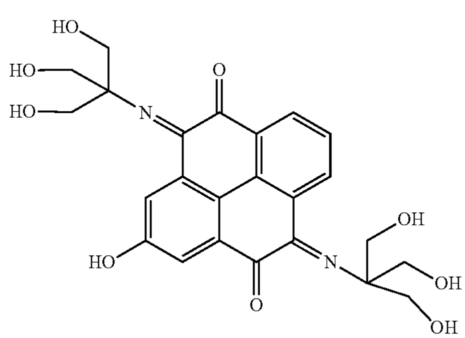 [SMILES: O=c1c(=NC(CO)(CO)CO)c2cccc3c2-c2c1cc(O)cc2c(=NC(CO)(CO)CO)c3=O] |
| II-150 (PKL-150) | 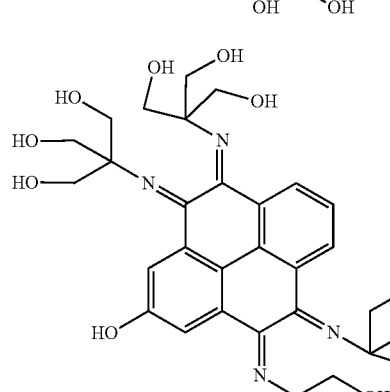 |
| II-151 (PKL-151) | |
| II-152 (PKL-152) | |

TABLE 1-continued

| Formula # (other identifiers) | Structure |
|---|---|
| II-153 (PKL-153) | 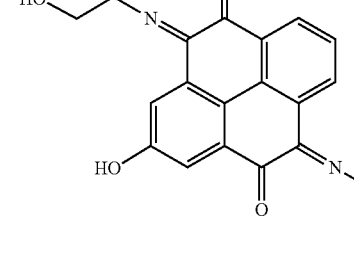 |
| II-154 (PKL-154) | 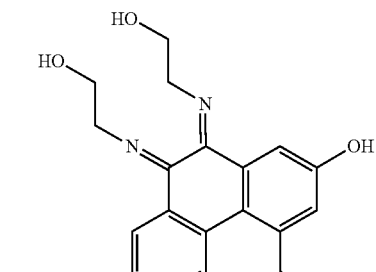 |
| II-155 (PKL-155) | 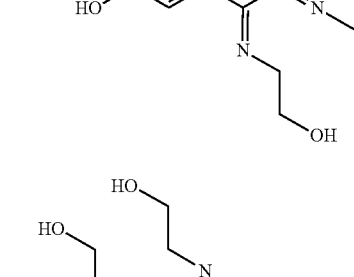 |
| II-156 (PKL-156) | 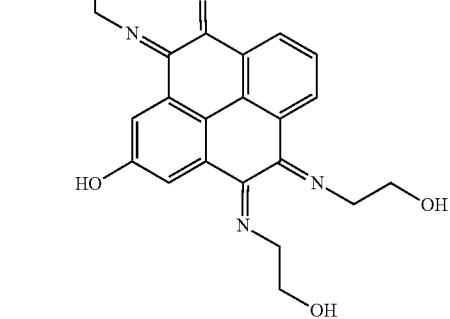 |
| II-157 (PKL-157) | 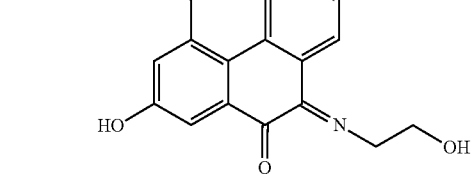 |
| III-031 (PKL-31) | 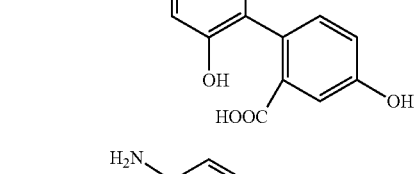 |
| III-035 (PKL-35) | 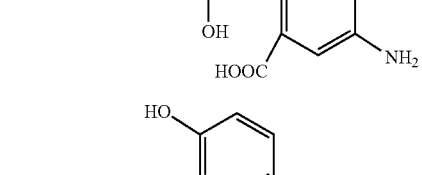 |
| III-082 (PKL-82) | 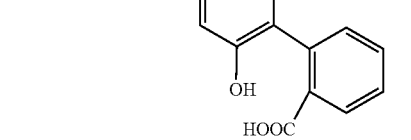 |

In some embodiments, one or more of compounds I-1, I-3, I-5, I-7, I-20, I-26, I-27, I-28, I-33, I-53, I-54, I-55, I-56, I-57, I-59, I-94, I-98, II-99, II-100, II-101, II-102, II-103, II-118, II-119, II-120, II-121, or II-122 are excluded from the compounds of the invention. In some embodiments, compounds I-1, I-3, I-5, I-7, I-20, I-26, I-27, I-28, I-33, I-53, I-54, I-55, I-56, I-57, I-59, I-94, I-98, II-99, II-100, II-101, II-102, II-103, II-118, II-119, II-120, II-121, and II-122 are excluded from the compounds of the invention.

In some embodiments, one or more of compounds I-1, I-2, I-3, I-5, I-7, I-20, I-26, I-27, I-28, I-33, I-53, I-54, I-55, I-56, I-57, I-59, I-94, I-98, II-99, II-100, II-101, II-102, II-103, II-118, II-119, II-120, II-121, or II-122 are excluded from the compounds of the invention. In some embodiments, compounds I-1, I-2, I-3, I-5, I-7, I-20, I-26, I-27, I-28, I-33, I-53, I-54, I-55, I-56, I-57, I-59, I-94, I-98, II-99, II-100, II-101, II-102, II-103, II-118, II-119, II-120, II-121, and II-122 are excluded from the compounds of the invention.

In some embodiments, one or more of compounds I-1, I-2, I-3, I-5, I-20, I-26, I-27, I-28, I-33, I-53, I-54, I-55, I-56, I-59, I-94, I-98, II-99, II-100, II-101, 11-102, II-103, II-118, II-119, II-120, II-121, or 11-122 are excluded from the compounds of the invention. In some embodiments, compounds I-1, I-2, I-3, I-5, I-20, I-26, I-27, I-28, I-33, I-53, I-54, I-55, I-56, I-59, I-94, I-98, II-99, II-100, II-101, II-103, II-118, II-119, II-120, II-121, and II-122 are excluded from the compounds of the invention.

In some embodiments, one or more of compounds I-20, I-26, I-27, I-28, I-33, I-53, I-54, I-55, I-98, II-99, II-100, II-101, II-102, II-103, II-118, II-119, II-120, II-121, or II-122 are excluded from the compounds of the invention. In some embodiments, compounds 1-20, I-26, I-27, I-28, I-33, I-53, I-54, I-55, I-98, II-99, II-100, II-101, II-102, II-103, II-118, II-119, II-120, II-121, and II-122 are excluded from the compounds of the invention.

In some embodiments, one or more of compounds I-1, I-2, I-3, I-5, I-7, 1-20, I-56, I-57, I-59, or I-94 are excluded from the compounds of the invention. In some embodiments, compounds I-1, I-2, I-3, I-5, I-7, I-20, I-56, I-57, I-59, and I-94 are excluded from the compounds of the invention.

In some embodiments, one or more of compounds I-1, I-2, I-3, I-5, I-20, I-56, I-59, or I-94 are excluded from the compounds of the invention. In some embodiments, compounds I-1, I-2, I-3, I-5, I-20, I-56, I-59, and I-94 are excluded from the compounds of the invention.

In some embodiments, one or more of compounds I-1, I-2, I-3, or I-5 are excluded from the compounds of the invention. In some embodiments, compounds I-1, I-2, I-3, and I-5 are excluded from the compounds of the invention.

In certain embodiments, compound I-1 is excluded from the compounds of the invention. In certain embodiments, compound I-2 is excluded from the compounds of the invention.

In some embodiments, the compounds of the invention comprise I-1, I-2, I-3, I-4, I-5, I-6, I-7, I-8, I-9, I-10, I-11, I-12, I-13 I-14, I-15, I-16, or I-17. In some embodiments, the compounds of the invention comprise I-1, I-2, I-3, I-4, I-5, I-15, I-16, or I-17.

In some embodiments, urolithin derivatives encompass one or more of Formula (I), Formula (IA), (II), or (III). In other embodiments, the compounds of Formula (I), Formula (IA), (II), or (III), or a combination thereof, encompass urolithin derivatives. In some embodiments, urolithin derivatives do not encompass one or more of Formula (I), Formula (IA), (II), or (III). In other embodiments, the compounds of Formula (I), Formula (IA), (II), or (III), or combinations thereof, do not encompass urolithin derivatives.

In some embodiments, the compounds of Formula (I), Formula (IA), (II), or (III) can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, simple derivatives of the compounds (e.g., ethers, esters, or amides) which have desirable retention and release characteristics but which are easily hydrolyzed by body pH, enzymes, or other suitable means, can be employed.

In some embodiments, the compounds of the invention having a chiral center and can exist in and be isolated in optically active and racemic forms. In other embodiments, compounds may exhibit polymorphism. Some embodiments of the present invention encompass any racemic, optically active, polymorphic, or stereoisomeric form, or mixtures thereof, of a compound described herein. The preparation of optically active forms can be accomplished by any suitable method, including but not limited to, resolution of the racemic form by recrystallization techniques, synthesis from optically-active starting materials, chiral synthesis, or chromatographic separation using a chiral stationary phase.

In some embodiments, the compounds of the invention (e.g., Formula (I), (IA), I-1, or I-2) can have an effect of (a) inhibiting Monoamino oxidase (MAO) enzyme activity, (b) inducing the expression of tight junction proteins (e.g., claudins family proteins (Cldn 1-27), Occludin, Zonula occludens (e.g., ZO-1, ZO-2), tight junction proteins (TJPs), junction-associated adhesion molecules (JAMs), or adherens junction proteins, such as vascular endothelial cadherins (VE-Cadherin)), (c) inducing the nuclear translocation and/or activation of AhR comprising, (d) inducing the nuclear translocation and/or activation of Nrf2, (e) inducing the expression of Cyp1A1 and/or Cyp1A2, or (f) increasing autophagy (e.g., mitophagy) in a cell (e.g., embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, or germ cells) or (g) a combination thereof.

Other Embodiments of Compounds—Urolithin Derivatives

"Urolithins" can generally be described as comprising two aromatic rings with a non-aromatic bridging ring containing an ester (i.e., the bridging ring of urolithins is a "cyclic ester"), in a fused, three-ring system.

As used herein, the term "urolithin derivative" refers to a compound having a structure derived from the structure of a urolithin and whose structure is sufficiently similar to a urolithin and based upon that similarity, would be expected by one skilled in the art to exhibit the same or similar activities and utilities as a urolithin, or to induce, as a precursor, the same or similar activities and utilities as a urolithin. In accordance with certain embodiments, urolithin derivatives can have a chemical group substitution of the urolithin cyclic ester. In some embodiments, the urolithin derivatives can have improved potency as compared to urolithin A, or improved stability at acidic pH and/or in presence of esterase and/or protease as compared to urolithin A (See FIG. 1A). The structure of Urolithin A is shown herein as PKL-01 (Table 1).

In various embodiments, the urolithin derivative has a cyclic ether in place of the urolithin cyclic ester. In some embodiments, the cyclic ether group comprises one or more substituents, such as (but not limited to) substituents independently selected from halo, amine, substituted amine (e.g., substituted with methyl, ethyl, or combinations thereof), hydroxyl, and a C5 or C6 heterocycle (e.g., heterocyclyl or heteroaryl), such as those having one or two heteroatoms independently selected from O, N, or S. In some embodiments, the urolithin derivative has, in place of the urolithin cyclic ester, a carbocycle (e.g., cycloalkyl or aryl) having adjacent carbonyl groups. In some embodiments, the urolithin derivative has, in place of the urolithin cyclic ester, a carbocyclic group (e.g., cycloalkyl or aryl), which optionally has one or more double bonds and is optionally aromatic, and optionally substituted (e.g., with any disclosed herein). In some embodiments, the carbocyclic group (e.g., cycloalkyl or aryl) has one or more substituents (e.g., with any disclosed herein). Exemplary substituents include those independently selected from ketone, optionally substituted imine, optionally substituted amine (e.g., substituted with methyl, ethyl, or combinations thereof), halo, and hydroxyl. In some embodiments, the urolithin derivative has, in place of the urolithin cyclic ester, a cyclic amide. In some embodiments, the urolithin derivative has, in place of the cyclic ester bridge, a non-cyclic bridge. In these embodiments, the ester group may be replaced with carboxylic acid and hydroxyl functional groups (in a non-cyclic structure). In other embodiments, the aromatic groups (e.g., aryl or heteroaryl) (flanking the bridging ring or group) may have one or more substituents. In some embodiments, the aromatic groups (e.g., aryl or heteroaryl) are optionally substituted (e.g., with any disclosed herein) phenyl groups. Exemplary substituents for the aromatic groups are independently selected from hydroxyl, alkoxy, halo, amine, a 5 or 6 membered carbocyclic (e.g., cycloalkyl or aryl) or heterocyclic (e.g., heterocyclyl or heteroaryl) ring, nitro, nitrile, alkyl, alkyl ether, and haloalkyl. In some embodiments, at least one of the aromatic rings is heterocyclic (e.g., heterocyclyl or heteroaryl). The heteroatoms of the heterocyclic ring (e.g., heterocyclyl or heteroaryl) may be independently selected from N, O, and S. In some embodiments, substituents of each aromatic ring may together form a second bridging ring, which optionally has the same or different structure of the first bridging ring.

In some embodiments, one or more of compounds I-1, I-3, I-5, I-7, I-20, I-26, I-27, I-28, I-33, I-53, I-54, I-55, I-56, I-57, I-59, I-94, I-98, II-99, II-100, II-101, II-102, II-103, II-118, II-119, II-120, II-121, or II-122 are excluded from the compounds of the invention. In some embodiments, compounds I-1, I-3, I-5, I-7, I-20, I-26, I-27, I-28, I-33, I-53, I-54, I-55, I-56, I-57, I-59, I-94, I-98, II-99, II-100, II-101, II-102, II-103, II-118, II-119, II-120, II-121, and II-122 are excluded from the compounds of the invention.

In some embodiments, one or more of compounds I-1, I-2, I-3, I-5, I-7, I-20, I-26, I-27, I-28, I-33, I-53, I-54, I-55, I-56, I-57, I-59, I-94, I-98, II-99, II-100, 11-101, II-102, II-103, II-118, II-119, II-120, II-121, or II-122 are excluded from the compounds of the invention. In some embodiments, compounds I-1, I-2, I-3, I-5, I-7, I-20, I-26, I-27, I-28, I-33, I-53, I-54, I-55, I-56, I-57, I-59, I-94, I-98, II-99, II-100, II-101, II-102, II-103, II-118, II-119, II-120, II-121, and II-122 are excluded from the compounds of the invention.

In some embodiments, one or more of compounds I-1, I-2, I-3, I-5, I-20, I-26, I-27, I-28, I-33, I-53, I-54, I-55, I-56, I-59, I-94, I-98, II-99, II-100, II-101, 11-102, II-103, II-118, II-119, II-120, II-121, or II-122 are excluded from the compounds of the invention. In some embodiments, compounds I-1, I-2, I-3, I-5, I-20, I-26, I-27, I-28, I-33, I-53, I-54, I-55, I-56, I-59, I-94, I-98, II-99, II-100, II-101, II-102, II-103, II-118, II-119, II-120, II-121, and II-122 are excluded from the compounds of the invention.

In some embodiments, one or more of compounds 1-20, I-26, I-27, I-28, I-33, I-53, I-54, I-55, I-98, II-99, II-100, II-101, II-102, II-103, II-118, II-119, II-120, II-121, or II-122 are excluded from the compounds of the invention. In some embodiments, compounds 1-20, I-26, I-27, I-28, I-33, I-53, I-54, I-55, I-98, II-99, II-100, II-101, II-102, II-103, II-118, II-119, II-120, II-121, and II-122 are excluded from the compounds of the invention.

In some embodiments, one or more of compounds I-1, I-2, I-3, I-5, I-7, I-20, I-56, I-57, I-59, or I-94 are excluded from the compounds of the invention. In some embodiments, compounds I-1, I-2, I-3, I-5, I-7, I-20, I-56, I-57, I-59, and I-94 are excluded from the compounds of the invention.

In some embodiments, one or more of compounds I-1, I-2, I-3, I-5, I-20, I-56, I-59, or I-94 are excluded from the compounds of the invention. In some embodiments, compounds I-1, I-2, I-3, I-5, I-20, I-56, I-59, and I-94 are excluded from the compounds of the invention.

In some embodiments, one or more of compounds I-1, I-2, I-3, or I-5 are excluded from the compounds of the invention. In some embodiments, compounds I-1, I-2, I-3, and I-5 are excluded from the compounds of the invention.

In certain embodiments, compound I-1 is excluded from the compounds of the invention. In certain embodiments, compound I-2 is excluded from the compounds of the invention.

In some embodiments, the compounds of the invention comprise I-1, I-2, I-3, I-4, I-5, I-6, I-7, I-8, I-9, I-10, I-11, I-12, I-13 I-14, I-15, I-16, or I-17. In some embodiments, the compounds of the invention comprise I-1, I-2, I-3, I-4, I-5, I-15, I-16, or I-17.

In some embodiments, urolithin derivatives encompass one or more of Formula (I), Formula (IA), (II), or (III). In other embodiments, the compounds of Formula (I), Formula (IA), (II), or (III), or a combination thereof, encompass urolithin derivatives. In some embodiments, urolithin derivatives do not encompass one or more of Formula (I), Formula (IA), (II), or (III). In other embodiments, the compounds of Formula (I), Formula (IA), (II), or (III), or combinations thereof, do not encompass urolithin derivatives.

In some embodiments, the compounds of Formula (I), Formula (IA), (II), or (III), or the urolithin derivatives can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, simple derivatives of the compounds (e.g., ethers, esters, or amides) which have desirable retention and release characteristics but which are easily hydrolyzed by body pH, enzymes, or other suitable means, can be employed.

In some embodiments, the compounds of the invention having a chiral center and can exist in and be isolated in optically active and racemic forms. In other embodiments, compounds may exhibit polymorphism. Some embodiments of the present invention encompass any racemic, optically active, polymorphic, or stereoisomeric form, or mixtures thereof, of a compound described herein. The preparation of optically active forms can be accomplished by any suitable method, including but not limited to, resolution of the racemic form by recrystallization techniques, synthesis from optically-active starting materials, chiral synthesis, or chromatographic separation using a chiral stationary phase.

In some embodiments, the compounds of the invention (e.g., Formula (I), (IA), I-1, or I-2, or urolithin derivative) can have an effect of (a) inhibiting Monoamino oxidase (MAO) enzyme activity, (b) inducing the expression of tight junction proteins (e.g., claudins family proteins (Cldn 1-27), Occludin, Zonula occludens (e.g., ZO-1, ZO-2), tight junction proteins (TJPs), junction-associated adhesion molecules (JAMs), or adherens junction proteins, such as vascular endothelial cadherins (VE-Cadherin)), (c) inducing the nuclear translocation and/or activation of AhR comprising, (d) inducing the nuclear translocation and/or activation of Nrf2, (e) inducing the expression of Cyp1A1 and/or Cyp1A2, or (f) increasing autophagy (e.g., mitophagy) in a cell (e.g., embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, or germ cells) or (g) a combination thereof.

Compositions Including Pharmaceutical Compositions

In certain embodiments, one or more compounds of the invention (e.g., Formula (I) or urolithin derivatives) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

In some embodiments, one or more compounds of the invention (e.g., Formula (I) or urolithin derivatives) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more compounds of the invention (e.g., Formula (I) or urolithin derivatives). In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

"Therapeutically effective amount" means an amount effective to achieve a desired and/or beneficial effect. An effective amount can be administered in one or more administrations. For some purposes of this invention, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any suitable method, such as measurement of tumor size.

In some embodiments, one or more compounds of the invention (e.g., Formula (I) or urolithin derivatives) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or *arachis* oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., one or more compounds of the invention such as Formula (I)) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Other embodiments of the invention can include methods of administering or treating an organism, which can involve treatment with an amount of at least one compound of the invention (e.g., Formula (I) or urolithin derivatives) that is effective to treat the disease, condition, or disorder that the organism has, or is suspected of having, or is susceptible to, or to bring about a desired physiological effect. In some embodiments, the composition or pharmaceutical composition comprises at least one compound of the invention (e.g., Formula (I) or urolithin derivatives) which can be administered to an animal (e.g., mammals, primates, monkeys, or humans) in an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight or about 6.5 mg/kg human body weight. In some instances, some animals (e.g., mammals, mice, rabbits, feline, porcine, or canine) can be administered a dosage of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention (e.g., Formula (I) or urolithin derivatives) can be administered in combination with one or more other therapeutic agents for a given disease, condition, or disorder.

In some embodiments, the compositions can include a unit dose of one or more compounds of the invention (e.g., Formula (I) or urolithin derivatives) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

In certain embodiments, the composition or pharmaceutical composition further comprises 5-florouracil (e.g., for cancer treatment or chemoresistant cancer treatment), at any of the amounts or dosages disclosed herein.

Administration Routes, Treatments of Disease, and Other Uses

The compounds of the invention (e.g., Formula (I), (IA), I-1, or I-2, or urolithin derivatives) can be administered to animals by any number of suitable administration routes or formulations. The compounds of the invention (e.g., Formula (I), (IA), I-1, or I-2, or urolithin derivatives) can also be used to treat animals for a variety of diseases. Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

The route of administration of the compounds of the invention (e.g., Formula (I), (IA), I-1, or I-2, or urolithin derivatives) can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, subcutaneous administration, topical administration, intradermal administration, oral administration, sublingual administration, intranasal administration, or intramuscular administration. The choice of administration route can depend on the compound identity (e.g., the physical and chemical properties of the compound) as well as the age and weight of the animal, the particular disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis), and the severity of the disease. Of course, combinations of administration routes can be administered, as desired.

Some embodiments of the invention include a method for providing a subject with a composition comprising one or more compounds of the invention (e.g., Formula (I), (IA), I-1, or I-2, or urolithin derivatives) described herein (e.g., a pharmaceutical composition) which comprises one or more administrations of one or more such compositions; the compositions may be the same or different if there is more than one administration.

Diseases that can be treated in an animal (e.g., mammals, porcine, canine, avian (e.g., chicken), bovine, feline, primates, rodents, monkeys, rabbits, mice, rats, and humans) using a compound of the invention (e.g., Formula (I), (IA), I-1, or I-2, or urolithin derivatives) include, but are not limited to alcoholic liver disease (ALD), non-alcoholic steatohepatitis (NASH), intestinal permeability (e.g., leaky gut such as metal induced gut leakiness, stress induced gut leakiness, or radiation induced gut permeability), colitis, local inflammation (e.g., in brain, mouth, esophagus, stomach, and small intestine), systemic inflammation, inflammatory bowel disease (e.g., ulcerative colitis or Crohn's disease), infection-induced inflammatory disease (e.g., sepsis or sepsis-induced kidney injury or sepsis-induced lung injury), neuroinflammatory disorders, Alzheimer's Disease, Parkinson's Disease, anxiety, depression, metabolic stress, cardiovascular disease, sarcopenia, muscle degenerative disease, Duchenne muscular dystrophy, nonalcoholic fatty liver disease, drug-induced liver injury, alpha-antitrypsin deficiency, ischemia/reperfusion injury, obesity, metabolic syndrome, type II diabetes mellitus, hyperlipidemia, osteoarthritis, neurodegenerative disease, amyotrophic lateral sclerosis (ALS), cancer (e.g., cancerous tumors, breast cancer or colon cancer), cognitive disorder, stress, mood disorder, or fibrosis. In some embodiments, diseases that can be treated include, but are not limited to alcoholic liver disease (ALD), non-alcoholic steatohepatitis (NASH), intestinal permeability (e.g., leaky gut such as metal induced gut leakiness, stress induced gut leakiness, or radiation induced gut permeability), colitis, local inflammation (e.g., in brain, mouth, esophagus, stomach, and small intestine), systemic inflammation, inflammatory bowel disease (e.g., ulcerative colitis or Crohn's disease), infection-induced inflammatory disease (e.g., sepsis or sepsis-induced kidney injury or sepsis-induced lung injury), neuroinflammatory disorders, Alzheimer's Disease, Parkinson's Disease, cancer (e.g., cancerous tumors, breast cancer or colon cancer), or fibrosis. In some embodiments, diseases that can be treated include, but are not limited to alcoholic liver disease (ALD), non-alcoholic steatohepatitis (NASH), colitis, intestinal permeability, leaky gut, metal induced gut leakiness, stress induced gut leakiness, radiation induced gut permeability, local inflammation, systemic inflammation, inflammatory bowel disease, ulcerative colitis, Crohn's disease, infection-induced inflammatory disease, sepsis, sepsis-induced kidney injury, sepsis-induced lung injury, scleroderma, vasculitis, drug-induced vasculitis, neuroinflammatory disorders, Alzheimer's Disease, Parkinson's Disease, cancer (e.g., cancerous tumors, breast cancer or colon cancer), or fibrosis. Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or cancer, or by having a cancerous tumor).

In some embodiments, cancers that can be treated in an animal (e.g., mammals, porcine, canine, avian (e.g., chicken), bovine, feline, primates, rodents, monkeys, rabbits, mice, rats, and humans) using a compound of the invention (e.g., Formula (I), (IA), I-1, or I-2, or urolithin derivatives) include, but are not limited to, pancreatic cancer (e.g., pancreatic ductal adenocarcinoma), lung cancer, liver cancer, colorectal cancer (e.g., colon cancer or rectal cancer), melanoma (e.g., cutaneous malignant melanoma, melanoma tumorigenesis), bladder cancer, prostate cancer, malignant nerve sheath tumors, multiple myeloma, breast cancer, squamous cell carcinoma (e.g., head and neck squamous cell carcinoma), lymphoma, leukemia, bone marrow cancer, non-Hodgkin lymphoma (e.g., diffuse large B-cell lymphoma), glioblastoma multiforme, endometrial cancer, kidney cancer, basal cell carcinoma, thyroid cancer, neuroblastoma, ovarian cancer, renal cell carcinoma, hepatocellular carcinoma, colon cancer, chronic lymphocytic leukemia (CLL), acute lymphoblastic leukemia, rhabdomyosarcoma, meningioma, gastric cancer, Glioma, oral cancer, nasopharyngeal carcinoma, rectal cancer, stomach cancer, uterine cancer, medulloblastoma, cancers that can result in metastasis, cancers resulting from metastasis, or cancerous tumors thereof. In some embodiments, cancers that can be treated include, but are not limited to, breast cancer, colon cancer or cancerous tumors thereof. Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or cancer, or by having a cancerous tumor).

In some embodiments, diseases that can be treated include, but are not limited to vasculitis, drug-induced vasculitis, scleroderma, internal vascular bleeding, drug-induced internal bleeding, atopic dermatitis, perfusion-related injury, perfusion related inflammation, diabetic retinopathy, celiac disease, Non-Alcoholic SteatoHepatitis (NASH), Alcoholic SteatoHepatitis (ASH), metabolic stress, cardiovascular disease, sarcopenia, muscle degenerative disease, Duchenne muscular dystrophy, alcoholic liver disease, nonalcoholic fatty liver disease, drug-induced liver injury, chronic kidney disease, alpha-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, neuroinflammatory disorder, Alzheimer's disease, Parkinson's disease, multiple sclerosis, myotrophic lateral sclerosis (ALS), pulmonary fibrosis, chronic obstructive pulmonary disease (COPD), acute lung injury, blood transfusion related acute lung injury, acute respiratory distress syndrome, asthma, cancer, cognitive disorder, stress, or mood disorder.

In some embodiments, diseases that can be treated in an animal (e.g., mammals, porcine, canine, avian (e.g., chicken), bovine, feline, primates, rodents, monkeys, rabbits, mice, rats, and humans) using a compound of the invention (e.g., Formula (I), (IA), I-1, or I-2, or urolithin derivatives) include, but are not limited to diseases that can be treated by (a) enhancing gut barrier integrity, (b) enhancing vascular barrier integrity, (c) enhancing airway barrier integrity in lungs, (d) improving or increasing autophagy in an animal (e.g., human) in a tissue or organ (e.g., in a tissue or organ of the animal selected from the group consisting of brain, eye, skin, bone, marrow, cartilage, heart, lung, stomach, intestine, liver, pancreas, kidney, muscle, and fat) or cell (e.g., adult stem cells, differentiated cells, blood cells, hematopoietic cells, endothelial cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells), (e) inhibiting Monoamino oxidase (MAO such as MAO-A or MAO-B) enzyme activity, (f) inducing the expression of tight junction proteins (e.g., claudins family proteins (Cldn 1-27), Occludin, Zonula occludens (e.g., ZO-1, ZO-2), tight junction proteins (TJPs), junction-associated adhesion molecules (JAMs), or adherens junction proteins, such as vascular endothelial cadherins (VE-Cadherin)), (g) inducing the nuclear translocation and/or activation of AhR, (h) inducing the nuclear translocation and/or activation of Nrf2, (i) inducing the expression of Cyp1A1 and/or Cyp1A2, (j) increasing autophagy (e.g., mitophagy) in a cell (e.g., embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, or germ cells), or (k) a combination thereof.

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal.

As related to treating disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis), treating can include but is not limited to prophylactic treatment and therapeutic treatment. As such, treatment can include, but is not limited to: preventing disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis); reducing the risk of disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis); ameliorating or relieving symptoms of disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis); eliciting a bodily response against disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis); inhibiting the development or progression of disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis); inhibiting or preventing the onset of symptoms associated with disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis); reducing the severity of disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis); causing a regression of disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis) or one or more of the symptoms associated with disease (e.g., a decrease in inflammation); causing remission of the disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis); or preventing relapse of the disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis). In some embodiments, treating does not include prophylactic treatment of disease (e.g., preventing or ameliorating future disease).

Treatment of an animal can occur using any suitable administration method (such as those disclosed herein) and using any suitable amount of a compound of the invention (e.g., Formula (I), (IA), I-1, or I-2, or urolithin derivatives). In some embodiments, methods of treatment comprise treating an animal for a disease (e.g., alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis). Some embodiments of the invention include a method for treating a subject (e.g., an animal such as a human or primate) with a composition comprising a compound of the invention (e.g., Formula (I), (IA), I-1, or I-2, or urolithin derivatives) (e.g., a pharmaceutical composition) which comprises one or more administrations of one or more such compositions; the compositions may be the same or different if there is more than one administration.

In some embodiments, the method of treatment includes administering an effective amount of a composition comprising a compound of the invention (e.g., Formula (I), (IA), I-1, or I-2, or urolithin derivatives). As used herein, the term "effective amount" refers to a dosage or a series of dosages sufficient to affect treatment (e.g., to treat disease, such as but not limited to alcoholic liver disease (ALD), intestinal permeability (e.g., leaky gut), inflammation (e.g., local or systemic), inflammatory bowel disease, ulcerative colitis, Crohn's disease, sepsis, Alzheimer's Disease, Parkinson's Disease, cancer (e.g., cancerous tumors, breast cancer or colon cancer), or fibrosis) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one compound of the invention (e.g., Formula (I) such as but not limited to compounds I-1 or I-2, or urolithin derivatives) (which can be administered to an animal such as mammals, primates, monkeys or humans) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some embodiments, the dosage can be about 0.5 mg/kg human body weight or about 6.5 mg/kg human body weight. In some instances, an effective amount of at least one compound of the invention (e.g., Formula (I) such as but not limited to compounds I-1 or I-2, or urolithin derivatives) (which can be administered to an animal such as mammals, rodents, mice, rabbits, feline, porcine, or canine) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, an effective amount of at least one compound of the invention (e.g., Formula (I) such as but not limited to compounds I-1 or I-2, or urolithin derivatives) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In regard to some conditions, the dosage can be about 20 mg/kg human body weight or about 100 mg/kg human body weight. In some instances, an effective amount of at least one compound of the invention (e.g., Formula (I) such as but not limited to compounds I-1 or I-2, or urolithin derivatives) (which can be administered to an animal such as mammals, rodents, mice, rabbits, feline, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg.

"Therapeutically effective amount" means an amount effective to achieve a desired and/or beneficial effect (e.g., decreasing inflammation). A therapeutically effective amount can be administered in one or more administrations. For some purposes of this invention, a therapeutically effective amount is an amount appropriate to treat an indication (e.g., to treat disease). By treating an indication is meant achieving any desirable effect, such as one or more of palliate, ameliorate, stabilize, reverse, slow, or delay disease progression, increase the quality of life, or to prolong life. Such achievement can be measured by any suitable method, such as but not limited to extent of inflammation.

In some embodiments, the treatments can also include one or more of surgical intervention, chemotherapy, radiation therapy, hormone therapies, immunotherapy, and adjuvant systematic therapies. Adjuvants may include but are not limited to chemotherapy (e.g., temozolomide), radiation therapy, antiangiogenic therapy (e.g., bevacizumab), and hormone therapies, such as administration of LHRH agonists; antiestrogens, such as tamoxifen; high-dose progestogens; aromatase inhibitors; and/or adrenalectomy. Chemotherapy can be used as a single-agent or as a combination with known or new therapies.

In some embodiments, the treatments disclosed herein can include use of other drugs (e.g., antibiotics or 5-florouracil (e.g., for cancer treatment or chemoresistant cancer treatment)) or therapies for treating disease. For example, a compound of the invention (e.g., Formula (I), (IA), I-1, or I-2, or urolithin derivatives) can be combined with 5-florouracil to treat cancer (e.g., colon, breast cancer tumors, or chemoresistant). For example, antibiotics can be used to treat infections and can be combined with a compound of the invention to treat disease (e.g., infections associated with inflammation). In other embodiments, intravenous immunoglobulin (IVIG) therapy can be used as part of the treatment regime (i.e., in addition to administration of the compound(s) of the invention).

In certain embodiments, treatment can result in (a) enhancing gut barrier integrity, (b) enhancing vascular barrier integrity, (c) enhancing airway barrier integrity in lungs, (d) improving or increasing autophagy in an animal (e.g., human) in a tissue or organ (e.g., in a tissue or organ of the animal selected from the group consisting of brain, eye, skin, bone, marrow, cartilage, heart, lung, stomach, intestine, liver, pancreas, kidney, muscle, and fat) or cell (e.g., adult stem cells, differentiated cells, blood cells, hematopoietic cells, endothelial cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells), (e) inhibiting Monoamino oxidase (MAO such as MAO-A or MAO-B) enzyme activity, (f) inducing the expression of tight junction proteins (e.g., claudins family proteins (Cldn 1-27), Occludin, Zonula occludens (e.g., ZO-1, ZO-2), tight junction proteins (TJPs), junction-associated adhesion molecules (JAMs), or adherens junction proteins, such as vascular endothelial cadherins (VE-Cadherin)), (g) inducing the nuclear translocation and/or activation of AhR, (h) inducing the nuclear translocation and/or activation of Nrf2, (i) inducing the expression of Cyp1A1 and/or Cyp1A2, (j) increasing autophagy (e.g., mitophagy) in a cell (e.g., embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, or germ cells), or (k) a combination thereof.

Methods for Preparing Compounds of the Invention

Some embodiments of the present invention include methods for the preparation of compounds of Formula (I) (e.g., Formula (IA) or urolithin derivatives). The compounds of Formula (I) can be prepared using any suitable method or they can be purchased, if available. In certain embodiments, a compound of Formula (I) (e.g., Formula (IA) or urolithin derivatives) can be prepared comprising the step of reacting a compound of Formula (V) with a compound of Formula (VI) to result in Formula (VII), which is then made into Formula (I) (e.g., Formula (IA) or urolithin derivatives) (e.g., using one or more synthetic steps).

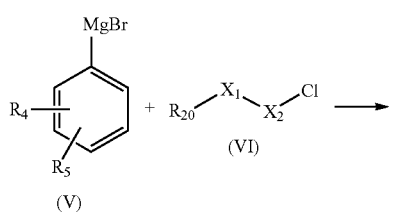

(V) + (VI)

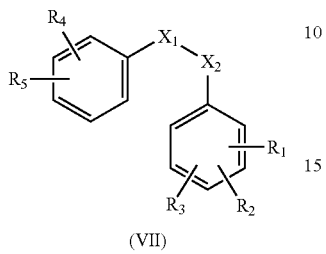

(VII)

In certain embodiments, Formula (V) can be

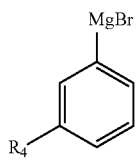

In some embodiments $R_{20}$ can be halogen (e.g., F, Cl, Br, or I) or

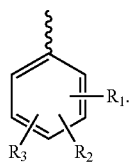

In other embodiments, $R_{20}$ can be Cl or

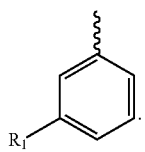

In certain embodiments, $R_1$, $R_2$, $R_3$, $R_4$, and $R_5$ are the same as those disclosed herein. In other embodiments, $X_1$ and $X_2$ are the same as those disclosed herein. Formula (V) can be prepared using any suitable method or can be purchased if available. Formula (VI) can be prepared using any suitable method or can be purchased if available.

In some embodiments, Formula (V) can be reacted with Formula (VI) under the following conditions: Formula (V) can be in a mixture comprising a solvent (e.g., THF), copper bromide and lithium bromide. The mixture can be cooled (e.g., using a dry ice acetone mixture) to a certain temperature (e.g., about −78° C.) for a certain amount of time (e.g., about 2 hours). Formula (VI) can be added (e.g., slowly) to the cooled mixture. The mixture can be stirred and/or allowed to reach room temperature (e.g., overnight). The mixture can then be cooled to 0° C., and optionally quenched (e.g., with aqueous ammonium chloride). Formula (VII) can then optionally be recovered (e.g., as disclosed herein).

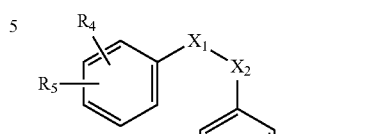

(VII)

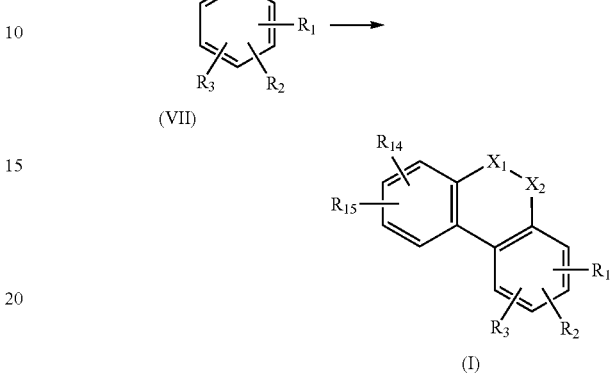

(I)

Formula (VII) can be prepared using any suitable method (e.g., see above) or can be purchased if available.

In some embodiments, Formula (VII) can be in a mixture comprising a solvent (e.g., dichloromethane). The mixture can be cooled (e.g., to about 0° C.). Ti(IV)chloride and/or molybdenum(V)chloride can then be added (e.g., slowly). The mixture can then be allowed to stir at room temperature (e.g., overnight). The mixture can then be cooled to 0° C., and optionally quenched (e.g., slowly with methanol). Formula (I) (e.g., Formula (IA)) can then optionally be recovered (e.g., as disclosed herein).

In some embodiments, Formula (I) (e.g., Formula (IA)) can be further reacted to change the identity of one or more of $R_1$, $R_2$, $R_3$, $R_4$, $R_5$, $X_1$ or $X_2$. Such further reactions can include but are not limited to one or more of: (a) reacting with aluminum chloride (e.g., anhydrous) or (b) reacting with acetic acid and ethanolamine (e.g., refluxed overnight at 110° C.).

In some embodiments, Formula (I) (e.g., Formula (IA)) (or any other formula recited above) can be recovered. Recovery can occur using any suitable method including but not limited to HPLC (e.g., reverse phase), LC, precipitation, filtration, centrifugation, column chromatography (e.g., size exclusion chromatography or ion exchange chromatography), use of silica gel, or combinations thereof.

In some embodiments, a method for the preparation of a compound of Formula (I) (e.g., Formula (IA)) can comprise one or more of the above-mentioned steps. In certain embodiments, a method for preparing a compound of Formula (I) (e.g., Formula (IA)) comprises (a) reacting a compound of Formula (V) with a compound of Formula (VI) to result in a mixture comprising a compound of Formula (VII);

(b) reacting a compound of Formula (VII) with a suitable compound (e.g., Ti(IV)chloride and/or molybdenum (V)chloride) to result in a mixture comprising a compound of Formula (I) (e.g., Formula (IA));

(c) optionally further reacting a compound of Formula (I) (e.g., Formula (IA)) to result in a different compound of Formula (I) (e.g., Formula (IA)) so that the identity of one or more of $R_1$, $R_2$, $R_3$, $R_4$, $R_5$, $X_1$ or $X_2$ is changed by the further reacting; and;

(d) recovering Formula (I) (e.g., Formula (IA)).

Additional Embodiments—A

1. A urolithin derivative having a chemical group substitution of the urolithin cyclic ester resulting in improved potency of the derivative as compared to urolithin A, or improved stability of the derivative at acidic pH and/or in presence of esterase and/or protease as compared to urolithin A.

2. The urolithin derivative of embodiment 1, wherein the urolithin cyclic ester is replaced with a cyclic ether.

3. The urolithin derivative of embodiment 2, wherein the urolithin cyclic ether comprises one or more substituents.

4. The urolithin derivative of embodiment 3, wherein the cyclic ether substituents are independently selected from halo, amine, substituted amine, hydroxyl, and a C5 or C6 heterocycle having one or two heteroatoms independently selected from O, N, or S.

5. The urolithin derivative of embodiment 1, wherein the urolithin cyclic ester is replaced with a carbocycle having adjacent carbonyl groups.

6. The urolithin derivative of embodiment 1, wherein the urolithin cyclic ester is replaced with a cyclic alkenyl group, which is optionally aromatic, and optionally substituted.

7. The urolithin derivative of embodiment 6, wherein the cyclic alkenyl group has one or more substituents.

8. The urolithin derivative of embodiment 7, wherein the cyclic alkenyl group substituents are independently selected from ketone, optionally substituted imine, optionally substituted amine, halo, and hydroxyl.

9. The urolithin derivative of embodiment 1, wherein the urolithin cyclic ester is replaced with a cyclic amide.

10. The urolithin derivative of embodiment 1, wherein the urolithin cyclic ester is replaced with a non-cyclic bridge.

11. The urolithin derivative of any one of embodiments 1 to 10, wherein the urolithin aromatic groups have one or more substituents.

12. The urolithin derivative of embodiment 11, wherein the aromatic groups are phenyl groups which are optionally substituted.

13. The urolithin derivative of embodiment 11 or 12, wherein the one or more aromatic substituents are independently selected from hydroxyl, alkoxy, halo, amine, a 5 or 6 membered carbocyclic or heterocyclic ring, nitro, nitrile, alkyl, alkyl ether, and haloalkyl.

14. The urolithin derivative of any one of embodiments 1 to 13, wherein one or more urolithin aromatic rings are heterocyclic.

15. The urolithin derivative of embodiment 14, wherein the heteroatoms of the heterocyclic ring are independently selected from N, O, and S.

16. The urolithin derivative of any one of embodiments 1 to 15, wherein substituents of each aromatic ring together form a second bridging ring.

17. The urolithin derivative of embodiment 16, wherein the second bridging ring is identical in structure to a first bridging ring.

18. The urolithin derivative of embodiment 16, wherein the second bridging ring is different in structure to the first bridging ring.

19. A method of inducing the expression of tight junction proteins in a tissue, comprising administering an effective amount of a pharmaceutical composition comprising a urolithin structural analogue to a subject in need.

20. A method of inducing the expression of tight junction proteins in a tissue, comprising administering an effective amount of a composition comprising a urolithin derivative of any one of embodiments 1-18 (or a composition comprising any compound disclosed herein) to a subject in need.

21. The method of embodiment 19 or 20, wherein the subject exhibits symptoms of gastrointestinal permeability or inflammation, and the composition is administered to the small and/or large intestine.

22. The method of embodiment 21, wherein the subject has an inflammatory bowel disease.

23. The method of embodiment 22, wherein the inflammatory bowel disease is Crohn's disease or ulcerative colitis.

24. The method of embodiment 21, wherein the subject has celiac disease.

25. The method of embodiment 24, wherein the inflammatory bowel disease comprises colonic inflammation.

26. The method of embodiment 19 or 20, wherein the composition is administered systemically in an amount effect to improve endothelial or vascular barrier integrity in organs.

27. The method of embodiment 26, wherein the organs are one or more selected from liver, kidneys, pancreas, heart, lungs, skin, muscle, fat, brain, eyes, bone, and intestine.

28. The method of embodiment 27, wherein the subject has a condition selected from vasculitis, drug-induced vasculitis, scleroderma, internal vascular bleeding, drug-induced internal bleeding, atopic dermatitis, perfusion-related injury, perfusion related inflammation, and diabetic retinopathy.

29. A method of treating systemic inflammation comprising administering to a patient in need thereof an effective amount of a composition comprising a urolithin derivative of any one of embodiments 1-18 (or a composition comprising any compound disclosed herein).

30. The method of embodiment 29, wherein the composition is administered enterally or parenterally.

31. The method of embodiment 30, wherein the subject has or is at risk of sepsis or an infection-induced inflammatory disease.

32. The method of embodiment 30, wherein the subject has or is at risk of alcoholic liver disease (ALD).

33. The method of embodiment 30, wherein the subject has or is at risk of Non-Alcoholic SteatoHepatitis (NASH) or Alcoholic SteatoHepatitis (ASH).

34. The method of embodiment 29, wherein the subject has inflammation of one or more organs or tissues selected from liver, kidneys, pancreas, heart, lungs, skin, muscle, fat, brain, eyes, bone, marrow, intestine, and cartilage.

35. A method for treating neuroinflammatory disorder comprising administering to a patient in need thereof an effective amount of a composition comprising a urolithin derivative of any one of embodiments 1-18 (or a composition comprising any compound disclosed herein).

36. The method of embodiment 35, wherein the neuroinflammatory disorder is Alzheimer's Disease.

37. The method of embodiment 35, wherein the neuroinflammatory disorder is Parkinson's Disease.

38. The method of embodiment 35, wherein the neuroinflammatory disorder is a neurodegenerative disease, which is optionally multiple sclerosis.

39. The method for treating anxiety or depression, comprising administering an effective amount of a composition comprising a urolithin derivative of any one of embodiments 1-18 (or a composition comprising any compound disclosed herein) to a subject in need, in an amount effective to inhibit monoamine oxidase enzymes in the subject.

40. The method of embodiment 39, wherein the composition is administered systemically or locally to the brain.

41. The method of embodiment 39, wherein the composition is administered enterally, parenterally, or intranasally.

42. A method of enhancing airway barrier integrity in lungs comprising administering to a subject in need thereof an effective amount of a composition comprising a urolithin derivative of any one of embodiments 1-18 (or a composition comprising any compound disclosed herein).

43. The method of embodiment 42, wherein the subject has pulmonary fibrosis, chronic obstructive pulmonary disease (COPD), acute lung injury, blood transfusion related acute lung injury, acute respiratory distress syndrome, or asthma.

44. A method of improving or increasing autophagy in a subject, comprising administering to a subject in need thereof an effective amount of a composition comprising a urolithin derivative of any one of embodiments 1-18 (or a composition comprising any compound disclosed herein).

45. The method of embodiment 44, wherein autophagy is improved or increased in a tissue or organ of the subject selected from brain, eye, skin, bone, marrow, cartilage, heart, lung, stomach, intestine, liver, pancreas, kidney, muscle, and fat.

46. The method of embodiment 45, wherein autophagy is improved or increased in cells of the subject selected from adult stem cells, differentiated cells, blood cells, hematopoietic cells, endothelial cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

47. The method of any one of embodiments 44 or 45, wherein the subject has a disease or condition selected from metabolic stress, cardiovascular disease, sarcopenia, muscle degenerative disease, Duchenne muscular dystrophy, alcoholic liver disease, nonalcoholic fatty liver disease, drug-induced liver injury, chronic kidney disease, alpha-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, amyotrophic lateral sclerosis (ALS), cancer, cognitive disorder, stress, and mood disorder, whereby the administering treats or ameliorates the disease or condition.

48. A method of increasing longevity in a subject, comprising administering to a subject a regimen of a composition comprising a urolithin derivative of any one of embodiments 1-18 (or a composition comprising any compound disclosed herein) effective to increase longevity in an animal.

49. The method of any one of embodiments 19-48, wherein the subject is a vertebrate animal.

50. The method of embodiment 49, wherein the subject is a mammal, which is optionally a primate.

51. The method of embodiment 50, wherein the subject is a human.

52. The method of embodiment 48, wherein the subject is a veterinary patient.

53. A method of increasing autophagy in a cell, comprising contacting a cell with an effective amount of a composition comprising a urolithin derivative of any one of embodiments 1-18 (or a composition comprising any compound disclosed herein).

54. The method of embodiment 53, wherein the autophagy is mitophagy.

55. The method of embodiment 53, wherein the cell is selected from: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

56. A method of increasing longevity of eukaryotic cells in vitro, comprising contacting the cells with a composition comprising a urolithin derivative of any one of embodiments 1-18 (or a composition comprising any compound disclosed herein) effective to increase longevity of the cells.

57. The method of embodiment 56, wherein the eukaryotic cells are eukaryotic cells in primary culture.

58. The method of embodiment 56 or 57, wherein the eukaryotic cells are part of a cell line.

59. The method of any one of the embodiments of 56-58, wherein, the eukaryotic cells are cells selected from: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

60. The method of embodiment 59, wherein the eukaryotic cells are cells selected from: embryonic stem cells, induced pluripotent stem cells, and adult stem cells.

Additional Embodiments—B

1. A compound having a structure shown in Table 2, or a pharmaceutically acceptable salt, solvate, or polymorph thereof.

61. Any pharmaceutical composition as disclosed herein, suitable for administration by a route selected from enteral, parenteral, rectal, inhalation, intranasal, and topical.

62. The pharmaceutical composition of embodiment 61, formulated for intravenous administration.

63. The pharmaceutical composition of embodiment 61, wherein the composition is an aerosol or mist formulated for pulmonary administration.

64. The pharmaceutical composition of embodiment 61, wherein the composition is formulated for topical administration to the skin, eyes, or mucus membranes.

65. The pharmaceutical composition of embodiment 61, wherein the composition is formulated for administration to the gastrointestinal tract.

66. The pharmaceutical composition of embodiment 65, wherein the composition is formulated for delivery of an effective amount of the derivative or compound to the mouth, esophagus, stomach, small intestine, large intestine, and/or colon.

67. The pharmaceutical composition of embodiment 61, wherein the composition is formulated for systemic administration.

68. The pharmaceutical composition of embodiment 67, wherein the derivative or compound is formulated for enteral or parenteral administration.

69. The pharmaceutical composition of embodiment 60, wherein the composition is administered to the central nervous system of a subject.

70. The pharmaceutical composition of embodiment 69, wherein the composition is formulated for intranasal administration.

71. The pharmaceutical composition of embodiment 69, wherein the composition is formulated for intrathecal administration.

Additional Embodiments—C

1. A method of preventing or treating inflammatory bowel diseases, comprising administering to a patient in need thereof an effective amount of a composition comprising any compound disclosed herein (e.g., Formula (I), (IA), I-1, or I-2).

2. The method of embodiment 2, wherein the inflammatory bowel disease is ulcerative colitis or Crohn's disease 3. A method of inducing the expression of tight junction proteins, comprising administering to a patient in need thereof an effective amount of a composition comprising any compound disclosed herein (e.g., Formula (I), (IA), I-1, or I-2).

4. The method of embodiment 3, wherein the tight junction protein are claudins family proteins (Cldn 1-27), Occludin, Zonula occludens (e.g., ZO-1, ZO-2), tight junction proteins (TJPs), junction-associated adhesion molecules (JAMs), or adherens junction proteins, such as vascular endothelial cadherins (VE-Cadherin).

5. A method of inducing the nuclear translocation and activation of AhR comprising administering to a patient in need thereof an effective amount of a composition comprising any compound disclosed herein (e.g., Formula (I), (IA), I-1, or I-2).

6. A method of inducing the nuclear translocation and activation of Nrf2 comprising administering to a patient in need thereof an effective amount of a composition comprising any compound disclosed herein (e.g., Formula (I), (IA), I-1, or I-2).

7. A method of inducing the expression of Cyp1A1 or/and Cyp1A2 comprising administering to a patient in need thereof an effective amount of a composition comprising any compound disclosed herein (e.g., Formula (I), (IA), I-1, or I-2).

8. A method of decreasing inflammation in the mouth, esophagus, stomach, and small intestine, comprising administering to a patient in need thereof an effective amount of a composition comprising any compound disclosed herein (e.g., Formula (I), (IA), I-1, or I-2).

9. A method of decreasing systemic inflammation comprising administering to a patient in need thereof an effective amount of a composition comprising any compound disclosed herein (e.g., Formula (I), (IA), I-1, or I-2).

10. A method of decreasing neural or brain inflammation comprising administering to a patient in need thereof an effective amount of a composition comprising any compound disclosed herein (e.g., Formula (I), (IA), I-1, or I-2).

11. A method of preventing or treating infectious disease and infection-induced inflammatory disease, comprising administering to a patient in need thereof an effective amount of a composition comprising any compound disclosed herein (e.g., Formula (I), (IA), I-1, or I-2).

12. The method of embodiment 11, wherein the infectious disease or infection-induced inflammatory disease is sepsis or sepsis-induced kidney injury or sepsis-induced lung injury.

13. A method of reducing neutrophil infiltration in the colon comprising administering to a patient in need thereof an effective amount of a composition comprising any compound disclosed herein (e.g., Formula (I), (IA), I-1, or I-2).

14. A method of reducing vascular components infiltration into organs or tissue comprising administering to a patient in need thereof an effective amount of a composition comprising any compound disclosed herein (e.g., Formula (I), (IA), I-1, or I-2).

15. A method of reducing neutrophil infiltration into organs or tissue comprising administering to a patient in need thereof an effective amount of a composition comprising any compound disclosed herein (e.g., Formula (I), (IA), I-1, or I-2).

16. A method of reducing cytokines infiltration into organs or tissue comprising administering to a patient in need thereof an effective amount of a composition comprising any compound disclosed herein (e.g., Formula (I), (IA), I-1, or I-2).

17. The method of any one of embodiments 14-16, wherein the organ or tissue is selected from the group consisting of: brain, eye, skin, bone, marrow, cartilage, heart, lung, stomach, intestine, liver, pancreas, kidney, muscle, and fat.

18. A method of enhancing gut barrier integrity comprising administering to a patient in need thereof an effective amount of a composition comprising any compound disclosed herein (e.g., Formula (I), (IA), I-1, or I-2).

19. A method of enhancing vascular barrier integrity comprising administering to a patient in need thereof an effective amount of a composition comprising any compound disclosed herein (e.g., Formula (I), (IA), I-1, or I-2).

20. A method of enhancing airway barrier integrity in lungs comprising administering to a patient in need thereof an effective amount of a composition comprising any compound disclosed herein (e.g., Formula (I), (IA), I-1, or I-2).

21. A method of treating neuroinflammatory disorders comprising administering to a patient in need thereof an effective amount of a composition comprising any compound disclosed herein (e.g., Formula (I), (IA), I-1, or I-2)

22. The method of embodiment 21, wherein the neuroinflammatory disorder is Alzheimer's Disease.

23. The method of embodiment 21, wherein the neuroinflammatory disorder is Parkinson's Disease.

24. A method of inhibiting Monoamino oxidase (MAO) enzyme activity comprising administering to a patient in need thereof an effective amount of a composition comprising any compound disclosed herein (e.g., Formula (I), (IA), I-1, or I-2).

25. A method of treating neurodegenerative disorders comprising administering to a patient in need thereof an effective amount of a composition comprising any compound disclosed herein (e.g., Formula (I), (IA), I-1, or I-2).

26. The method of embodiment 25, wherein the neurodegenerative disorder is anxiety.

27. The method of embodiment 25, wherein the neurodegenerative disorder is depression.

28. A method of increasing autophagy in a cell, comprising contacting a cell with an effective amount of a composition comprising any compound disclosed herein (e.g., Formula (I), (IA), I-1, or I-2), thereby increasing autophagy in the cell.

29. The method of embodiment 28, wherein the autophagy is mitophagy.

30. The method of embodiment 28, wherein the cell is selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

31. A method of increasing longevity in an animal, comprising administering to an animal in need thereof an effective amount a composition comprising any compound disclosed herein (e.g., Formula (I), (IA), I-1, or I-2) or a precursor thereof, thereby increasing longevity of the animal.

32. The method of embodiment 31 wherein the animal is a mammal.

33. The method of embodiment 32 wherein the animal is a human.

34. A method of increasing longevity of eukaryotic cells in vitro, comprising contacting eukaryotic cells in vitro with an effective amount of a composition comprising any compound disclosed herein (e.g., Formula (I), (IA), I-1, or I-2), thereby increasing longevity of the eukaryotic cells in vitro.

35. The method of embodiment 34, wherein the eukaryotic cells are eukaryotic cells in primary culture.

36. The method of embodiment 34 or 35, wherein the eukaryotic cells are part of a cell line.

37. The method of any one of the embodiments of 34-36, wherein, the eukaryotic cells are cells selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

38. The method of any of the previous embodiments, wherein the eukaryotic cells are cells selected from the group consisting of: embryonic stem cells, induced pluripotent stem cells, and adult stem cells.

39. A method of improving or increasing autophagy in an animal, comprising administering to an animal in need thereof an effective amount of a composition comprising any compound disclosed herein (e.g., Formula (I), (IA), I-1, or I-2), or a precursor thereof, thereby improving or increasing autophagy in the animal.

40. The method of embodiment 39, wherein the animal is a mammal.

41. The method of embodiment 40, wherein the mammal is a human.

42. The method of any of the previous embodiments, wherein autophagy is improved or increased in a tissue or organ of the animal selected from the group consisting of: brain, eye, skin, bone, marrow, cartilage, heart, lung, stomach, intestine, liver, pancreas, kidney, muscle, and fat.

43. The method of any of the previous embodiments, wherein autophagy is improved or increased in cells of the animal selected from the group consisting of adult stem cells, differentiated cells, blood cells, hematopoietic cells, endothelial cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

44. The method of any of the previous embodiments, wherein the animal has a disease or condition selected from the group consisting of metabolic stress, cardiovascular disease, sarcopenia, muscle degenerative disease, Duchenne muscular dystrophy, alcoholic liver disease, nonalcoholic fatty liver disease, drug-induced liver injury, alpha-antitrypsin deficiency, ischemia/reperfusion injury, inflammation, inflammatory bowel disease, Crohn's disease, obesity, metabolic syndrome, type II diabetes mellitus, hyperlipidemia, osteoarthritis, neurodegenerative disease, Alzheimer's disease, Parkinson's disease, amyotrophic lateral sclerosis (ALS), cancer, cognitive disorder, stress, and mood disorder, whereby the administering treats the disease or condition.

45. The method of any of the previous embodiments, wherein the composition is administered by oral ingestion.

46. The method of any of the previous embodiments, wherein the composition is administered intravenously.

47. The method of any of the previous embodiments, wherein the composition is administered intraperitoneally.

48. The method of any of the previous embodiments, wherein the composition is administered by inhalation or aerosol.

49. The method of any of the previous embodiments, wherein the composition is administered topically.

The presently-disclosed subject matter is further illustrated by the following specific but non-limiting examples. The following examples may include compilations of data that are representative of data gathered at various times during the course of development and experimentation related to the present invention.

EXAMPLES

Example Set A

Materials: General laboratory chemicals and reagent solutions were purchased from Sigma-Aldrich (St. Louis, MO). ELISA kits for IL-6 and TNF-α were purchased from Bio-legend. ELISA kit for CXCL1 was purchased from R&D systems. All antibodies were purchased from Santacruz unless otherwise specified. LPS was purchased from Sigma Aldrich. Colitis grade DSS (36,000-50,000 M.W) was purchased from MP Bio. UroA was custom synthesized as previously described (SAHA et al. (2016) "Gut Microbiota Conversion of Dietary Ellagic Acid into Bioactive Phytoceutical Urolithin A Inhibits Heme Peroxidases" PLoS One, Vol. 11, Article e0156811).

Mice: C57BL/6 mice were either bred in our animal facility or purchased from Jackson Laboratories. Breeding pairs of Nrf2$^{-/-}$ mice (B6.129x1-Nfe2/2$^{tm1Ywk}$/J, stock #0170009) were purchased from Jackson Laboratories and bred at U of L animal facility to generate experimental animals. AhR$^{-/-}$ mice (Model #9166) were purchased from Taconic Laboratories. We utilized the mice at the ages of between 7-9 weeks age old for colitis experiments. Mice were kept in specific pathogen free (SPF) barrier conditions with temperature-controlled room with alternate 12 hours cycles of dark and light. Animals were allowed free excess to feed and water ad libitum. All studies were performed under approved protocols from Institutional Animal Care and Use Committee (IACUC), University of Louisville, Louisville, KY, USA.

Synthetic procedure for synthesis of UAS03: Chemically UroA (3,8-dihydroxy-6H-dibenzo[b,d]pyran-6-one) structure has a bridge ester, lactone, and two hydroxyl on two phenyl rings. UroA has a lactone (cyclic ester) bond that connects two phenyl rings and leads to the planar structure. Gastric pH or digestive enzymes can hydrolyze the lactone bond leading to opening of the ring. This will result in losing the planar structure, becomes propeller structure, and potentially loses its activities. To generate more stable and potent compounds, we have synthesized non-hydrolyzable cyclic ether derivative, UAS03 by the following procedure (FIG. 10).

Sodium borohydride (0.165 g, 4.38 mmol) was added to dry THF (10 ml), and the mixture was cooled 10° C. before borontrifluoride etherate (0.80 g, 5.7 mmol) was added drop wise over a period of 1 h. Then 3,8-dihydroxy-6H-benzo[c] chromen-6-one (Uro-A) (0.5 g, 2.19 mmol) in THF (5 ml) was added over a period of 10 mins. The mixture was allowed to stir for 5 hrs at 50° C. The completion of reaction was monitored by thin layer chromatography (TLC). The reaction was quenched with methanol. 3N aqueous HCl solution (10 ml) was added, and the mixture was gently heated to 50° C. for 30 mins. The reaction mixture was adjusted to neutral with 10% NaOH solution, and the volatiles were evaporated under reduced pressure. The crude product was purified by column chromatography using 50% ethylacetae in Hexane with 60-120 mesh silica gel to get pure 6H-benzo[c]chromene-3,8-diol product.

MS (M+1)=215.2. $^1$H-NMR (DMSO-$d_6$): (δ: 9.49 (2H, s), 7.51-7.50 (1H, d, J=6.6 Hz), 7.48-7.47 (1H, d, J=6.6 Hz), 6.75-6.73 (1H, m), 6.61 (1H, s), 6.48-6.46 (1H, m), 6.32 (1H, s), 4.96 (2H, s). $^{13}$C-NMR (DMSO-$d_6$): (δ: 158.10, 156.71, 154.93, 131.88, 123.86, 122.79, 121.66, 115.72, 114.89, 111.84, 110.07, 103.95, 68.18.

Cell cultures: Human colon epithelil carcinoma cell lines, HT29 (ATCC #HTB-38™) and Caco2 cells (ATCC #HTB-37™) were maintained in DMEM-high glucose and EMEM-high glucose (Cornings; 10-009CV) respectively, supplemented with 10% fetal bovine serum, 1× penicillin-streptomycin solution (100 U/ml penicillin, and 100 μg/ml streptomycin; Sigma Aldrich) in a humidified atmosphere (5% $CO_2$, 95% air, 37° C.). Mouse bone marrow derived macrophages (BMDMs) were isolated and cultured using the following procedure (KUROWSKA-STOLARSKA et al. (2009) "IL-33 amplifies the polarization of alternatively activated macrophages that contribute to airway inflammation" The Journal of Immunology, Vol. 183, pp. 6469-6477). Briefly, mice were sacrificed by $CO_2$ anesthesia, rinsed in 70% ethanol and bone marrow was isolated from tibias and femurs. Bone marrow cells were plated ($2\times10^6$ cell/ml) in DMEM-high glucose (HyClone) supplemented with 10% FBS, 1% glutamine, 1× penicillin-streptomycin solution and 50 ng/mL mouse M-CSF (R&D Systems Inc., Minneapolis, MN) for 7 days for differentiation.

Measurements of IL-6 and TNF-α in BMDM: BMDM were plated in 96 (10,000 cells/well) and 12 wells ($0.1\times10^6$ cells/well) plate for ELISA and RNA isolation. To evaluate the anti-inflammatory properties, BMDMs were stimulated with E. coli-derived lipopolysaccharides (LPS; 055:B5; Sigma) at 50 ng/mL concentration for six hours alone or in combination with UroA or UAS03 at indicated concentrations (0.01, 0.1, 1, 10, 25, 50 μM) in quadruplicates. For cytokine production via ELISA, the supernatant was collected and centrifuged at 10,000×g for 10 min at 4° C. to pellet down any cell and cytokines were quantified using IL-6 and TNF-α specific ELISA kit (Biolegend) following manufacturer's instruction.

LPS-induced peritonitis: Male mice (C57BL/6J; 6-8 weeks old) were randomly divided in 3 groups viz. vehicle (0.25% sodium carboxymethylcellulose (CMC)), UroA and UAS03. UroA and UAS03 groups received oral gavage of respective compounds (20 mg/kg in 100 μl of volume) at 0, 6, 12, 18 and 24 h. Vehicle group received same volume of CMC at same time. After 24 h, mice were injected intraperitoneally with LPS (2 mg/kg; Sigma-Aldrich). Post 4 h LPS challenge, mice were sacrificed and blood was collected. The serum was prepared using BD Microtainer separator tubes. The serum samples were analyzed for Il-6 and TNF-α using respective ELISA assay kit (Biolegend).

Real time PCR: Total RNA was isolated from cells/tissue using Maxwell® 16 LEV simplyRNA tissue kit (Promega) and reverse transcribed with TaqManC Reverse transcription Kit (Applied Biosystems, CA, USA). The transcribed cDNA (after dilution) was mixed with 100 nM gene specific primers (Real time primers LLC) and 1×SYBR green reaction mix (Power SYBR® Green PCR Master Mix; Applied Biosystems, CA, USA). Changes in gene expression was analyzed using CFX96™ Real-Time System (Bio Rad) and fold change in expression was calculated using $2^{\Delta\Delta CT}$ method using GAPDH/β-actin as house keeping gene and normalized with untreated control.

In vitro permeability study: For in vitro cellular permeability studies, Caco2 cells or HT29 cells ($2\times10^4$ cells/$cm^2$) were seeded in 24-well Transwell® plates (Cornings; USA), on polyester membrane filters (pore size 0.4 μm, surface area 1.12 $cm^2$) (KOWAPRADIT et al. (2010) "In vitro permeability enhancement in intestinal epithelial cells (Caco-2) monolayer of water soluble quaternary ammonium chitosan derivatives" Aaps Pharmscitech, Vol. 11, pp. 497-508). Culture medium was added to both apical and basal chamber and the medium was changed every other day up to 21 days for Caco2 cells or 5-7 days for HT29 cells. For Caco2 cells, transepethelial electrical resistance (TEER) was calculated using EMD Millipore Millicell-ERS2 Volt-Ohm Meter (Millipore). Filters (with cell monolayer) showing more than 600 $\Omega \cdot cm^2$ were used for permeability study. After cells reach desired confluence (monolayered cells), cells were pretreated with vehicle (0.01% DMSO) UroA (50 μM) and UAS03 (50 NM) for 24 hours. After treatment, monolayer was washed with PBS to remove any residual drug and 200 μL of LPS (50 ng/ml in HBSS) was added to each well and incubated for 2 hours. After LPS treatment, the monolayer was washed with PBS twice and 200 μL of FITC-Dextran (FD-4; Sigma Aldrich, USA) solution (1 mg/mL in HBSS) was added. After 2 h, a sample from the basal chamber was withdrawn and FD4 concentration was determined using fluorescence 96-wells plate reader at excitation and emission wavelengths were 480 and 525 nm, respectively.

RNA sequencing: Total RNA was isolated from HT29 cells treated with vehicle and UroA (50 μM) (n=3) for 24 h and RNA was isolated using Trizol based lysis followed by Qiagen RNeasy kits. The isolated RNA was checked for integrity (RIN>9.5) using the Agilent Bioanalyzer 2100 system (Agilent Technologies, Santa Clara, CA) and quantified using a Qubit fluorometric assay (Thermo Fisher Scientific, Waltham, MA). Poly-A enriched mRNASeq libraries were prepared following Illumina's TruSeq Stranded mRNA LT library preparation protocol (Illumina Inc., San Diego, CA) using 1 μg of total RNA. All 15 samples were individually barcoded and quantitated with the KAPA Library Quantitation Kit for Illumina Platforms (Kapa Biosystems, Wilmington, MA) in conjunction with an Agilent Bioanalyzer DNA 1000 analysis (Agilent Technologies, Santa Clara, CA) for fragment size determination. The average fragment size was approximately 300 bp. 1.8 μM of the pooled libraries with 1% PhiX spike-in was loaded on one NextSeq 500/550 75 cycle High Output Kit v2 sequencing flow cell and sequenced on the Illumina NextSeq 500 sequencer. The quality of the 1×75 bp sequences was checked using FASTQC (version 0.10.1) (ANDREWS (2014) "FastQC: A Quality Control Tool for High Throughput Sequence Data"). Trimming was not necessary with the median quality score above 30 (error probability=0.001 or 1 base call in 1,000 is predicted to be incorrect) across the entire length of the read and the lower quantile above a score of 20 (error probability=0.01) at the end of the read where there is an expected decrease in quality. The raw reads for each sample were directly aligned to the *Homo sapiens* (hg38) reference genome assembly (hg38.fa) using tophat2 (version 2.0.13) (KIM et al. (2013) "TopHat2: accurate alignment of transcriptomes in the presence of insertions, deletions and gene fusions" Genome biology, Vol. 14, Article R36), generating alignment files in bam format. Optional parameters include-no-coverage-search and -library-type fr-firststrand. The human ENSEMBL (FLICEK et al., (2014) "Ensembl 2014" Nucleic acids research, Vol. 42, pp. D749-D755) transcriptome gtf v82 was used for transcript identification, resulting in 60,903 total genes. On average, 26 million reads were aligned per sample with a mean alignment rate of 97 percent. Following sequence mapping, differentially expressed genes were determined using tuxedo suite of programs including cuffdiff2 (version 2.2.1) (TRAPNELL et al. (2013) "Differential analysis of gene regulation at transcript resolution with RNA-seq" Nature biotechnology, Vol. 31, pp. 46-53; TRAPNELL et al., (2012) "Differential gene and transcript expression analysis of RNA-seq experiments with TopHat and Cufflinks" Nature protocols, Vol. 7, pp. 562-578) with the optional parameter-library-type fr-firststrand. The RNA-seq data was deposited in gene data base (GEO #GSE113581).

Immunoblots (Western blots): The total protein lysates were collected either from colon tissue/cells using radioimmunoprecipitation assay (RIPA) buffer (Sigma-Aldrich, USA) and quantified using BCA protein quantification kit (Thermo Scientific) as per instructional manual. Total protein (20-50 µg) of was resolved on NuPAGE™ 4-12% Bis-Tris gel (Novex Life technologies) and transferred to polyvinylidene difluoride membrane (0.22 µm pore; Millipore, USA). After blocking with 5% (w/v) skim milk powder (containing 1×TBS) for 1 h, the membrane was then incubated with respective antibodies at 4° C. overnight (dilutions of respective antibodies is given in Table A1). Next day, respective secondary antibody conjugated with Horseradish peroxidase were probed and the chemiluminescent substrate was used to detect the protein bands (ImageQuant LAS 4000). Densitometry analysis of bands were done using ImageJ software. Antibodies for Cldn4, Ocln, Cldn1, Cyp1A1, AhR, HO1, NQO1, Keap1, β-actin and Lamin B were purchased from Santa Cruz Biotechnologies (USA) and Nrf2 from Novus Biologicals (USA). Source and list of antibodies are provided in Table A1.

TABLE A1

List of antibodies used for Western blots.

| Sr No | Antibody | Source | Dilution |
|---|---|---|---|
| 1 | Nrf2 (NBP1-32822) | Novus Biologicals | 1:1000 |
| 2 | HO-1 (sc-10789) | Santa Cruz Biotechnology | 1:500 |
| 3 | Cldn4 (sc-376643) | Santa Cruz Biotechnology | 1:1000 |
| 4 | ZO-1 (5406) | Cell Signaling Technology | 1:2000 |
| 5 | Ocln (sc-133256) | Santa Cruz Biotechnology | 1:1000 |
| 6 | NQO1 (sc32793) | Santa Cruz Biotechnology | 1:1000 |
| 7 | β-actin (Sc-47778 HRP) | Santa Cruz Biotechnology | 1:5000 |
| 8 | Lamin B (sc-6216) | Santa Cruz Biotechnology | 1:100 |
| 9 | AhR (sc-133088) | Santa Cruz Biotechnology | 1:1000 |
| 10 | Cyp1A1 (H00001543-D01P) | Novus Biologicals | 1:100 |

Confocal Imaging: HT29 or CaCo2 or BMDM cells (50,000 cells/well) were plated on to 8-well chambered slides (154534PK; ThermoFisher Scientific) allowed them to grow overnight. The cells were induced with vehicle (0.01% DMSO) or UroA (50 µM) or UAS03 (50 µM) for desired time points and fixed with cold methonol. The AhR or Nrf2 or Cldn4 stained with respective antibodies (1:200 dilution) followed by fluorecently labelled (Alexa flour 594 for AhR and Alexa flour 488 for Nrf2 and Cldn4) secondary ab (1:500 dilution; ThermoFisher Scientific). The nucleus was stained with DAPI (Sigma Aldrich). The confocal images were captured using Nikon AIR confocal microscope using 60× magnification lense with appropriate laser channels.

AhR Reporter assay: AhR-reported assay was performed using AhR Reporter Assay system (Indio Biosciences). The AhR Reporter cells (expressing luciferase under AhR promoter) as well as positive control MeBio (AhR ligand) compound were provided in the kit. The cells were treated with Vehicle or UroA or UAS03 or ellagic acid or MeBio for 6 hr and luminoscence was measured according to manufacture's instructions.

Nrf2-Reporter assay: ARE-luciferase plasmid vector was obtained from Cayman Chemicals. HT29 cells were transfected at 50% confluency using lipofectamine 3000 reagent (ThermoFisher Scientific). Briefly, cells were seeded in 6-well plates ($0.5 \times 10^6$ cells) and grown for 24 h. The transfection complex containing 1 µg of plasmid DNA and transfection reagent was added to each well in absence of FBS. After 6 hr medium containing 10% FBS was added and cells were incubated for another 16-18 hr. These cells were treated with vehicle (0.01% DMSO) or UroA (50 µM) or UAS03 (50 µM) or sulforaphane (10 µM) for 24 h. After incubation with inducers, cells were lysed and firefly luciferase activities (luminiscence) were measured with Luciferase Assay System (Promega) using multiwell plate luminometer (BMG, LABTECH).

Measurements of Cyp1A1 enzyme activity (Ex vivo): Mice were treated with Vehicle or UroA or UAS03, BNF or FICZ daily for one week at indicated concentration either through oral or i.p. route. After one week, mice were euthanized and the colon and liver tissues were dissected. Microsomes from these tissues were prepared using the following procedure (SINGH et al., (2013) "Evaluation of memory enhancing clinically available standardized extract of Bacopa monniera on P-glycoprotein and cytochrome P450 3A in Sprague-Dawley rats" PloS one, Vol. 8, Article e72517). For hepatic microsomes, liver was first perfused with 0.9% sodium chloride solution and excised out. Adhering blood and saline was removed by blotting on tissue paper and tissue was homogenized in tissue homogenization buffer (50 mM Tris-HCl, pH 7.4 with 250 mM sucrose). Homogenate was centrifuged at 10,000×g for 30 minutes at 4° C. supernatant obtained was further centrifuged at 105,000×g for 60 minutes at 4° C. The pellet was washed with homogenization buffer and centrifuged again at 105,000×g for 60 minutes at 4° C. The pellet was suspended in homogenization buffer and used for protein and CYP assay. For intestinal microsome preparation, intestine was removed and washed with 0.9% sodium chloride. The intestine was longitudinally cut open to expose mucosal layer and mucosa was scrapped with help of glass slide. The scraped tissue was collected in homogenization buffer (50 mM Tris-HCl buffer containing glycerol (20% v/v), protease inhibitor (1%) and heparin (3 U/ml)). This suspended mucosa was homogenized and centrifuged at 10,000×g for 20 minutes at 4° C. Supernatant obtained was further centrifuged at 105,000×g for 60 minutes at 4° C. The pellet was washed with buffer and centrifuged again at 105,000×g for 60 minutes at 4° C. The pellet was suspended homogenization buffer and used for protein and CYP enzymes assays.

Ethoxyresorufin-O-deethylase (EROD) assay: The microsomal proteins (0.5 mg) were mixed with 200 μL Tris buffer (0.1 M, pH 7.4) containing ethoxyresorufin (0.01 mM). To start reaction, NADPH (0.1 mM) was added and incubated at 37° C. for 10 min. After 10 min, reaction was terminated by adding equal volume of acetonitrile and reaction mixture was centrifuged at 13000×g for 10 min at 4° C. Supernatant was used to determine resorufin by measuring fluorescence (Ex. 530 nm, Em. 580 nm). Pure resorufin (Sigma Aldrich) was used to generate standard curve.

P450-Glo Cyp1A1 luminiscence assay: The above microsomes (20 μg) were used for P450-Glo Cyp1A1 luminiscence assays as per manufacturer's instructions.

Measurment of Cyp1A1 enzyme activities in vitro. EROD assay: HT-29 cells (15,000 cells/well) treated with vehicle, UroA and UAS03 (24 hrs), were rinsed with HBSS buffer, and then fresh HBSS buffer was added along with 5 μM of 7-ethoxyresorufin. Cells were further incubated at 37° C. for 1 h. After the incubation time, fluorescence (Exc. 530 nm, Em. 580 nm) was measured and product (resorufin) formed was calculated from calibration standard and normalized with protein concentration.

P450-Glo Cyp1A1 luminiscence assay: HT29 cells (25,000 cells/well) were plated in 48 well plate. Cell were then treated with UroA (0.1, 1, 10, 25 and 50 μM) or UAS03 (0.1, 1, 10, 25 and 50 μM) or FICZ (0.1, 1, 10, 25 and 50 nM) for 24 hrs. After treatment, cells were washed to remove any residual drugs, and fresh medium containing Cyp1A1 substrate (as per protocol provided with kit Cat. #V8751; Promega) for 3 hr. After incubation, 25 μl of culture medium was removed from each well and transferred to a 96-well white opaque plate and 25 μl of luciferin detection reagent was added to initiate the luminescence reaction and plate was incubated at room temperature for 20 min. After incubation, luminescence was recorded in luminometer. The data reported as fold change over vehicle treatment.

Small interfering RNA (siRNA) mediated knockdown experiment: The AhR siRNA (SR300136) and Cyp1A1 siRNA (SR301093) was purchased from Origene. For knockdown experiments, HT29 cells ($0.5 \times 10^6$ cells/well) were plated in 6 well plate and grown for 24 hr. The AhR, Cyp1A1 and control-siRNA was transfected into HT29 cells using Lipofectamine® RNAiMAX reagent (ThermoFisher Scientific) as per instruction given. After 24 hr of transfections, cell were induced with vehicle (0.01% DMSO), UroA (50 μM) and UAS03 (50 μM) for 24 hr. After treatment with inducers, cells were lysed using RIPA buffer and total protein was used to analyse the expression of AhR, Cyp1A1 and cldn4 by western blot.

Cyp1A1 deletion by CRISPR/Cas9 method: HT29 cells ($1.5 \times 10^5$) were plated in 6-well in antibiotic free standard growth medium 24 h prior to transfection. At 60% confluency cells, cell were co-transfected with 2 μg each of CRISPR/Cas9 KO Plasmid (sc-400511-KO-2; Santa cruz) and HDR Plasmid (sc-400511-HDR-2; Santa cruz) using UltraCruz® Transfection Reagent (sc-395739; Santa Cruz). Medium was replaced with selective medium (containing 4 μg/mL puromycin) 96 hr post transfection. Transfection was confirmed with fluorescence microscopy and western blot (CYP1A1). The double positive cells for GFP and RFP were sorted using MoFlo XDP sorting instrument (Beckman Coulter). The deletion of Cyp1A1 in these sorted was confirmed by Western blots. These cells were then plated in 6-well plate for in standard medium for evaluating the effect of UroA/UAS03 on Cldn4 expression. After 24 hr of UroA/UAS03 treatment cells were harvested for protein and Cldn4 expression was investigated along with normal HT29 cells.

NF-κB EMSA assay: RAW 264.7 cells or BMDM were plated in 100 mm dishes ($1 \times 10^6$) in DMEM supplemented with 10% fetal bovine serum (FBS), 100 U/ml penicillin, and 100 U/ml streptomycin. Cells were allowed to grow for 24 hr and after incubation, cells were treated with LPS (50 ng/mL) with and without UroA (50 μM) and UAS03 (50 μM) for 6 hr. After treatments, culture medium was removed and washed with PBS. Cells were scraped and pelleted down in PBS. Supernatant was discarded and pellet was used for isolation of nuclear and cytosolic protein using NE-PER Nuclear and Cytoplasmic kit (Thermo Scientific; Cat #78833). Later nuclear protein (2 μg) was used for EMSA using Non-Radioactive EMSA Kits with IR Fluo-Probes for Nuclear factor kappa B p65 (Viagene Biotech Inc Cat #IRTF282 60).

Colon explant culture: Colon tissue pieces (0.5-1 cm length) from wild type (C57BL/6) or $Nrf2^{-/-}$ or $AhR^{-/-}$ mice were cultured in triplicates for 24 h in complete DMEM-high glucose medium (supplemented with 10% fetal bovine serum, 1× penicillin-streptomycin solution) in a humidified atmosphere in the presence of vehicle (0.01% DMSO), UroA (50 μM) or UAS03 (50 μM). The tissues were processed for protein preparation (tissue lysates with RIPA plus buffer) or total RNA isolation. These tissue lysates or RNA were used to determine the expression of Nrf2, Cldn4 and AhR.

Tissue processing for RNA and protein analysis: Mice were treated with as described in results section. Mice were euthanized with $CO_2$ asphyxiation followed by cervical dislocation. Colon was dissected out and luminal contents were flushed out with cold PBS (containing PMSF and Sodium orthvandate). Small portion of colon was snap frozen in liquid nitrogen and stored at −80° C. for RNA analysis. For preparation of protein samples, colon was opened longitudinally and mucosa was scraped in ice-cold 1×PBS using pre-chilled glass slide and centrifuged at 300×g for 10 min at 4° C. Supernatant was discarded and pellet was suspended in RIPA buffer (containing 1× protease inhibitor) and vortexed at high speed. After 30 min incubation on ice, samples were centrifuged at 13,000×g for 20 min at 4° C. Supernatant was collected and protein was quantified using BCA protein quantification kit. The lysates were used appropriately for Western blots.

28-day repeated dose toxicity study: To evaluate toxicity of UroA and UAS03, we performed 28-days repeated dose toxicity study. Mice were fed (oral gavage) with UroA (20 and 40 mg/kg/day) and UAS03 (20 and 40 mg/kg/day) daily for 28 days. Body weight, food and water intake were assessed weekly. After 28 days, mice were sacrificed and gross examination of all major organs were performed. Blood was collected to obtain serum. Serum alanine aminotransferase (ALT) and asparate aminotransferase (AST) were analyzed using ALT/AST kit (BioVision) as per instructional manual.

2,4,6-Trinitrobenzenesulfonic acid (TNBS)-induced colitis: Male C57BL/6 or $Nrf2^{-/-}$ mice (6-8 week old age mice) were anesthetized with ketamine/xylazine (100 mg/12.5 mg/kg IP) mixture and administered with single dose of TNBS (2.5 mg/mice; Sigma Aldrich, USA) in 50% ethanol. After administration of TNBS, mice were held upside down for 30-60 sec to ensure proper distribution of TNBS in the colon. Control group received 50% ethanol without TNBS. Mice with TNBS were randomly divided into three groups, viz. vehicle (0.25% sodium carboxymethylcellulose (CMC)), UroA and UAS03. UroA or UAS03 was resuspended in 0.25% sodium-CMC at desired concentrations. The mice were given orally Veh or UroA or UAS03 in 100 μl at desired concentrations (4 or 20 mg/kg/body weight). The treatment started after 12 hours of TNBS administration and every 12 hours thereafter up to 72 hours. The experiment was terminated post 60 h TNBS, where AhR$^{-/-}$ mice were involved. In some experiments, we treated only once at post 12 h TNBS administration. TNBS administered and control mice were euthanized for tissue and plasma collection after 80 hours of TNBS/ethanol treatment. Mice were examined for colitis phenotype.

DSS-induced colitis: Acute experimental colitis in mice was induced by giving 3% (w/v) colitis grade DSS (MP Biomedicals) in drinking water for 7 days. Control animal received drinking water without DSS. All colitis group mice were randomly divided into three groups viz. vehicle treated (0.25% Na-CMC), UroA (20 mg/kg/day) and UAS03 (20 mg/kg/day) on the 4$^{th}$ and 6$^{th}$ day of DSS treatment. After 7 days, animals were put back on regular water for a period of 7 days. For chronic DSS colitis model, we used three cycles of 2.0% (w/v) DSS and each DSS cycle consisted or 7 days followed by 10 days of regular water and mice were treated with UroA (20 mg/kg/day) on every 4$^{th}$ and 6$^{th}$ day of DSS cycle.

Assessment of colitis severity and tissue collection: Mice were evaluated daily for change in body weight, stool consistency and rectal bleeding and score was given and combined to obtained disease activity index (MURTHY et al., (1993) "Treatment of dextran sulfate sodium-induced murine colitis by intracolonic cyclosporin" Dig Dis Sci, Vol. 38, pp. 1722-1734). After euthanasia, the colon was removed and flushed with PBS containing (1 mM PMSF and 0.2 mM sodium orthovanadate). Colon length and colon weight were measured and small parts of colon were excised for myeloperoxidase (MPO) activity and RNA isolation. Tissues for MPO and RNA extraction were snap frozen in liquid nitrogen and stored in −80° C. until further analysis. Tissue for histological examination was stored in 10% phosphate buffered saline formalin. Blood was collected and serum was separated by centrifugation at 3500×g for 15 min. Serum cytokines (IL-6, TNF-α; Biolegend) and chemokines (CXCL1; R&D Systems) levels were measured by ELISA according to manufacturer's instructions.

In vivo intestinal permeability assay: The gut barrier function was evaluated by in vivo intestinal permeability using FITC-Dextran (MW 4000; FD4, Sigma-Aldrich, USA) (FURUTA et al., (2001) "Hypoxia-inducible factor 1-dependent induction of intestinal trefoil factor protects barrier function during hypoxia" J Exp Med, Vol. 193, pp. 1027-1034). Briefly, mice were orally administered with FITC-dextran (60 mg/100 gm body weight). Mice were fasted for 4 h prior to euthanization. The FITC-dextran concentration in serum was determined using the standard curve of FITC-dextran in serum (excitation, 485 nm; emission, 525 nm; BMG LABTECH).

Myeloperoxidase (MPO) activity: The MPO activity in the colons was determined using the following procedure (KIM et al. (2012) "Investigating intestinal inflammation in DSS-induced model of IBD" J Vis Exp, Vol. 60, Article e3678 (6 pages)). Briefly, colon tissue was homogenized in 0.5% (w/v) hexadecyltrimethylammonium bromide (H6269; Sigma-aldrich, USA) in 50 mM PBS, pH 6.0. This homogenate underwent 3 freeze-thaw cycles and 10-15 sec sonication to obtain homogenous suspension. The supernatant from this suspension was collected after centrifiguaton at 13000×g for 20 min at 4° C. The supernatant (10 μl) was then added to 50 mM potassium phosphate buffer (pH 6.0) containing 0.167 mg/ml o-dianisidine (Sigma-Aldrich, USA) and 0.0005% $H_2O_2$(Sigma-Aldrich USA) and absorbance was taken at 450 nm (BMG, LABTECH) at 2 min interval. Units of MPO in each sample was determined by considering that one unit (U) of MPO=1 μmol of $H_2O_2$ split with molar extinction coefficient of $1.13 \times 10^{-2}$ nm/min and MPO in each sample calculated by using $[\Delta A(t_2-t_1)]/\Delta \text{min} \times (1.13 \times 10^{-2})$ formula and MPO units were normalized with per mg tissue.

Histopathology: Collected colon tissue were fixed in 10% buffered formaldehyde solution overnight and fixed tissue underwent standard histopathological processing. Briefly, after fixation tissue underwent dehydration and cleaning with xylene before paraffin embedding. The paraffin section of 5 μm were cut (Leica microtome) and stained for H&E staining. The H&E images were captured using Aperio Scanscope. H&E sections were scored blindly using index scoring described by Erben et al. (ERBEN et al., (2014) "A guide to histomorphological evaluation of intestinal inflammation in mouse models" Int J Clin Exp Pathol, Vol. 7, pp. 4557-4576).

The methods used in the results discussed below are those as discussed in Example Set A, unless otherwise indicated.

Example Set B

Synthesis and Anti-inflammatory Activities of UroA and UAS03

Figure 1:
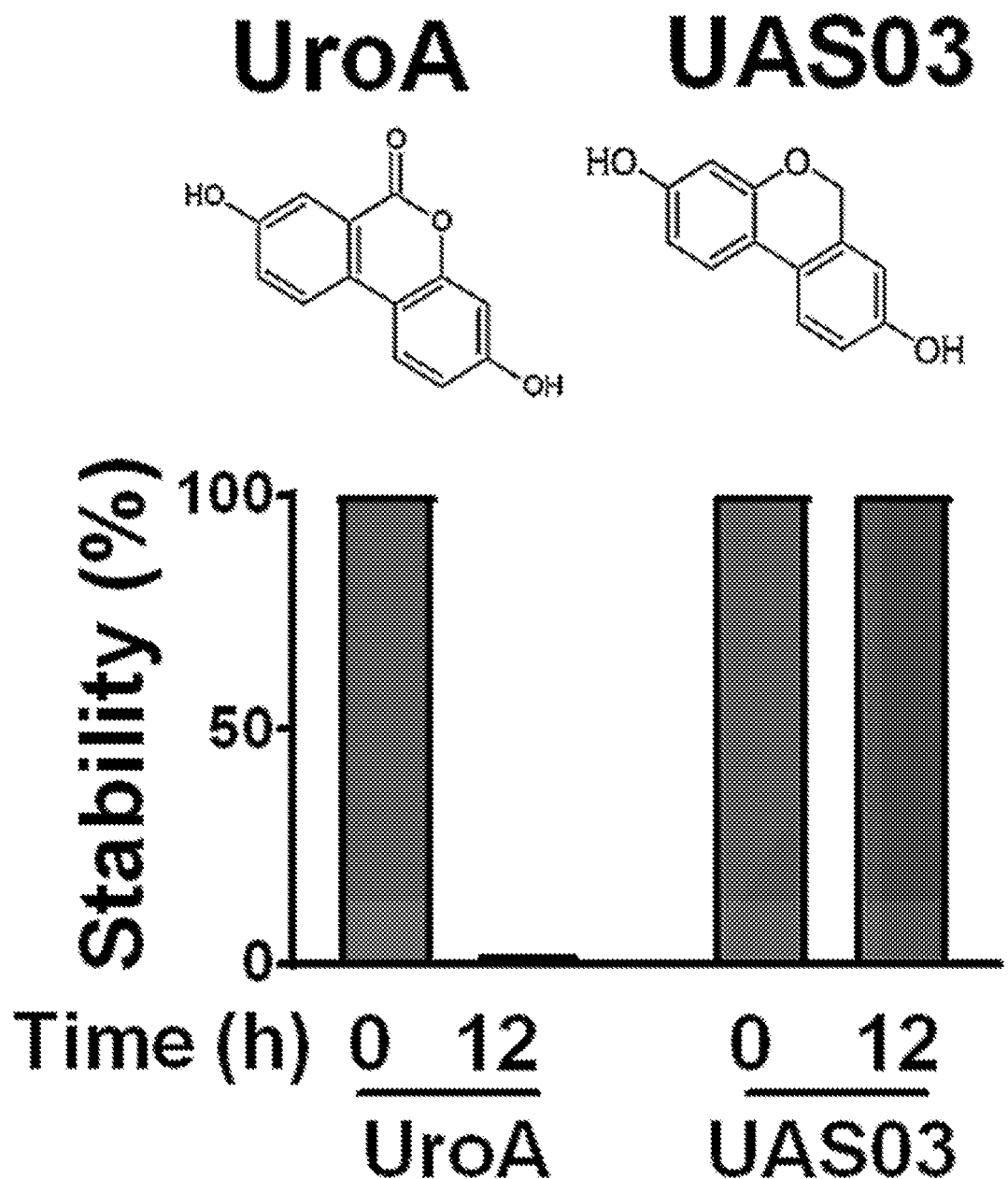
FIG. 1: UAS03 is a potent anti-inflammatory structural analogue of UroA and induces tight junction proteins. (A) Chemical structures of UroA, UAS03. UroA/UAS03 stability was examined in the presence of gastric pH 2.0 and digestive enzymes. UroA and UAS03 (0.2 mg/ml) were incubated with digestive enzymes (esterases and proteases, 100 U/ml) for 12 h at 37° C. and compound levels were quantified. (B) BMDMs were stimulated with LPS (50 ng/ml) without or with UroA (blue line)/UAS03 (purple line) (0.1, 1, 10, 25 and 50 µM) for 6 hours. IL-6 and TNF-α levels in supernatants were measured. (C) C57BL/6 mice (n=3-4) were pretreated with UroA (20 mg/kg) and UAS03 (20 mg/kg). After 4 hours, LPS (2 mg/kg) was injected intraperitoneally. Post 4 h of LPS administration, serum levels of IL-6 and TNF-α was measured. (D) Canonical pathway analysis of RNA-Seq data. HT29 cells were treated with Vehicle or UroA (50 µM) for 24 h and total RNA was isolated and performed RNA-Seq using Illumina HiSeq as described in methods. Pathway analysis was performed using Ingenuity pathway analysis by uploading genes that are up or down regulated (p<0.05). Pathways that are more than 2.5 log p-value are shown. AhR and Nrf2 pathways that are of interest are highlighted. (E-F) RNA-seq analysis-UroA upregulated HMOX1, CLDN4 and CYP1A1 genes. HT29 cells were treated with Vehicle or UroA (50 µM) for 24 h and total RNA was isolated and performed RNA-Seq using Illumina Next Seq 500 as described in methods. (E) Genes with a Log Fc>0.8 were clustered using Euclidian Distance as dissimilarity measure. Genes of interest are highlighted from left: HMOX1, CLDN4, CYP1A1. Heat map generated using Partek program. (F) Gene counts and respective fold changes of selected genes, Claudin 4 (Cldn4), Cytochrome P450 1A1 (Cyp1A1) and hemoxygenase (HMOX1, HO1) are shown. (G-I) HT29 or Caco2 cells were treated with vehicle (DMSO-0.01%) or UroA/UAS03 (50 µM) for 24 h. (G) The fold changes in mRNA levels of claudin 4 (Cldn4), occludin (Ocln) and Zona occludens 1 (ZO1) in HT29 cells were determined by RT PCR method. (H) UroA/UAS03 induced protein expression of Cldn4, Ocln and ZO1 in HT29 cells were determined by immunoblots and quantified by Image J software. (I) Caco2 or HT29 cells were grown on coverslip bottom FluroDish and treated with Vehicle, UroA/UAS03 for 24 h. The cells were stained with anti-Cldn4 followed by secondary antibody tagged with Alexa-488. Nucleus was stained using DAPI. The confocal images were captured. The green intensity (n=15-20 cell membrane regions) was measured. Scale bars for Caco2 and HT29 cells indicate 50 and 25 µm respectively. (J-K) UroA/UAS03 treatment upregulate expression of Cldn4, HO1, Nrf2 and AhR in colons of mice. C57BL/6 mice (7-8 week age old mice, n=3-4) were orally supplemented daily with Vehicle or UroA or UAS03 (20 mg/kg/bodyweight) for 7 days. The protein lysates were prepared from colon scrapes and subjected to immunoblots and detected the expression of the (J) Nrf2, HO1, Cldn4 and (K) AhR using appropriate antibodies as described in methods. (L) Monolayer HT29 or Caco2 cells on transmembranes were treated with vehicle or UroA/UAS03 (50 µM) for 24 h followed by treatment with LPS (50 ng/ml) for 2 h. FITC-dextran was added to these cells (top of the membrane) and incubated for 2 h and FITC-dextran levels in bottom chamber well was measured. Results are representative of three independent experiments with triplicates for each concentration. $*p<0.05$, $p<0.01$, $*\ p<0.001$, unpaired t-test between Veh, UroA or UAS03. Error bars, ±SEM.
Figure 1:
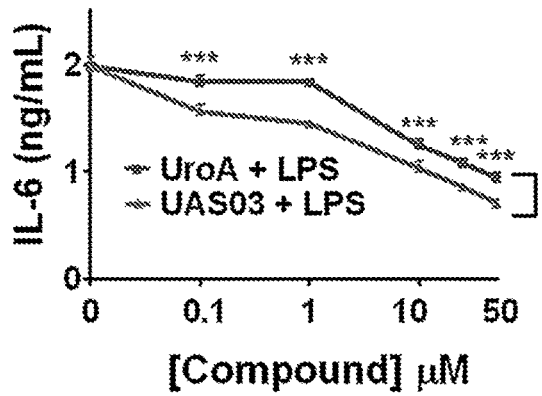
Figure 1:
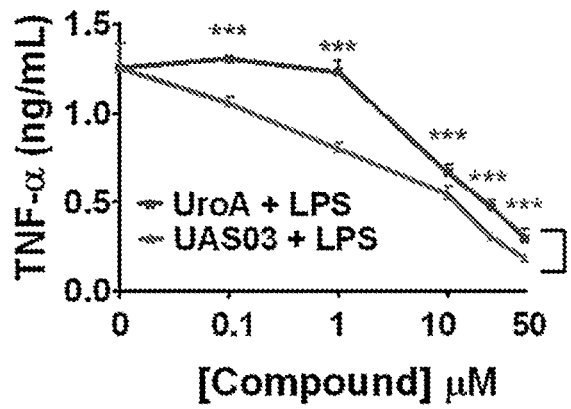
Figure 1:
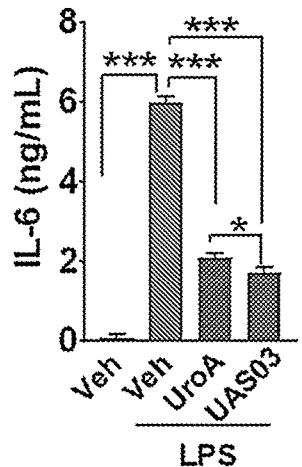
Figure 1:
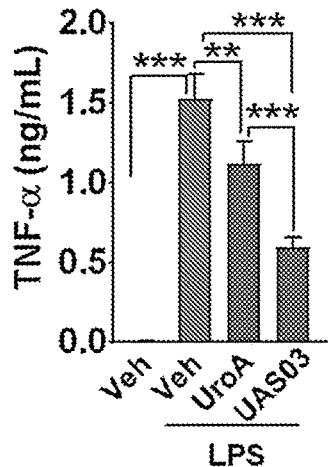
Figure 1:
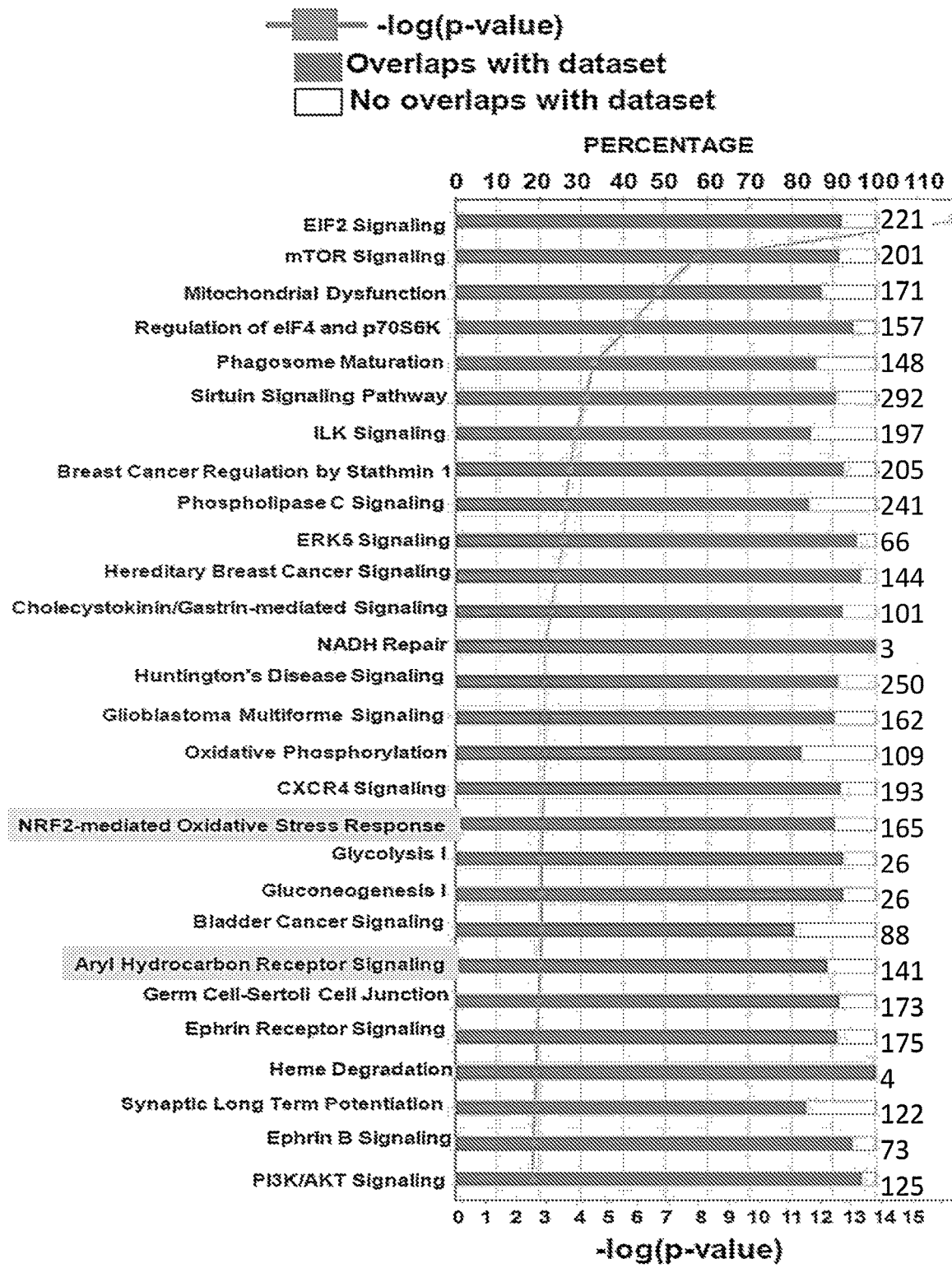
Figure 1:
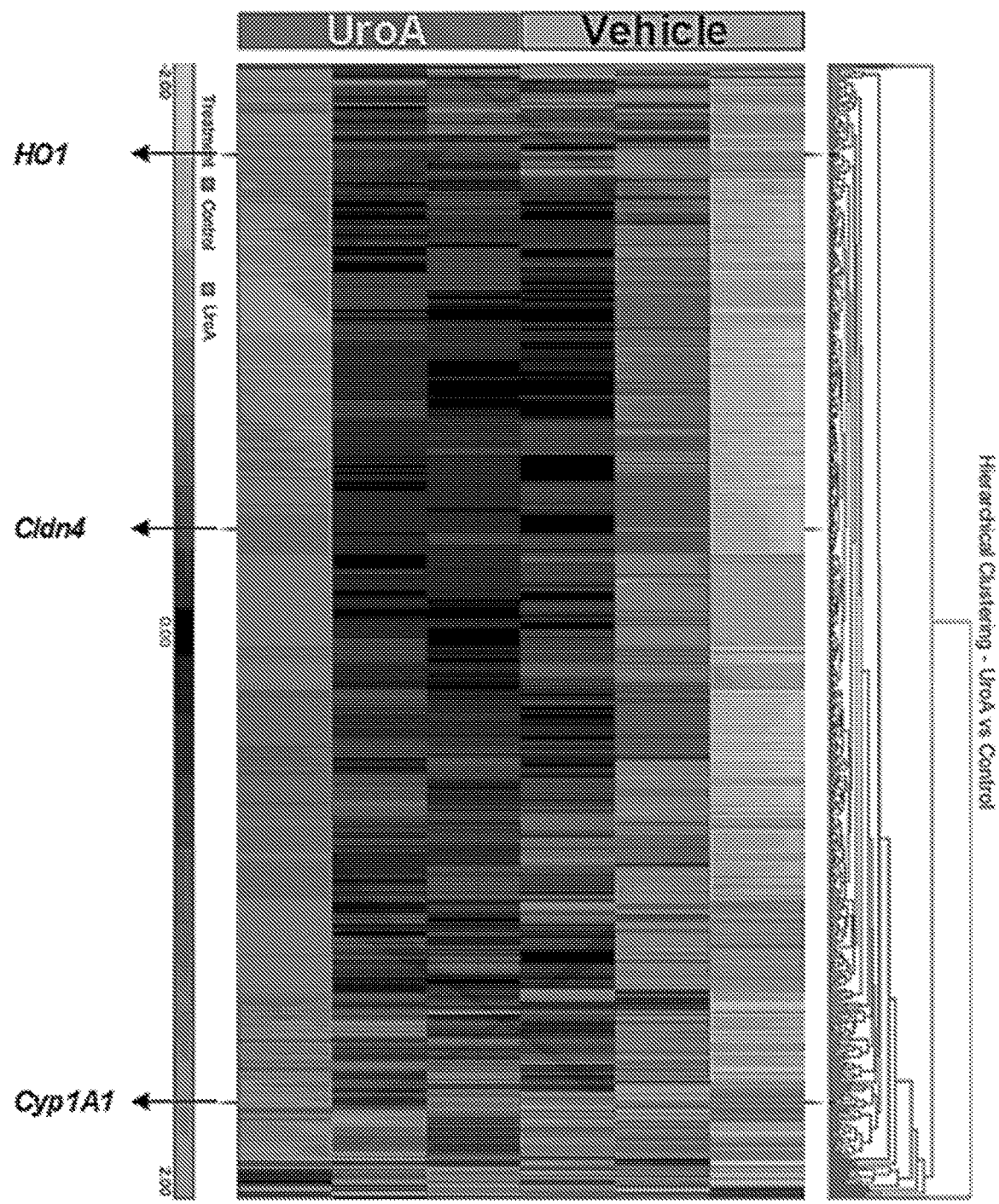
Figure 1:
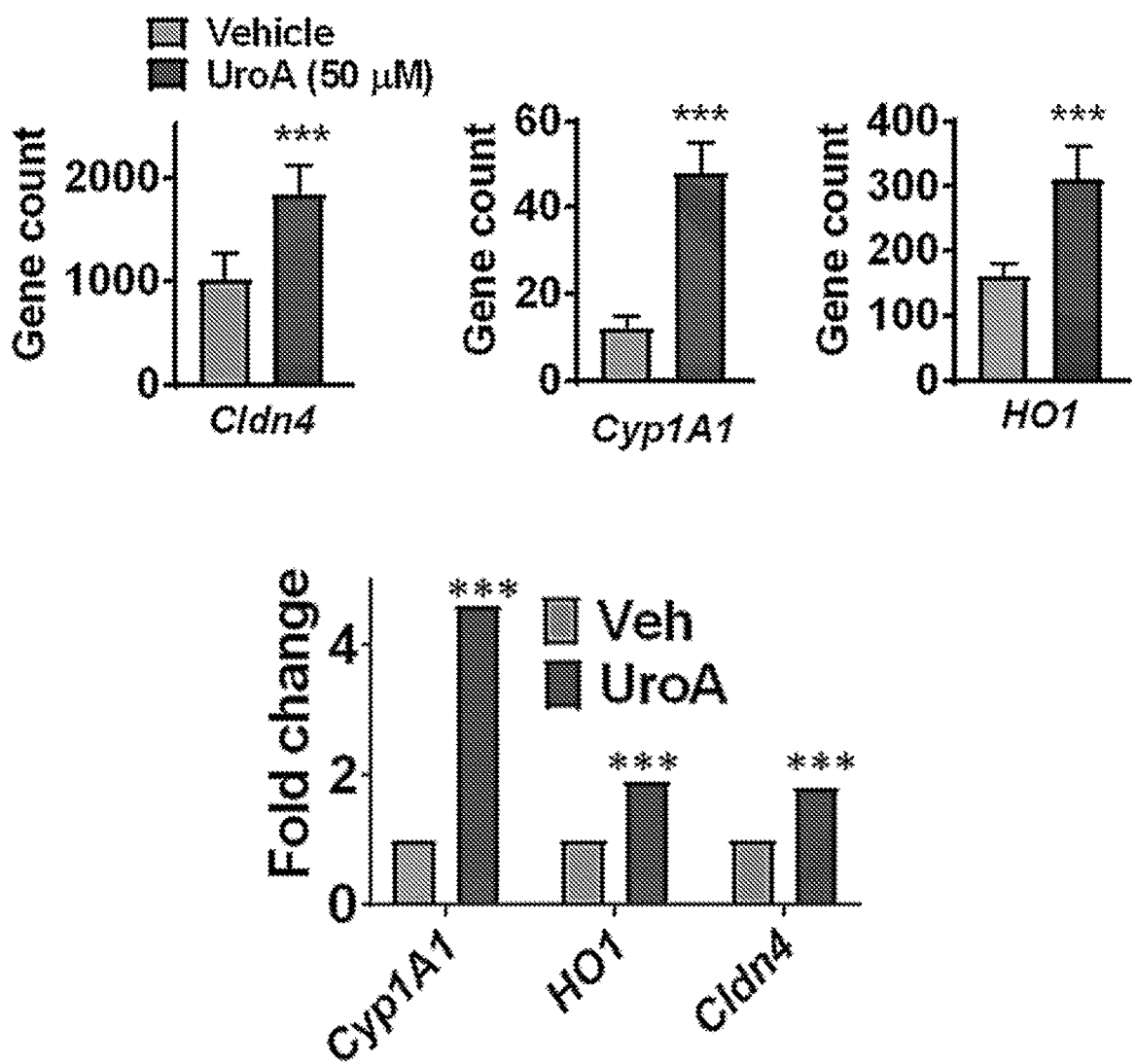
Figure 1:
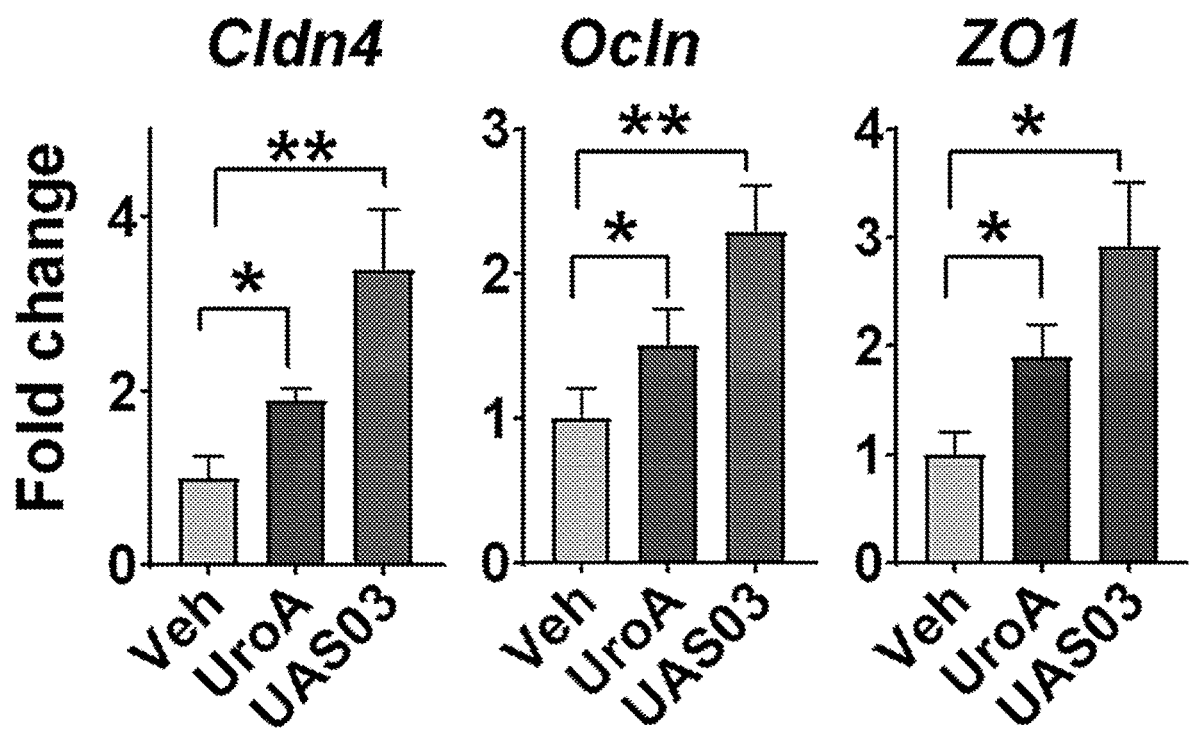
Figure 1:
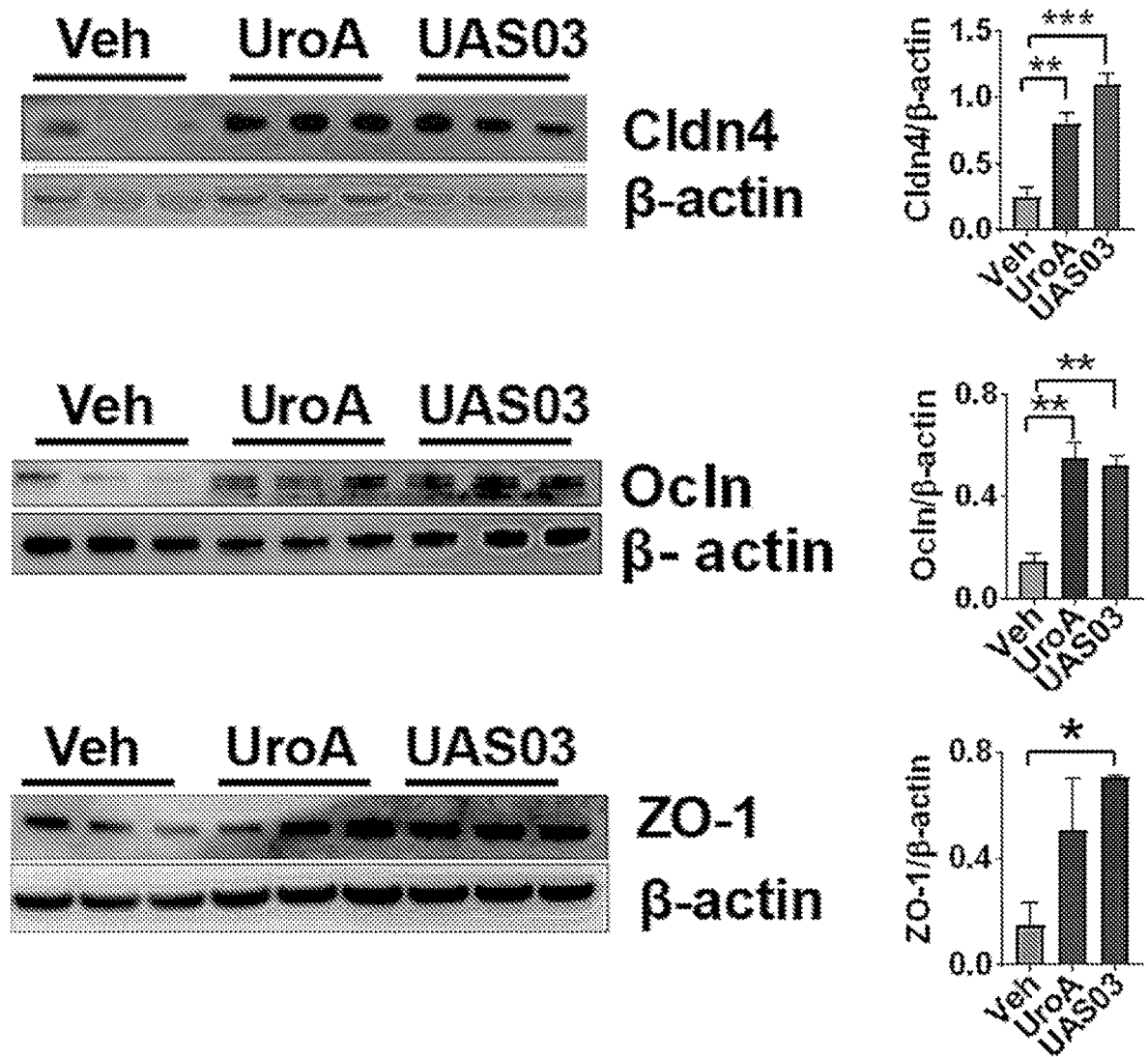
Figure 1:
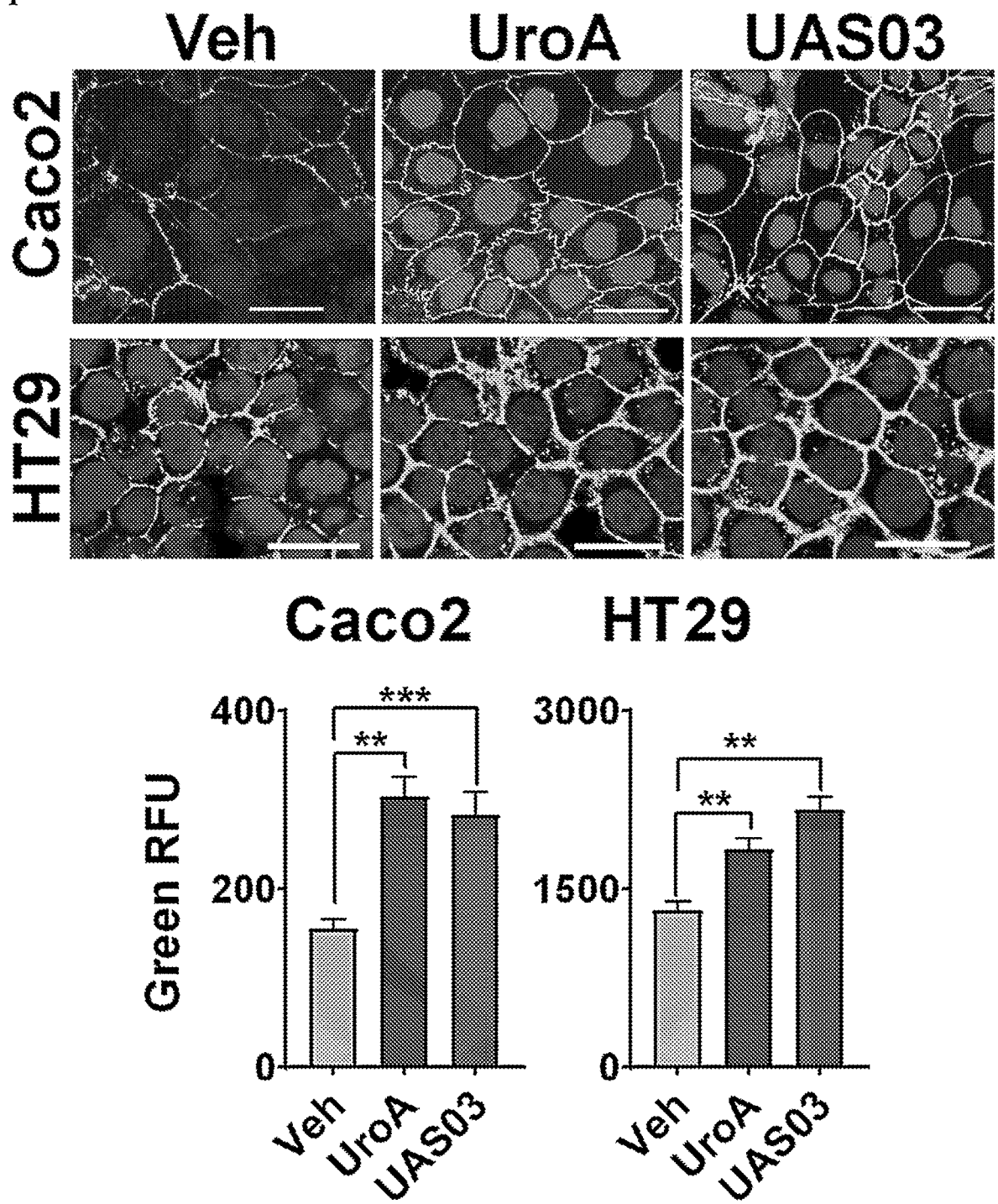
Figure 1:
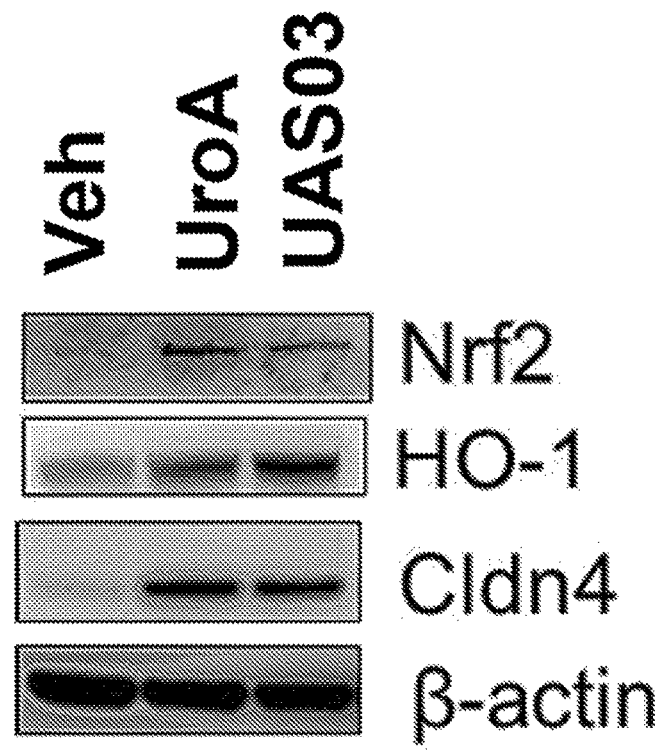
Figure 1:
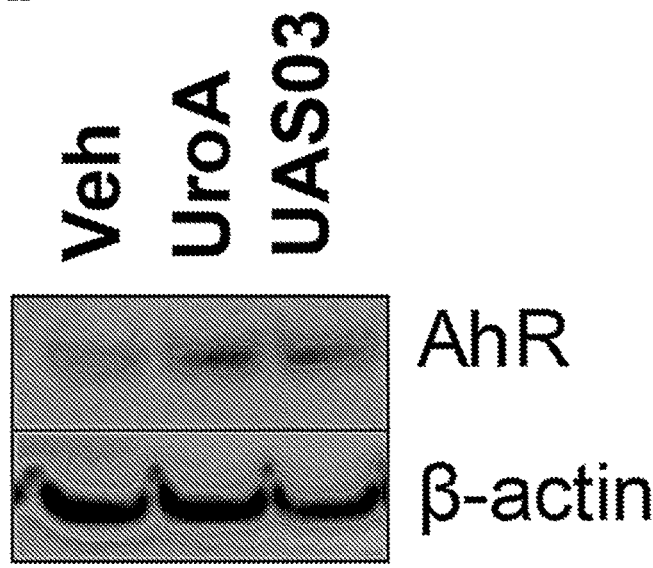
Figure 1:
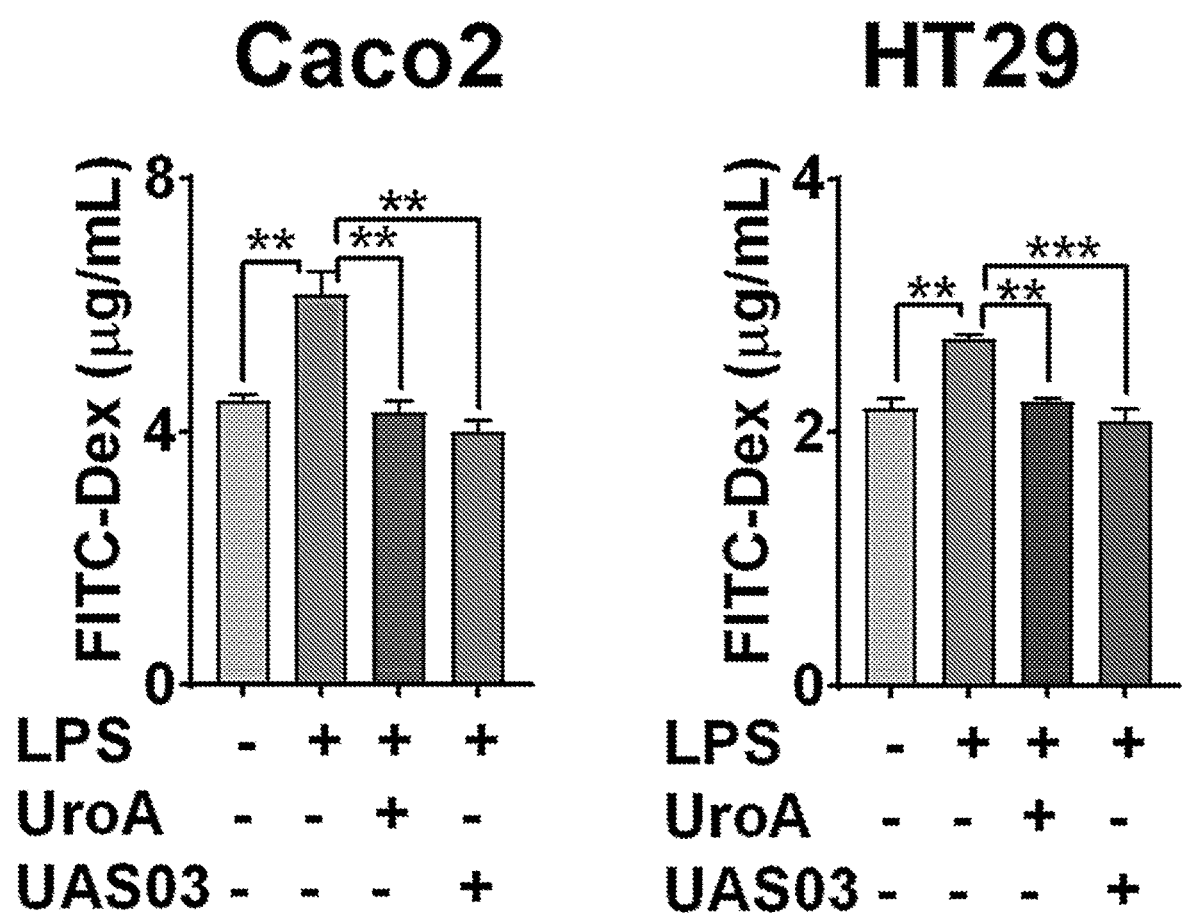

UroA (3,8-dihydroxy-6H-dibenzo[b,d]pyran-6-one) has a lactone (cyclic ester bond) that connects two mono-hydroxyl phenyl rings leading to a planar structure (FIG. 1A). Gastric pH or digestive enzymes can hydrolyze the lactone ring, which opens the ring resulting in the loss of the planar structure and possibly its activities (without wishing to be bound by theory). To generate more stable and possibly more potent compounds, we synthesized non-hydrolyzable cyclic ether derivative, UAS03 (6H-benzo[c]chromene-3,8-diol) (FIG. 1A). The stability of both compounds was examined under conditions of gastric pH and digestive enzymes. The results showed that UAS03 indeed is stable at gastric pH and also in the presence of gastric enzymes e.g., esterases and proteases (FIG. 1A). Both UroA and UAS03 decreased LPS induced IL-6 and TNF-α in mouse bone marrow derived macrophages (BMDMs) with UAS03 showing anti-inflammatory activities at nano molar concentrations (FIG. 1B). Next, anti-inflammatory activities of UroA and UAS03 were examined in vivo in a LPS-induced peritonitis mouse model. UroA or UAS03 treatment reduced the LPS-induced increase in serum IL-6 and TNF-α levels (FIG. 1C). These results suggest that UAS03 is a potent structural analogue of UroA with increased anti-inflammatory activities.

UroA/UAS03 Induce Tight Junction Proteins

Since, microbial metabolites are in close proximity to gut epithelium; we surmise (without wishing to be bound by theory) that metabolites could have a direct impact on epithelial cell function. To examine such effects, we performed RNA-Seq analysis of epithelial cell line (HT29) exposed to UroA. The analysis was performed as described in methods and to determine significance of differential gene expression, cuffdiff2 algorithm was used. Based on an uncorrected p-value cutoff of 0.05, 1,960 genes were determined to be differentially expressed as a result of UroA treatment in HT29 cells. Further restricting this list, 437 genes were found to be differentially expressed at FDR corrected q value <0.05 in UroA treated HT29 cells (FIG.

1D). The pathway analysis using these restricted gene lists was performed using Ingenuity Pathway Analysis (IPA) software (FIG. 1D). The Eukaryotic Initiation Factor 2 (eIF2), mammalian target of rapamycin (mTOR) and mitochondrial dysfunction pathways emerged as top 3 pathways. The impact of UroA on mTOR and eIF2 pathways needed to be established in the context of colon epithelial functions. The RNA-Seq analysis showed that cytochrome P450 1A1 (Cyp1A1) is among the top 3 UroA upregulated genes. The pathways analysis further indicated that the Nrf2 and AhR signaling pathways are in top 25 (FIG. 1D). We surmise (without wishing to be bound by theory) that regulation of barrier function can sometimes help mitigate IBDs. Therefore, we examined the expression of the tight junction proteins in RNA-Seq data and found that claudin 4 (Cldn4) is upregulated in UroA treated cells (FIG. 1E-F). In addition to Cldn4 and Cyp1A1, UroA also increased the expression of heme oxygenase 1 (HMOX1 or HO1) (FIG. 1E-F). HO1 is a Nrf2-dependent gene, which can exert some beneficial activities including removal of toxic heme, protection against oxidative stress, regulation of apoptosis and inflammation. Based on these observations, we hypothesized that UroA and UAS03 could induce tight junction proteins and enhance barrier function through AhR and Nrf2 pathways Ingenuity Pathway Analysis (IPA) revealed enrichment of Nrf2 and AhR signaling pathways (FIG. 1D), supporting a role for these pathways in UroA signaling. A potential therapeutic avenue in IBD is the ability to increase barrier function. It was therefore of interest that we observed an increase in expression of the tight junction protein Cldn4 in UroA treated cells. Although not statistically significant in our RNA-seq dataset, we further observed an increase in expression of additional tight junction proteins ZO-1 and Ocln1 using real time PCR (FIG. 1G). The increased levels of these proteins by UroA or UAS03 was confirmed by Western blots (FIG. 1H) and Cldn4 by confocal imaging (FIG. 1I) in both HT29 and another colon epithelial cell line, Caco2. Further, we observed elevated expression of Cldn4 in the colons of mice treated with UroA/UAS03 (FIG. 1J). The functional consequence of increased tight junction proteins was examined using in vitro FITC-dextran permeability assay in transwell plates. As shown in FIG. 1L, pretreatment of Caco2 or HT29 cells with UAS03 or UroA inhibited LPS induced leakage of FITC-dextran into bottom chambers. Overall, these results suggest that treatment with UroA/UAS03 increased the expression of tight junction proteins potentially enhancing the gut barrier integrity.

AhR Mediates the Activities of UroA/UAS03

RNA-Seq data and real time PCR data suggested that UroA upregulated Cyp1A1 (FIG. 1E-F, FIG. 2A-B). The P450-Glo Cyp1A1 assay (FIG. 2C) as well as 7-ethoxyresorufin-O-deethylase (EROD) assay (FIG. 2D) were performed to determine, whether the Cyp1A1 enzyme activity was similarly affected. UroA/UAS03 induced Cyp1A1 activity in colon epithelial cells (FIG. 2C and FIG. 2D). Since Cyp1A1 is a downstream target of AhR signaling, we examined whether UroA/UAS03 mediate their actions through AhR. In these assays, we utilized potent AhR ligands [2,3,7,8-tetrachlorodibenzo-p-dioxin (TCDD) or 6-Formylindolo[3,2-b]carbazole (FICZ) and low affinity AhR ligand (beta-naphthoflavone (BNF)] to compare the Cyp1A1 activities with UroA/UAS03. UroA/UAS03 activated Cyp1A1 similar to low affinity AhR ligand BNF at 50 µM. As expected, the high affinity ligands such as FICZ and TCDD showed increased Cyp1A1 activity even at nano molar concentrations compared to UroA/UAS03/BNF (FIG. 2C and FIG. 2D). We tested whether UroA/UAS03 induce the Cyp1A1 activities in vivo using wild type and AhR$^{-/-}$ mice. As shown in FIG. 2E, UroA/UAS03 activated Cyp1A1 activity in colon and liver of wild type but not in AhR$^{-/-}$ mice. Moreover, UroA/UAS03 treated wild type mice showed relatively more Cyp1A1 activity in colon tissues compared to BNF and FICZ treated mice (FIG. 2F-G). FICZ and BNF that are delivered through intra peritoneum (i.p) showed more Cyp1A1 activity in liver compared to UroA/UAS03 that are delivered through oral route (FIG. 2F-G). It could be attributed to first pass effect. To directly compare the administration route, we delivered UroA or UAS03 or FICZ through i.p. and determined Cyp1A1 enzyme activities. As expected, high affinity AhR ligand, FICZ, induced ~30 fold in liver compared to 5-6 fold by UroA/UAS03 (FIG. 2H). In colons, FICZ increased Cyp1A1 activity up to ~ 5 fold, whereas UroA/USA03 increased by only ~ 3 fold. In summary, these results suggest that UroA/UAS03 upregulate expression of Cyp1A1 and enhances the enzyme activity through AhR albeit at low levels in vivo.

The direct activation of AhR by UroA/UAS03 was examined in HT29 cells by XRE-luciferase reporter assay as well as nuclear translocation of AhR. The data showed that UroA/UAS03 treatment resulted in 2 to 4 fold induction of luciferase activity (FIG. 2I) compared to the high affinity ligand MeBio that caused higher levels (~15 fold) of AhR activation. Both UroA and UAS03 induced the nuclear translocation of AhR (FIG. 2J-K). AhR was upregulated in mice treated with UroA or UAS03 (FIG. 1K). Next, we asked whether AhR or Cyp1A1 are involved in UroA/UAS03 mediated upregulation of tight junction protein, Cldn4. For this purpose, AhR or Cyp1A1 expression was suppressed using siRNA knockdown and Cldn4 expression was examined. As shown in FIG. 2L-0, UroA/UAS03 does not appear to induce Cldn4 both in AhR or Cyp1A1 knockdown cells. In addition, we also deleted Cyp1A1 in HT29 cells using CRISPR/Cas9 methods and examined UroA/UAS03 mediated activities. Deletion of Cyp1A1 did not show effect on basal levels of Cldn4 compared to parental HT 29 cells (FIG. 2P). As shown in FIG. 2Q-S, that UroA/UAS03 did not appear to upregulate Cldn4 or NQO1 in Cyp1A1 deleted cells. These results suggest that UroA/US03 induce the expression of tight junction proteins through activation of AhR-Cyp1A1 dependent pathway.

UroA/UAS03 Enhance Gut Barrier Function Through Nrf2

Since AhR appears to play a role in UroA mediated activities, we analyzed existing AhR-ligand Chip analysis using ChIP-Atlas (<<http://chip-atlas.org/target_genes>>) that were performed on breast cancer cell line MCF-7 (<<http://dbarchive.biosciencedbc.jp/kyushu-u/hg19/target/AHR.1.html>>). The analysis suggested that Nrf2 is a target of AhR signaling cascade (FIG. 3A). Similarly, AhR also has influence on tight junction proteins such as Ocln, TJP3, Cldn2, 3 and 5 (FIG. 3B). Furthermore, the pathway analysis of RNA seq data (Ingenuity) also revealed that AhR and Nrf2 pathways are listed in top 25. As TCDD mediates some of its activities through Nrf2 pathways, we hypothesized that UroA/UAS03 could induce tight junction proteins through activating AhR-Nrf2 dependent pathways. We tested this hypothesis in colon epithelial cells as well as in mice deficient in AhR and Nrf2. Treatment with UroA/UAS03 upregulated Nrf2 both at mRNA and protein levels (FIG. 3C & FIG. 3G) and induced its nuclear translocation in HT29 cells (FIG. 3H-I). Nrf2-promoter activities were validated utilizing ARE-luciferase assays, where UroA/UAS03 enhanced luminescence upon treatment (FIG. 3D) similar to known Nrf2 activator sulforaphane (SFN) albeit at lower levels. Nrf2 and its target gene HO1 are upregulated in the colons of wild type mice treated with UroA/UAS03 (FIG. 1J-K) as well as in HT29 cells (FIG. 3E). To examine the precise function and interdependency of AhR-Nrf2 pathways in UroA/UAS03 induced Cldn4 upregulation, we utilized colon explants from C57BL/6 (wild type, WT), AhR$^{-/-}$ and Nrf2$^{-/-}$ mice. NAD(P)H:quinone oxidoreductase (NQO1) encodes cytoplasmic 2-electron reductase and the induction is shared by both AhR and Nrf2 pathways. We examined whether UroA/UAS03 upregulate expression of NQO1 in colon explants of these mice. Treatment with UroA/UAS03 induced the expression of both Nrf2, NQO1 and Cldn4 in WT colon explants (FIG. 3J-N). But these compounds did not appear to induce Cldn4 and NQO1 in both Nrf2$^{-/-}$ and AhR$^{-/-}$ colon explants as well as Nrf2 in AhR$^{-/-}$ mice colon explants (FIG. 3J-N) suggesting a possible requirement of AhR and Nrf2 expression for UroA/UAS03 mediated activities. The basal level comparison of expression of Cldn4 and NQO1 in WT, AhR$^{-/-}$ and Nrf2$^{-/-}$ mice colon explants suggests that lack of AhR and Nrf2 reduced the expression of NQO1 and Cldn4 (FIG. 3L). The data suggest that expression of Clnd4 is reduced in AhR$^{-/-}$ and Nrf2$^{-/-}$ but not in Cyp1A1 knock down cells.

To define the possible in vivo requirement of AhR and Nrf2 for UroA/UAS03 mediated upregulation of tight junction proteins, we utilized WT, Nrf2$^{-/-}$ and AhR$^{-/-}$ mice. Examination of basal level expression of Cldn4, NQO1 in the colon tissues of these mice suggests that lack of AhR or Nrf2 have reduced NQO1 levels, but did not show statistical significance for reduction of Cldn4 albeit there was a trend towards reduced expression. (FIG. 3Q). The mice were treated daily with UroA/UAS03 (orally, 20 mg/kg bodyweight) for seven days and barrier functions were analyzed. Treatment with UroA/UAS03 upregulated Nrf2 and tight junction proteins (Cldn4, NQO1, Ocln, ZO1 and TJP3) in WT mice (FIG. 3O-T). In contrast, UroA/UAS03 did not appear to induce these proteins in Nrf2$^{-/-}$ and AhR$^{-/-}$ mice (FIG. 3O-T). UroA/UAS03 induced NQO1 expression was also confirmed in HT29 cells (FIG. 3F). Overall these results suggest that both AhR and Nrf2 play a role in UroA/UAS03 mediated upregulation of tight junction proteins and NQO1.

Treatment with UroA/UAS03 Mitigates Colitis

Figure 4:
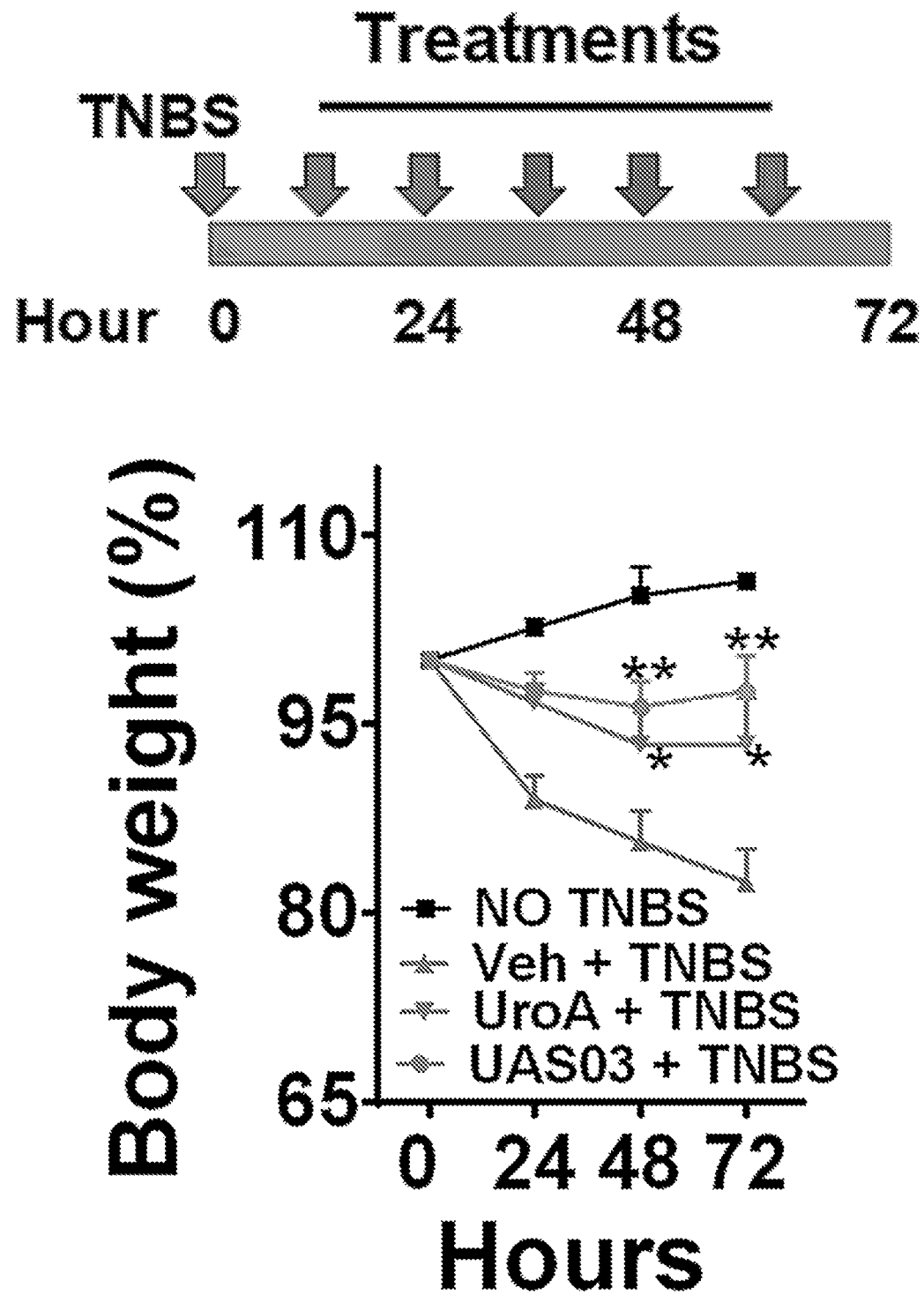
FIG. 4: UroA/UAS03 treatment attenuates TNBS-induced colitis in mice. Colitis was induced by intrarectal administration of TNBS (2.5 mg/mouse) in C57BL/6 (8 week age old, n=5/group) mice. Mice were orally treated with vehicle or UroA (20 mg/kg) or UAS03 (20 mg/kg body weight) every 12 h post-TNBS instillation for 60 h and the experiment terminated at 72 h. Representative data from one of three independent experiments is shown. (A) Percent body weight loss (No TNBS– Solid black line; Veh+TNBS– Solid red line; UroA+TNBS– Solid blue line; UAS03+TNBS– Solid purple line). (B) disease activity index, (C) intestinal permeability, (D) colon lengths were measured. (E) Gross morphological changes of colon, (F) ratio of colon weight/length, (G) colonic myeloperoxidase (MPO) levels, (H) serum IL-6, TNF-α, CXCL1 and IL-1β levels, (I) microphotographs of hematoxylin and eosin (H&E) stained sections of colons and inflammation scores are shown. Scale bar indicates 300 μm. (J) Cldn4 expression in the colons of these mice (n=3) was measured by immunoblots and quantified. (K-P) Single dose of UroA and UAS03 protects against TNBS-induced colitis in mice. TNBS (2.5 mg/mouse) was administered intrarectally in C57BL/6 male (n=3-4/group) to induce colitis. A single dose of UroA (4 or 20 mg/kg bodyweight) or UAS03 (4 or 20 mg/kg body weight) or vehicle (0.25% sodium carboxymethylcellulose) were administered orally post 12 h of TNBS instillation. Mice were euthanized at 72 h post TNBS administration. (K) Experimental design and changes in body weights (%) are shown. (No TNBS– Solid black line; Veh+TNBS– Solid red line; UroA (20 mg/kg)+TNBS– Solid blue line; UAS03 (20 mg/kg)+TNBS– Solid purple line; UroA (4 mg/kg)+TNBS– dashed blue line; UAS03 (20 mg/kg)+TNBS– dashed purple line). (L) Representative colon images (M) colon lengths are shown. (N) Intestinal permeability was measured using FITC-dextran permeability assay. (O) Serum cytokines IL-6, TNF-α, CXCL1 and IL-were measured using standard ELISA methods. (P) Representative H&E section images captured using Aperio Imagescope. Scale bar indicates 100 microns. (Q) Detail analysis of percent body weight loss of data presented in FIG. 4K. (No TNBS– Solid black line; Veh+TNBS– Solid red line; pre-TNBS+UroA– Solid blue line; Pre-TNBS+UAS03– solid purple line; Post-TNBS+UroA– dashed blue line; Post-TNBS+UAS03– dashed purple line). The data is separately presented for each time point. (R-S) Evaluation of UroA/UAS03 toxicity in mice. C57BL/6 mice (7-8 week age old mice, n=4-5) were orally supplemented daily with Vehicle (Veh) or UroA or UAS03 (20 or 40 mg/kg/bodyweight) for 28 days. (R) Changes in body weight were measured once a week. (Vehicle—Solid gray line; UroA (20 mg/kg)—dashed blue line; UroA (40 mg/kg)—Solid blue line; UAS03 (20 mg/kg)—dashed purple line; UAS03 (40 mg/kg)—Solid purple line) (S) Serum AST and ALT levels at day 28 were measured using standard ELISA kits—no significant differences were observed. Statistical analysis was performed (unpaired t-test) using Graphpad Prism software. Error bars, ±SEM *p<0.001; p<0.01 *p<0.05.
Figure 4:
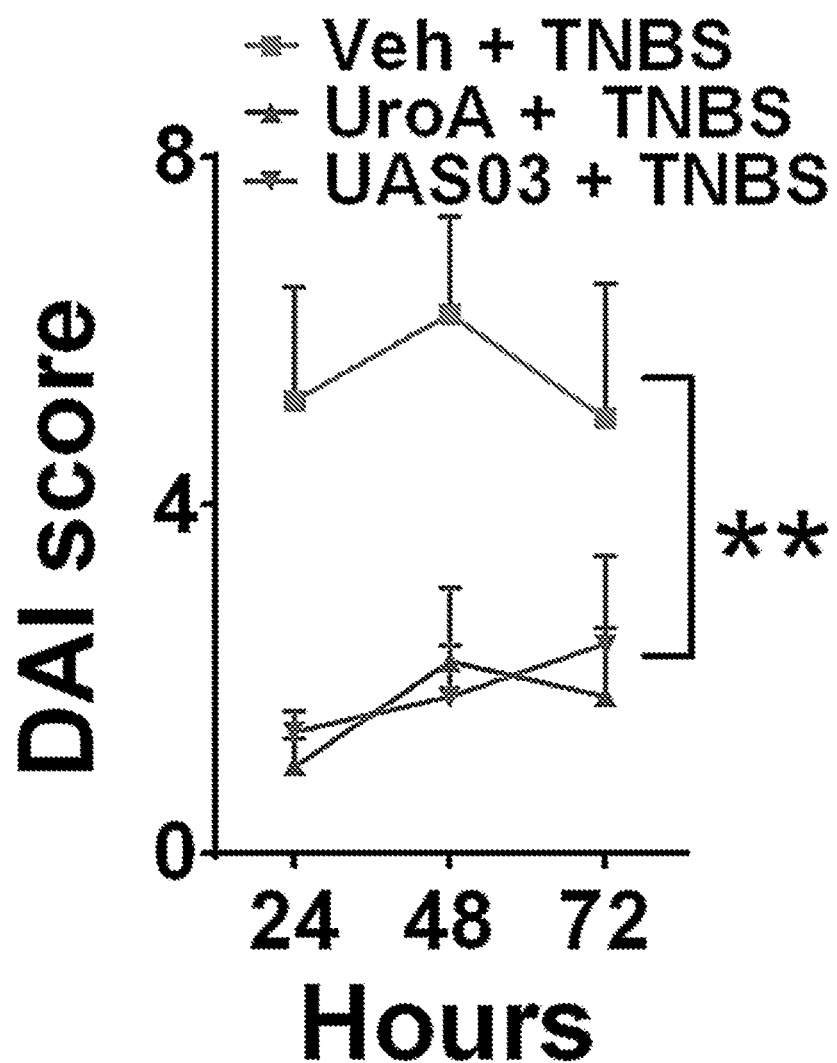
Figure 4:
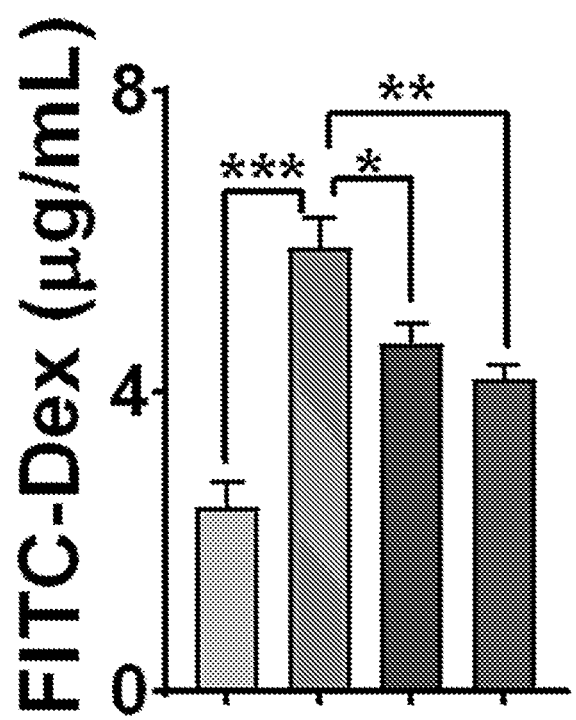
Figure 4:
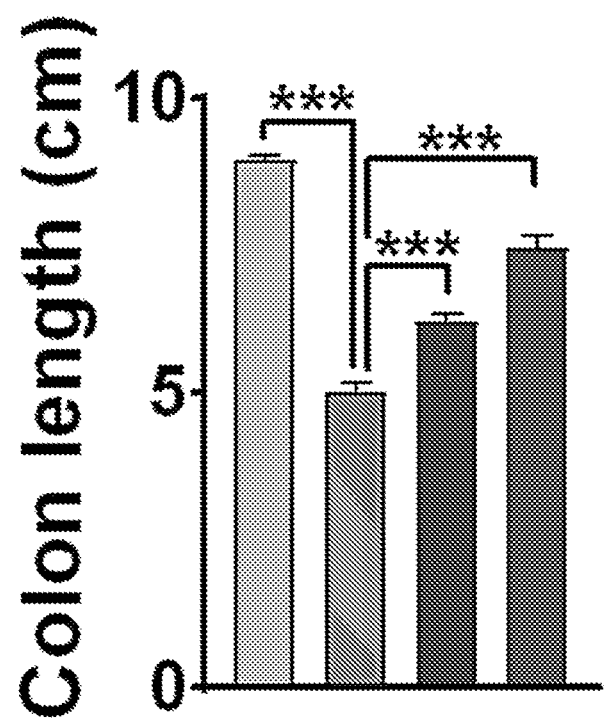
Figure 4:
Figure 4:
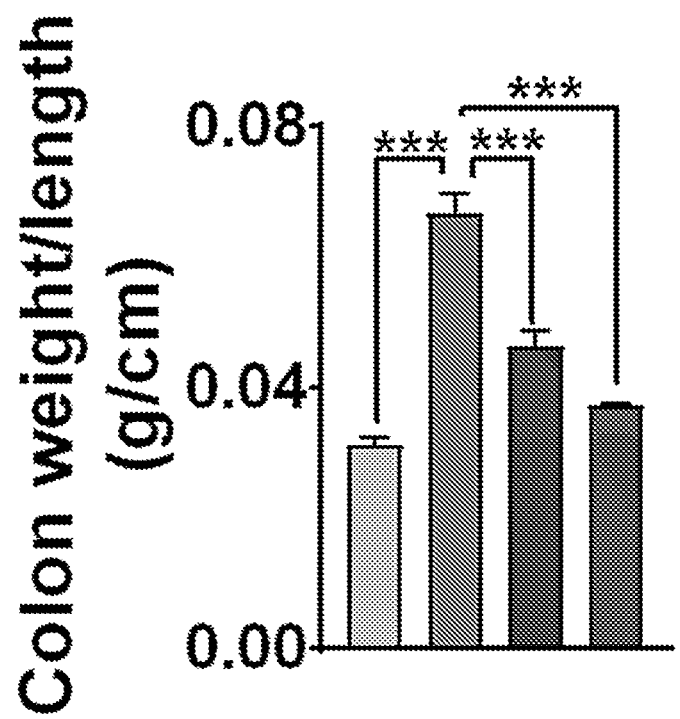
Figure 4:
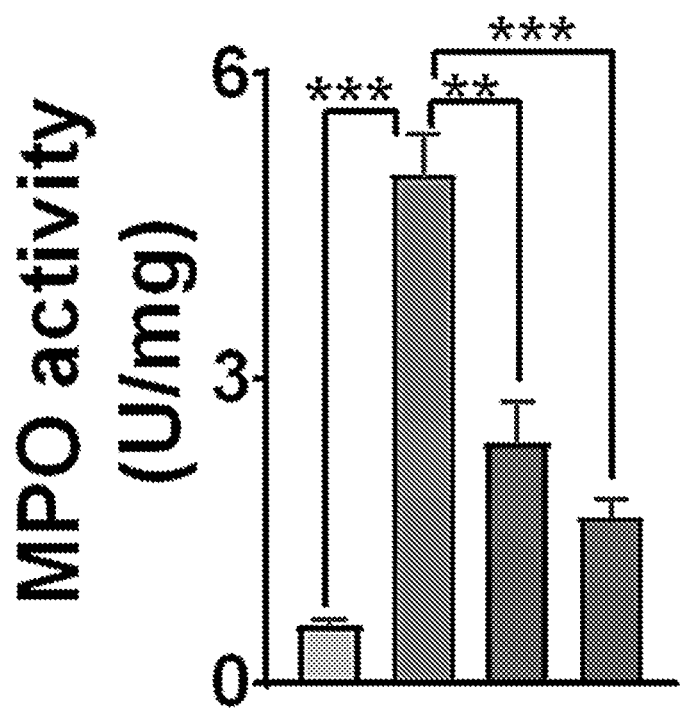
Figure 4:
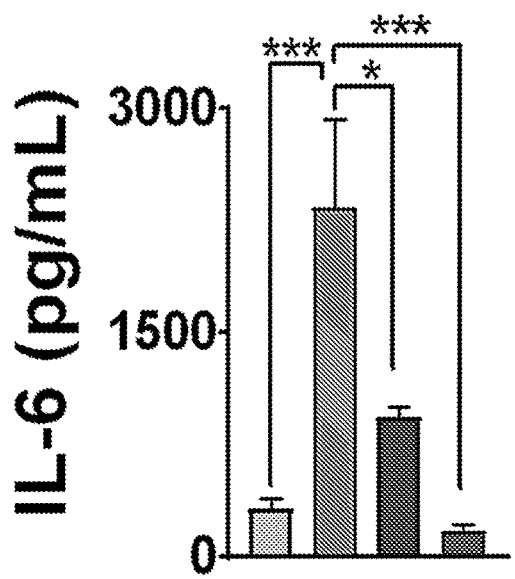
Figure 4:
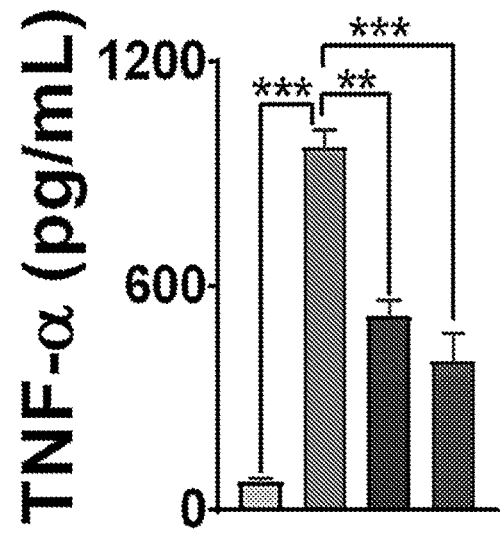
Figure 4:
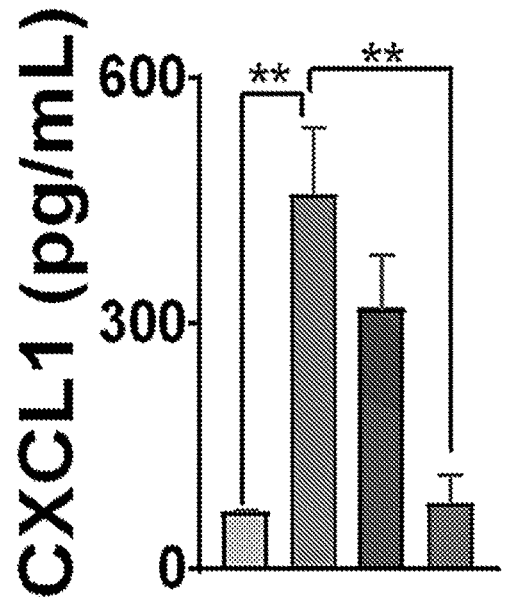
Figure 4:
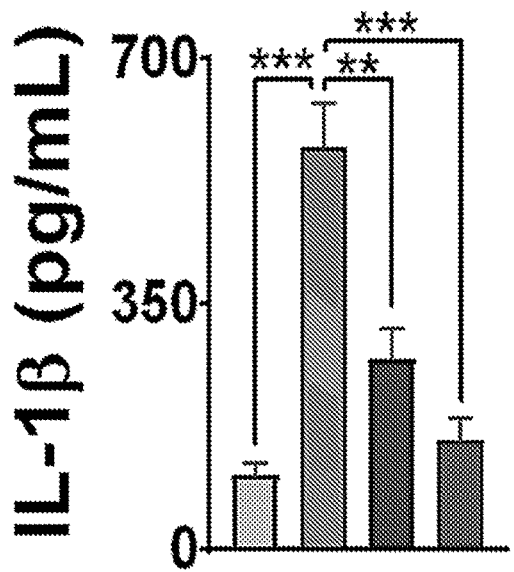
Figure 4:
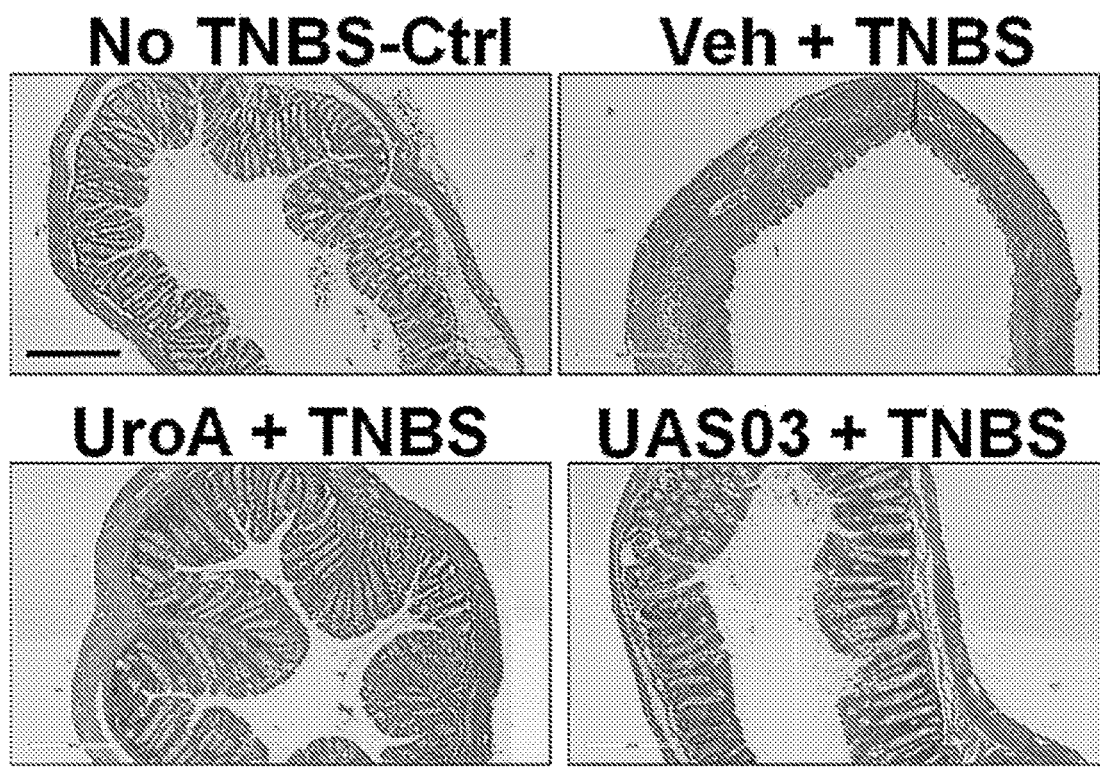
Figure 4:
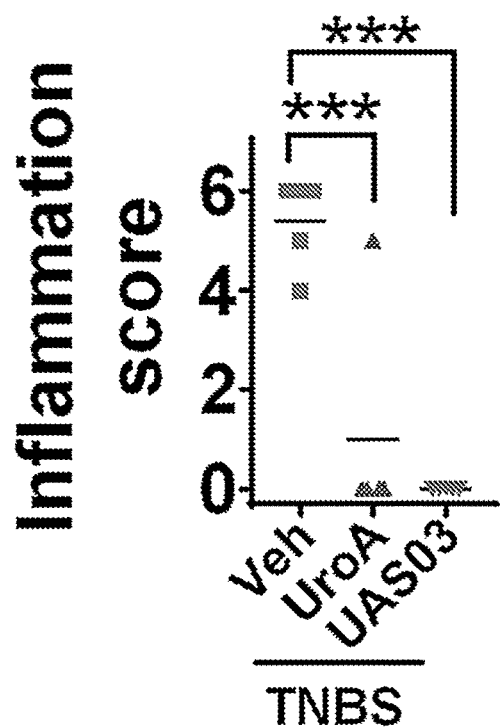
Figure 4:
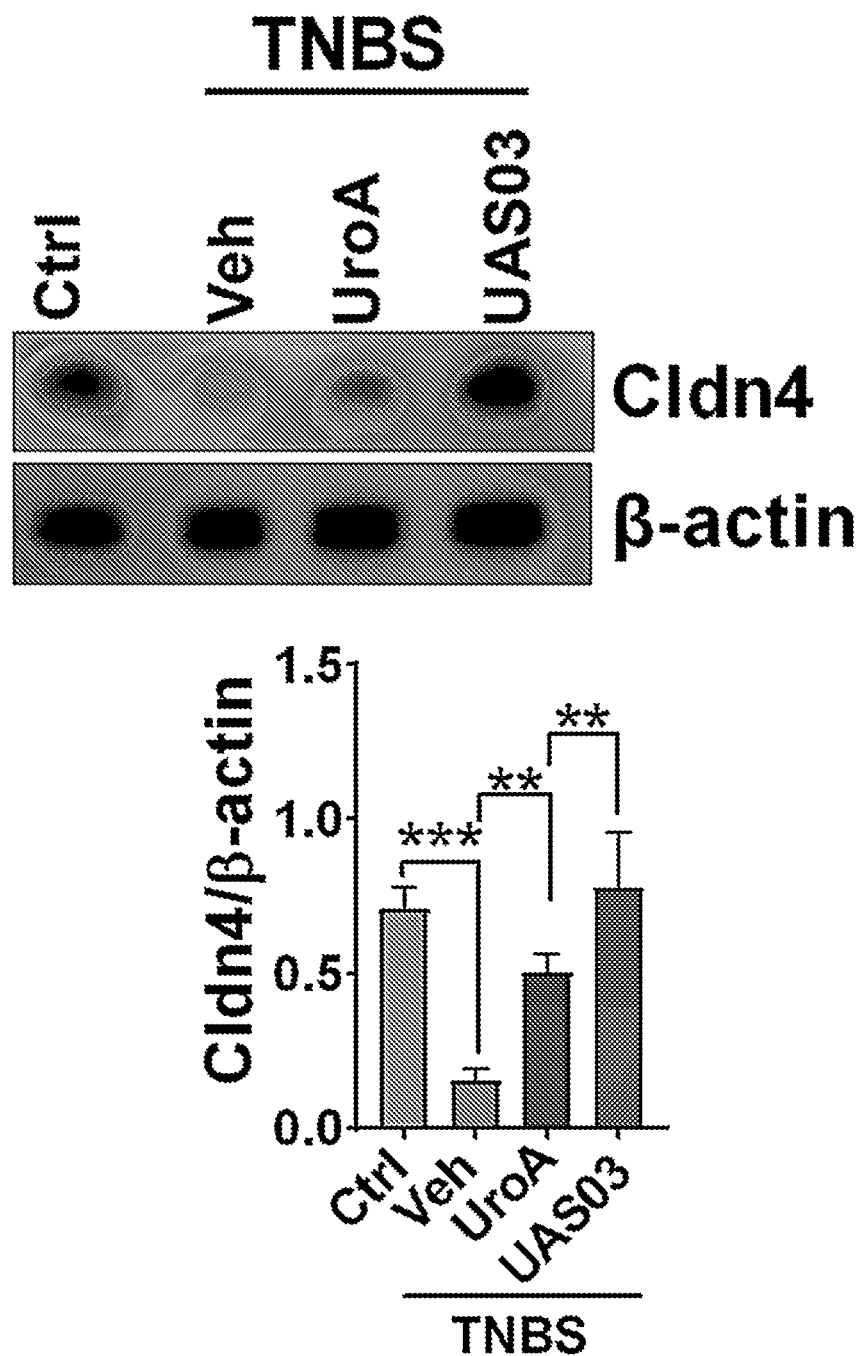
Figure 4:
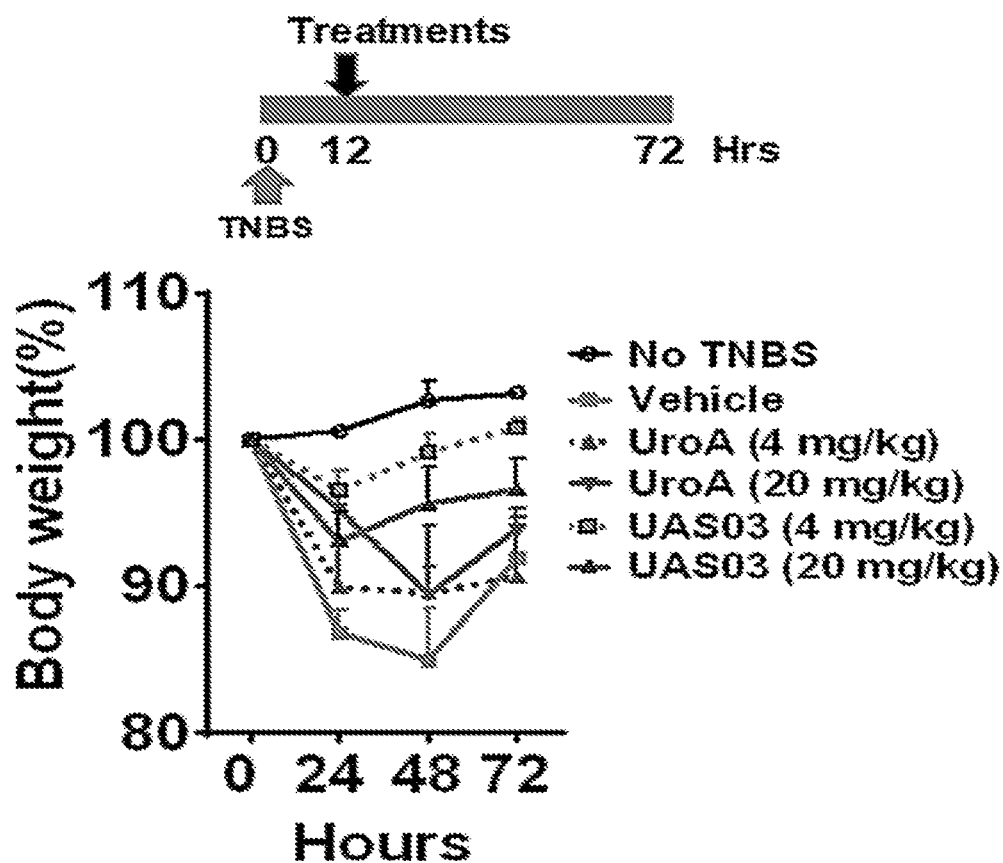
Figure 4:
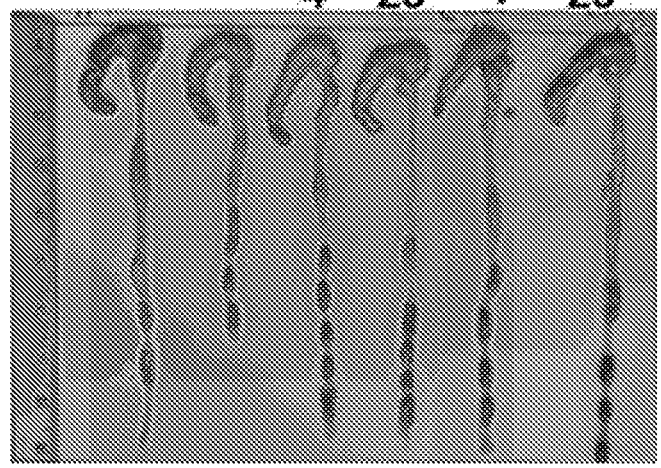
Figure 4:
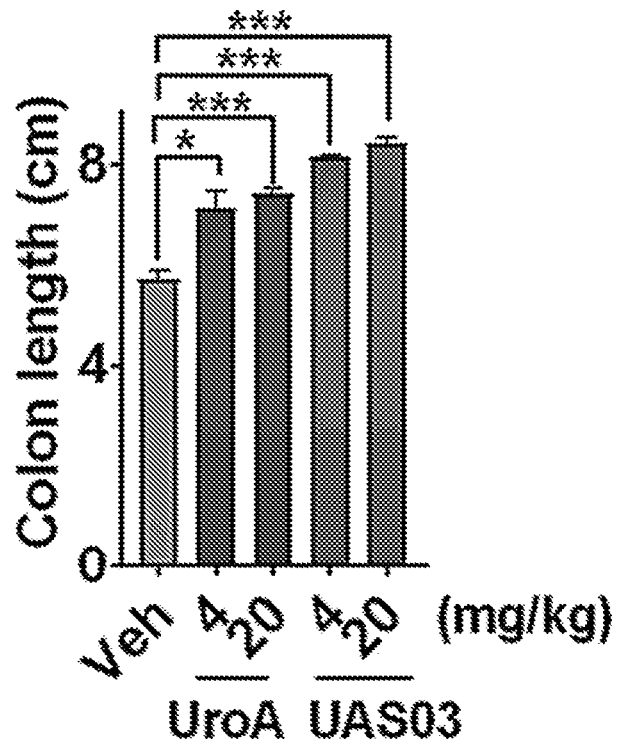
Figure 4:
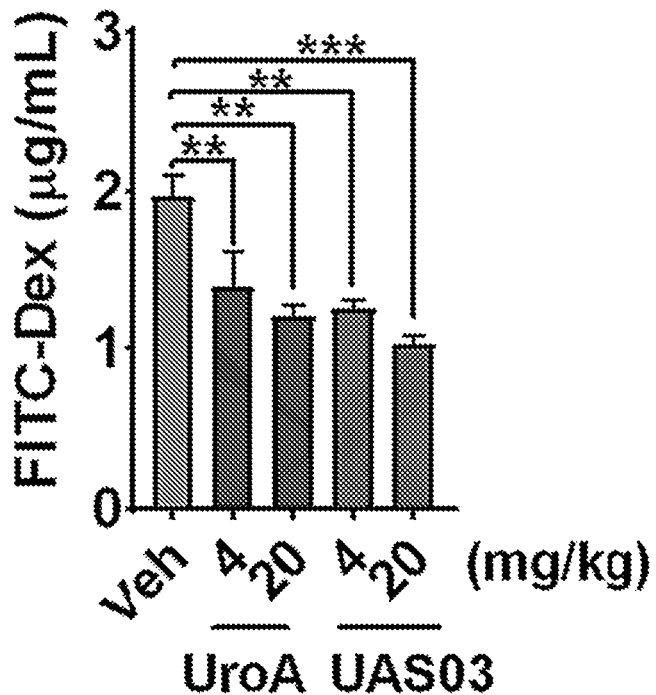
Figure 4:
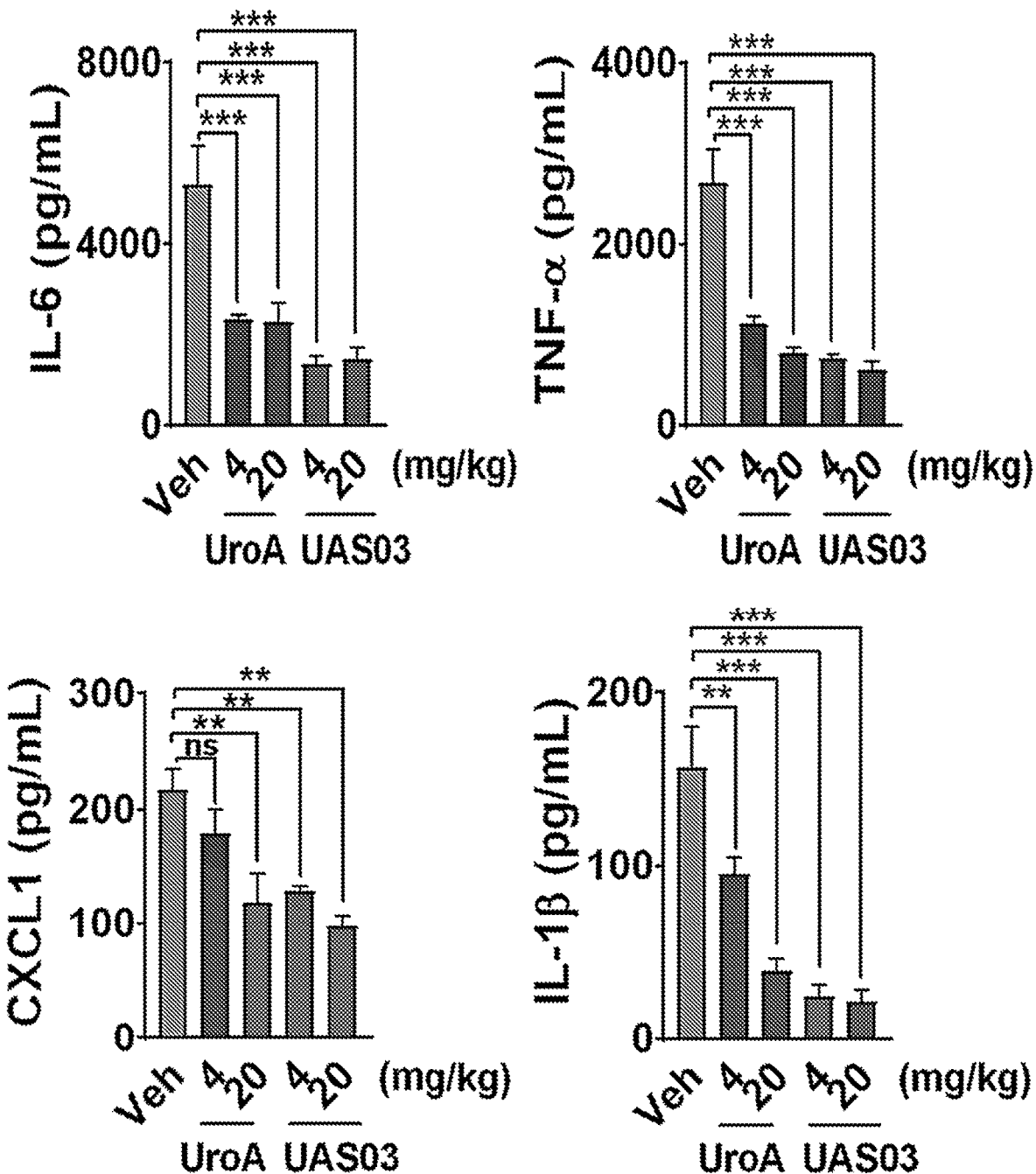
Figure 4:
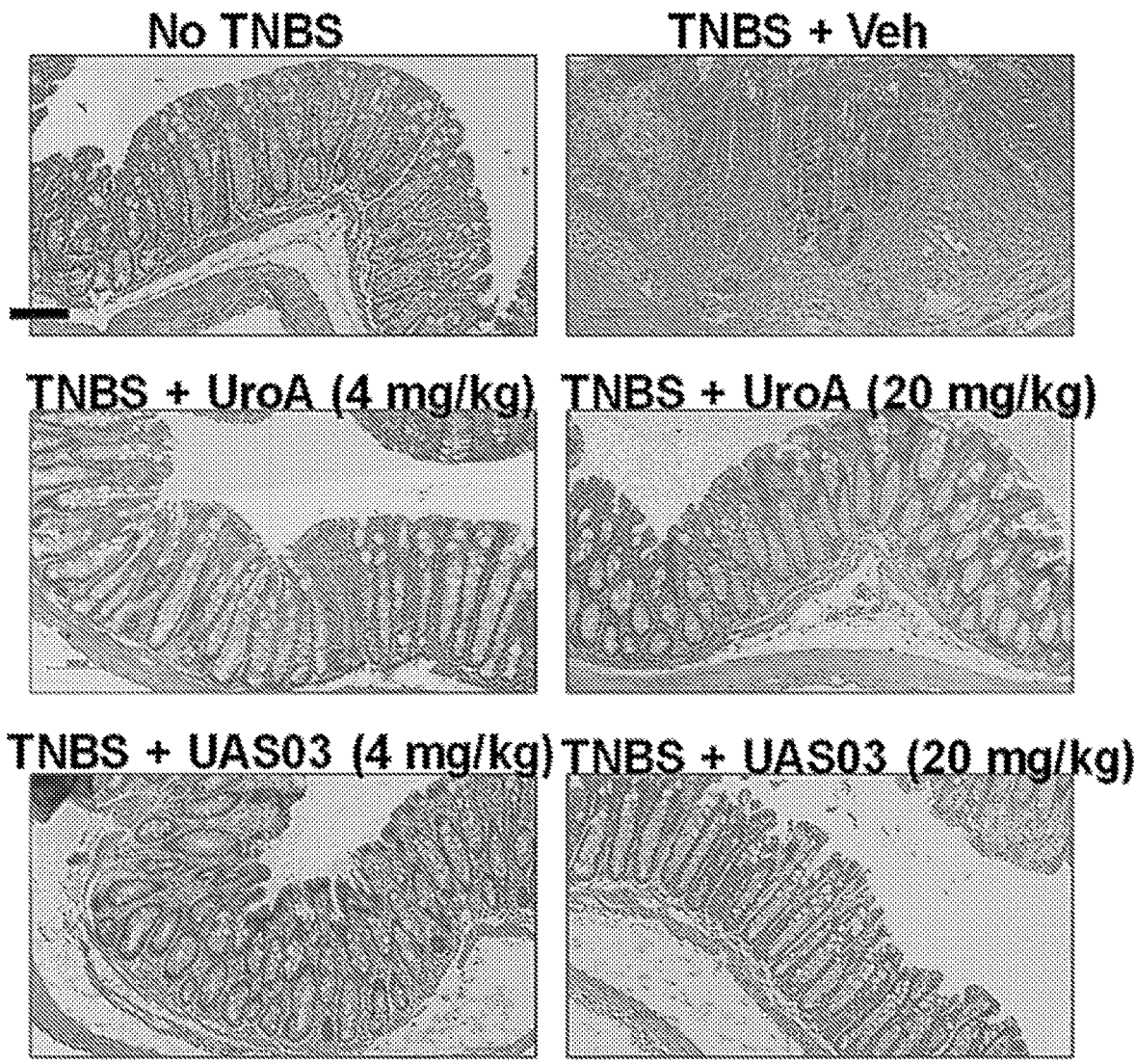
Figure 4:
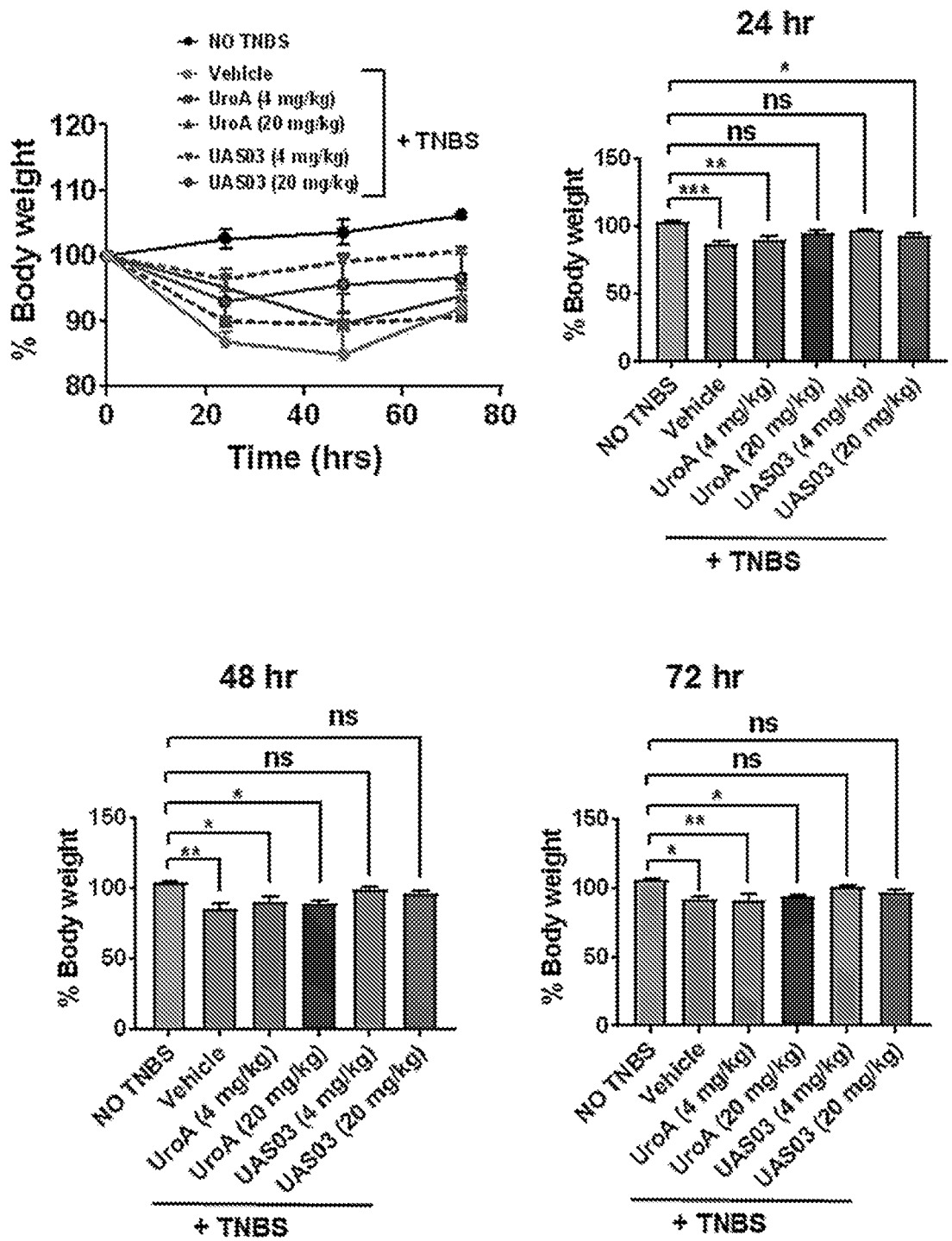
Figure 4:
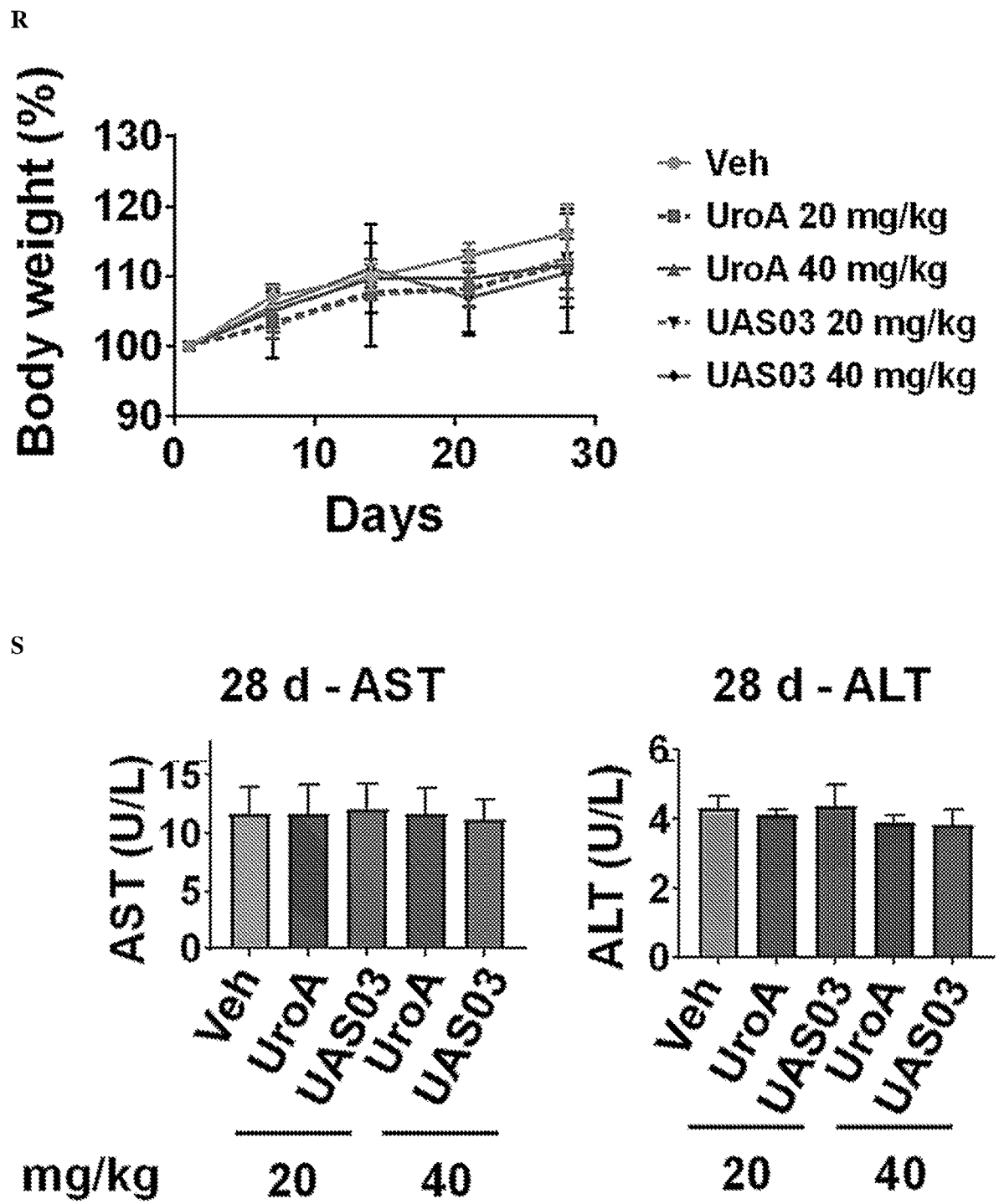

The physiological relevance of UroA/UAS03 regulated barrier function was examined in the 2,4,6-Trinitrobenzenesulfonic acid (TNBS)-induced colitis model (ANTONIOU et al. (2016) "The TNBS-induced colitis animal model: An overview" Ann Med Surg (Lond), Vol. 11, pp. 9-15.). Oral treatment with UroA/UAS03 (20 mg/kg at 12 h intervals) protected from TNBS-induced body weight loss (FIG. 4A), reduced disease activity index (DAI) score (FIG. 4B) and intestinal permeability (FIG. 4C). UroA/UAS03 treatment protected from TNBS-induced colon shortening (FIGS. 4D-E) and reduced weight to length ratio (FIG. 4F) suggesting decreased colonic inflammation. UroA/UAS03 treatment also reduced neutrophil infiltration as evident from myeloperoxidase (MPO) activity (FIG. 4G) as well as serum inflammatory markers such as IL-6, TNF-α, CXCL1 and IL-10 (FIG. 4H) that are hallmarks of ulcerative colitis. Consistent with these findings, H&E analysis of colon sections showed less tissue damage and inflammation scores (FIG. 4I). Furthermore, UroA/UAS03 also protected from TNBS-induced downregulation of Cldn4 in the colons of these mice (FIG. 4J). We further examined the effects of dose and frequency of UroA/UAS03 treatments as well as their preventive efficacy in mitigating colitis. As shown in FIG. 4K-P, UroA/UAS03 mitigated TNBS-induced colitis with a single treatment at 4 or 20 mg/kg body weight. The comparisons bodyweights at each time points suggest that TNBS treatment in all the groups led to decrease in body weight and treatment seems to decrease the loss of body weight, but did not reach significance (FIG. 4Q). However, treatments showed impact on other parameters such as protecting from shortening of colons, blocking inflammatory mediators. Supplementing wild type mice with UroA or UAS03 did not exhibit any signs of toxicity as evident from no observed changes in their body weights, CBC counts as well as serum ALT and AST levels (FIG. 4R-S).

Since UroA/UAS03 exhibited barrier protective activities by upregulating tight junction proteins, we investigated whether regular exposure to these metabolites would have sustained beneficial effects in preventing colitis. The prophylactic activity profile of UroA/UAS03 was examined in the TNBS-induced colitis model. WT mice were orally fed daily with vehicle or UroA/UAS03 for one week followed by TNBS administration to induce colitis. These mice did not receive any further UroA/UAS03. The treatment regimen and percent bodyweights are shown in FIG. 5A and FIG. 5H. The pre-treated mice were protected from TNBS-induced colon shortening and colonic inflammation (colon length/weight) similar to a therapeutic regimen (FIG. 5B-D). Pre-treatment also enhanced barrier function and decreased TNBS-induced inflammation (FIG. 5E-F). These results suggest that UroA/UAS03 mediated enhanced gut barrier function will likely have long-term beneficial effects in preventing colitis. In therapeutic regimen, mice were treated with UroA or UAS03 24 h post-TNBS, where mice develop severe colitis. In this setting, treatment with UroA/UAS03 also reversed the colitis phenotype by reducing shortening of colons, gut permeability and inflammation compared to vehicle treatment.

The therapeutic applications of UroA/UAS03 were also examined in the dextran sodium sulphate (DSS)-induced colitis model. DSS chemically disrupts the epithelial cell barrier and leads to increased penetration of bacteria resulting in inflammation and colonic tissue damage. As shown in FIG. 2N-O, the mice treated with UroA/UAS03 were protected from 3% DSS induced acute colitis. UroA/UAS03 treatment mice displayed overall decreased DAI scores during the disease progression. UroA/UAS03 treatments protected from shortening of colons, decreased gut permeability and reduced inflammation compared to vehicle treatment (FIG. 5I-M) at the end of experiment on day 15. Further, the therapeutic efficacies of UroA/UAS03 were also examined in a chronic DSS model, where mice were given 4 cycles of 2% DSS in drinking water for 7 days with an interval of 14 days in each cycle on regular water (FIG. 6A). Treatment with UroA/UAS03 protected from DSS-induced colitis as evident from decreased gut permeability (FIG. 6B), reduced shortening of colons (FIG. 6C-D), increased colon weight/length ratio (FIG. 6E), reduced inflammation (serum IL-6, IL-10, TNF-α as well as colonic tissue MPO levels) (FIG. 6F-G). Analysis of tight junction proteins in these mice also suggest that treatment with UroA/UAS03 enhanced the expression of Cldn4 (FIG. 6H). These results highlight the model independent beneficial activities of UroA/UAS03 in preserving the barrier integrity and mitigating colonic inflammation.

UAS03/UroA Mediated Protection Against Colitis May Use AhR-Nrf2 Pathways

Figure 7:
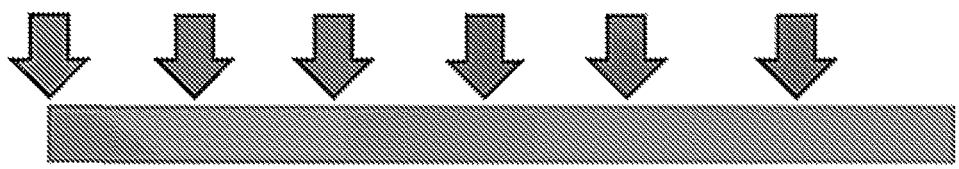
FIG. 7: UroA/UAS03 utilize Nrf2 pathways to mitigate colitis. (A-F) Colitis was induced using TNBS in C57BL/6 (WT) and Nrf2$^{-/-}$ mice (n=4-5/group 7-8 week old age). Mice were treated with Veh or UroA/UAS03 (20 mg/kg bodyweight) every 12 h post TNBS administration ending at 72 h. Representative data from two independent experiments is shown. (A) TNBS-induced colitis experimental design and treatment regimen. (B) Percent body weight loss (No TNBS– Solid black line; Veh+TNBS– Solid red line; UroA+TNBS– Solid blue line; UAS03+TNBS– Solid purple line), (C) representative colon images, (D) colon lengths, (E) gut permeability, (F) serum levels of IL-6 and TNF-α were determined. Statistical analysis was performed (unpaired t-test) using Graphpad Prism software. Error bars, ±SEM *$p<0.001$; $p<0.01$ *$p<0.05$.
Figure 7:
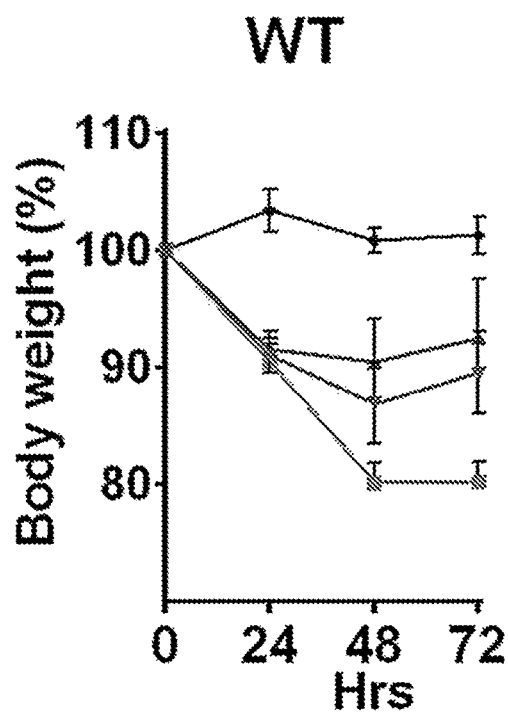
Figure 7:
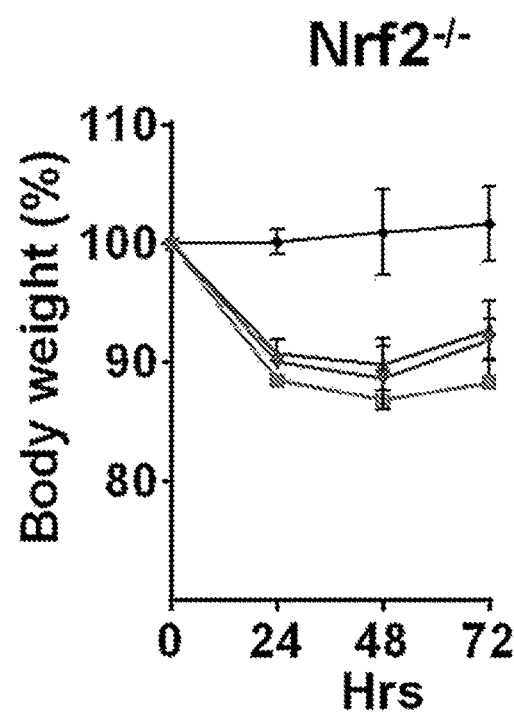
Figure 7:
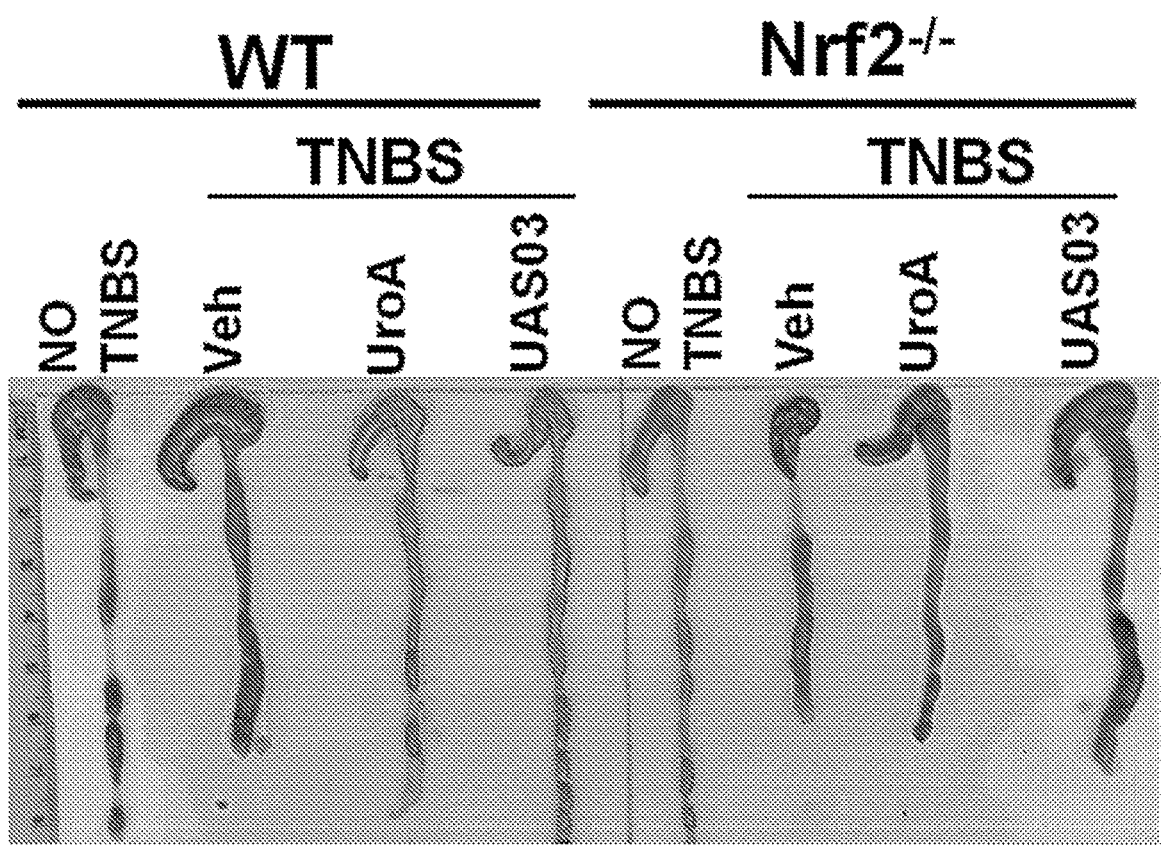
Figure 7:
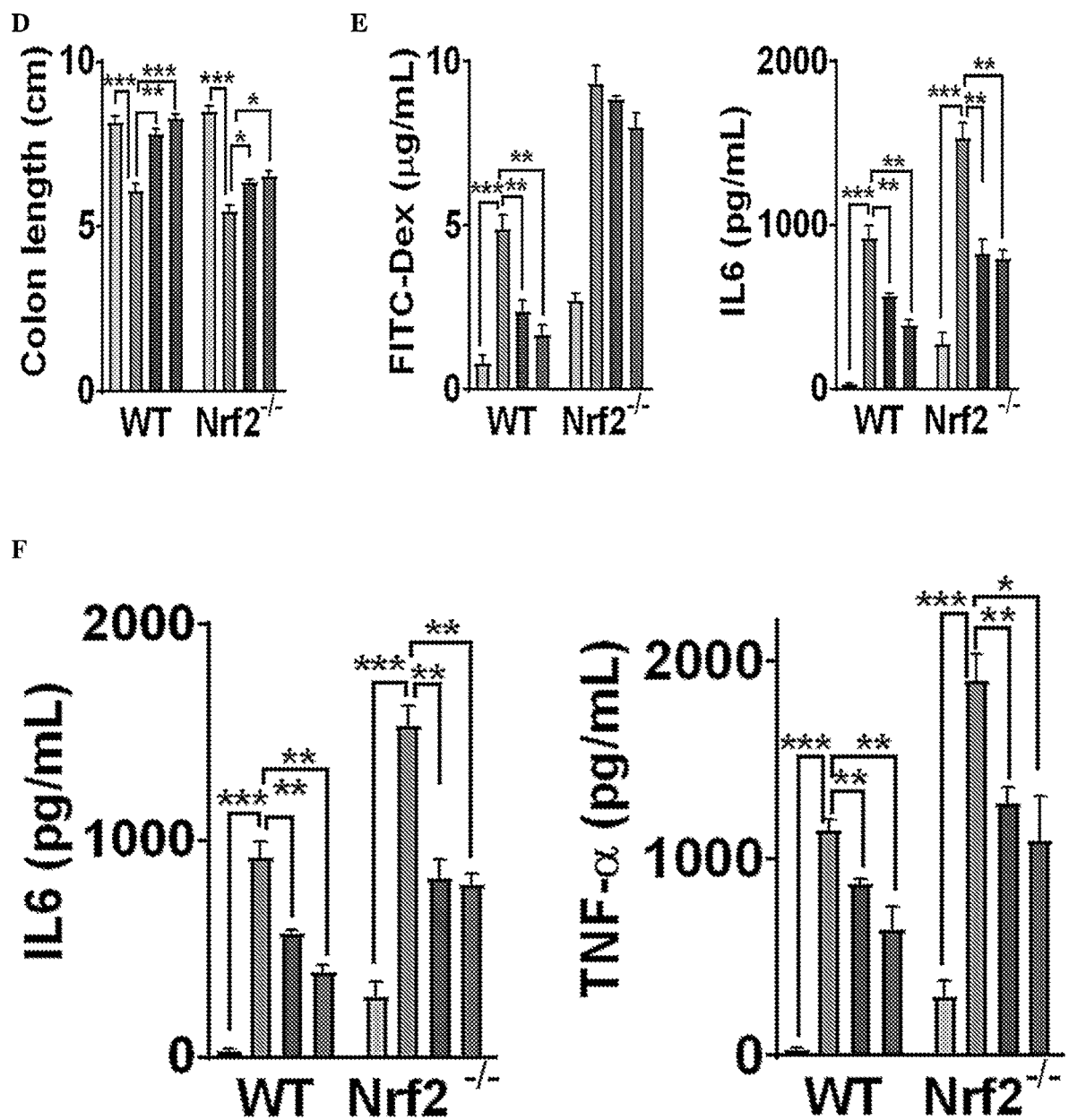
Figure 8:
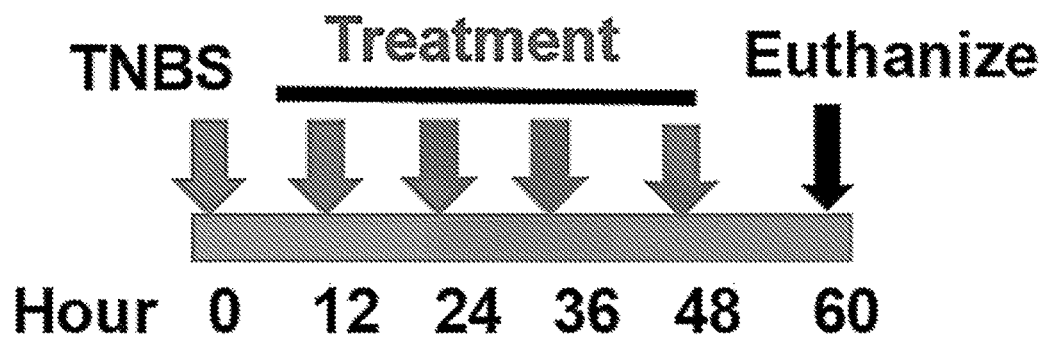
FIG. 8: UroA/UAS03 exert beneficial activities through AhR-dependent pathways. (A-F) Colitis was induced using TNBS in C57BL/6 (WT) and AhR$^{-/-}$ mice (n=4/group 7-8 week old age). Mice were treated with Veh or UroA/UAS03 (20 mg/kg bodyweight) every 12 h post TNBS administration and mice were euthanized at post 60 h TNBS administration. (A) TNBS-induced colitis experimental design and treatment regimen. (B) Percent body weight loss (No TNBS-Solid black line; Veh+TNBS– Solid red line; UroA+TNBS– Solid blue line; UAS03+TNBS– Solid purple line), (C) representative colon images, (D) colon lengths, (E) gut permeability, (F) serum levels of IL-6 and TNF-α were determined. Statistical analysis was performed (unpaired t-test) using Graphpad Prism software. Error bars, ±SEM *$p<0.001$; $p<0.01$ *$p<0.05$. (G) AhR-Nrf2 dependent tight junction protein regulation by UroA/UAS03. UroA/UAS03 (L:ligands) bind to AhR and activate its nuclear translocation to induce expression of Cyp1A1 and Nrf2. Further, UroA/UAS03 appears to cause Nrf2 dependent upregulation of tight junction proteins and enhanced barrier function. (H) LPS (50 ng/ml)-induced IL-6 levels were measured in the presence of Vehicle or UroA or UAS03 (0.1, 1, 10, 20, 30 and 50 µM) in bone marrow derived macrophages (BMDM) from wild type (WT), Nrf2$^{-/-}$ and AhR$^{-/-}$ mice. The data is representative of two independent experiments with triplicates. Statistical analysis was performed (unpaired t-test) using Graphpad Prism software. Error bars, ±SEM *$p<0.001$; $p<0.01$ *$p<0.05$.
Figure 8:
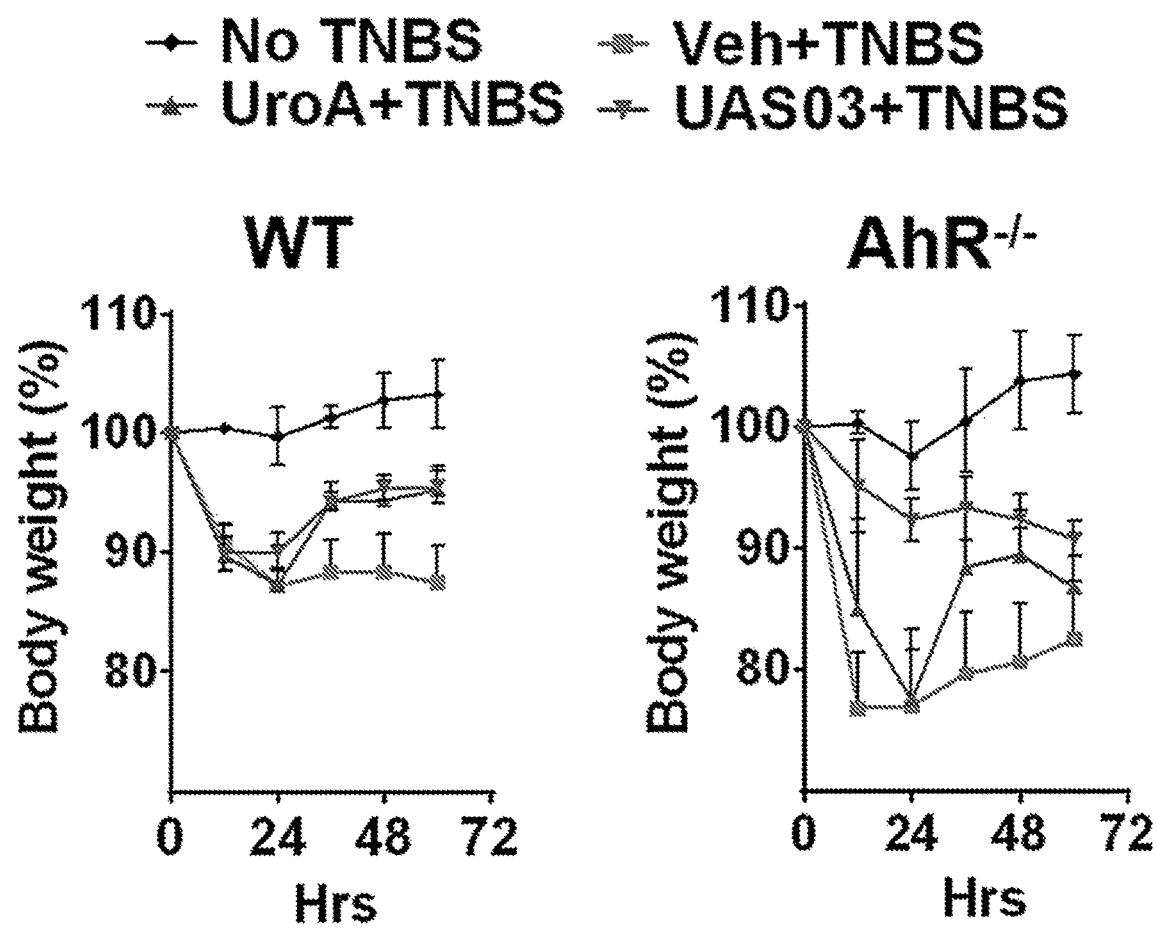
Figure 8:
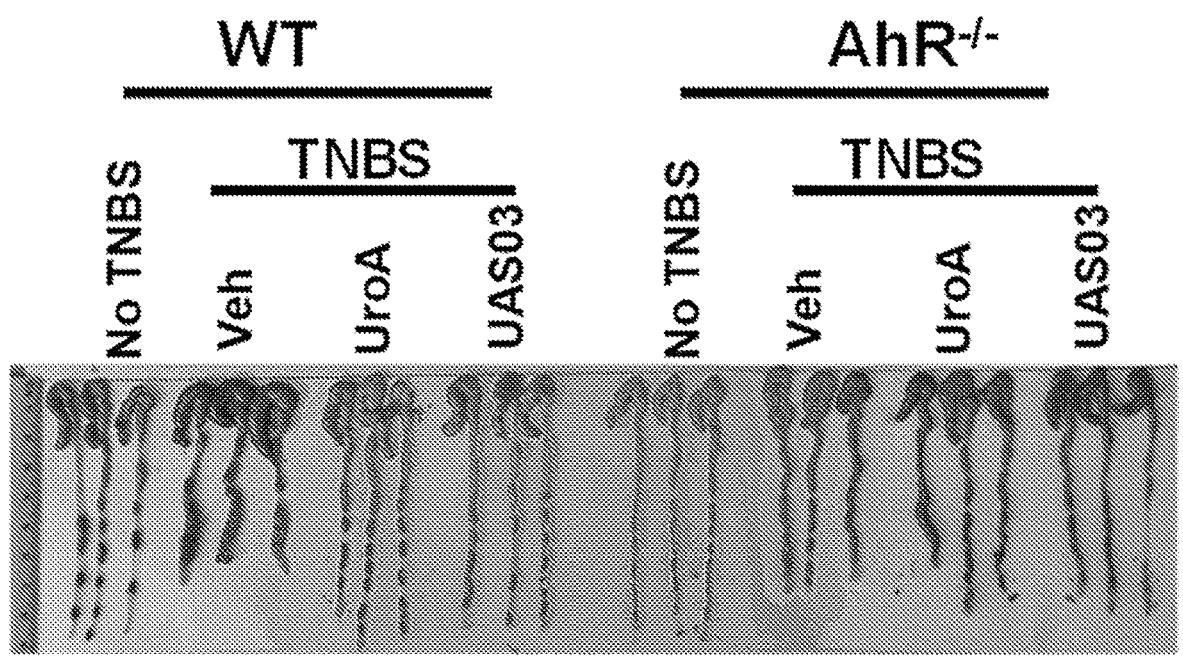
Figure 8:
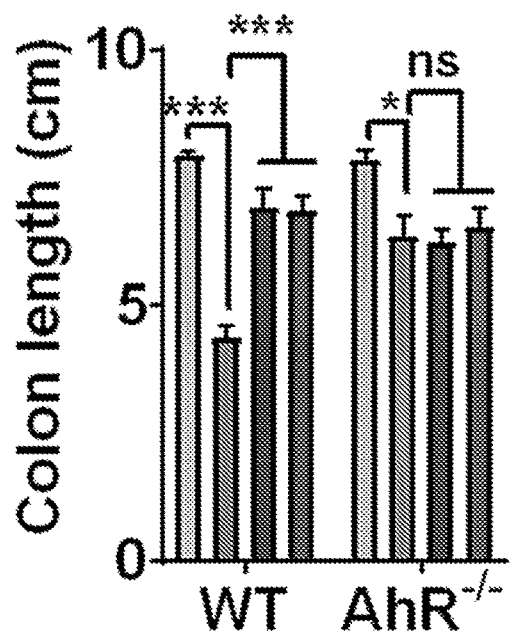
Figure 8:
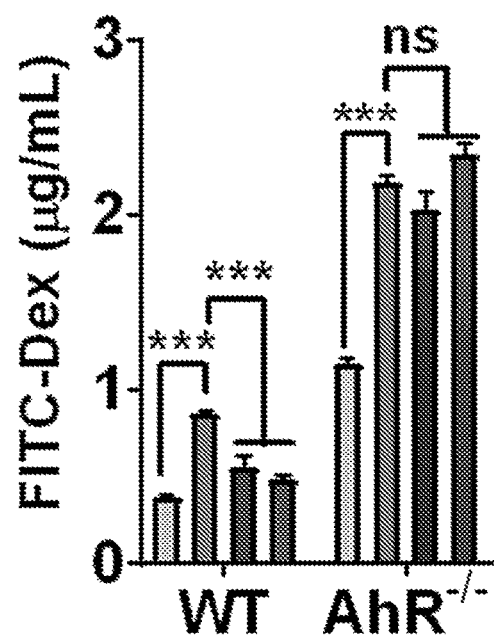
Figure 8:
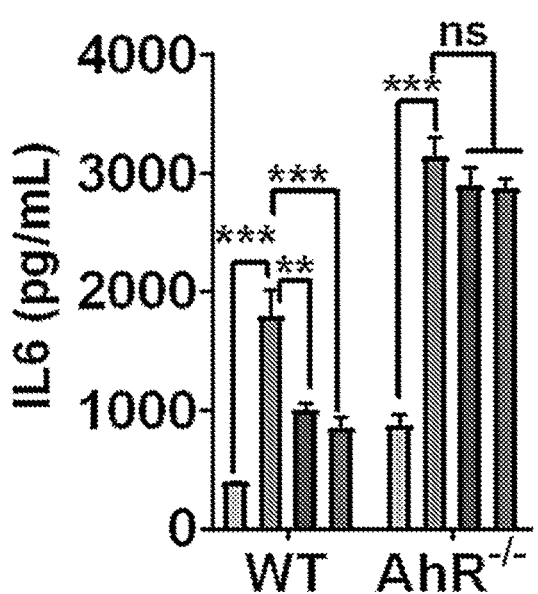
Figure 8:
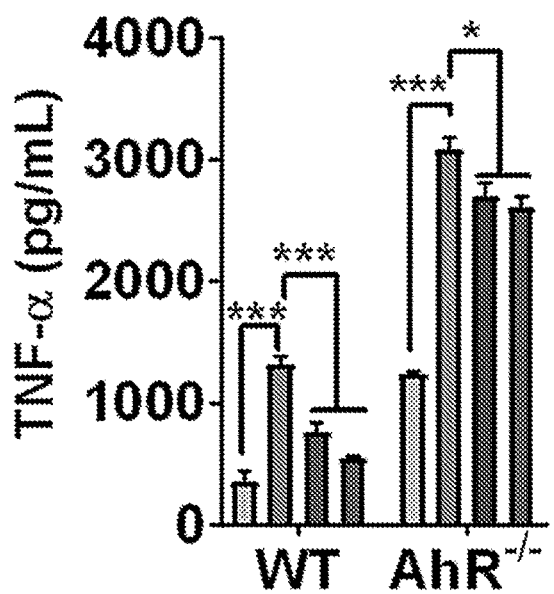
Figure 8:
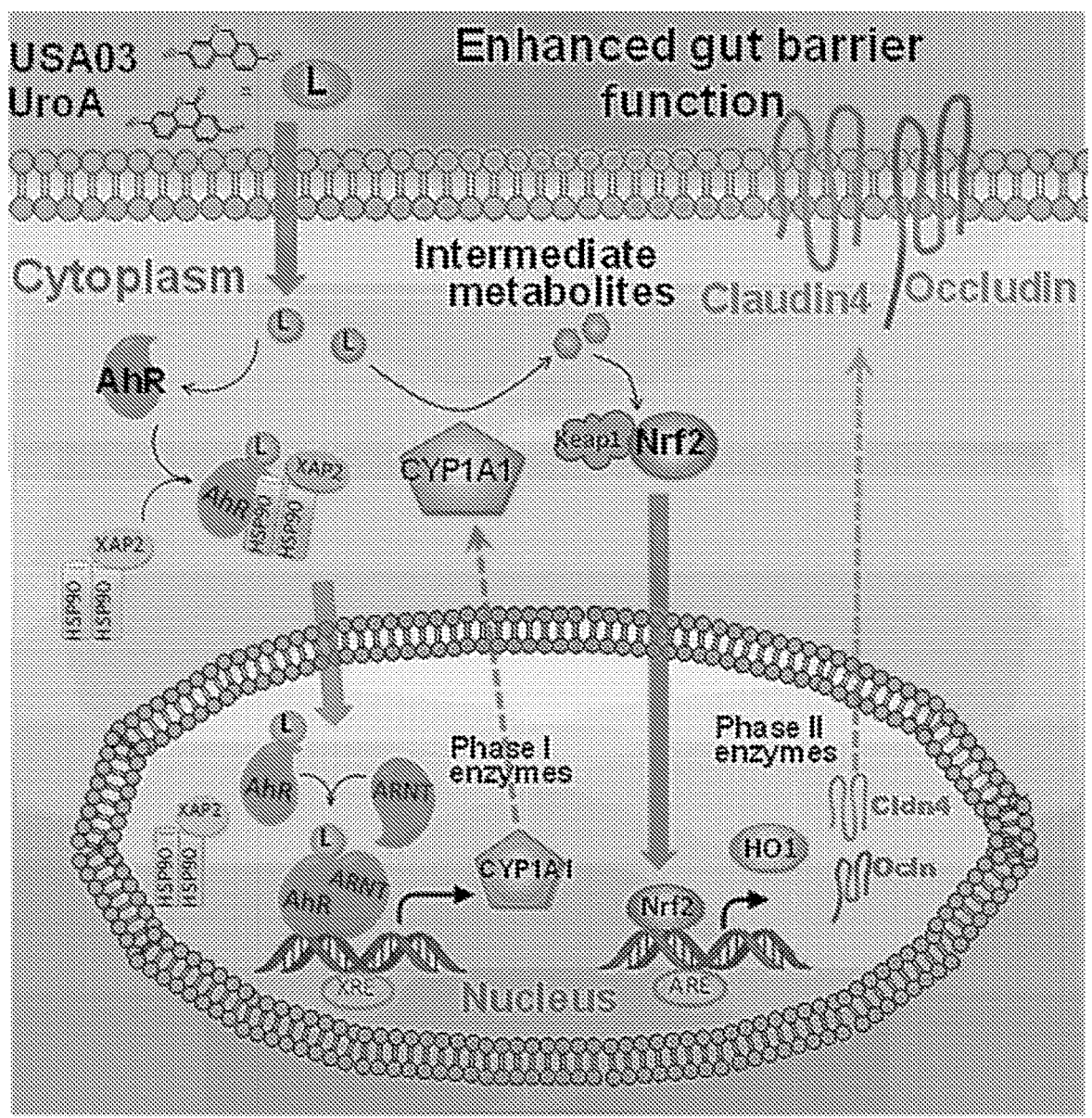
Figure 8:
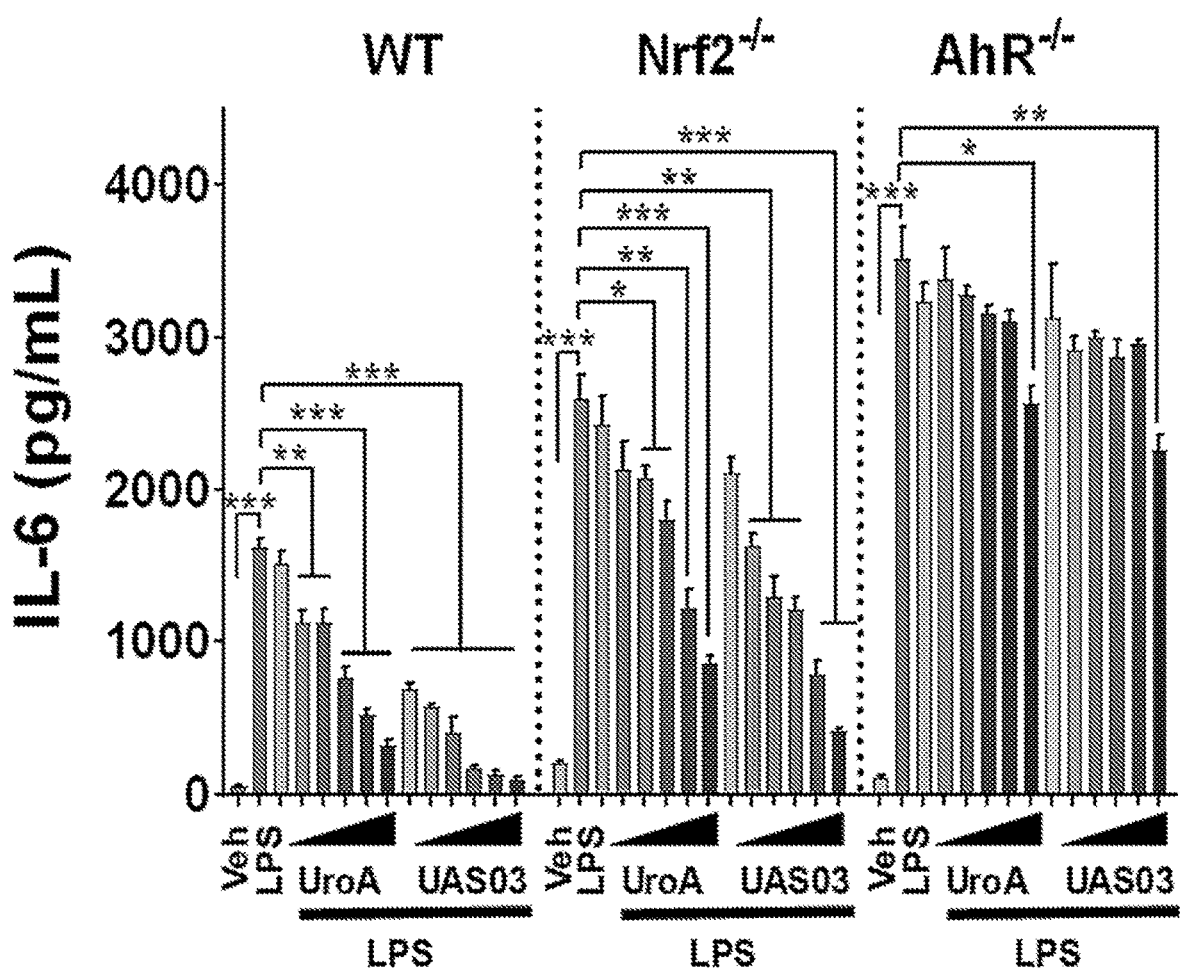
Figure 9:
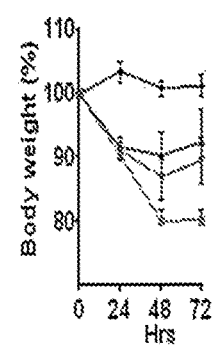
FIG. 9: (A) Detail analysis of percent body weight loss of data presented in FIG. 7B. The data is separately presented for each time point (No TNBS– Solid black line; Veh+TNBS– Solid red line; UroA+TNBS– Solid blue line; UAS03+TNBS– Solid purple line). (B) Detail analysis of percent body weight loss of data presented in FIG. 8B. The data is separately presented for each time point. (No TNBS– Solid black line; Veh+TNBS– Solid red line; UroA+TNBS– Solid blue line; UAS03+TNBS– Solid purple line). (C-G) UroA/UAS03 activate Nrf2-dependent pathways in BMDM. (C) Wild type BMDM were isolated and cultured for 7 days. BMDM were treated with Veh (0.01% DMSO) or UroA or UAS03 (50 µM) for 6 h and total RNA was isolated. Nrf2 levels were measured using SyBR green Real Time PCR method. (D) Veh or UroA or UAS03 treated BMDM cell lysates were immunoblotted for Nrf2. (E) The nuclear and cytosolic fractions of BMDMs were immnunoblotted for Nr2. Lamin B and β-actin were used as normalizing proteins. (F) BMDM cells were grown on cover slip bottom fluorodishes overnight and treated with Vehicle or UroA (50 µM) or UAS03 (50 µM) for 6 h. The expression of Nrf2 was determined by immunofluorescence staining using anti-Nrf2 followed by secondary antibody tagged with Alexa-488 dye and DAPI was used to stain nucleus. The fluorescence images were captured using Nikon A1R confocal microscope at 60× magnification and green fluorescence (n=>15 cells) was measured using Nikon elements software. The scale bar indicates 25 μm. Statistics performed using unpaired t-test using Graphpad Prism software. Error bars, ±SEM *p<0.001; p<0.01; *p<0.05 (G) BMDMs treated with Vehicle or UroA (50 μM) or UAS03 (50 μM) for 24 h and mRNA levels was estimated using SyBR RT PCR as described in methods. (H-I) UroA/UAS03 reduce LPS-induced NF-κB activation in AhR-dependent manner. NF-κB activation was evaluated by EMSA assays. Raw 267.4 cells (H) or BMDMs (I) were treated with LPS (50 ng/mL) in the presence or absence of UroA or UAS03 (25 μM) for 6 hr and nuclear extract (2 μg) was used to determine NF-κB binding by EMSA. (J-L) UroA/UAS03 mediate anti-inflammatory activities through AhR. (J-K) The IL-6 data represented as fold over its own basal level. The absolute values are provided in main figures (FIGS. 7F and 8F). Serum IL-6 changes in TNBS-induced colitis model in (J) WT and Nrf2$^{-/-}$ mice; (K) WT and AhR$^{-/-}$ mice. (L). LPS-induced levels of IL-6 in the presence or absence of UroA/UAS03. The absolute values and detailed legend are provided in FIG. 8H. The fold change over basal was calculated using its own control. WT+Veh or Nrf2$^{-/-}$+Veh or AhR2$^{-/-}$+Veh were used to normalize to 1. Statistics performed using unpaired t-test using Graphpad Prism software. Error bars, ±SEM *p<0.001; p<0.01; *p<0.05.
Figure 9:
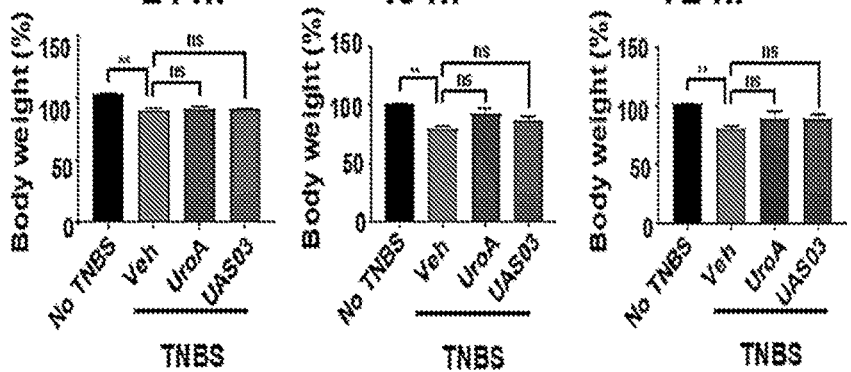
Figure 9:
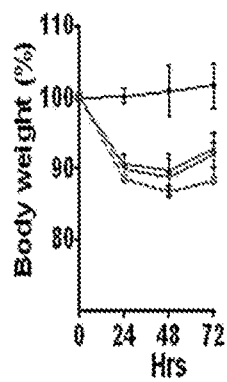
Figure 9:
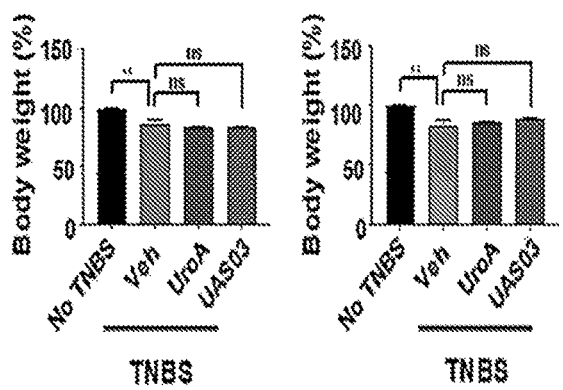
Figure 9:
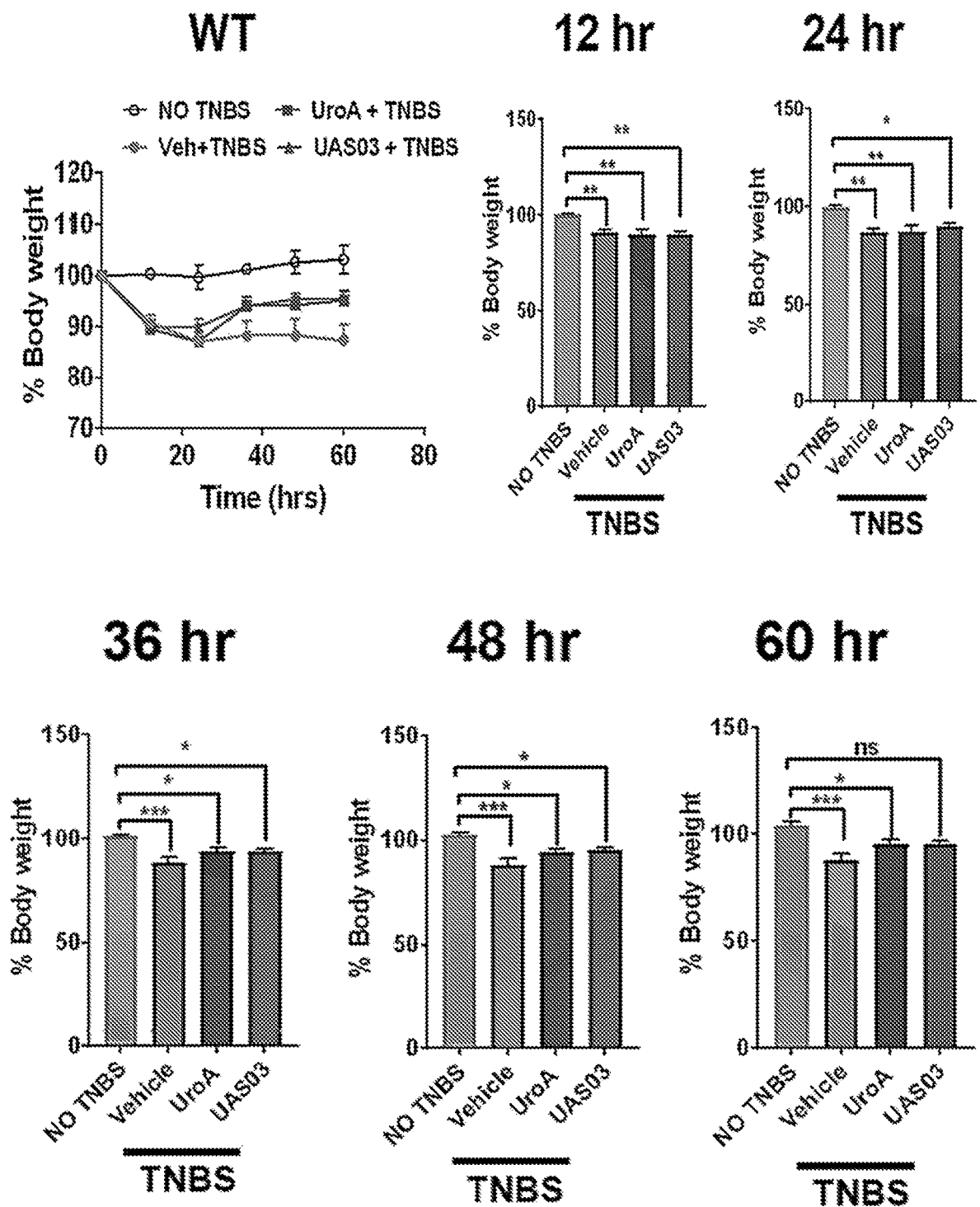
Figure 9:
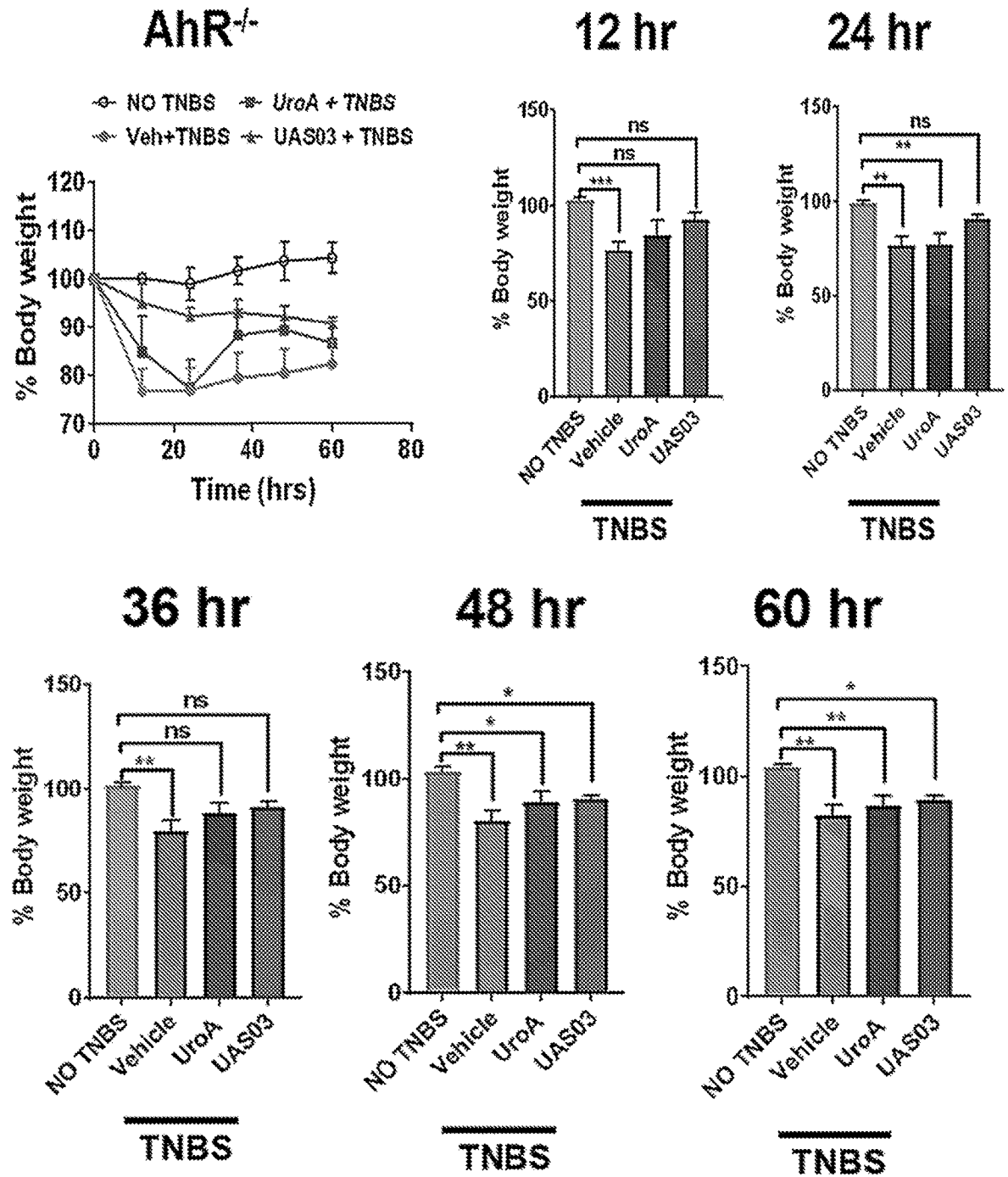
Figure 9:
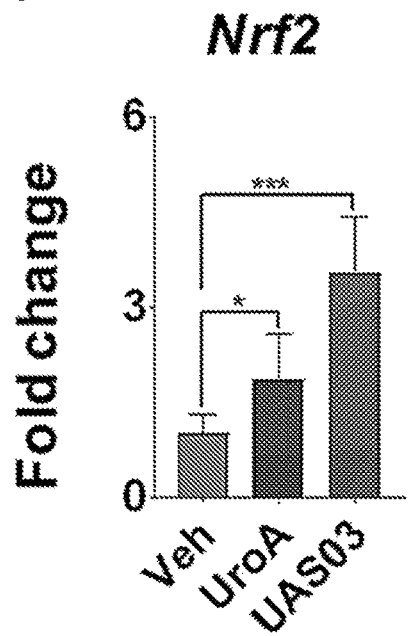
Figure 9:
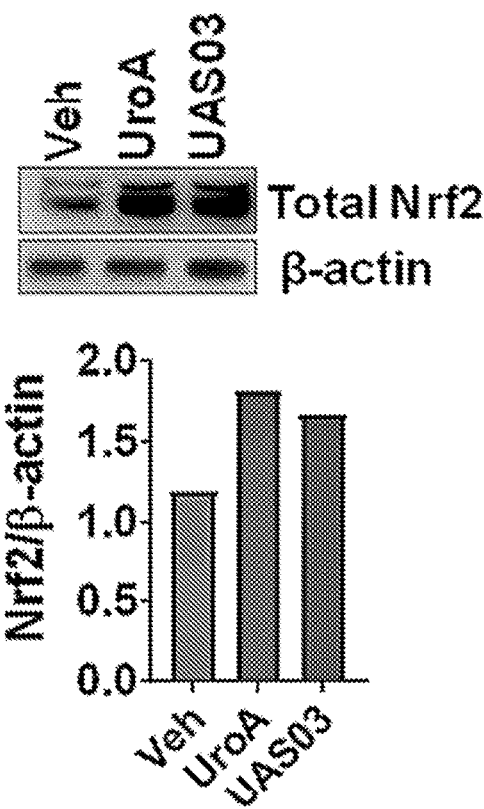
Figure 9:
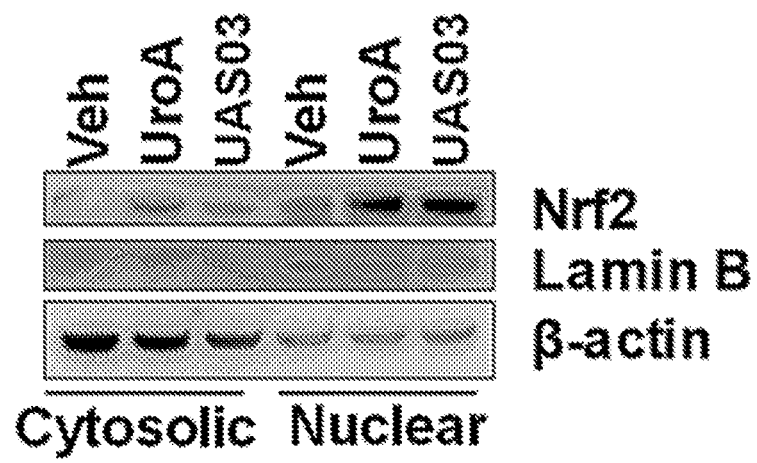
Figure 9:
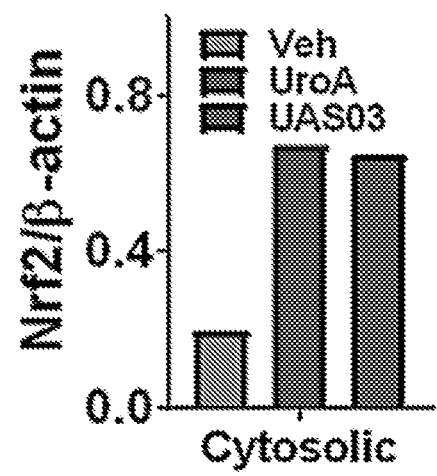
Figure 9:
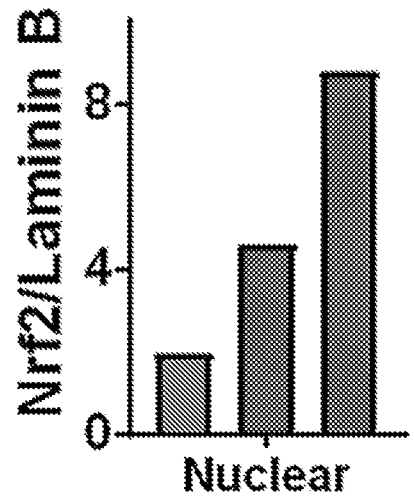
Figure 9:
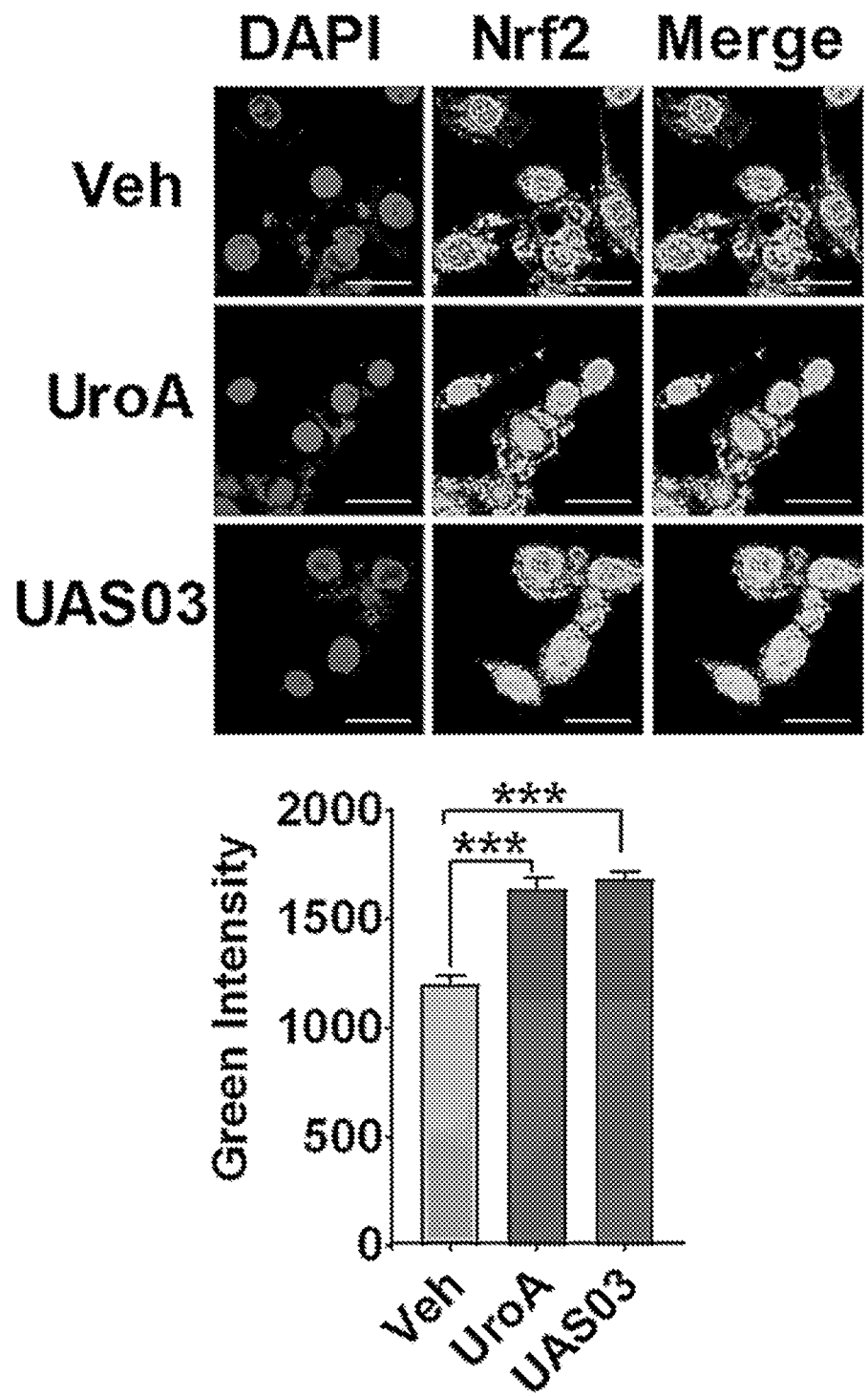
Figure 9:
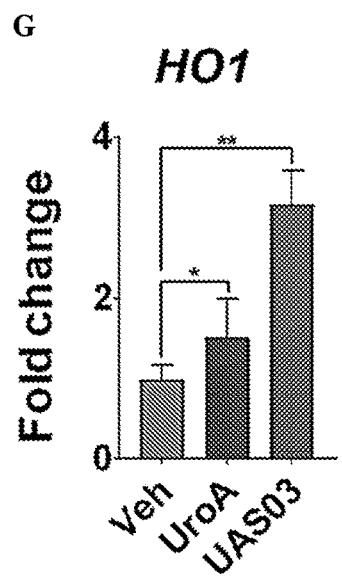
Figure 9:
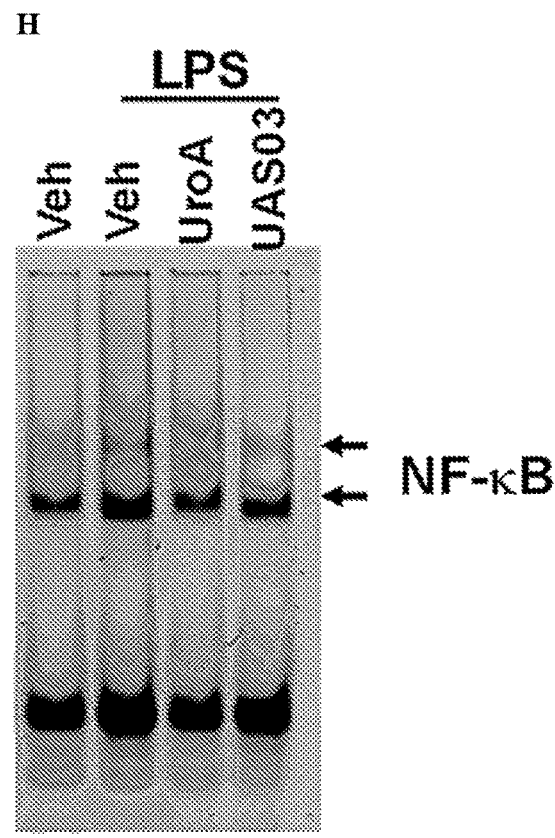
Figure 9:
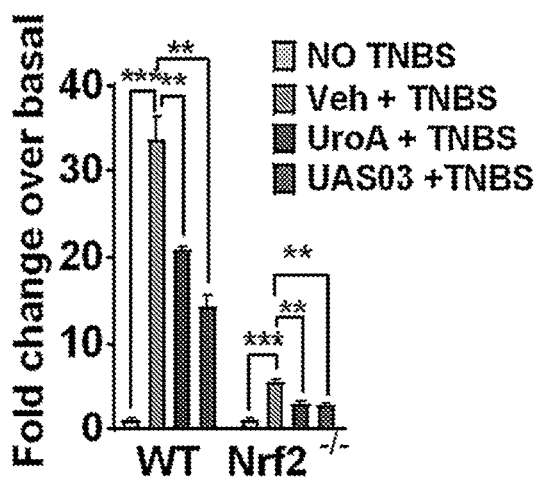
Figure 9:
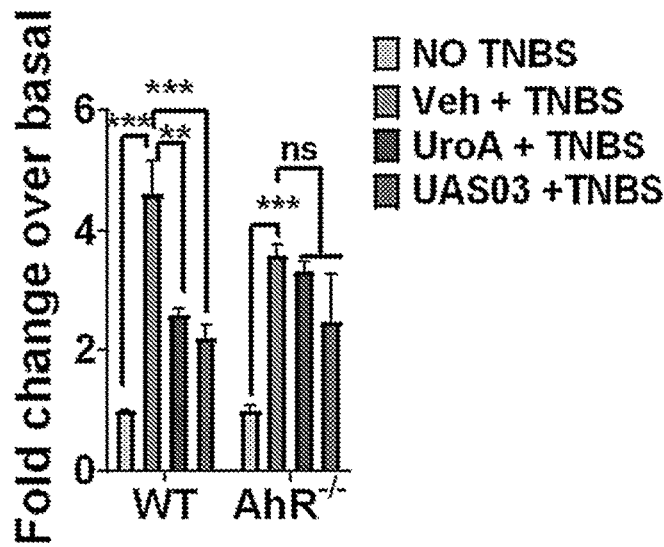
Figure 9:
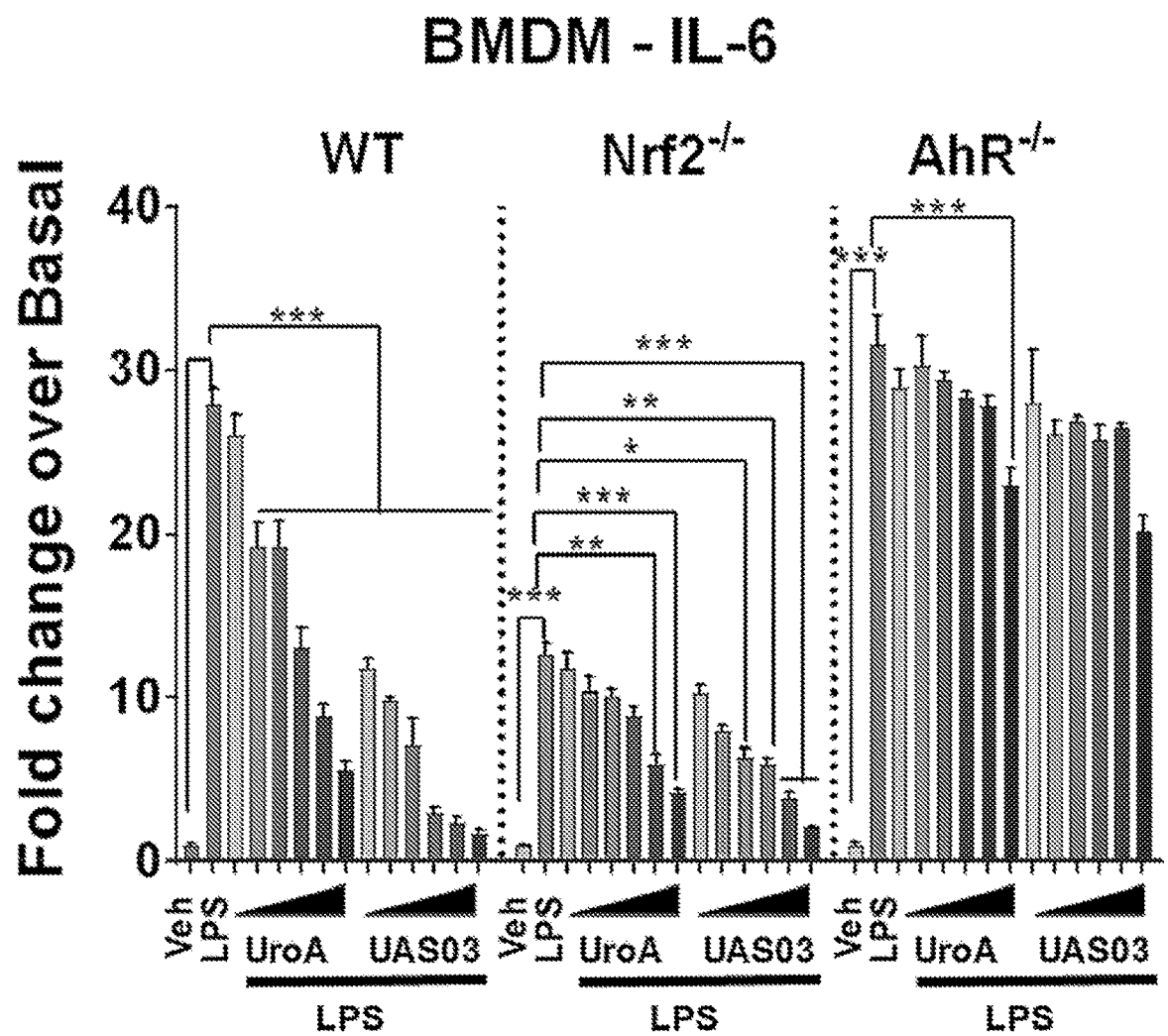

The studies described above indicated the role of AhR-Nrf2 pathway in UroA/UAS03 enhanced barrier function. To examine the relevance of these pathways in colitis, we tested the in vivo use of Nrf2 (FIG. 7) and AhR (FIG. 8). Treatment of Nrf2$^{-/-}$ mice with UroA/UAS03 did not appear to restore body weight loss caused by TNBS-induced colitis (FIGS. 7A-B and FIG. 9A) or protect from shortening of colons (FIG. 7C). UroA/UAS03 treatment did not enhance barrier function in Nrf2$^{-/-}$ mice as evident from similar FITC-dextran leakage in UroA/UAS03 treated mice compared to vehicle treatment (FIG. 7D). These results demonstrated that UroA/UAS03 enhanced gut barrier integrity involves the expression of Nrf2. UroA/UAS03 partially reduced serum inflammatory mediators such as IL-6 and TNF-α levels in Nrf2$^{-/-}$ mice (FIG. 7E), suggesting that UroA/UAS03 could mediate some of the anti-inflammatory activities in Nrf2-independent manner. To define the role of AhR in UroA/UAS03 mediated protective activities, the TNBS-induced colitis model was executed in AhR$^{-/-}$ mice along with wild type mice (FIG. 8A). As expected AhR$^{-/-}$ mice were more susceptible to TNBS-induced colitis model as evident from rapid loss of body weight (FIG. 8B and FIG. 9B). Therefore, we terminated the experiment at post 60 h TNBS administration (FIG. 8A). Treatment with UroA/UAS03 did not appear to protect from shortening of colon lengths in AhR$^{-/-}$ mice compared to wild type mice (FIG. 8C-D). Additionally, UroA/UAS03 did not appear to correct the barrier dysfunction in AhR$^{-/-}$ mice as evident from in vivo permeability assays (FIG. 8E). Analysis of serum inflammatory mediators suggest that UroA/UAS03 did not appear to reduce IL-6 and slightly reduced the TNF-α in AhR$^{-/-}$ mice, whereas UroA/UAS03 treatments reduced IL-6 and TNF-α in wild type mice as observed above (FIG. 8F). Based on these results we propose that UroA/UAS03 exert protective barrier functional activities through AhR-Nrf2 dependent pathways by inducing tight junction proteins (FIG. 8G).

Since the macrophages can be mediators of colonic inflammation in IBDs, we determined if UroA/UAS03 mediated anti-inflammatory activities are involved in the AhR-Nrf2 pathways in macrophages. First, we examined whether UroA/UAS03 activates Nrf2-dependent pathways in macrophages. The results showed that treatment with UroA/UAS03 upregulated Nrf2 expression and induced its nuclear translocation, as well as upregulation of Nrf2-target genes such as HO1 expression in macrophages (FIG. 9C-G). Further, analysis of UroA/UAS03 mediated down regulation of LPS-induced IL-6 production in macrophages from WT, Nrf2$^{-/-}$ and AhR$^{-/-}$ mice showed that LPS-induces much higher levels of IL-6 in Nrf2$^{-/-}$ and AhR$^{-/-}$ macrophages relative to WT (FIG. 8H). UroA/UAS03 also reduced the NF-κB activation in an AhR-dependent manner in macrophages (FIG. 9H). AhR$^{-/-}$ BMDM are hyper responsive to LPS stimulation as evident from increased NF-κB activation as well as increased levels of IL-6 compared to wild type (FIG. 8H and FIG. 9I). Despite lowering of IL-6 levels by UroA/UAS03 in Nrf2$^{-/-}$ macrophages, these reduced levels are still higher compared to LPS-induced IL-6 in WT macrophages. When compared, the fold reduction upon treatments (FIG. 9J-L), UroA/UAS03 reduced IL-6 in Nrf2$^{-/-}$ similar to WT indicating Nrf2-independent anti-inflammatory activities both in vivo (TNBS model) and in vitro BMDM (LPS-induced IL-6). In contrast, UroA/UAS03 did not block LPS-induced IL-6 production in AhR$^{-/-}$ macrophages up to 30 NM as well as in AhR$^{-/-}$ mice in TNBS-induced colitis model suggesting that UroA/UAS03 mediate anti-inflammatory activities through AhR-dependent manner. AhR$^{-/-}$ BMDM slight decrease in IL-6 levels at 50 μM dose may suggest some of unknown AhR-independent anti-inflammatory activities. The results presented here highlight that single microbial metabolite regulates the barrier function in epithelial cells via the activating AhR-Nrf2 signaling pathways and also anti-inflammatory activities in AhR dependent pathways.

DISCUSSION

UroA and UAS03 increases overall gut health by enhancing barrier function in addition to their anti-inflammatory activities. UroA/UAS03 activate the phase I (AhR-Cyp1A1) and phase II (Nrf2-anti-oxidative pathways) metabolic pathways to enhance expression of tight junction proteins and inhibit inflammation. We further demonstrate that treatment with these compounds mitigated colitis both in preventive and therapeutic settings.

Our approach of searching for an epithelial cell function for these metabolites by RNA-Seq analysis revealed several clues for their function as well potential mechanisms. UroA/UAS03 mediated up regulation of tight junction proteins (e.g., Cldn4, Ocln and ZO1) and protection from LPS induced leakage in epithelial monolayers showed that these metabolites clearly play a role in the regulation of barrier function. Tight junctions consist of both transmembrane proteins (e.g., occludin, claudins, junctional adhesion molecules and tricellulin) as well as peripheral membrane proteins (e.g., ZO-1 and cingulin) to regulate paracellular permeability and maintain gut barrier function. The disruption of tight junctions leads to barrier dysfunction and is implicated in IBDs and other disorders.

Our RNA-seq studies and expression analysis showed that in addition to upregulation of Cldn4, UroA also induced the expression of Cyp1A1 and HO1 in colon epithelial cells. Since Cyp1A1 and HO1 represent the activation of phase I and phase II drug metabolic pathways, these results suggested the potential involvement of AhR and Nrf-2 in mediating UroA/UAS03 functions. AhR is a nuclear transcription factor that responds to both xenobiotic and endogenous ligands leading to cell-specific gene regulation and cellular functions. AhR activation is responsible for the induction of multiple Phase I and Phase II xenobiotic chemical metabolizing enzymes such as Cyp1A1. Our studies revealed that UroA/UAS03 treatments induced the expression and nuclear translocation of AhR and enhanced transcription of XRE-target genes as well as induced Cyp1A1 enzyme activities without exhibiting toxicity.

UroA/USA03 did not appear to exert their activities in cells lacking AhR or in AhR$^{-/-}$ colon explants as well as in AhR$^{-/-}$ mice suggesting a role for the AhR pathway in mediating UroA/UAS03 activities. Our current studies highlight this pathway in epithelial cells to regulate tight junction proteins and barrier function.

Figure 2:
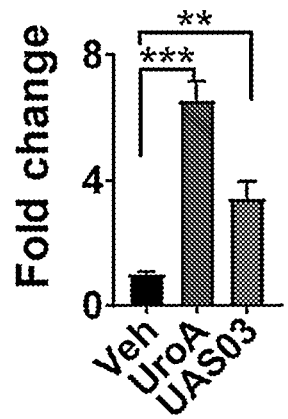
FIG. 2: UroA/UAS03 enhance tight junction proteins in AhR dependent manner. (A) HT29 cells were treated with vehicle (DMSO-0.01%)/UroA/UAS03 (50 µM) for 24 h. mRNA levels of Cytochrome P450 1A1 (Cyp1A1) was measured by RT PCR. (B) Cyp1A1 protein levels were measured using immunoblots and quantified band intensities by Image J software. (C) Cyp1A1 enzyme activity was measured by P450-Glo Cyp1A1 assay. HT29 cells were treated with UroA or UAS03 (0.1, 1, 10, 25, 50 µM) or FICZ (0.1, 1, 10, 25, 50 nM) for 24 h and enzyme Cyp1A1 activity was measured. (D) HT29 cells treated (quadruplicate wells) with UroA or UAS03 (50 µM) or TCDD (10 nM) or FICZ (100 nM) or BNF (50 µM) for 24 h and Cyp1A1 enzyme activity was measured using EROD assay as described in methods. Statistics performed using unpaired t-test using Graphpad Prism software. Error bars, ±SEM; $*p<0.001$; $p<0.01$; $p<0.05$. (E) C57BL/6 and AhR$^{-/-}$ (n=3) mice were treated orally with Vehicle (0.25% CMC), UroA or UAS03 (20 mg/kg) for 1 week and Cyp1A1 activity was measured in colons and livers by ethoxyresorufin-O-deethylase (EROD) assay. (F-H) In vivo Cyp1A1 enzyme activities. (F-G). C57BL/6 (n=3, 7 week old age) mice were treated orally with Vehicle (0.25% Na-CMC), or UroA (20 mg/kg/day) or UAS03 (20 mg/kg/day) for one week. 0-naphthoflavone (BNF, 40 mg/kg/day) or 5,11-Dihydroindolo[3,2-b]carbazole-6-carboxaldehyde (FICZ, 1 µg/mouse/day) were delivered i.p daily for one week. At day 7, the mice were euthanized and microsomes from colon and liver were isolated. The Cyp1A1 enzyme activity was measured using EROD and P450-Glo Cyp1A1 assay methods. (H) C57BL/6 (n=3, 7 week old age) mice were treated i.p. with Vehicle or UroA (5 mg/kg/day) or UAS03 (5 mg/kg/day) or FICZ, (1 µg/mouse/day) for week. The Cyp1A1 enzyme activities were measured from microsomes isolated from colon and liver tissues by P450-Glo Cyp1A1 assay method. Statistics were performed using unpaired t-test using Graphpad Prism software. Error bars, ±SEM * p<0.001; ** p<0.01; *p<0.05. ns: not significant. (I) The cells expressing AhR-reporter (luciferase) were treated with Veh or UroA/UAS03 or ellagic acid (EA) or MeBio (AhR high affinity ligand) for 6 h and fold change of luminescence over vehicle treatment was measured. (J) Immunofluorescence confocal images of HT29 cells treated with vehicle/UroA/UAS03 (50 µM) for 6 h. The cells were stained with anti-AhR antibody (red) and DAPI (blue). Relative fluorescence (n=~20 cells) in the cytosol and nucleus was measured. The scale bar indicates 10 µm. (K) AhR levels in cytosol and nuclear fractions of HT29 cells treated for 2 h with Veh or UroA/UAS03 (50 µM). (L) AhR or (M) Cyp1A1 was knocked down using siRNA in HT29 cells and the cells were treated with vehicle/UroA/UAS03 (50 µM) for 24 h and immnunoblots were performed to detect expression of AhR, Cyp1A1 and Cldn4. Scrambled (Sc) siRNA transfections were used as controls. Immunoblots were quantified using Image J software. The data is representative of two independent repeats with triplicate wells for each treatment. (N—O) UroA/UAS03 induce Cldn4 in AhR and Cyp1A1 dependent manner. Expression of (N) AhR or (O) Cyp1A1 was suppressed using respective siRNAs and Cldn4 expression was evaluated upon UroA/UAS03 treatments as described in FIGS. 2L-M. These are additional biological replicates (n=3 for AhR siRNA and n=4 for Cyp1A1 siRNA) of immunoblots and were used for quantification in FIGS. 2L-M. Statistics performed using unpaired t-test using Graphpad Prism software. (P)—(S) Expression of Cyp1A1 appears to play a role in UroA/UAS03 mediated upregulation of Cldn4. Cyp1A1 gene was deleted using CRISPR/Cas9 method in HT29 cells. (P) The basal level expression of Cldn4 were examined in parental HT29 or Cyp1A1 (CRISPR/Cas9) cells by Western blots and quantified. (Q) Parental HT29 or Cyp1A1 (CRISPR/Cas9) cells were treated with Veh or UroA or UAS03 (50 µM) for 24 h. Expression of Cyp1A1 and Cldn4 was measured by Western blots. Three independent replicates of Western blots were used to quantify band intensities by Image J software. (R) Cyp1A1 (CRISPR/Cas9) cells (n=3) were treated with Veh or UroA or UAS03 (50 µM) for 24 h and examined expression of Cldn4 and NQO1 and quantified. The fold changes were calculated by setting up vehicle's Cldn4 or NQO1/D-actin ratio average as 1 and compared with treatments. (S) mRNA levels of Cldn4 were measured by Real time PCR from treatments as described in FIG. 2Q. All in vitro studies were performed in triplicates. Error bars, ±SEM; *p<0.001; p<0.01; *p<0.05; ns: not significant.
Figure 2:
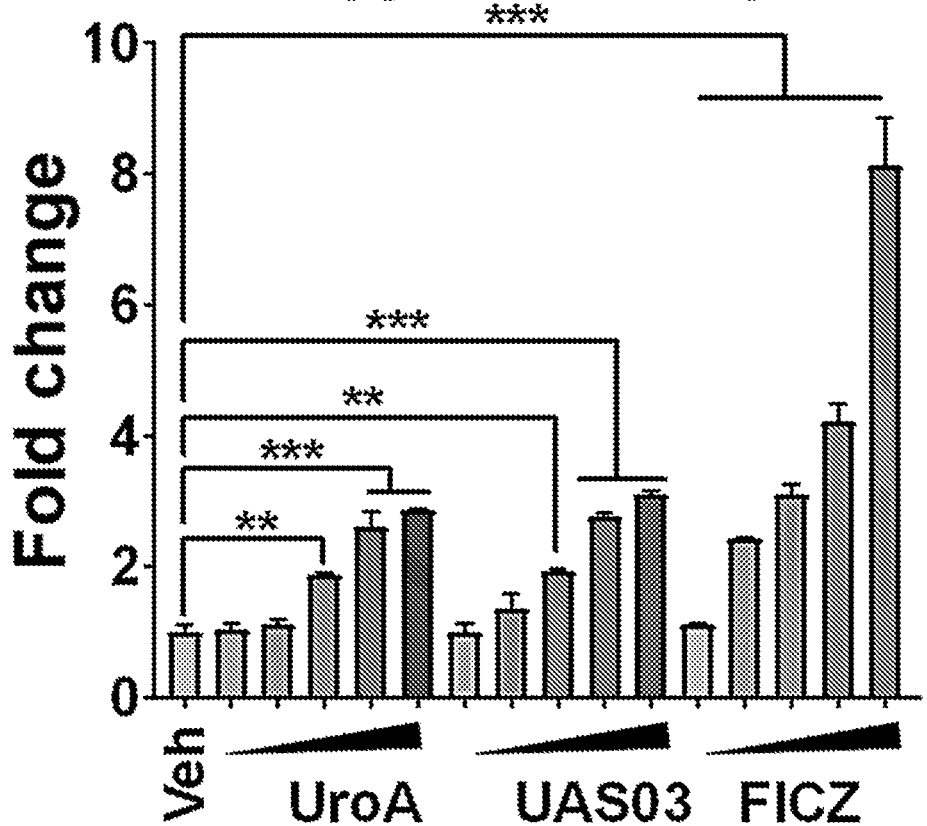
Figure 2:
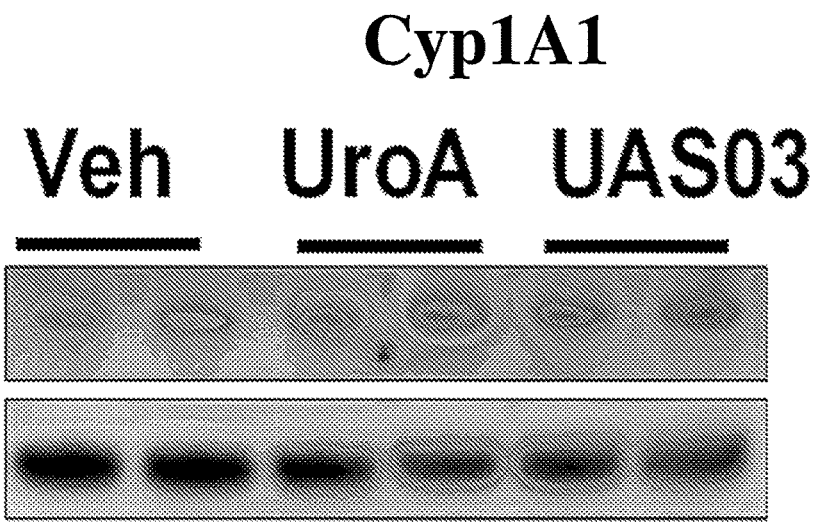
Figure 2:
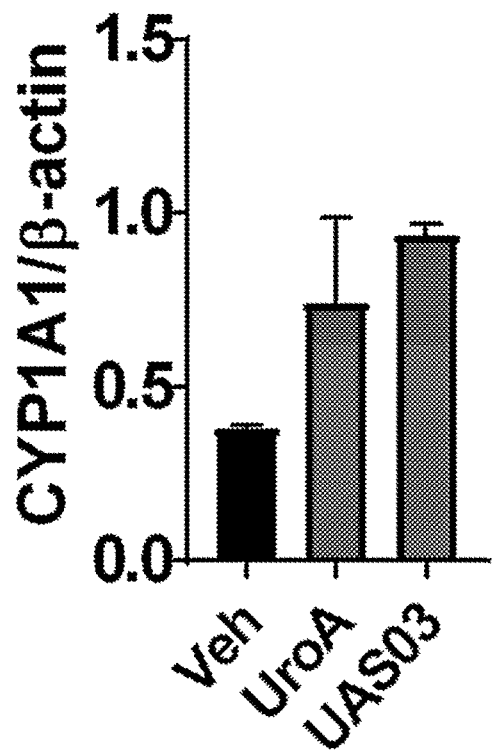
Figure 2:
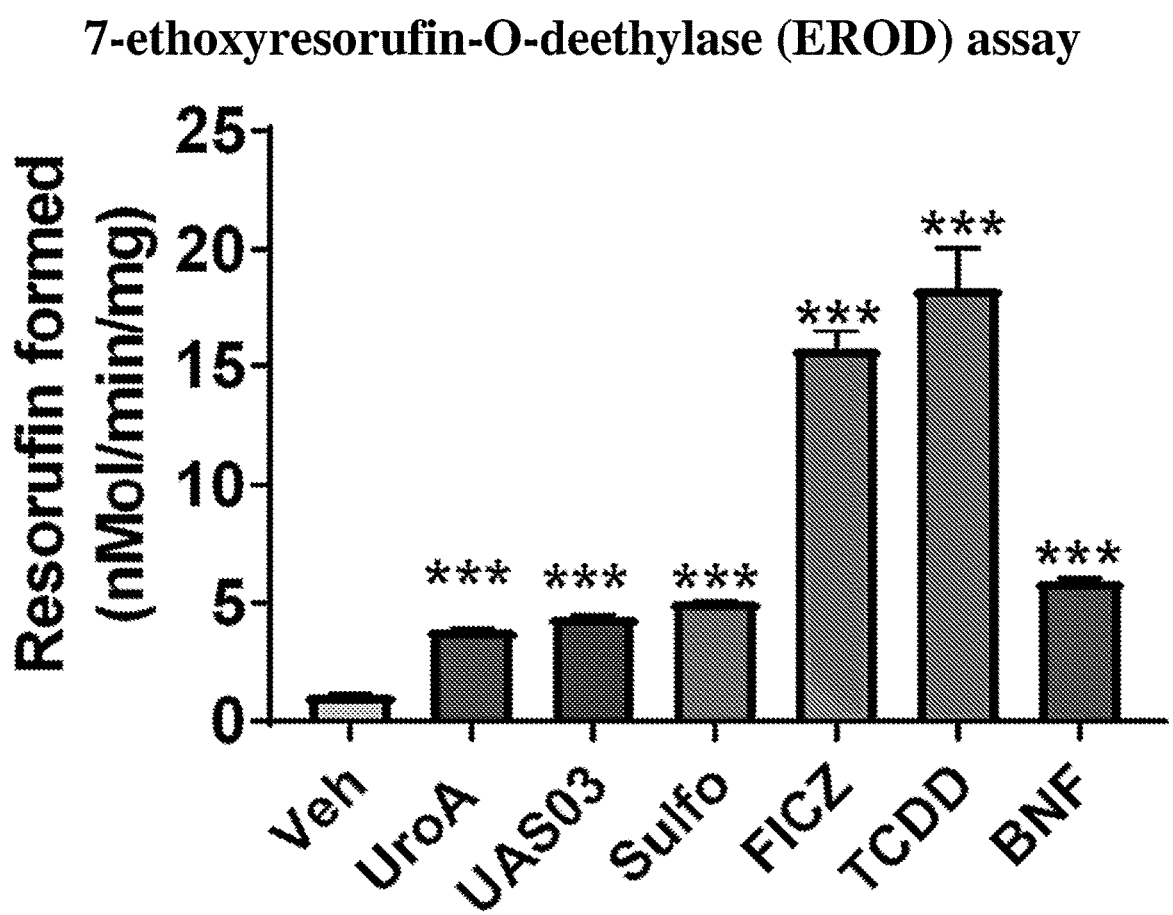
Figure 2:
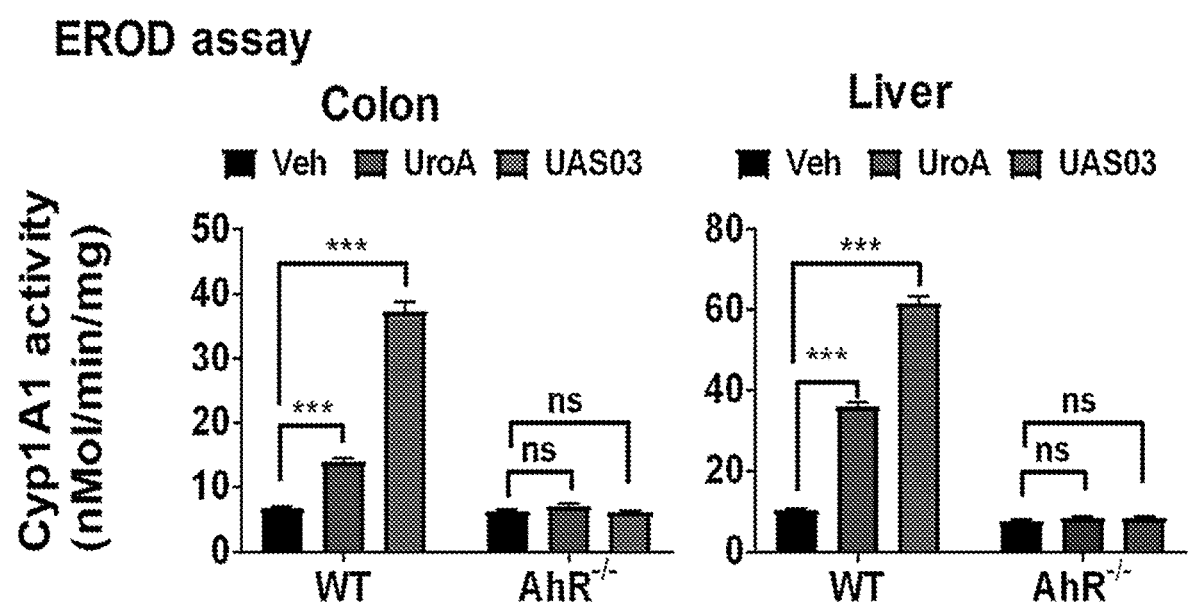
Figure 2:
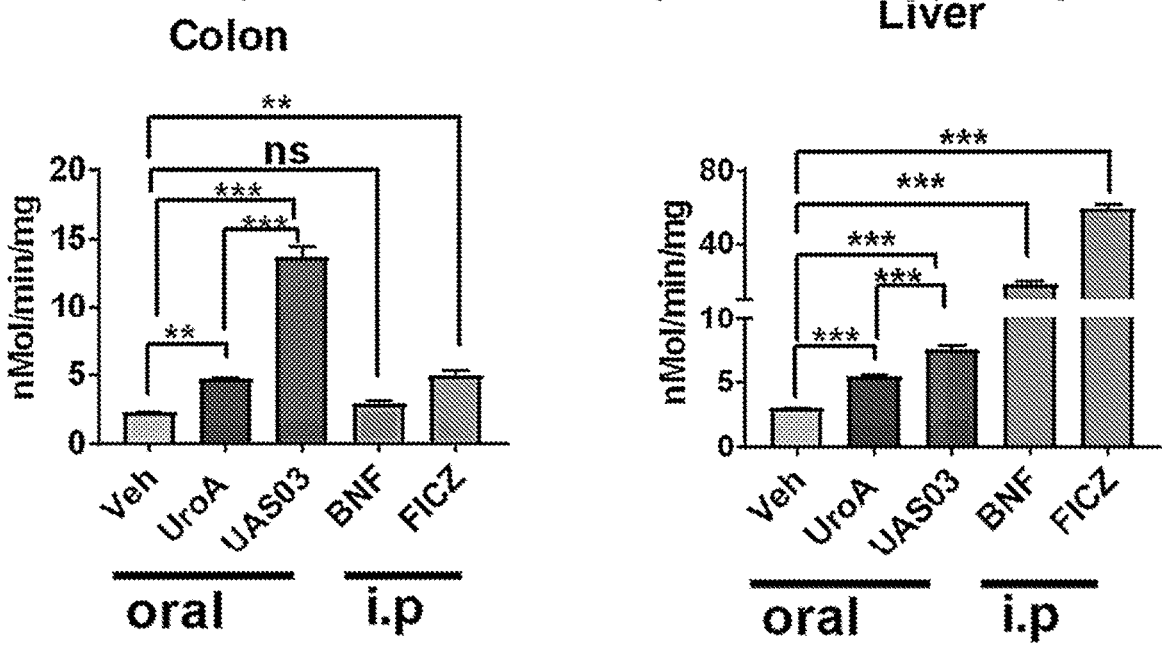
Figure 2:
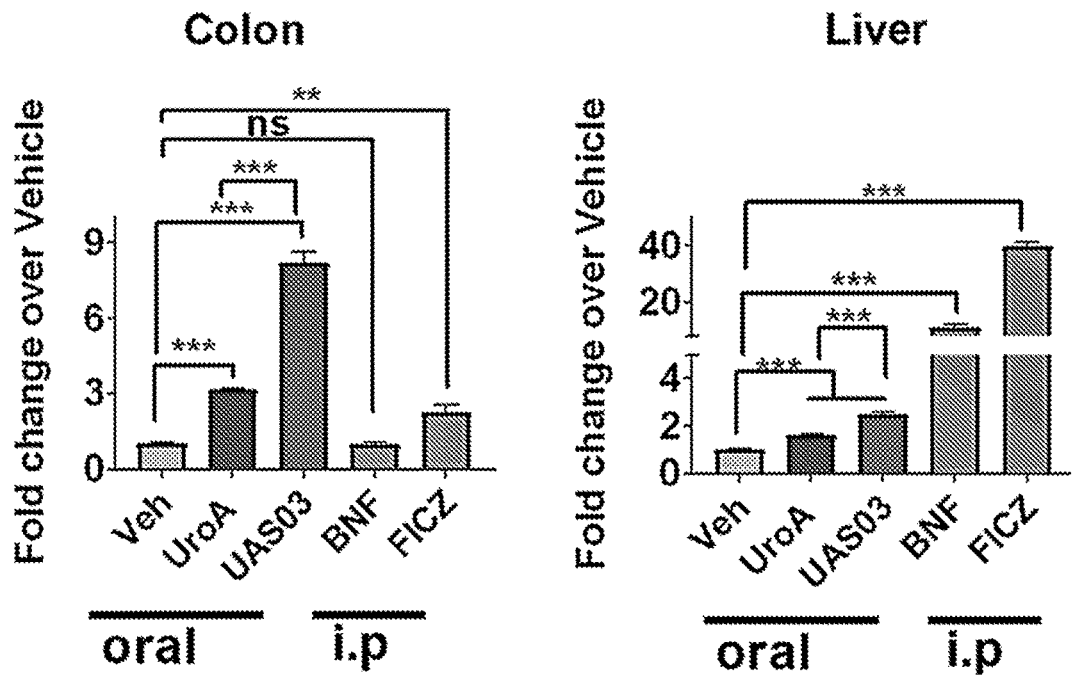
Figure 2:
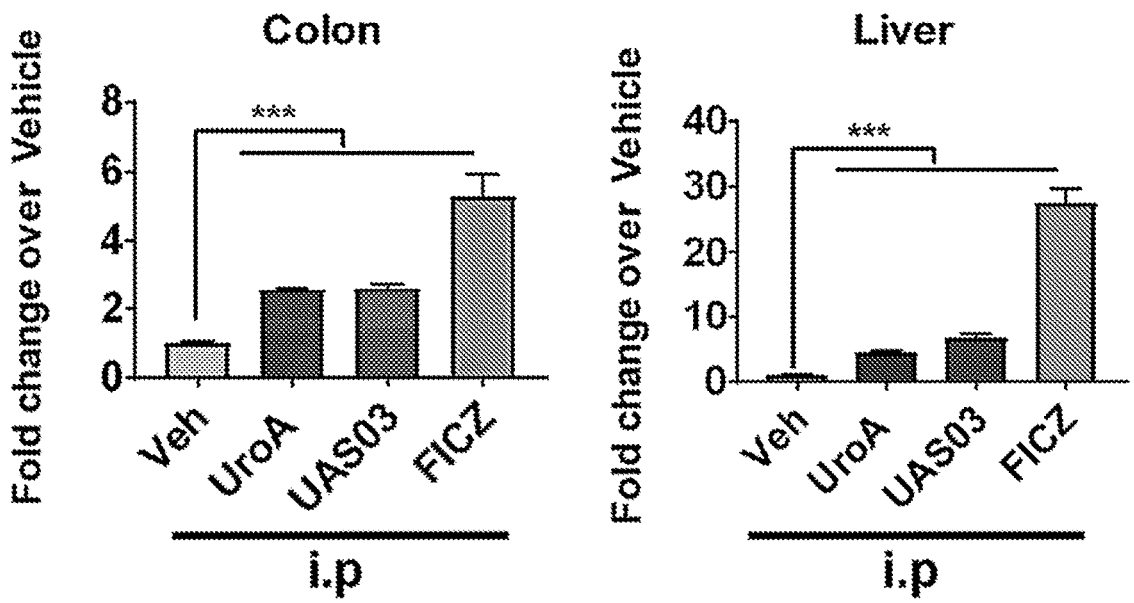
Figure 2:
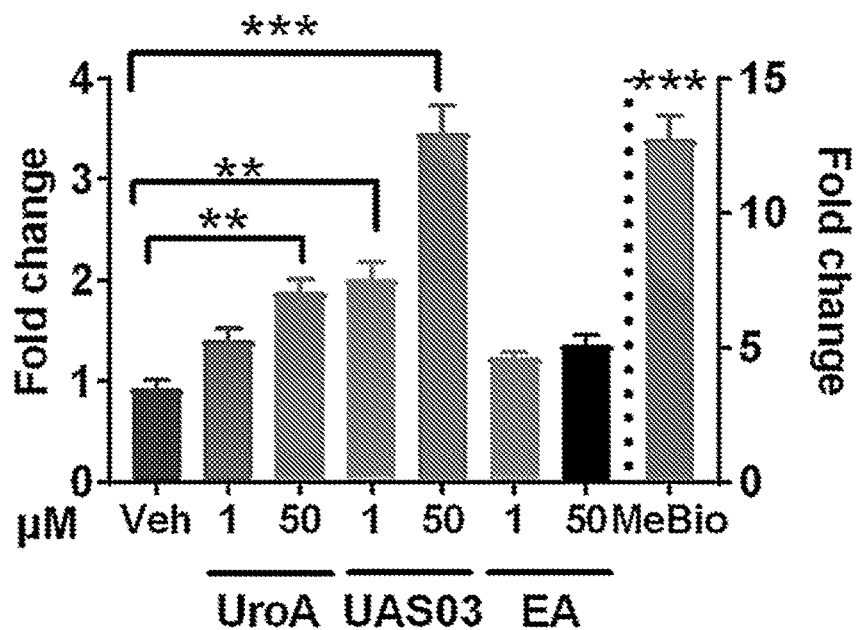
Figure 2:
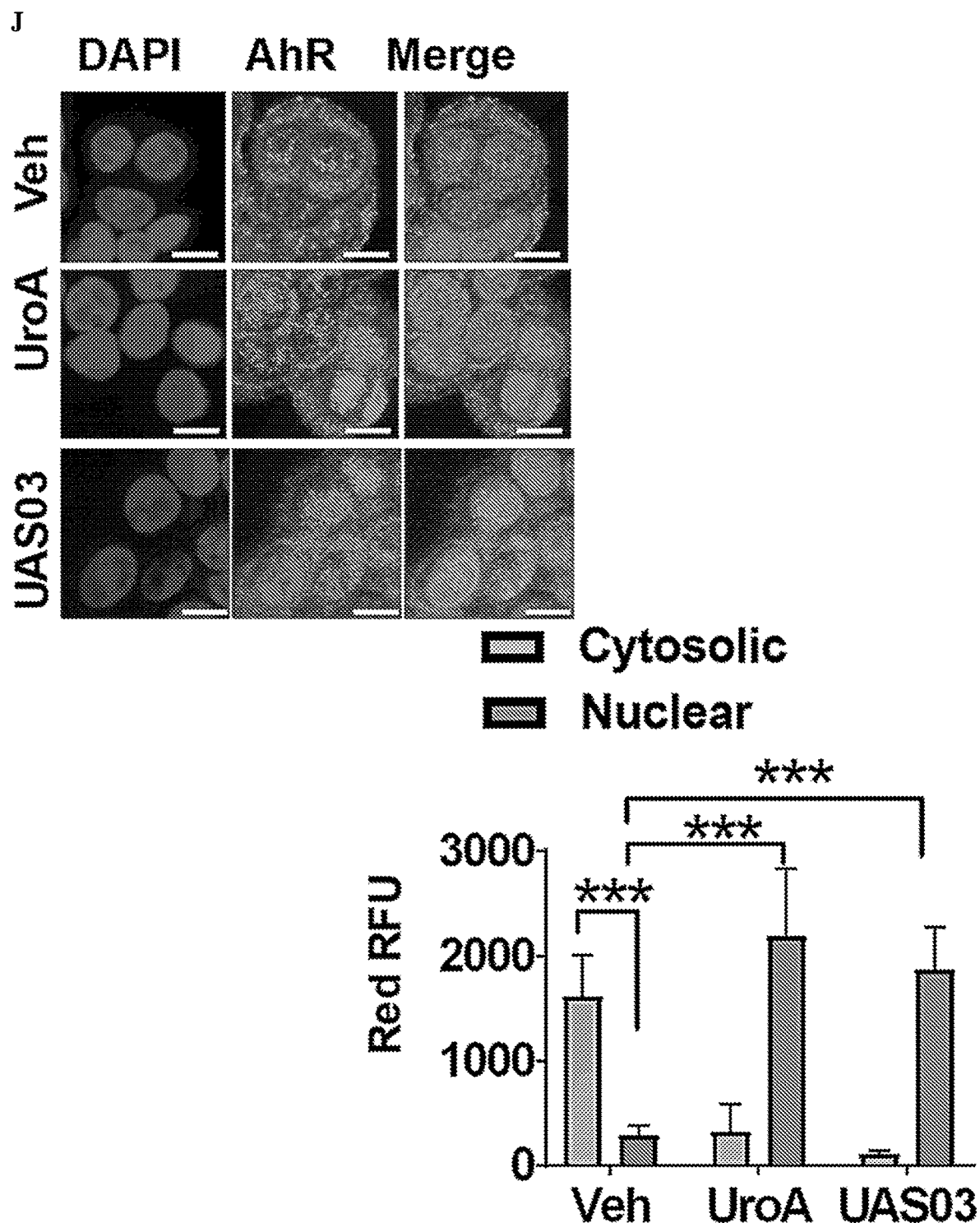
Figure 2:
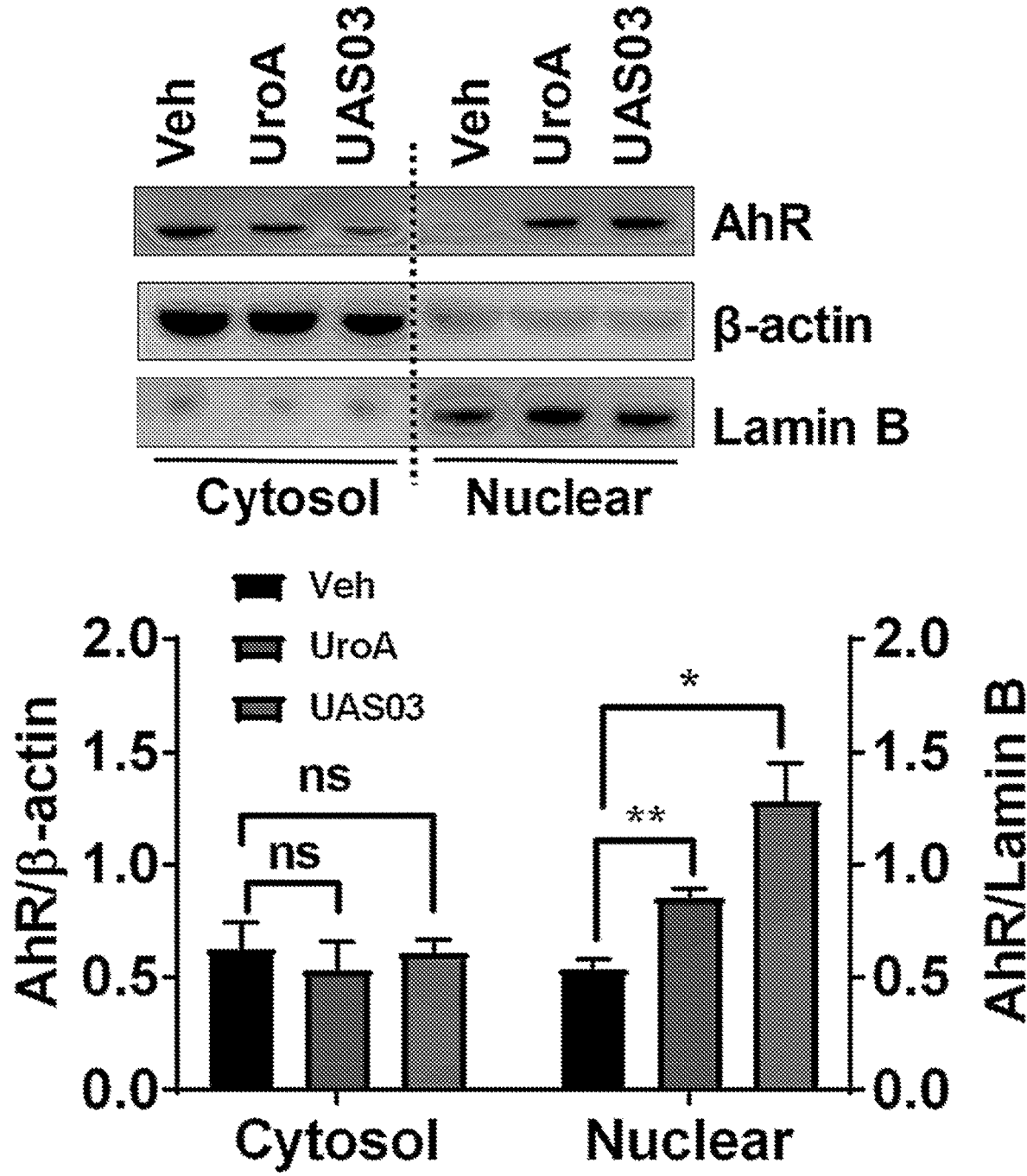
Figure 2:
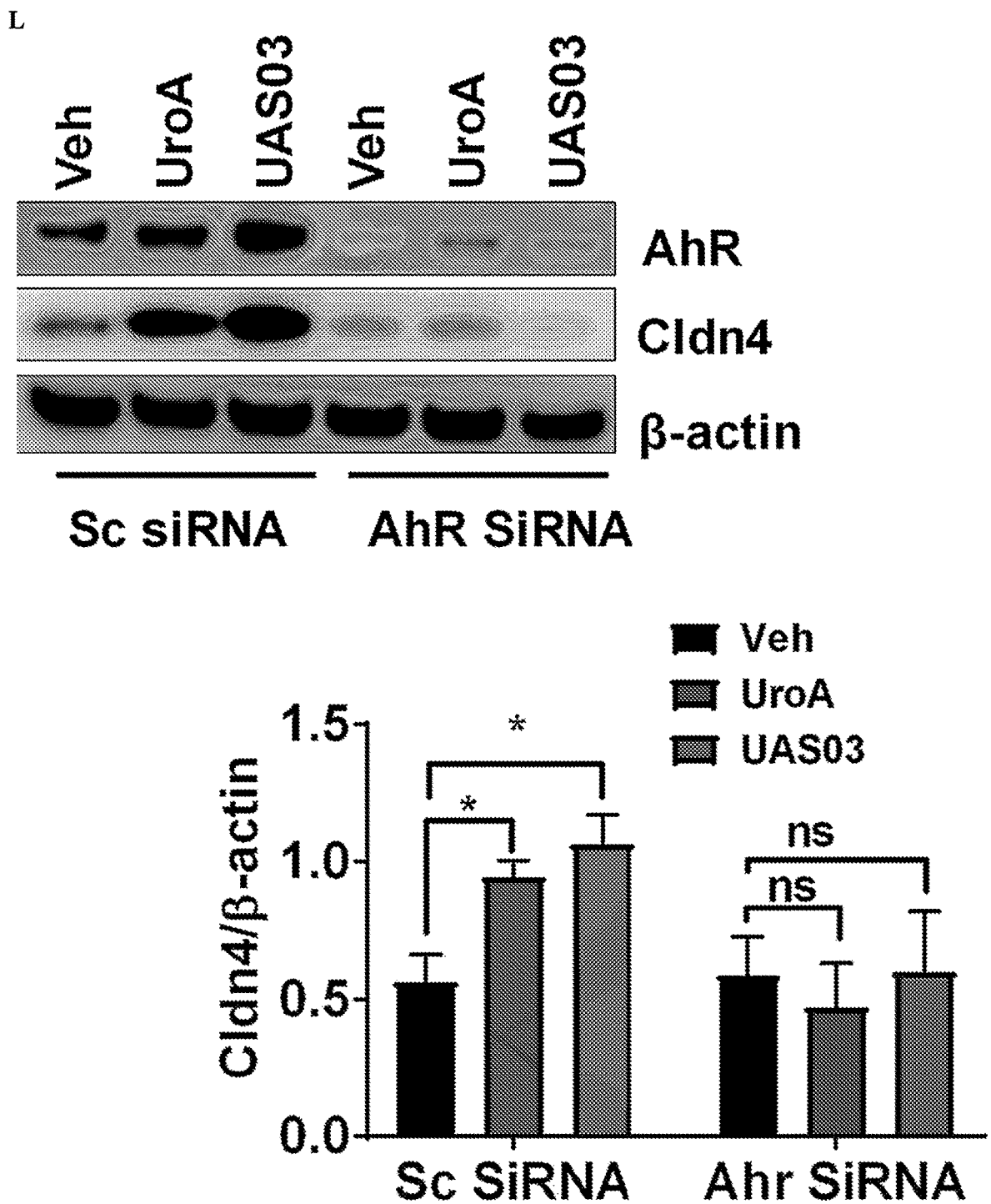
Figure 2:
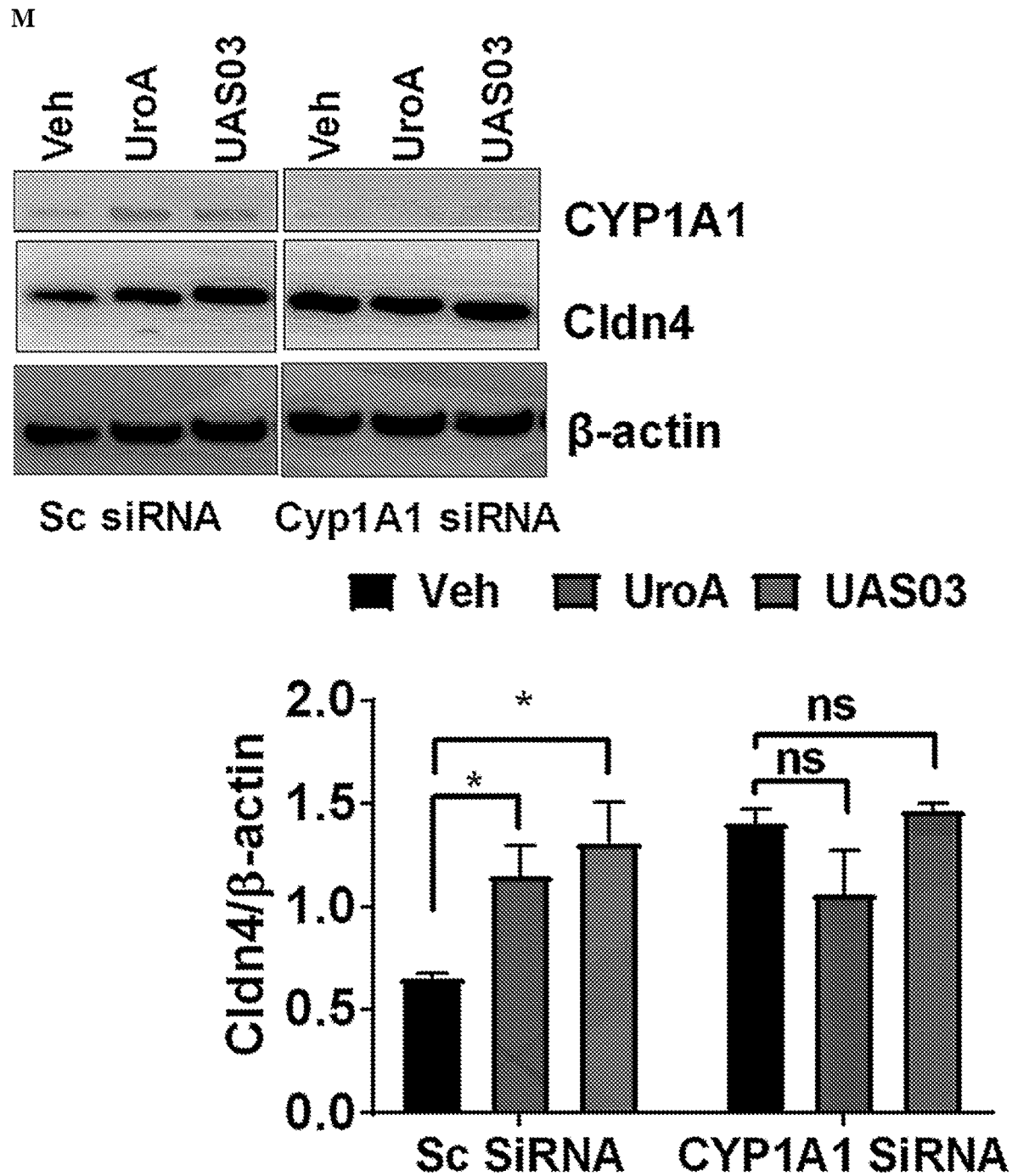
Figure 2:
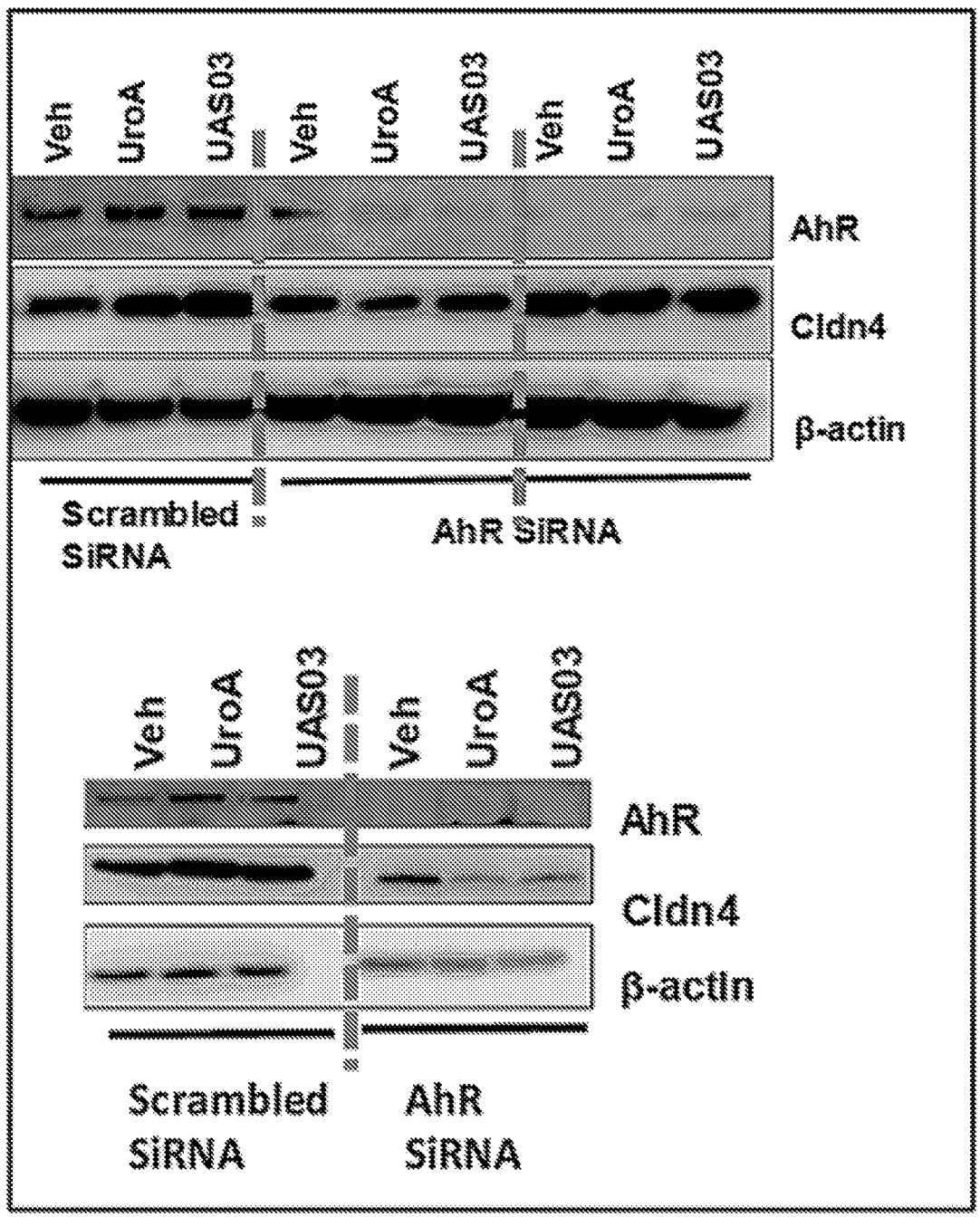
Figure 2:
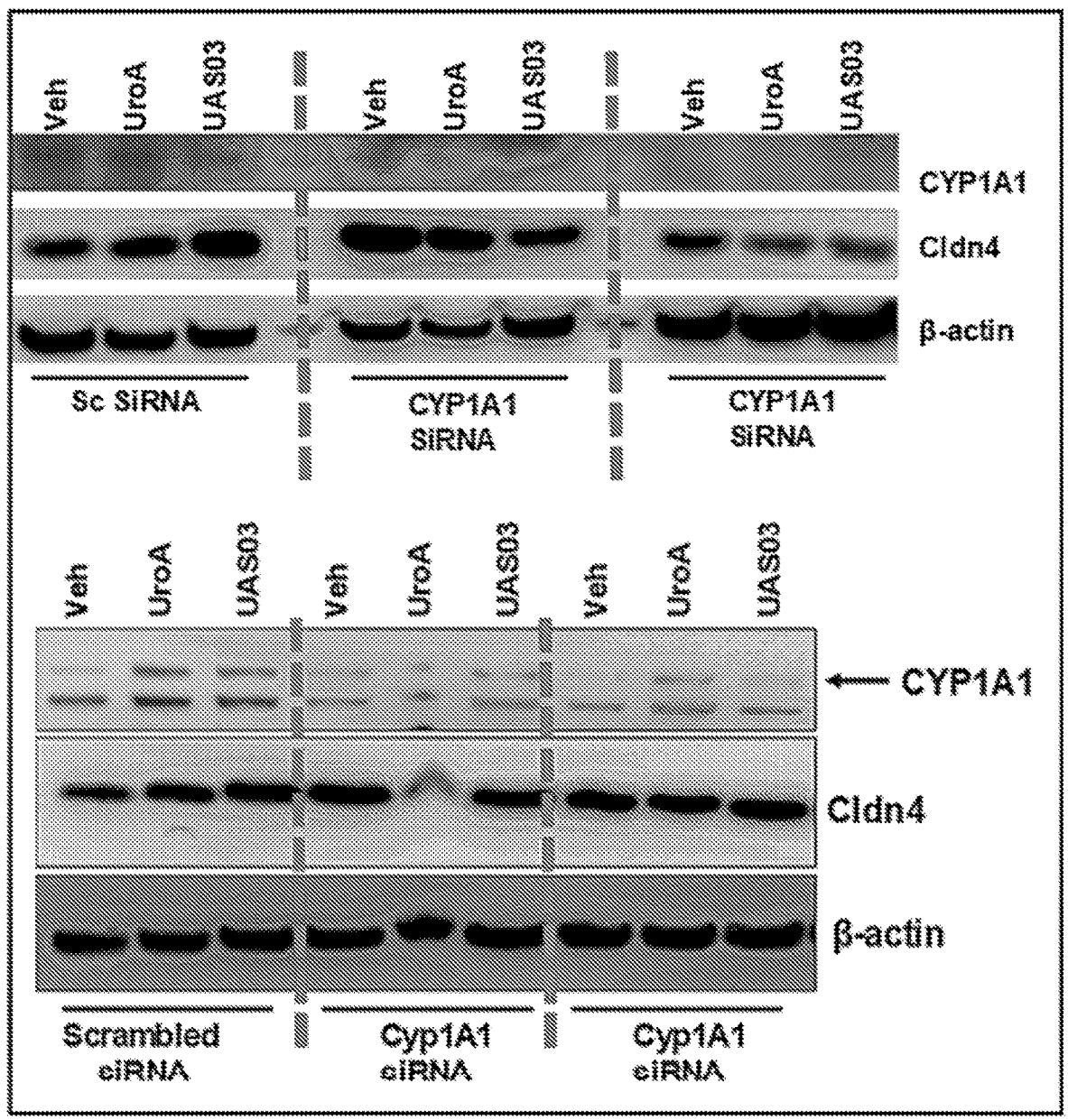
Figure 2:
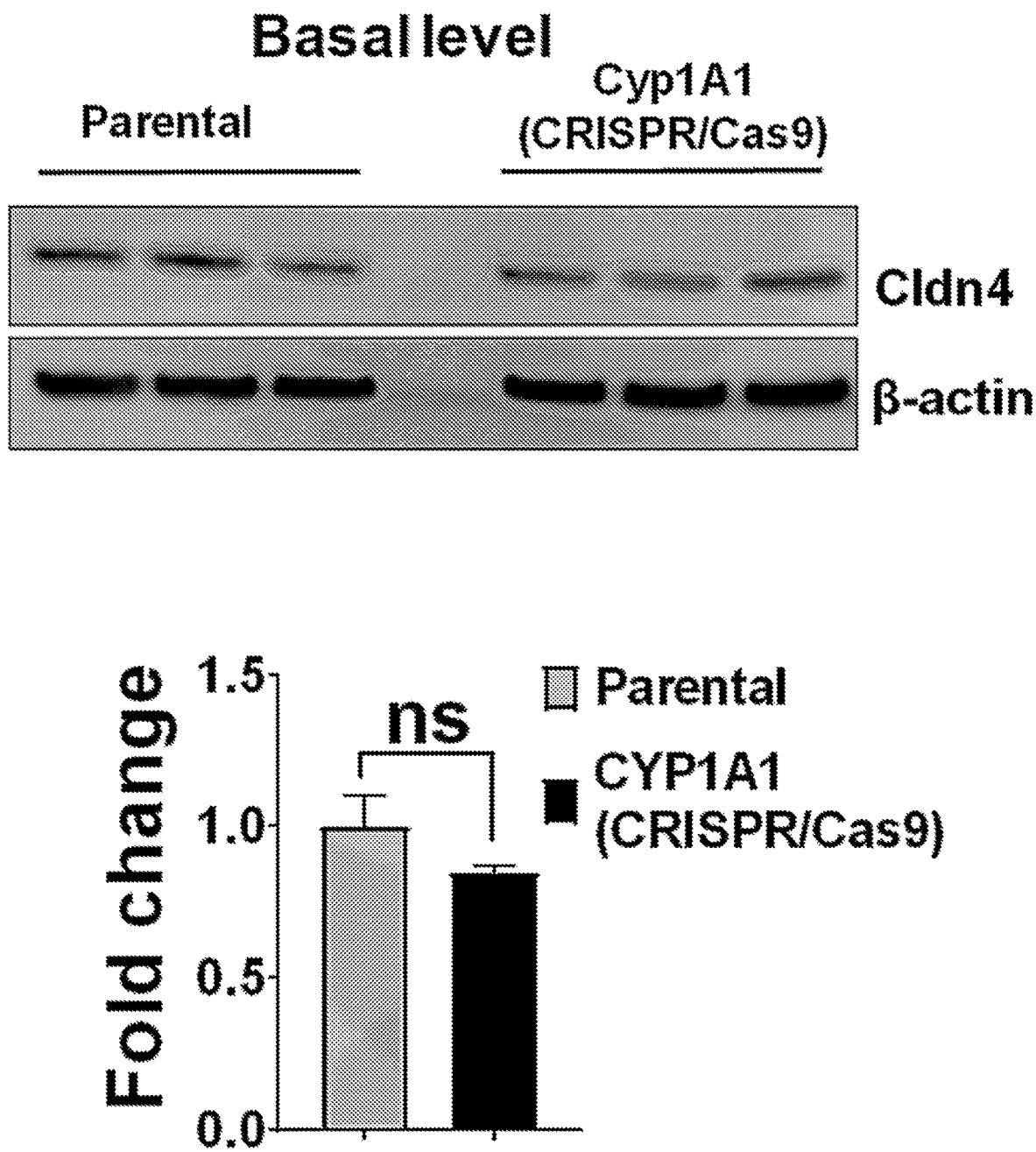
Figure 2:
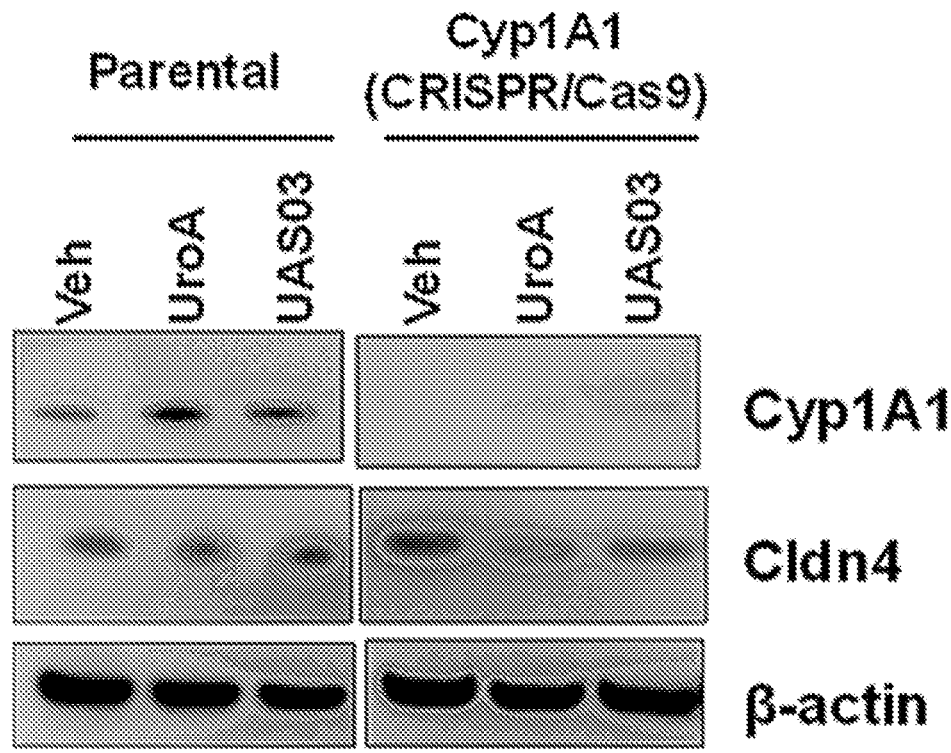
Figure 2:
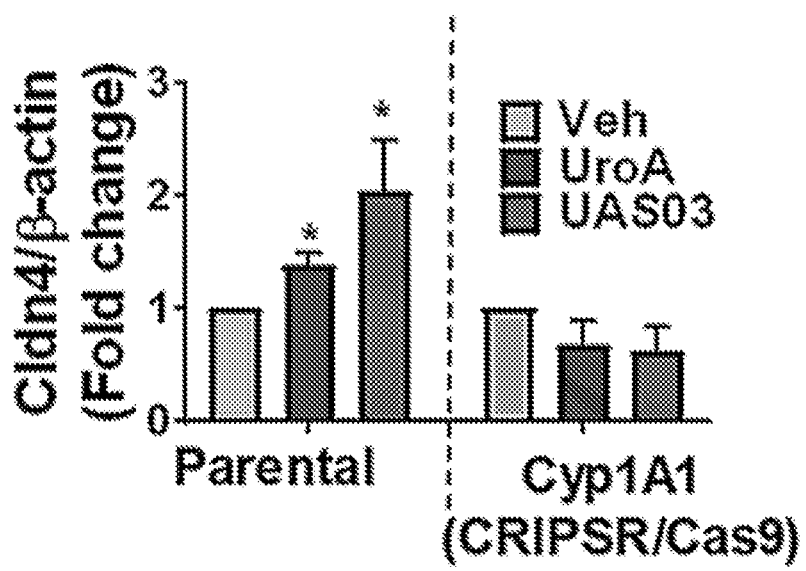
Figure 2:
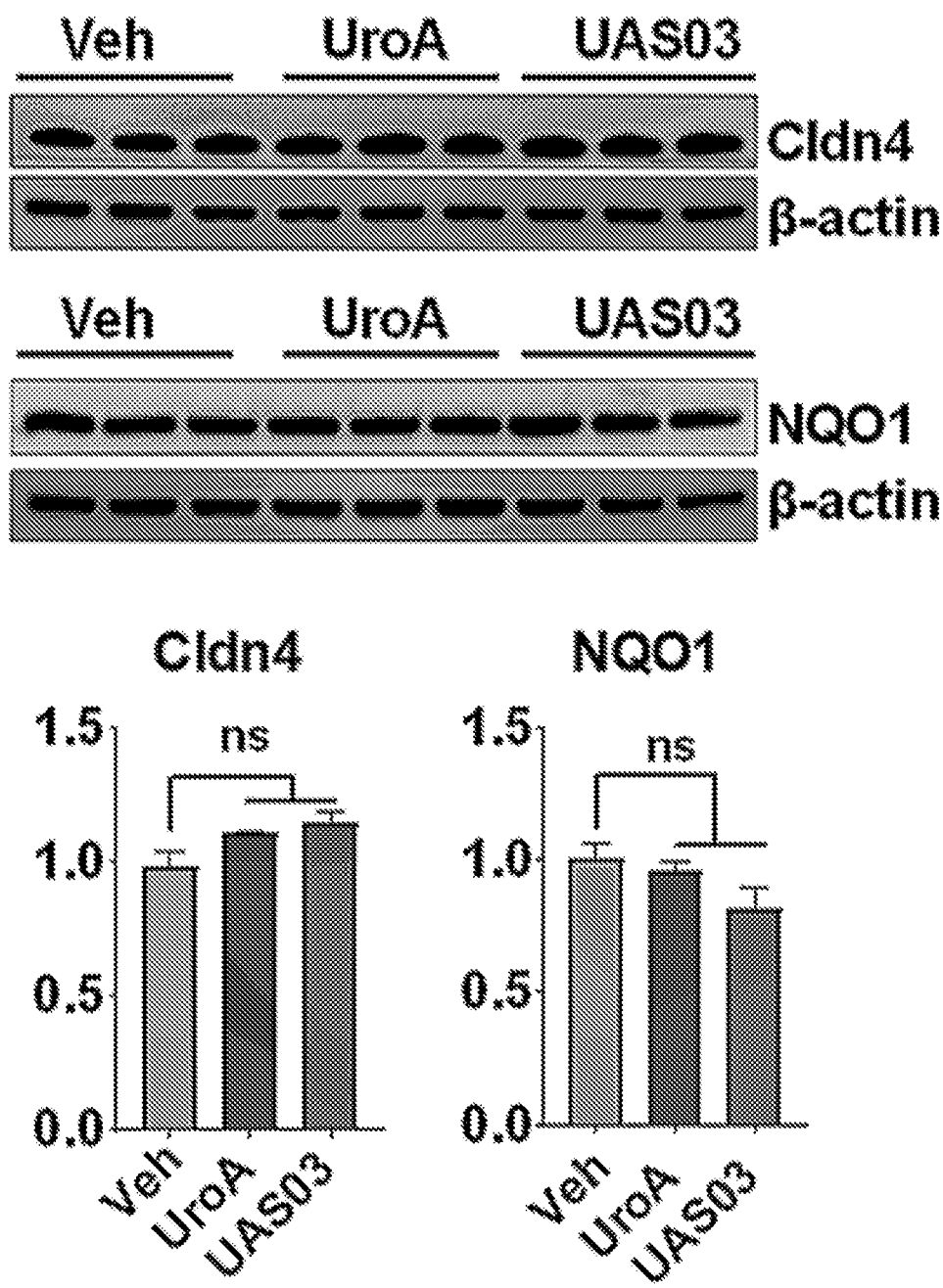
Figure 2:
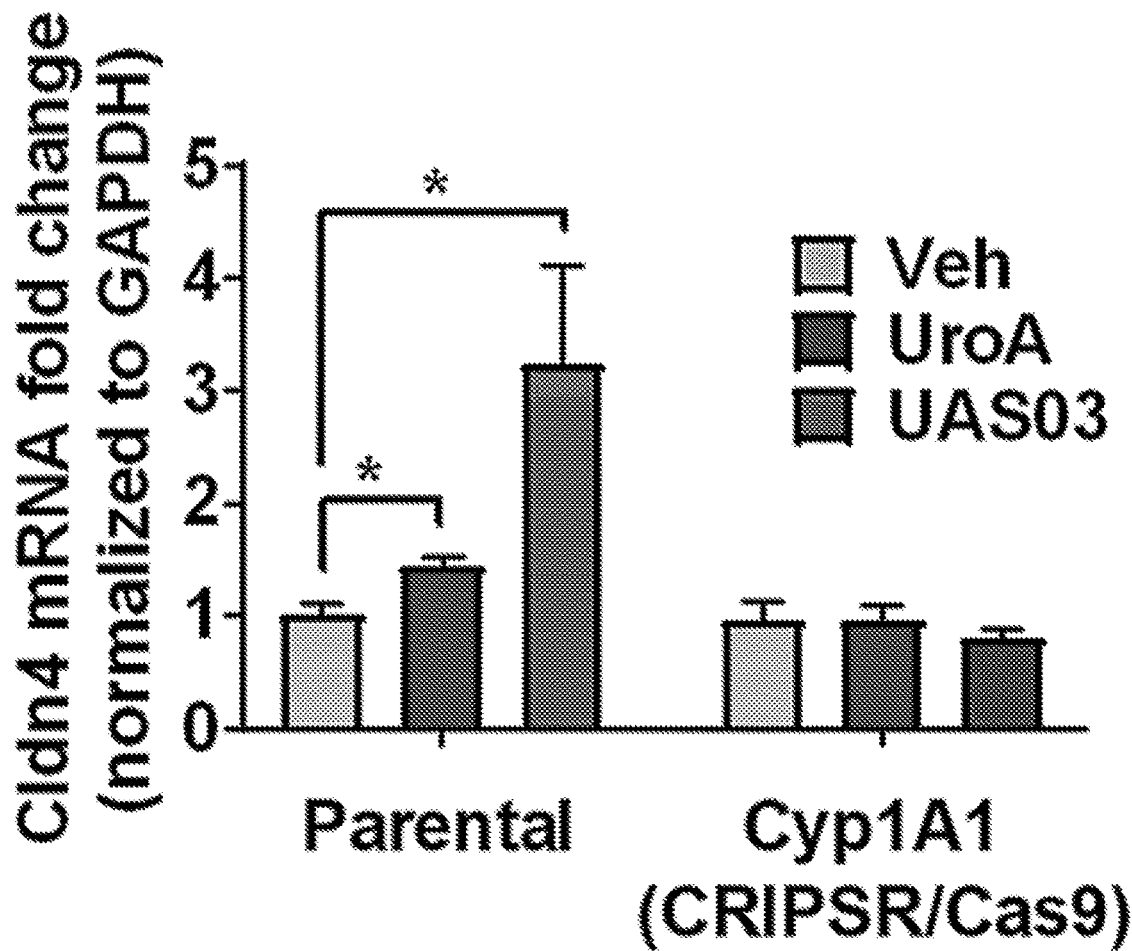
Figure 3:
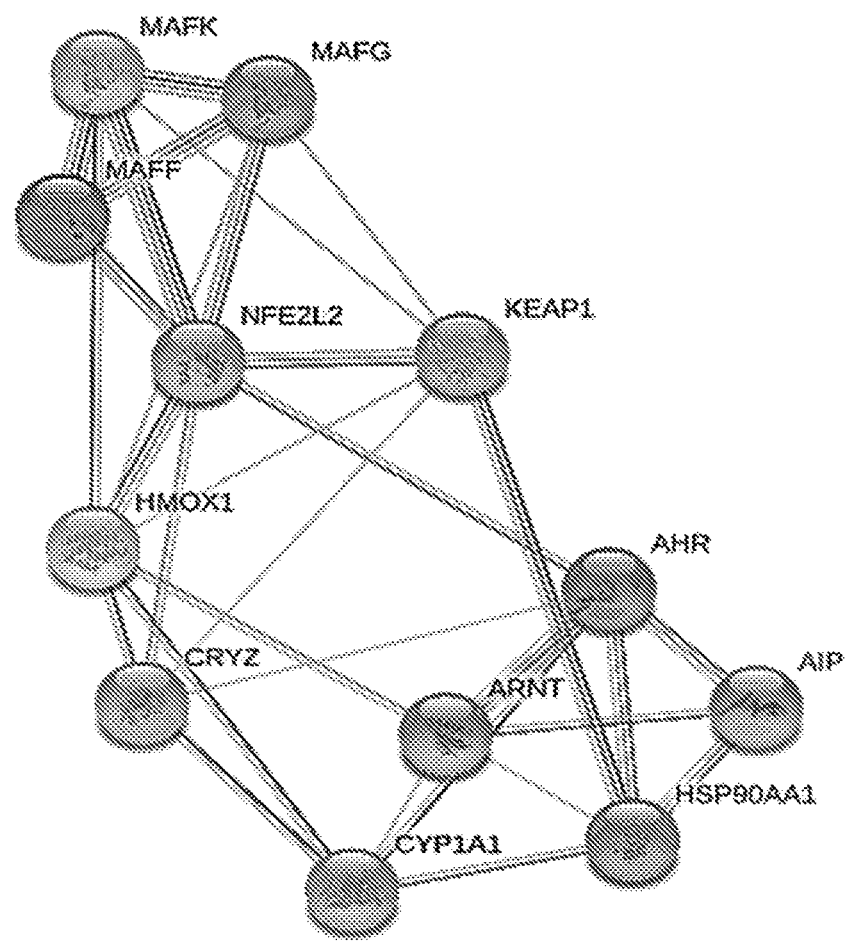
FIG. 3: Nrf2 has a role in UroA/UAS03 mediated upregulation of tight junction proteins. (A-B) AhR-ligand Chip-seq analysis of MCF-7 cells. Publically available ChIP-Atlas (<<http://chip-atlas.org/target_genes>>) Chip-seq analysis of AhR ligand. (A) AhR targets Nrf2 and Cyp1A1 genes. (<<http://dbarchive.biosciencedbc.jp/kyushu-u/hg19/target/AHR.1.html>>). (B) AhR also target tight junction proteins such as TJP1, 2, 3, Ocln, Clnd2, 3 and 5. (C-F) UroA and UAS03 upregulate expression of Nrf2-target genes. (C) HT29 cells were treated with Vehicle or UroA or UAS03 (50 μM) (n=3) and total RNA was isolated. The mRNA levels of Nrf2 was evaluated using SyBR green real time PCR method. (3-actin was used to normalize the expression. (D) HT29 cells were transfected with ARE-luciferase vector. Post 24 h transfection, cells were treated with Veh/UroA/UAS03 (50 μM) or sulforaphane (10 μM) for 24 h (n=3) and luminescence was measured. (E-F) HT-29 cell lysates prepared similar to described above and immunoblotted for HO1 using anti-HO1 (E) and NQO1 (F) using anti-NQO1. The quantification of immunoblots were performed using Image J software. (G) Nrf2 levels were determined by immunoblots in HT29 cells treated with vehicle/UroA/UAS03 (50 μM) for 24 h. (H) Nrf2 expression in cytosolic and nuclear fractions of HT29 cells treated with Veh/UroA/UAS03 (50 μM) for 6 h. (I) Immunofluorescence confocal images of HT29 cells treated with vehicle/UroA/UAS03 (50 μM) for 6 h. The cells were stained with anti-Nrf2 antibody and DAPI. Relative green fluorescence (n=~20 cells) intensity was measured. Scale bars indicate 25 μm. (J) Expression of Cldn4 and NQO1 in colon explants from WT, Nrf2$^{-/-}$ and AhR$^{-/-}$ mice treated with vehicle/UroA/UAS03 (50 μM) for 24 h. Immunoblots were quantified using Image J software. (K) mRNA levels of Cldn4, Nrf2 and HO1 from colon explant cultures was measured by real time PCR using SyBr green method. (L-N) UroA/UAS03 induce Cldn4 in AhR and Nrf2 dependent manner (Ex vivo colon explants study). These experiments represent biological replicates from different mice. The colon explants from WT and AhR$^{-/-}$ mice (L), and WT and Nrf2$^{-/-}$ mice (M) were prepared and induced with vehicle or UroA (50 μM) or UAS03 (50 μM) or FICZ (100 nM) for 24 h and measured the expression of indicated proteins. These are replicates supporting the data from FIG. 3J. (O-S) UroA/UAS03 induce Cldn4 in AhR and Nrf2 dependent manner (In vivo treatment studies). C57BL/6 (WT), Nrf2$^{-/-}$ and AhR$^{-/-}$ mice (n=4-6) were treated with vehicle (0.25% Na-CMC) or UroA (20 mg/kg/daily) or UAS03 (20 mg/kg/daily) for one week. Colons were isolated and scrapped the villi and the total protein was extracted as described in methods. (O) Nrf2 is upregulated upon UroA/UAS03 treatment of wild type mice. (P) Changes in mRNA levels of Nrf2, Cldn4, Ocln and TJP3 in colon tissues (WT and Nrf2$^{-/-}$ mice) were measured using RT PCR. (Q) Colons from untreated C57BL/6 (WT), Nrf2$^{-/-}$ and AhR$^{-/-}$ mice (n=3) were isolated and the basal level of expressions of NQO1 and Cldn4 were measured by immunoblots as described in methods. (R) C57BL/6 (WT), Nrf2$^{-/-}$ and AhR$^{-/-}$ mice (n=4) treated with vehicle (0.25% Na-CMC) or UroA (20 mg/kg/daily) or UAS03 (20 mg/kg/daily) for one week. Colon tissue lysates were prepared and examined expression of Cldn4 and NQO1 by Western blots. UroA/UAS03 failed to upregulate Cldn4 and NQO1 in Nrf2$^{-/-}$, AhR$^{-/-}$ mice. The immunoblots represent independent replicates to support the data in FIG. 3F. (S) Expression of Nrf2 was determined in same samples described in FIG. 3J by immunoblots. Immunoblots (n=3) were quantified using Image J and represented ratio of Nrf2/β-actin. (T) C57BL/6, Nrf2$^{-/-}$ and AhR$^{-/-}$ mice (n=3) treated orally daily with veh or UroA/UAS03 (20 mg/kg) for 1 week. Cldn4 and NQO1 protein levels in colons were measured by immunoblots and quantified by Image J software. All in vitro studies were performed in triplicates. The immunoblots of colon explants and colon tissues were quantified from at least 6 independent runs. The levels of proteins were normalized to R-actin and Wild type vehicle treatment was set to 1 and calculated the fold changes. Statistics performed using unpaired t-test using Graphpad Prism software. Error bars, ±SEM; * p<0.05; p<0.01; *p<0.001.
Figure 3:
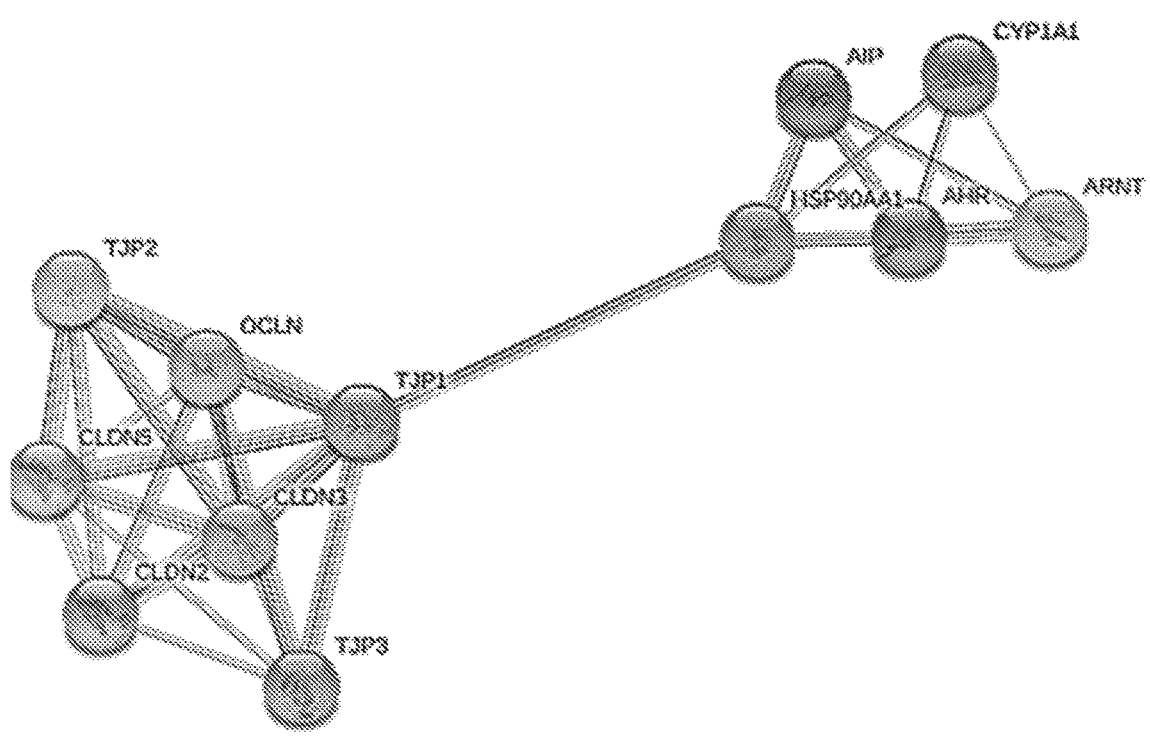
Figure 3:
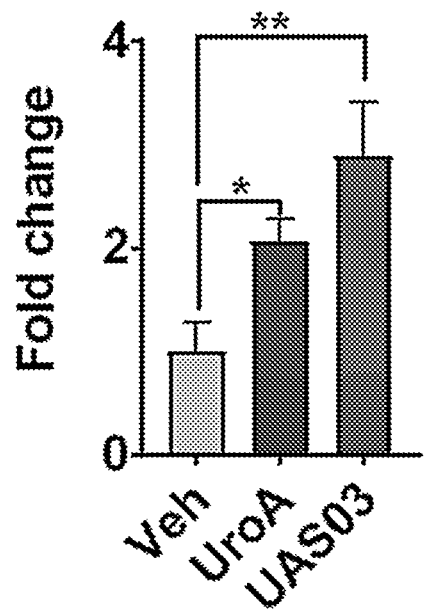
Figure 3:
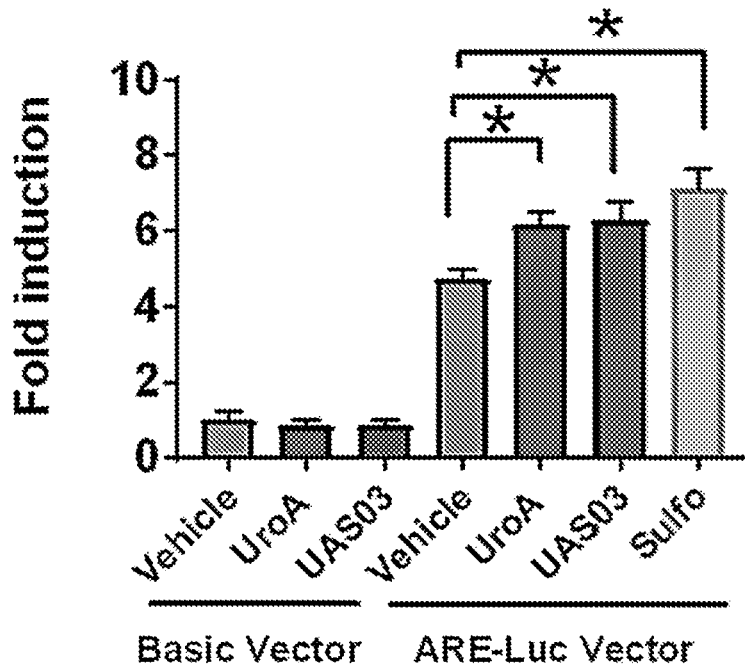
Figure 3:
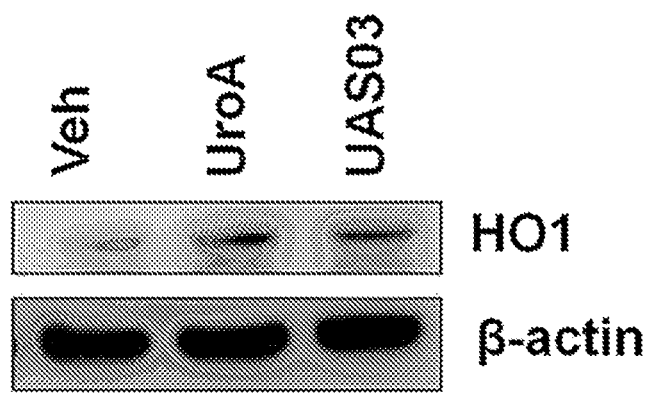
Figure 3:
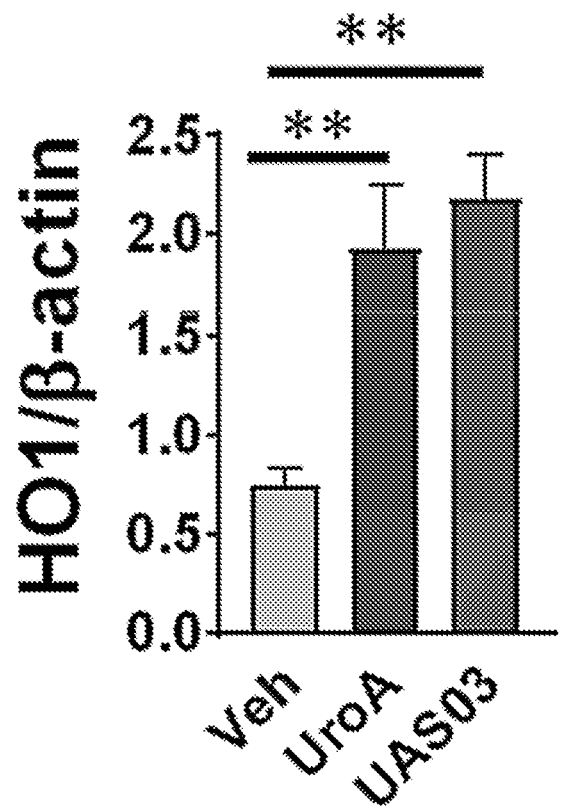
Figure 3:
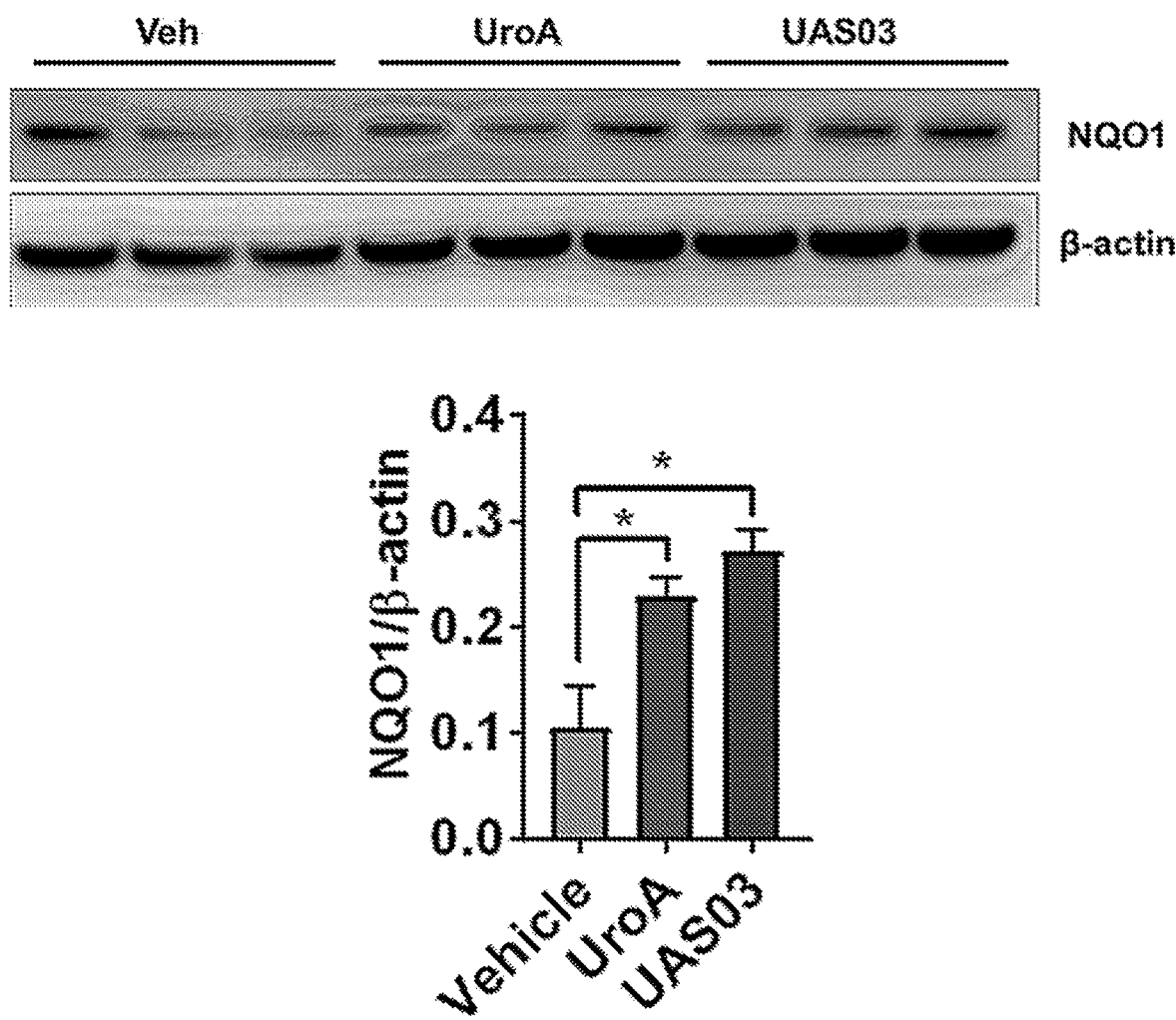
Figure 3:
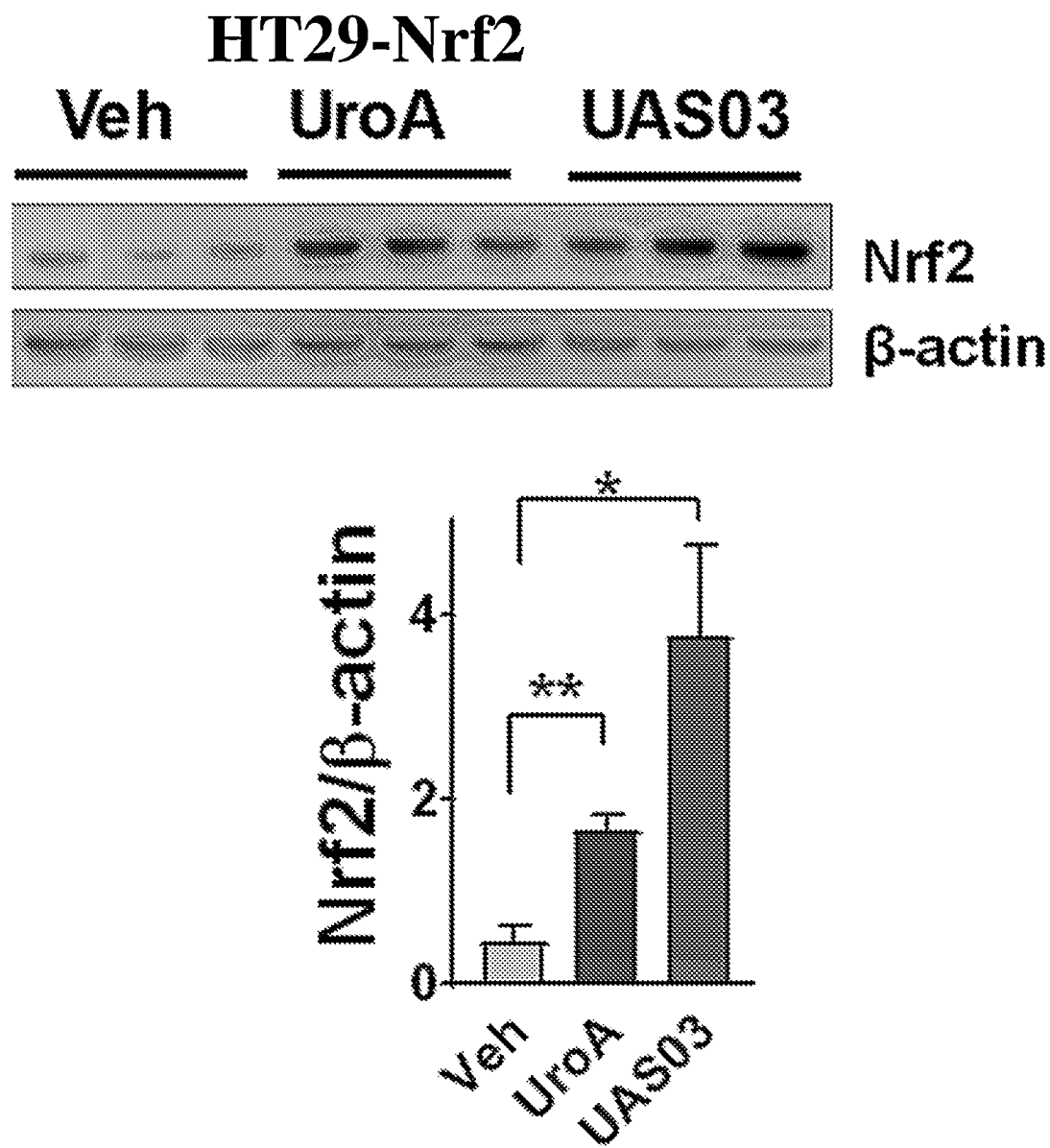
Figure 3:
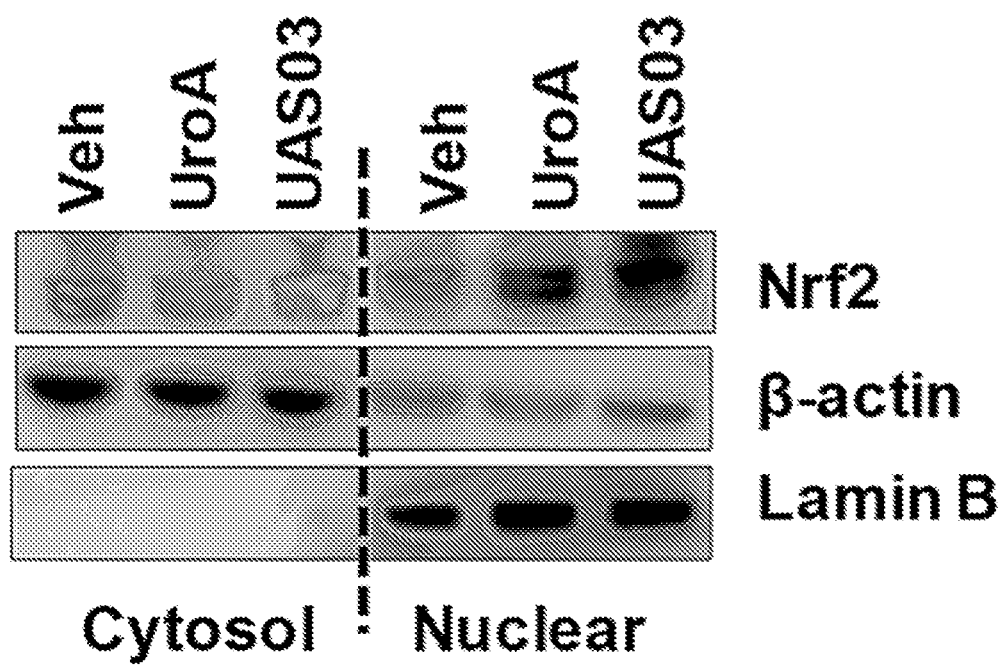
Figure 3:
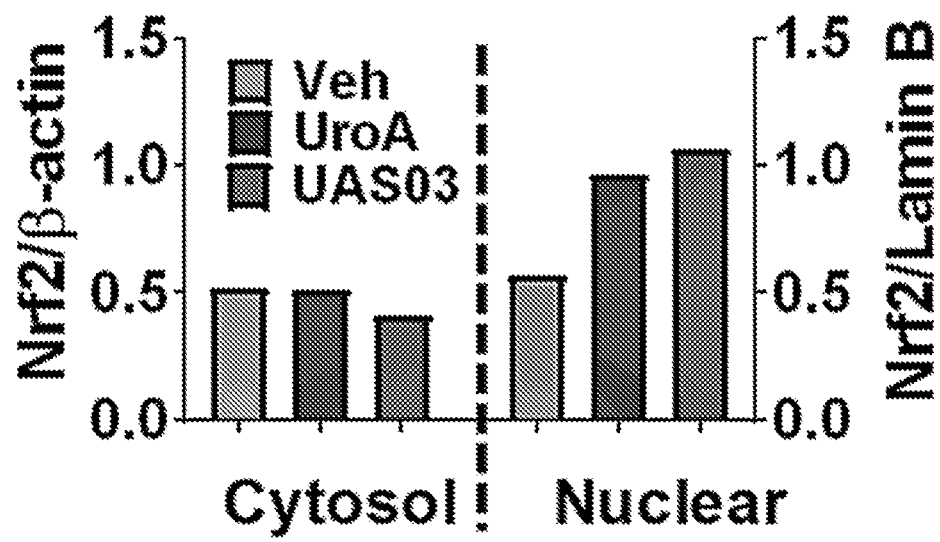
Figure 3:
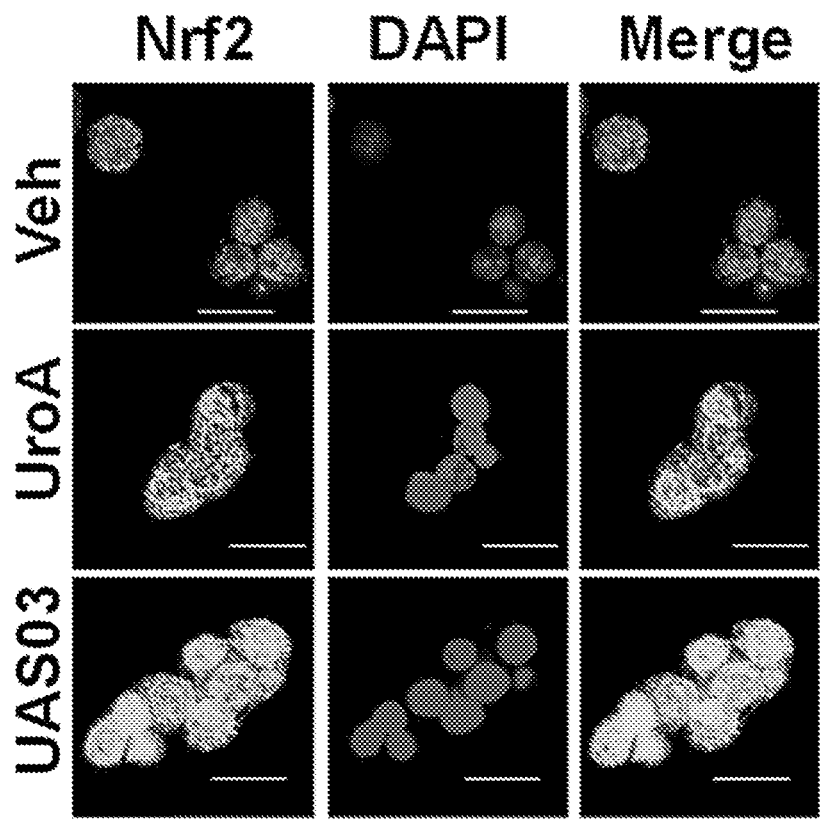
Figure 3:
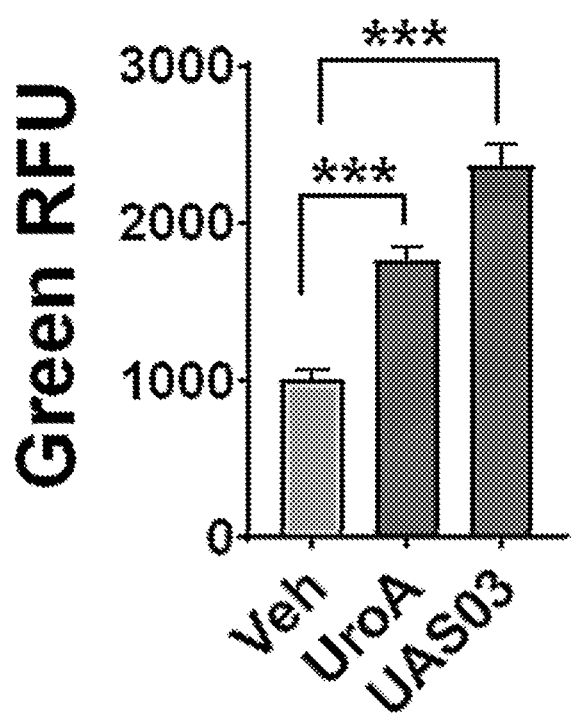
Figure 3:
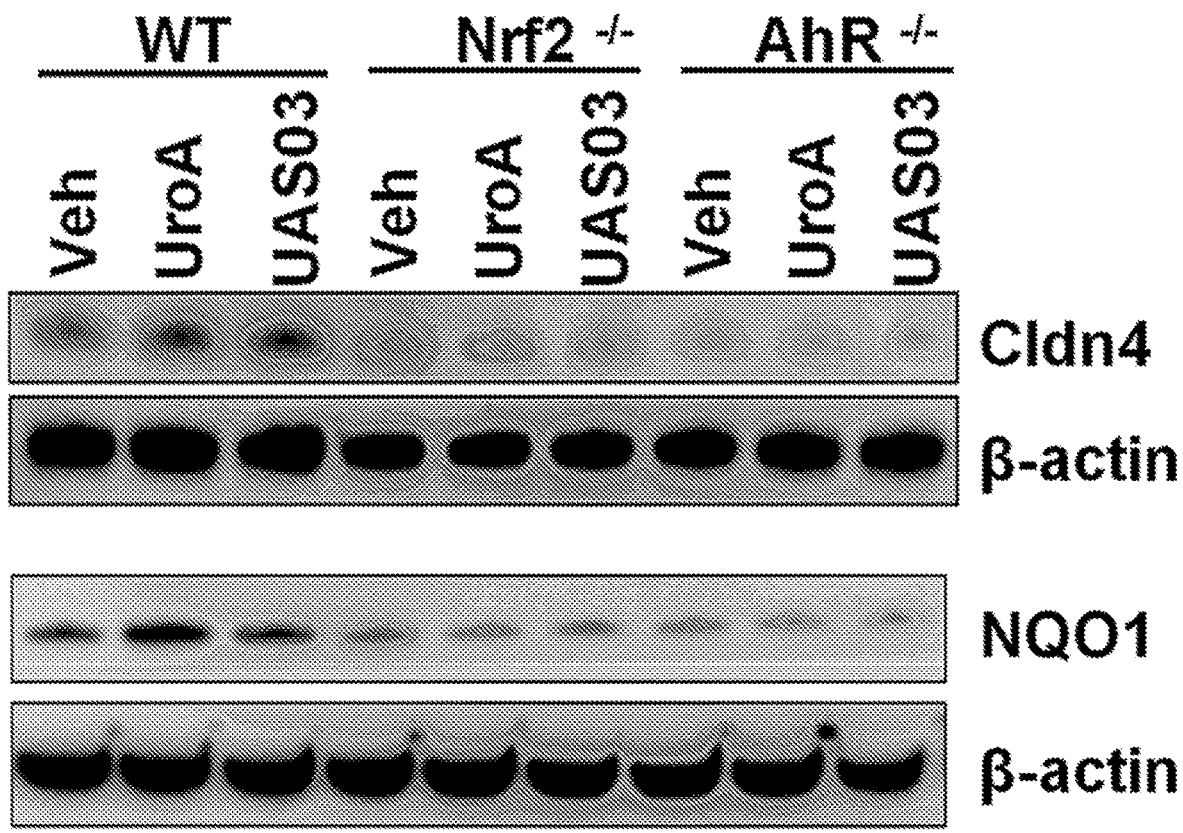
Figure 3:
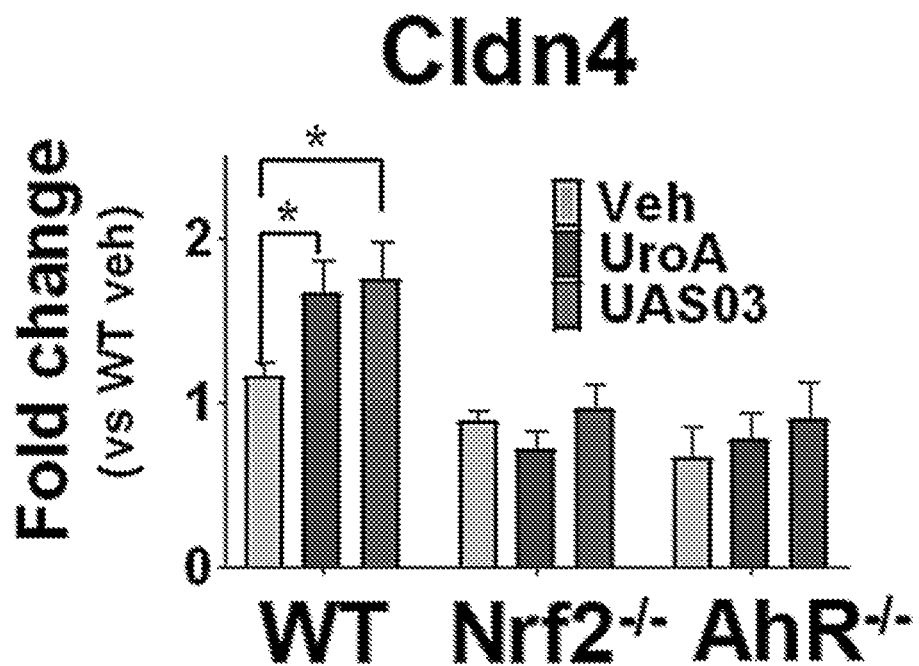
Figure 3:
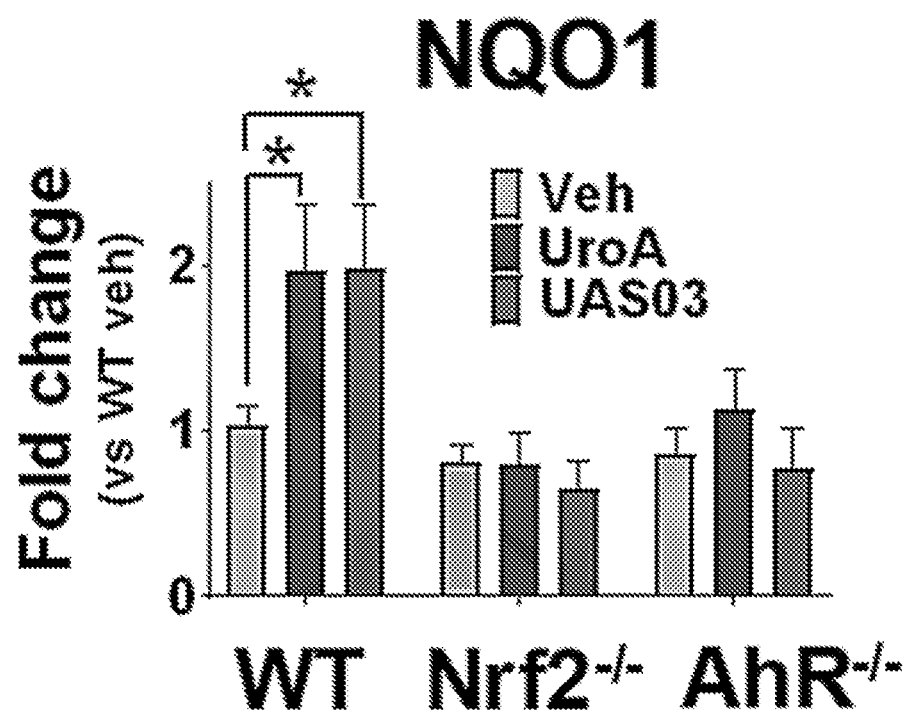
Figure 3:
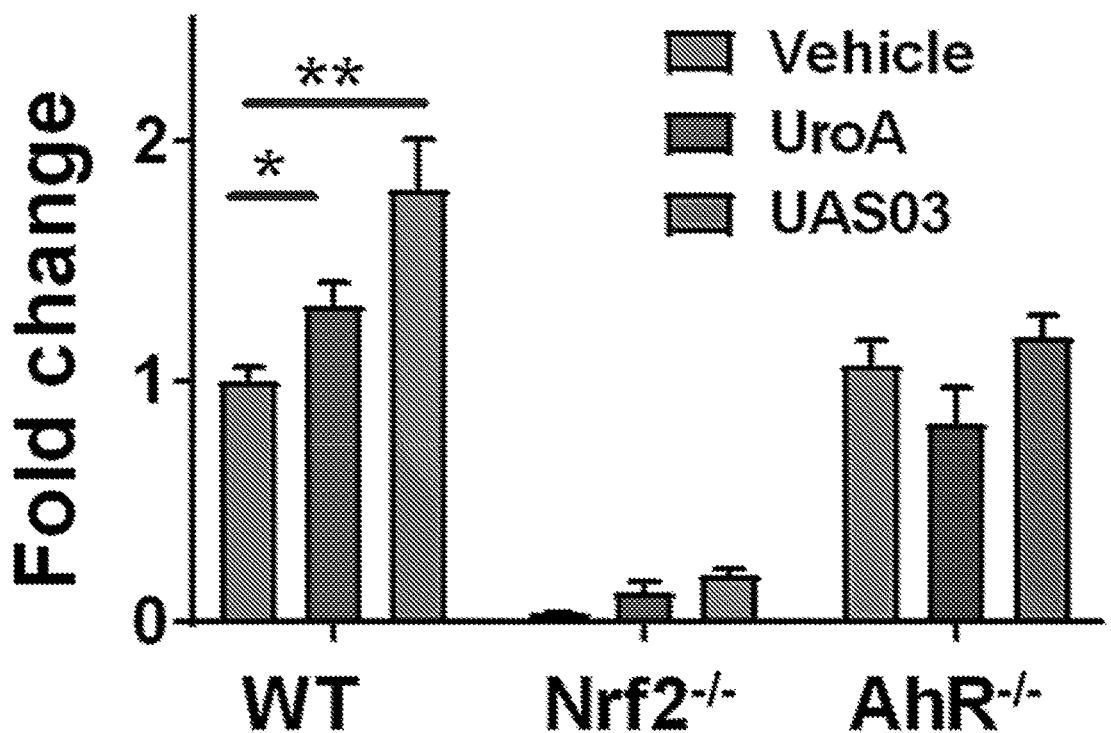
Figure 3:
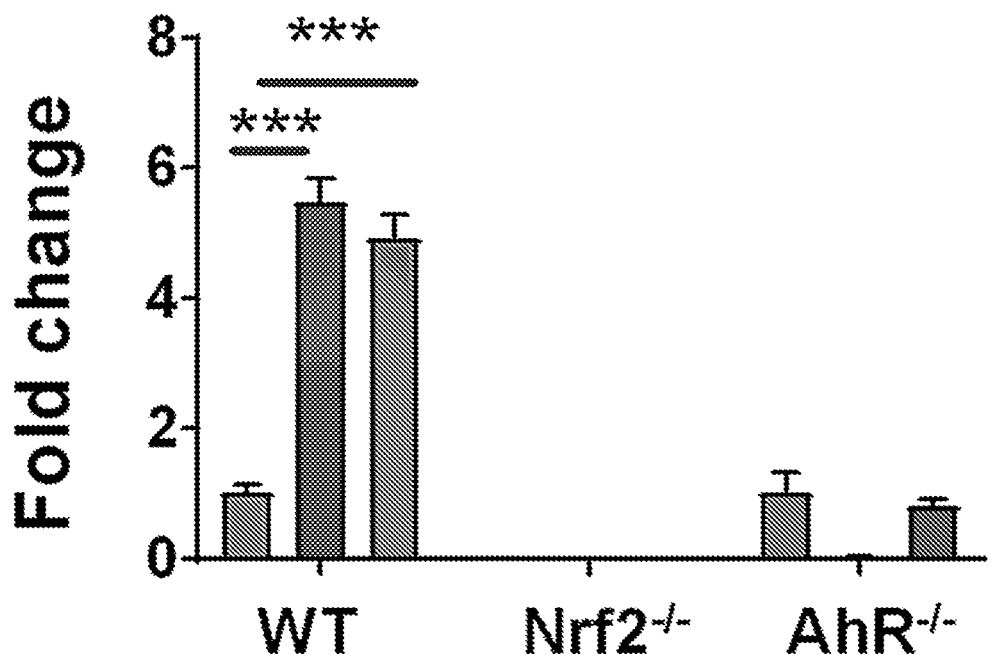
Figure 3:
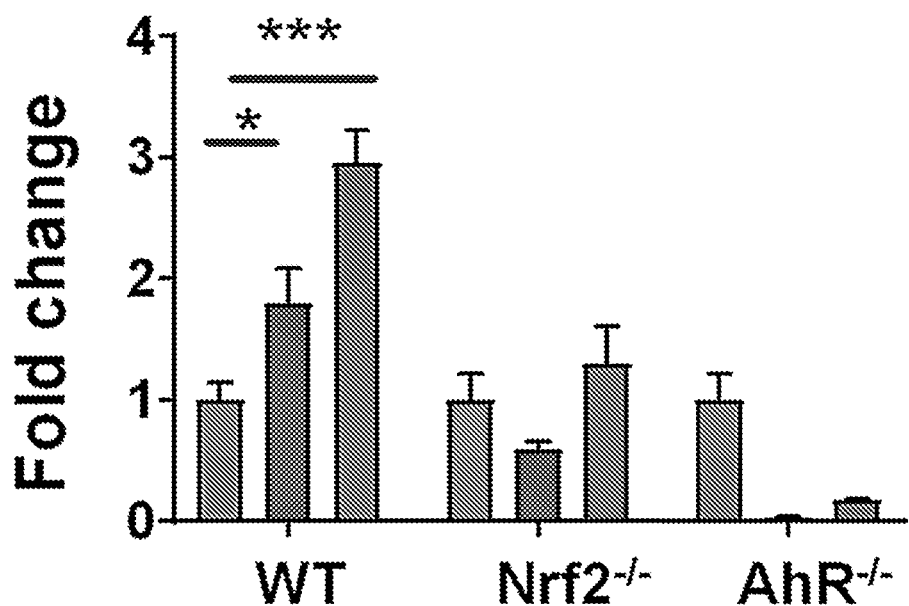
Figure 3:
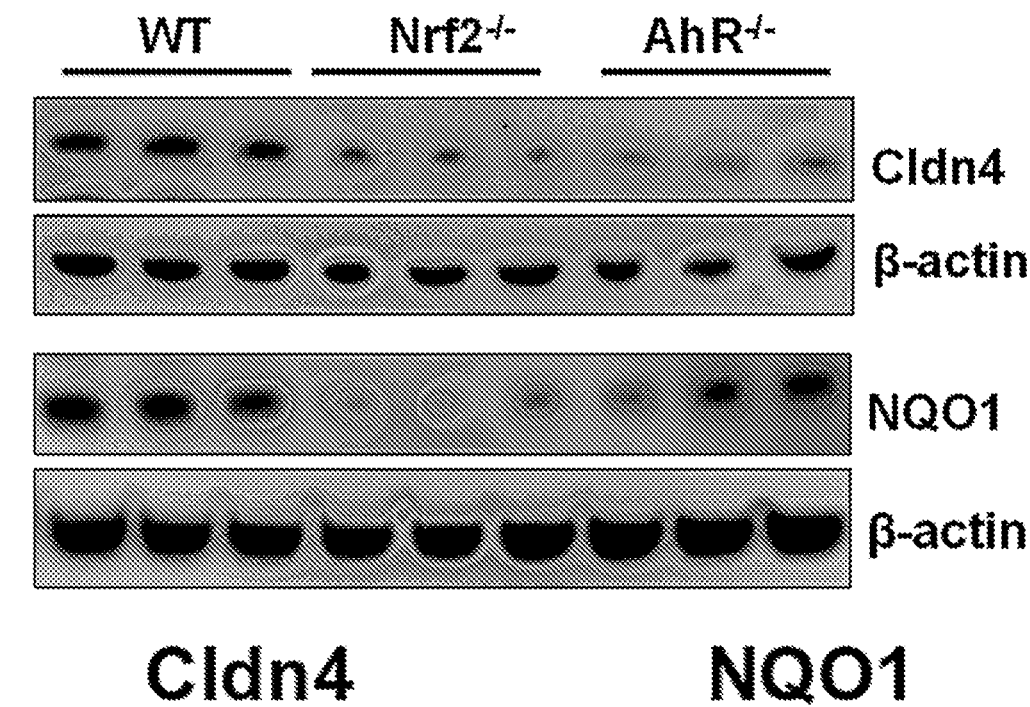
Figure 3:
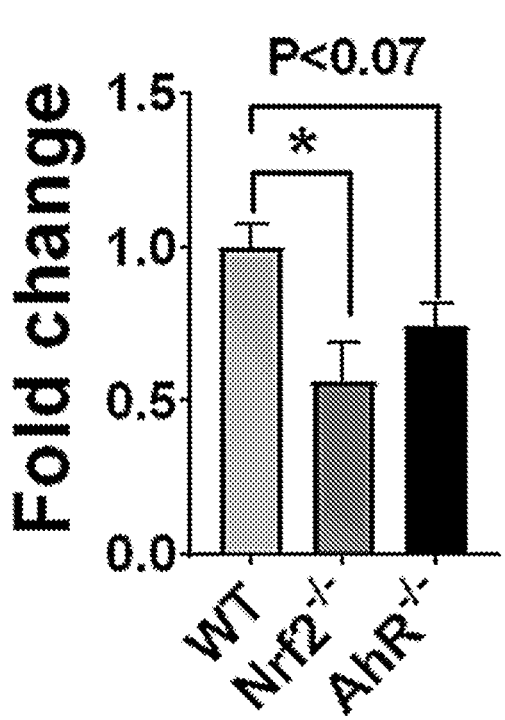
Figure 3:
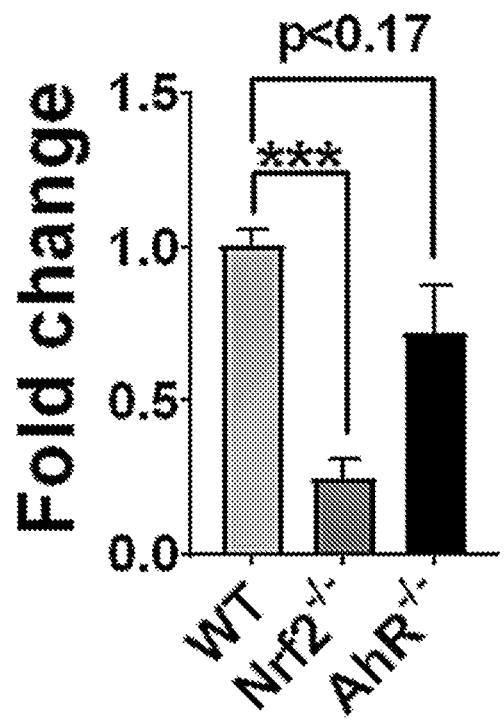
Figure 3:
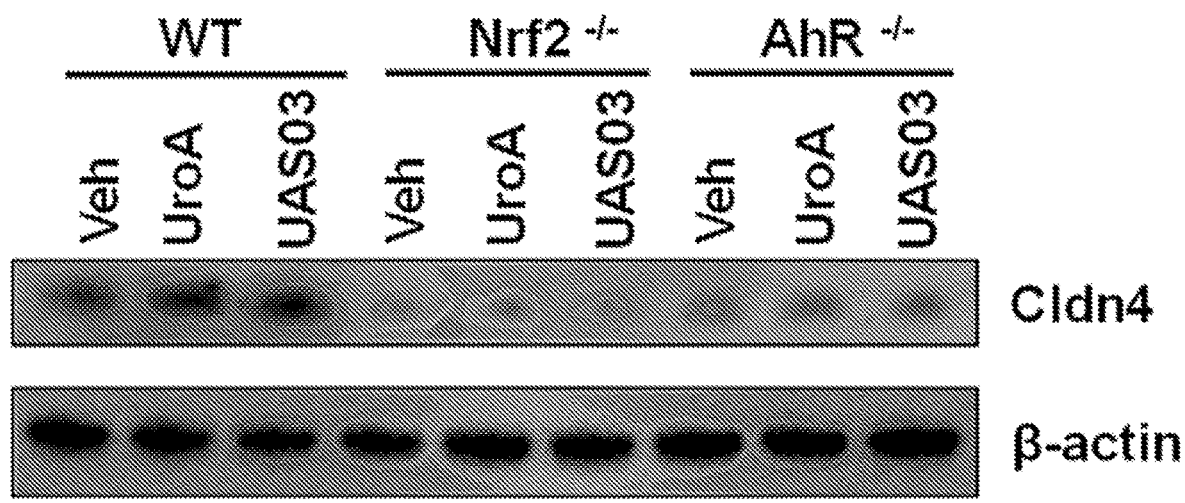
Figure 3:
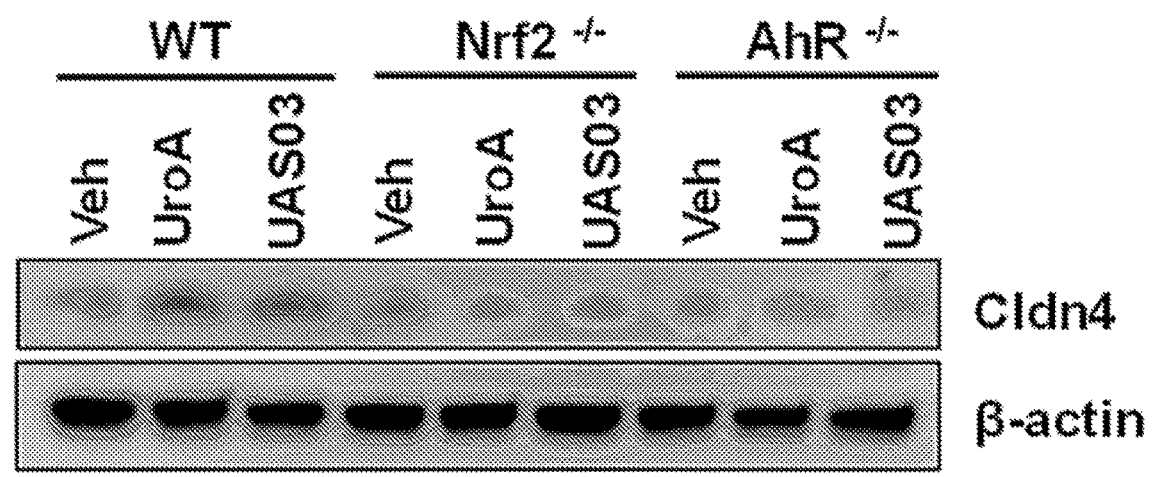
Figure 3:
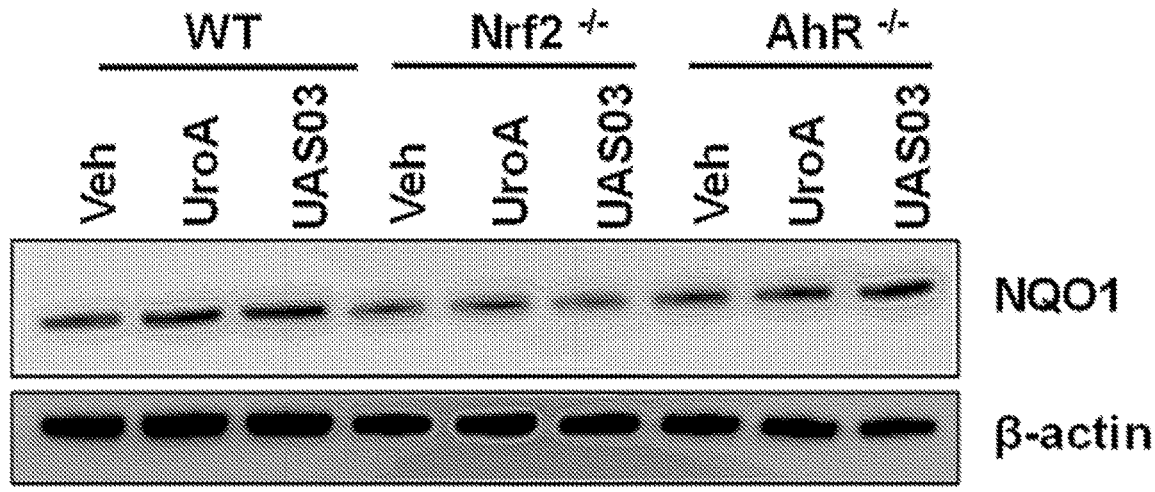
Figure 3:
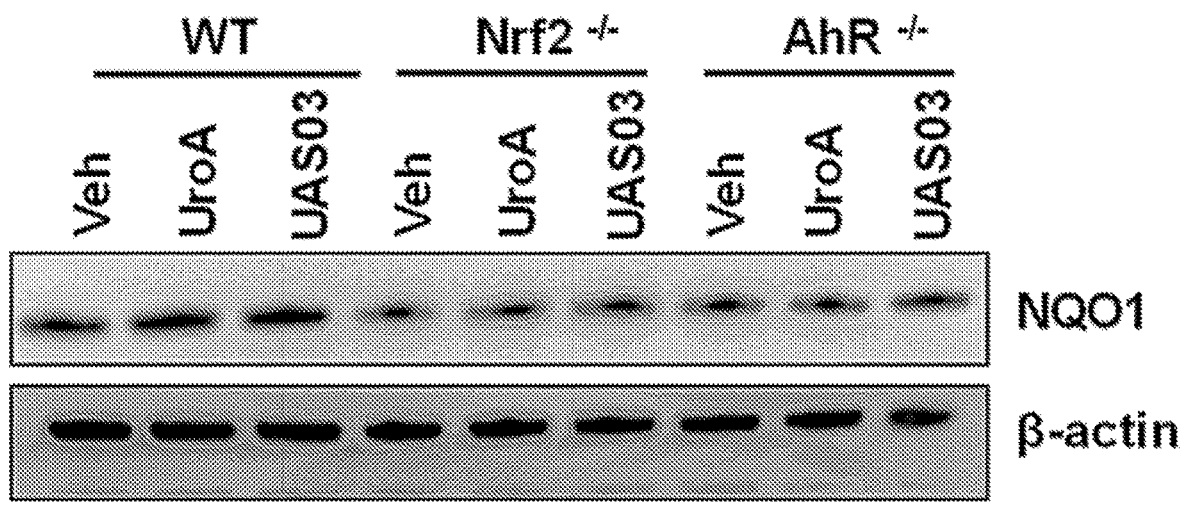
Figure 3:
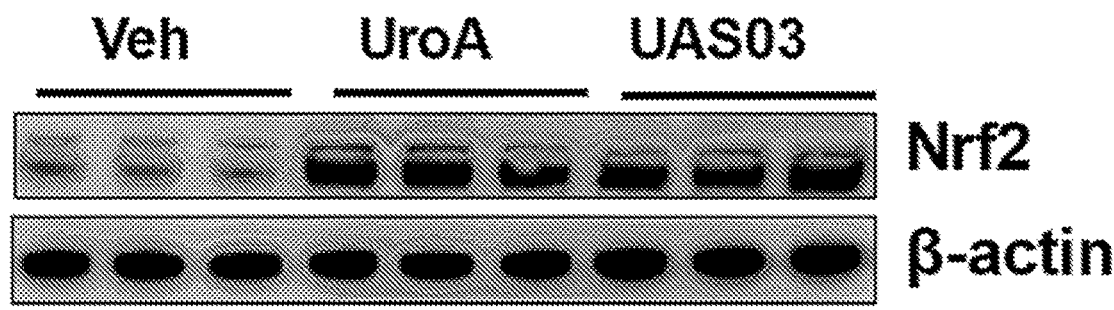
Figure 3:
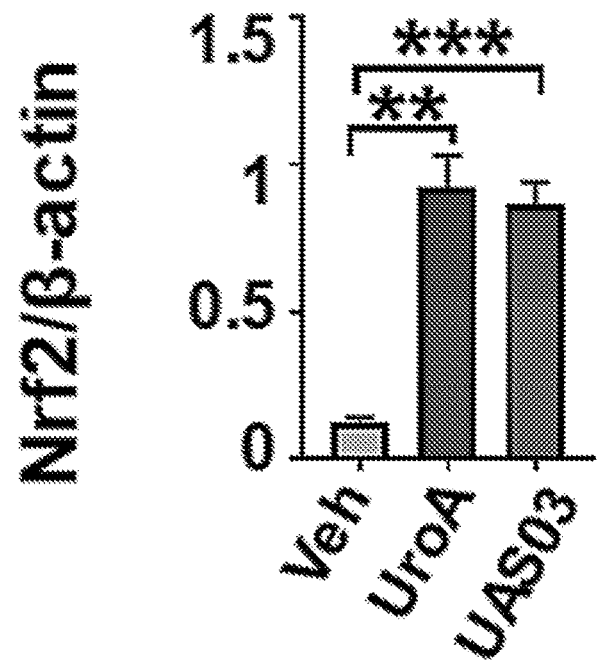
Figure 3:
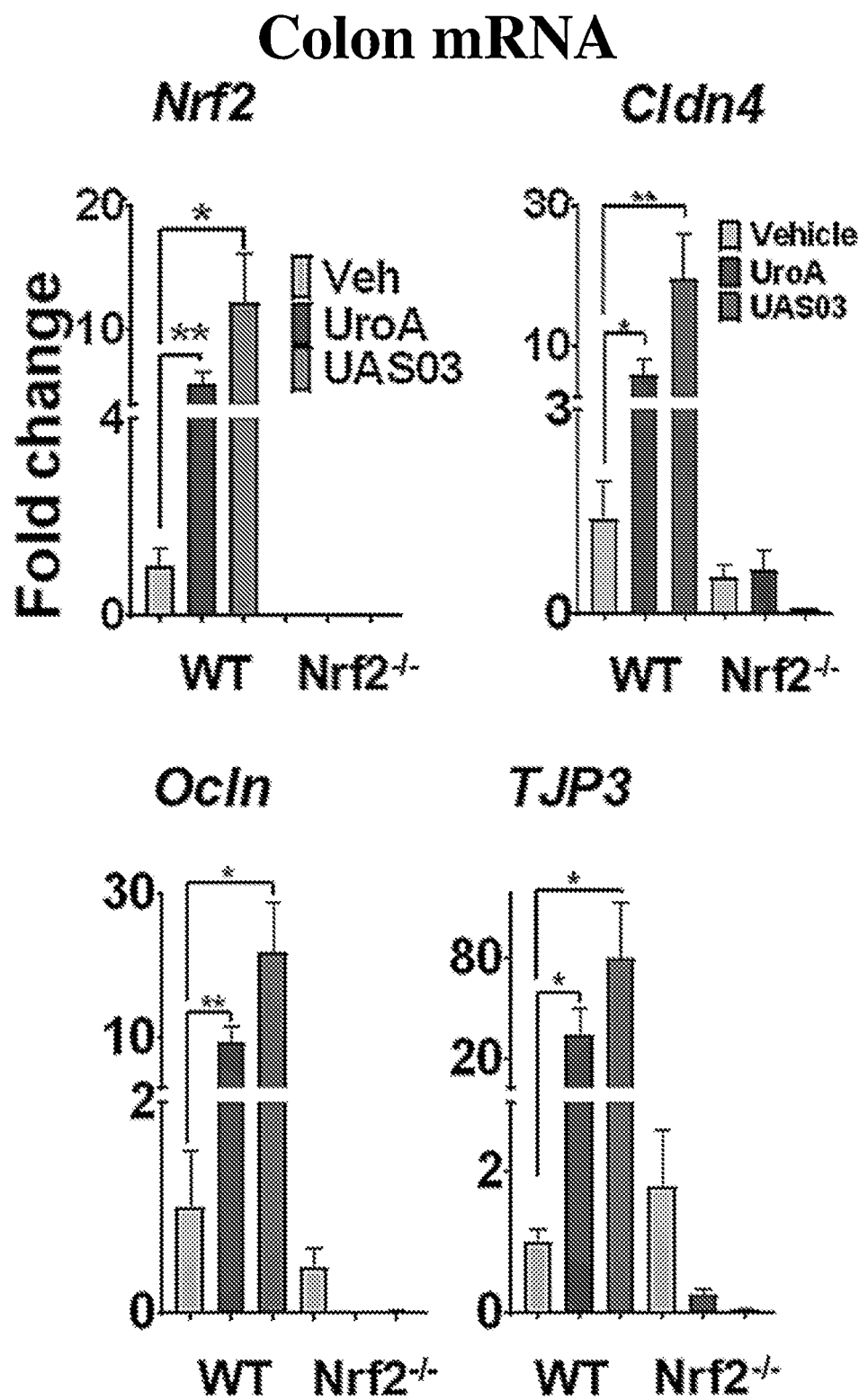
Figure 3:
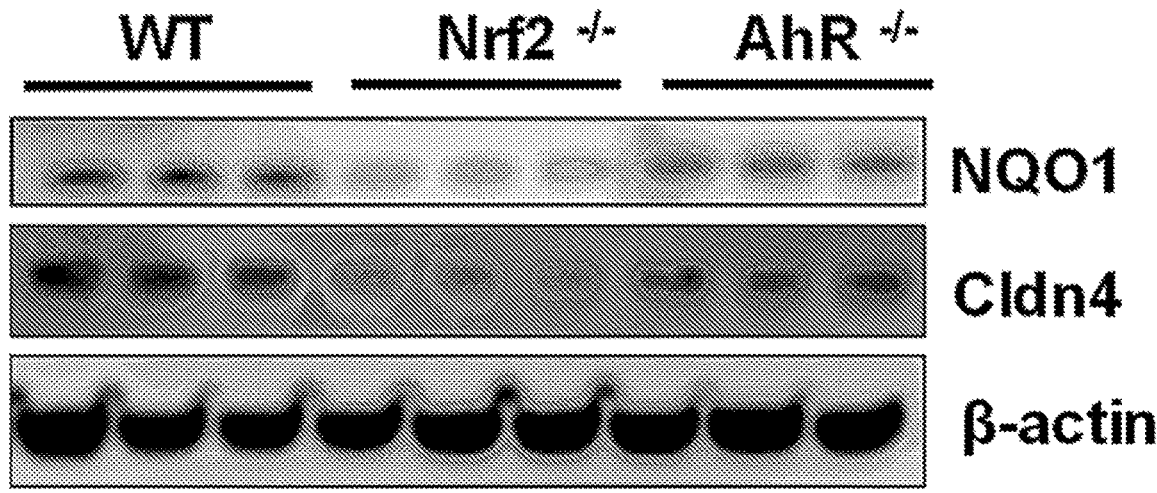
Figure 3:
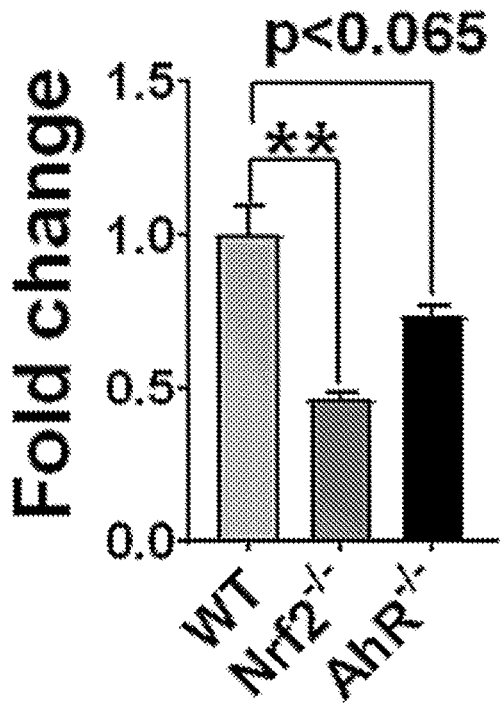
Figure 3:
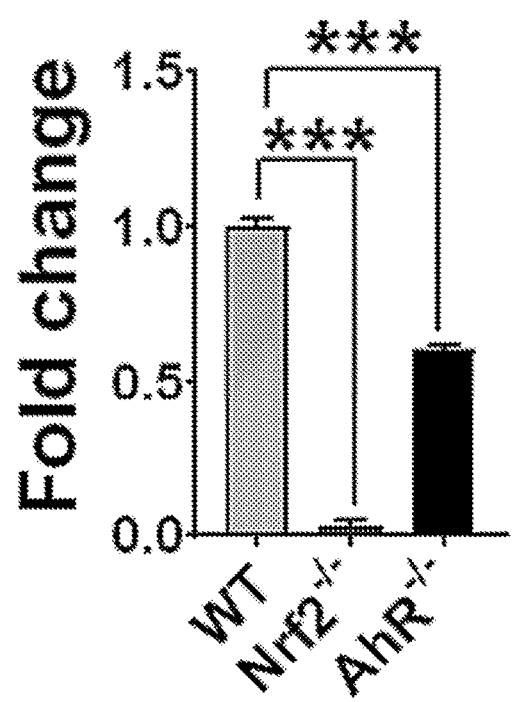
Figure 3:
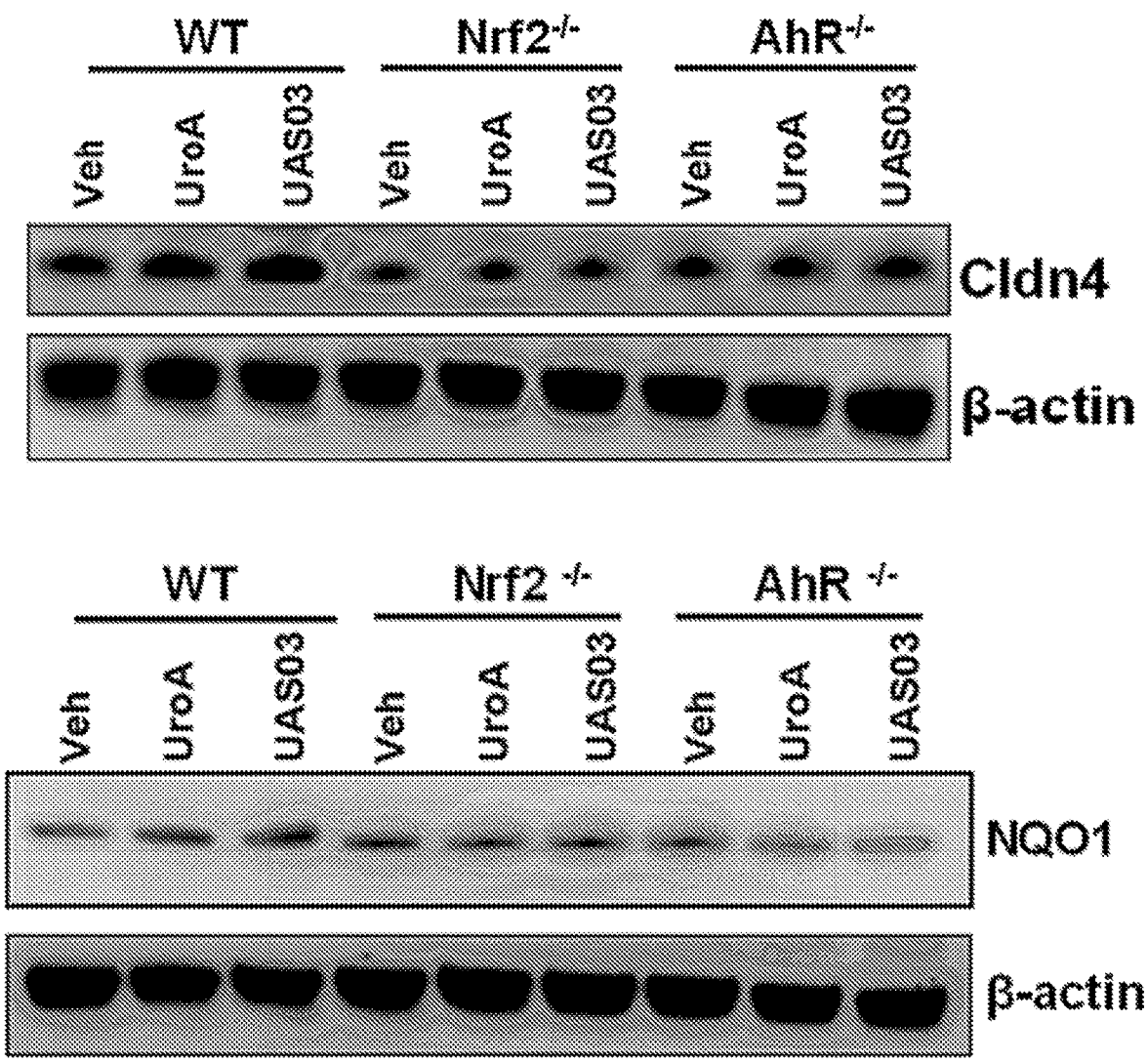
Figure 3:
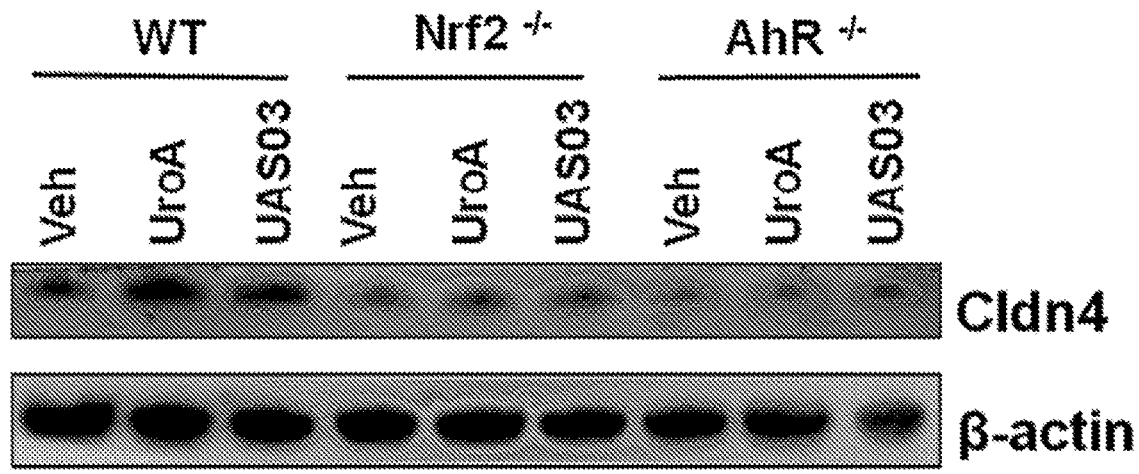
Figure 3:
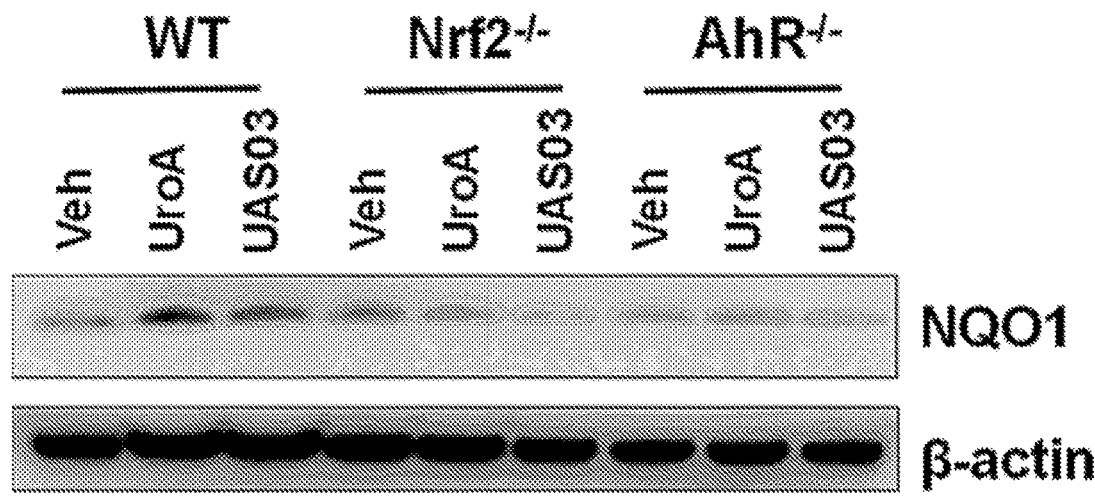
Figure 3:
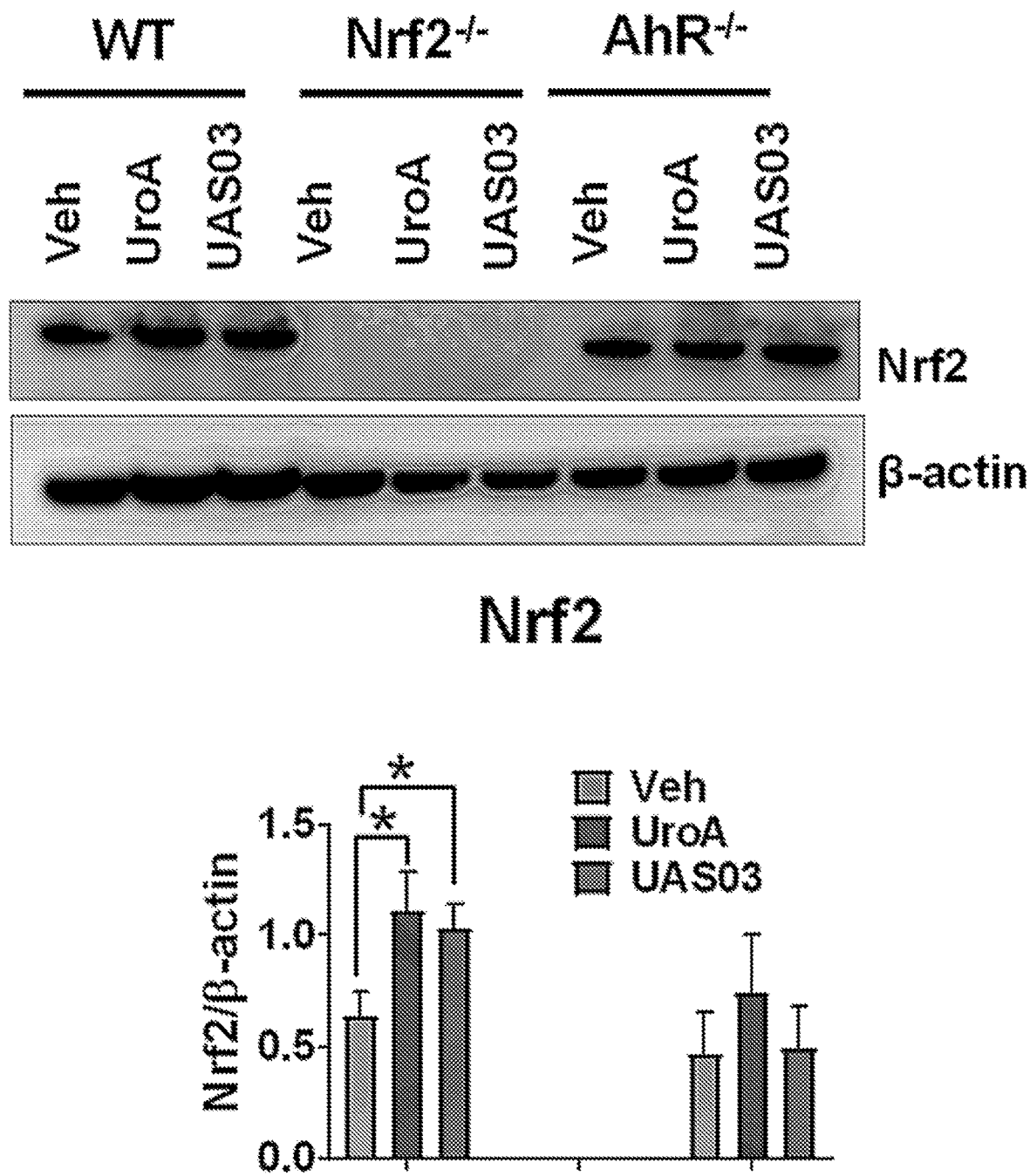
Figure 3:
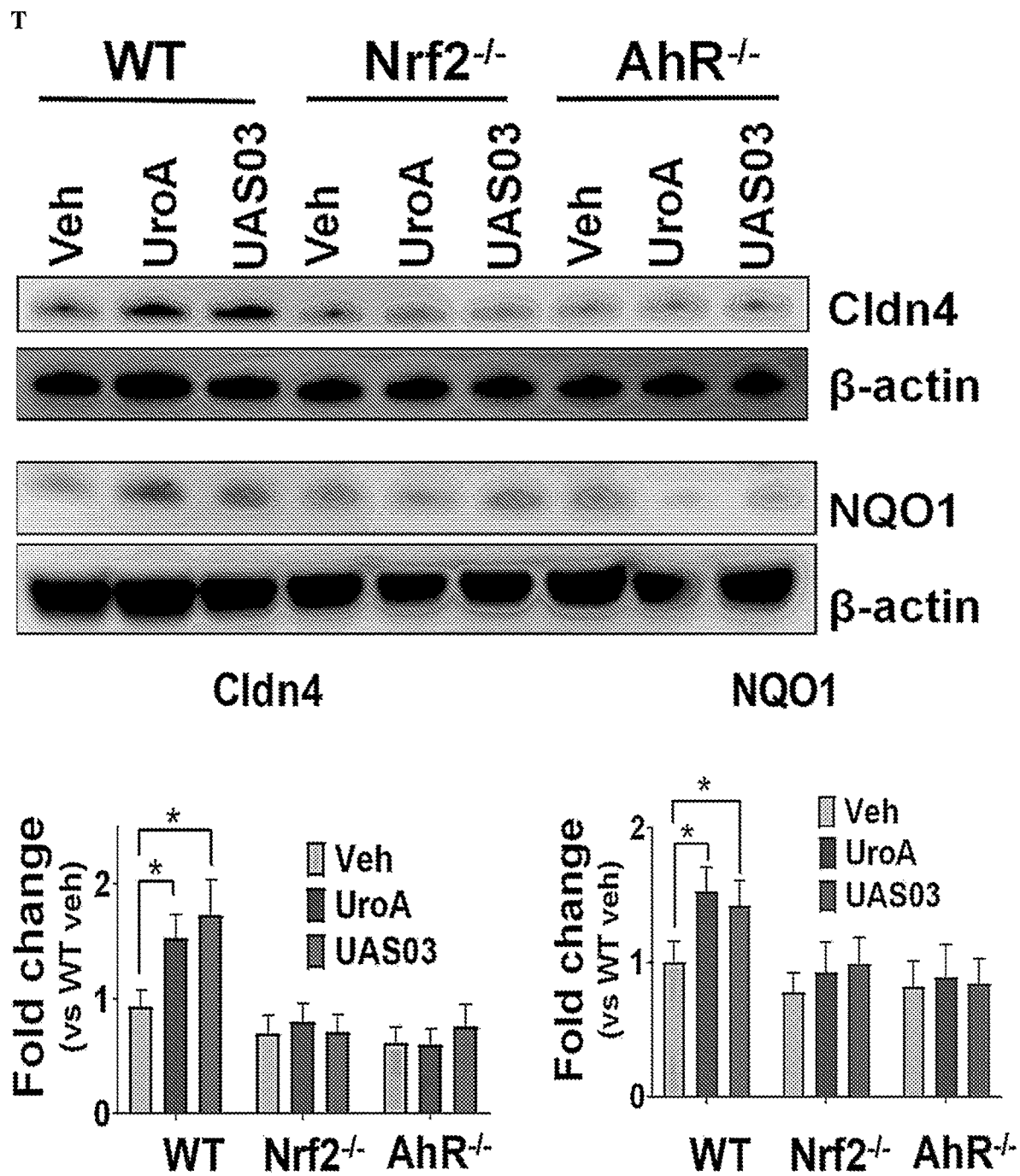

Our studies both in vitro and in vivo suggest that UroA/UAS03 induced the expression of Nrf2 as well as its target genes such as HO1 and NQO1 in colon epithelium. Furthermore, our results also showed that AhR-Cyp1A1-Nrf2 pathways have a role in UroA/UAS03 mediated upregulation of tight junction proteins (FIGS. 2 and 3).

Figure 5:
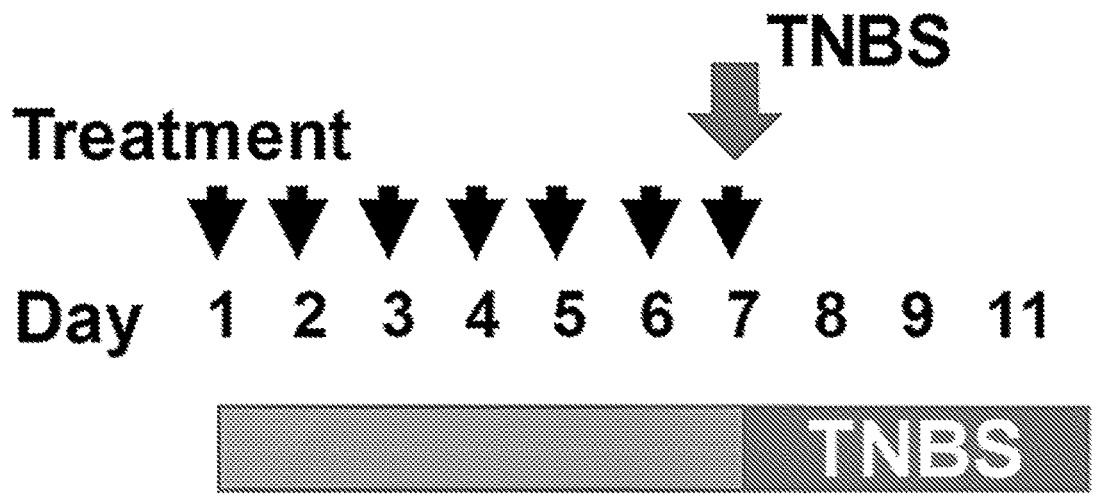
FIG. 5: UroA/UAS03 prevent TNBS-induced colitis and sustain beneficial barrier activities. (A) Pre-TNBS treatment. Male C57BL/6 mice (n=5 per group at 7-8 week old age) were given orally vehicle (Veh; 0.25% sodium carboxymethylcellulose) or UroA or UAS03 (20 mg/kg/bodyweight) daily for one week followed by rectal administration of TNBS to induce colitis. These mice did not receive any treatment post-TNBS administration. Mice were euthanized 72 h post-TNBS administration and characterized. (B) Post-TNBS treatment. Another set group of C57BL/6 mice (n=5 per group at 7-8 week old age) received Veh or UroA or UAS03 (20 mg/kg) 24, 48 and 72 h post-TNBS. (C) Percent body weight loss was recorded after TNBS-administration. (No TNBS– Solid black line; Veh+TNBS– Solid red line; Pre-TNBS+UroA-Solid blue line; Pre-TNBS+UAS03-solid purple line; Post-TNBS+UroA-dashed blue line; Post-TNBS+UAS03–dashed purple line). (D) Representative colon images of control (no TNBS) along with vehicle/UroA/UAS03 treated mice from pre- and post-treatment groups. (E) Ratio of colon weight/length. (F) Intestinal permeability was evaluated using FITC-dextran leakage assay. (G) Serum levels of IL-6 and TNF-α were measured using standard ELISA methods. (H) Detail analysis of percent body weight loss of data presented in FIG. 5C. The data is separately presented for each time point. (No TNBS– Solid black line; Veh+TNBS-Solid red line; pre-TNBS+UroA-Solid blue line; Pre-TNBS+UAS03-solid purple line; Post-TNBS+UroA-dashed blue line; Post-TNBS+UAS03-dashed purple line). (I-M) Treatment with UroA/UAS03 mitigates DSS-induced acute colitis. C57BL/6 mice (7-8 week age old mice, n=8) were administered with 3% DSS in drinking water for 7 days and allowed them to recover for 7 days with normal water. UroA (20 mg/kg) or UAS03 (20 mg/kg) or vehicle (0.25% sodium carboxymethylcellulose) was delivered orally in 100 µl of volume on day 4 and 6 post-DSS. On $15^{th}$ day, mice were euthanized and analyzed the colonic inflammation. (I) Experimental design and disease activity index (DAI) scores are shown (Vehicle-Solid red line; UroA-Solid blue line; UAS03-Solid purple line). (J) colon lengths, (K) Intestinal permeability with FITC-dextran assay were determined. (L) Serum cytokines were measured using standard ELISA kits. (M) Representative colon H&E section photomicrographs were captured using Aperio Image Scope. The scale bar indicates 1 mm. Statistical analysis was performed (unpaired t-test) using Graphpad Prism software. Error bars, ±SEM *$p<0.001$; $p<0.01$; *$p<0.05$. ns: not significant.
Figure 5:
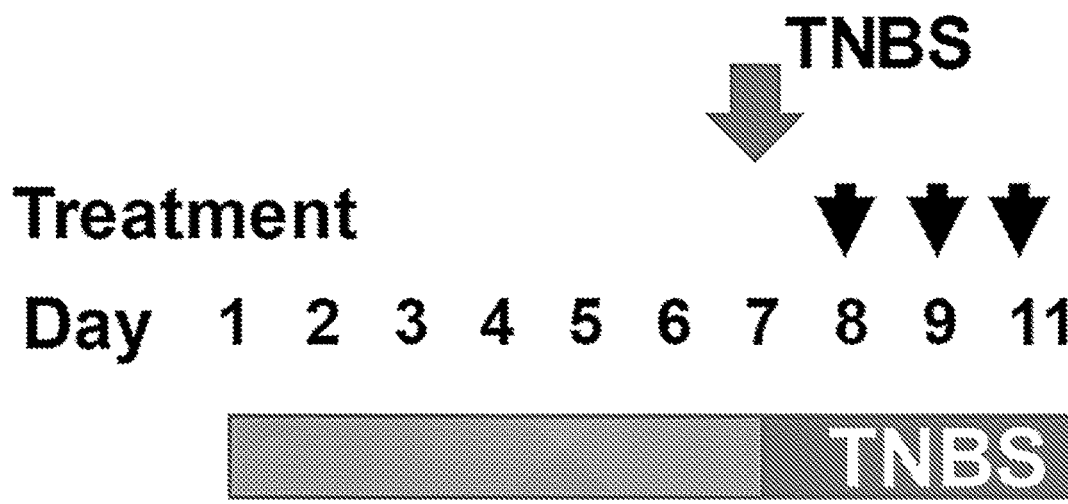
Figure 5:
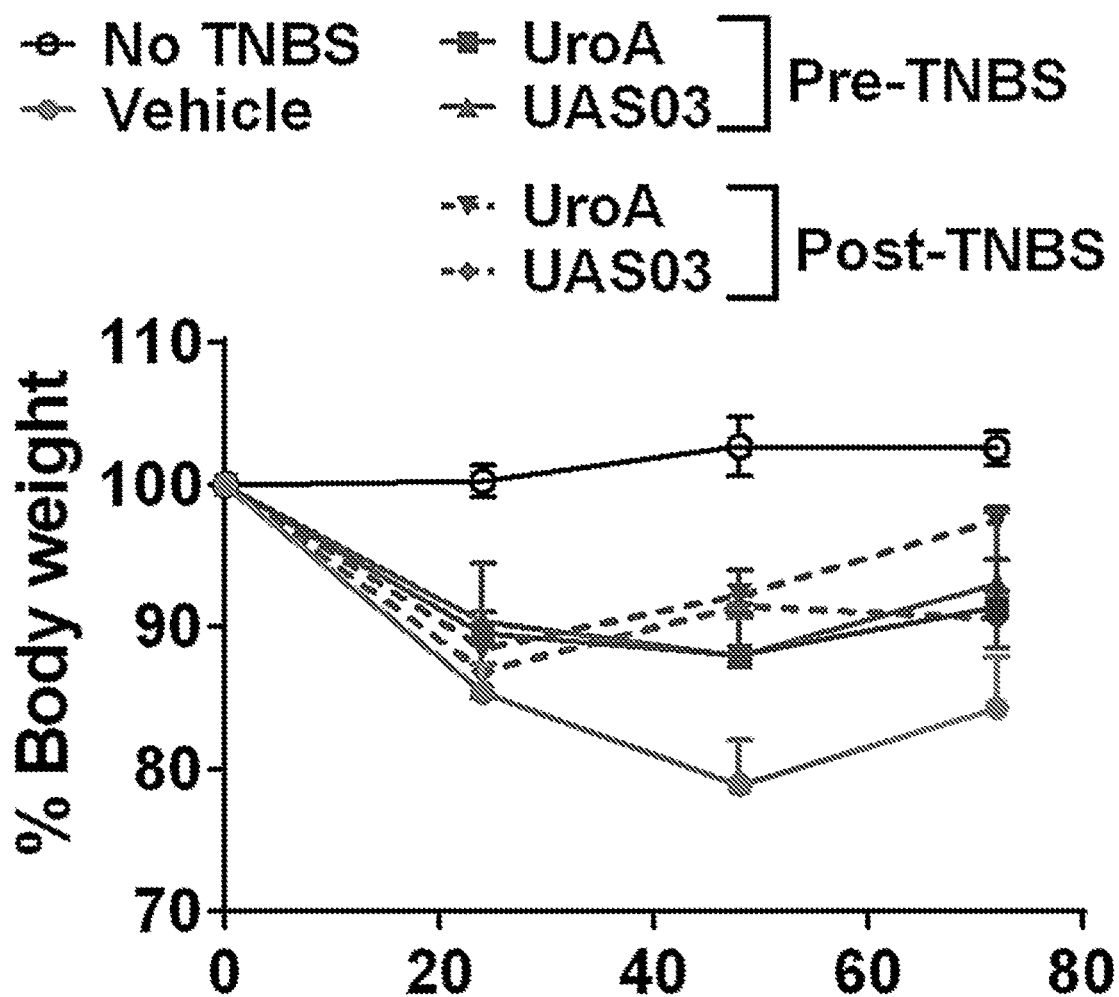
Figure 5:
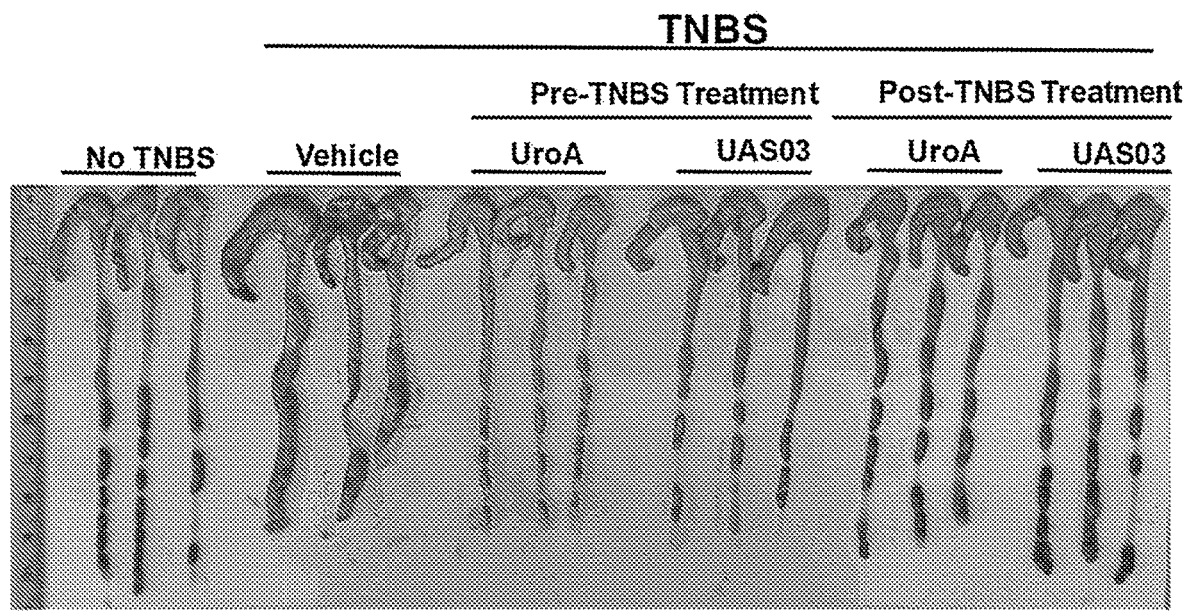
Figure 5:
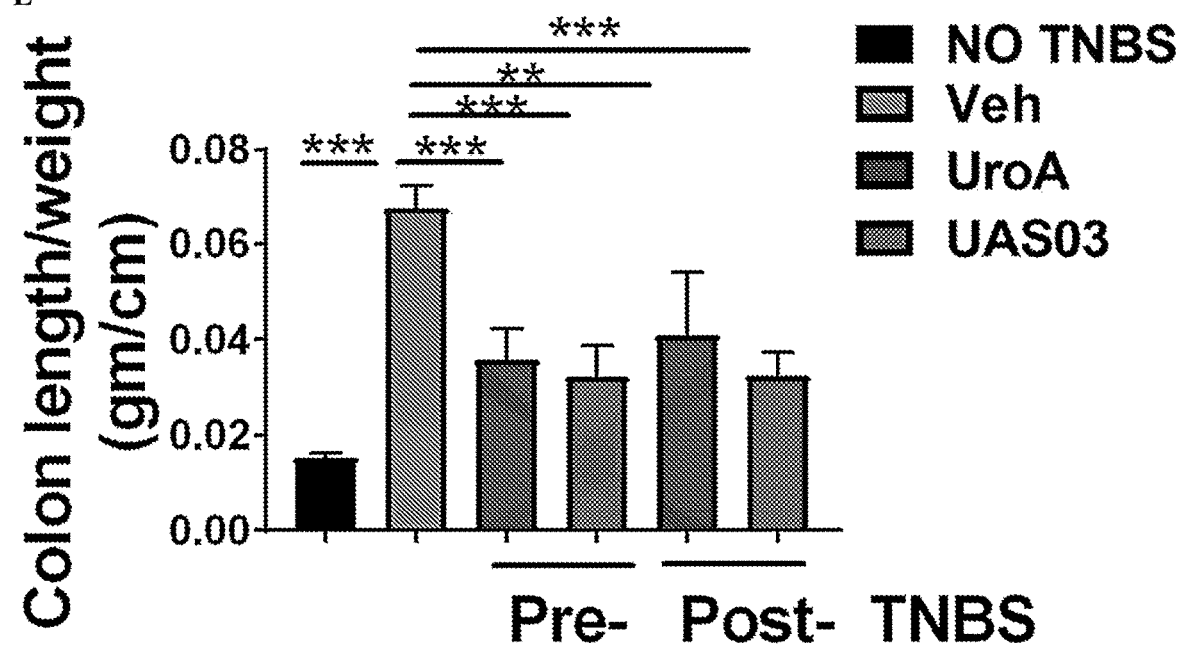
Figure 5:
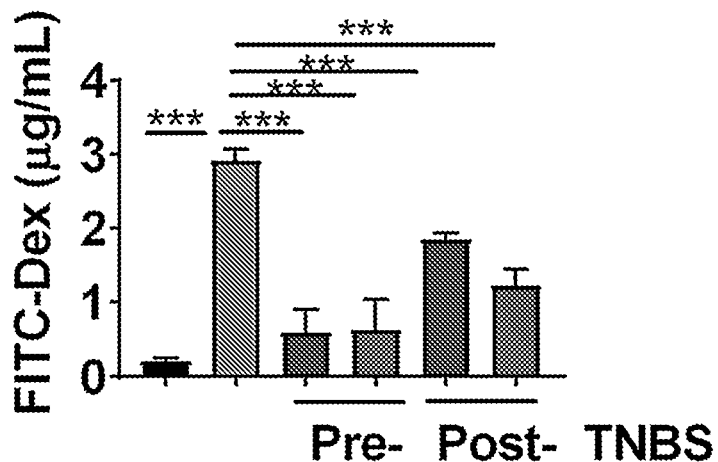
Figure 5:
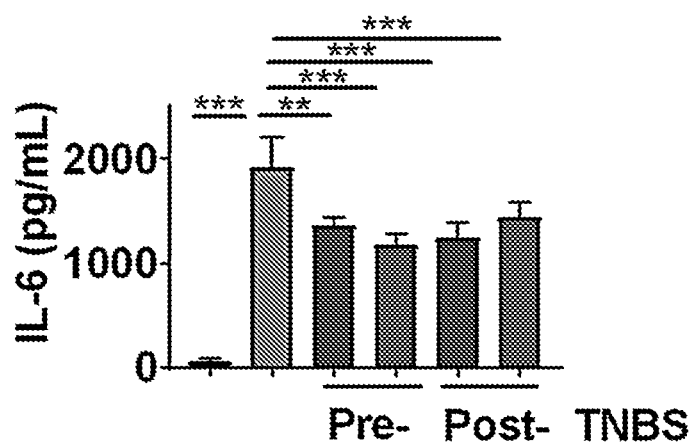
Figure 5:
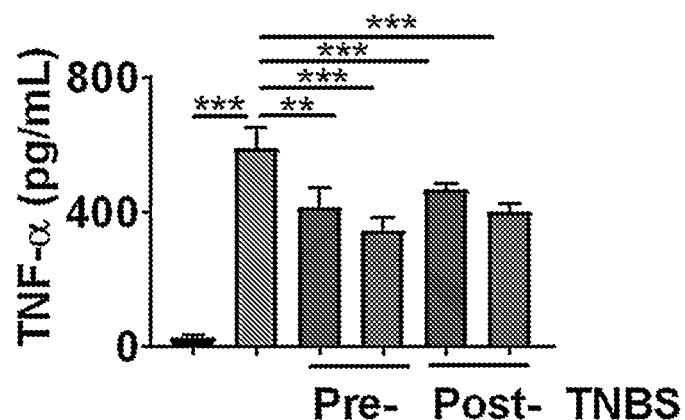
Figure 5:
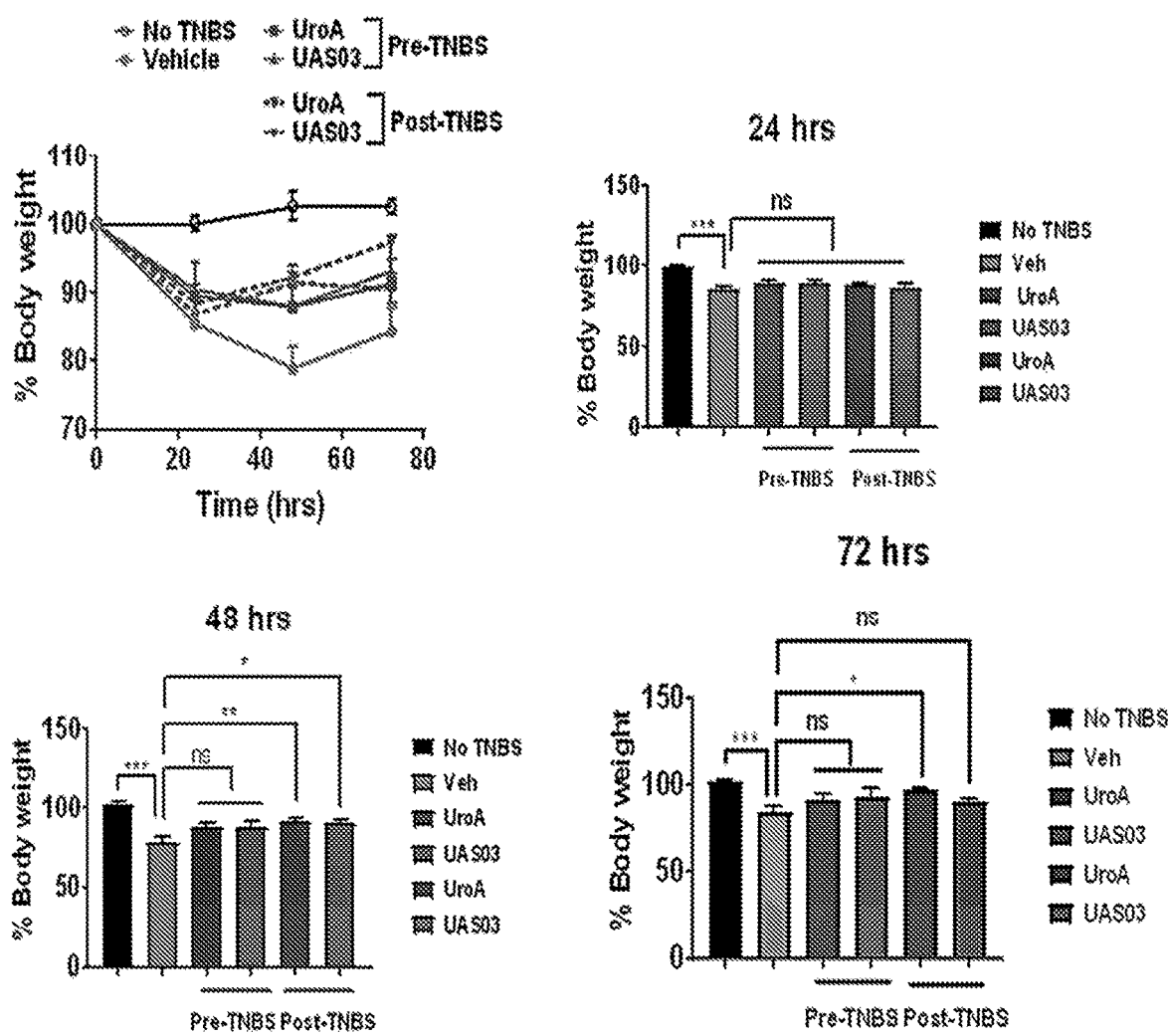
Figure 5:
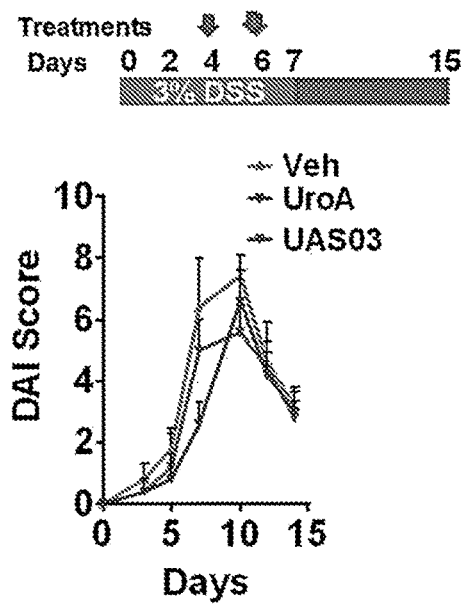
Figure 5:
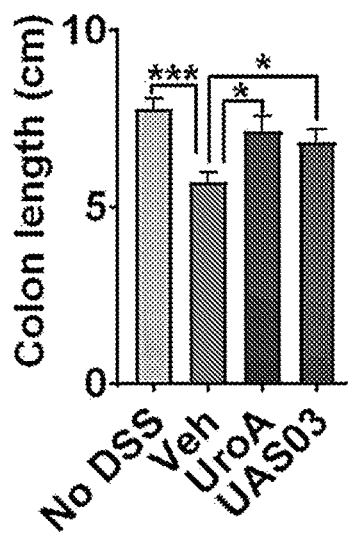
Figure 5:
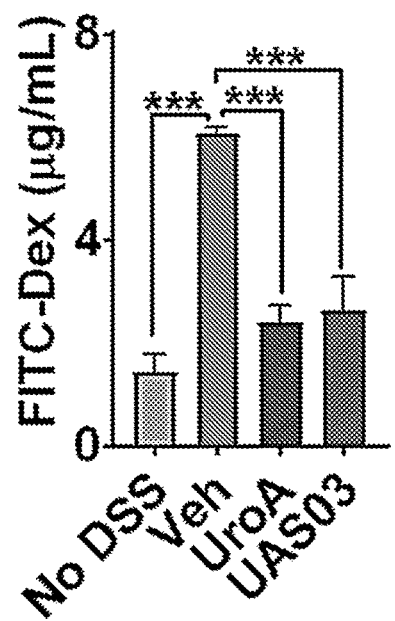
Figure 5:
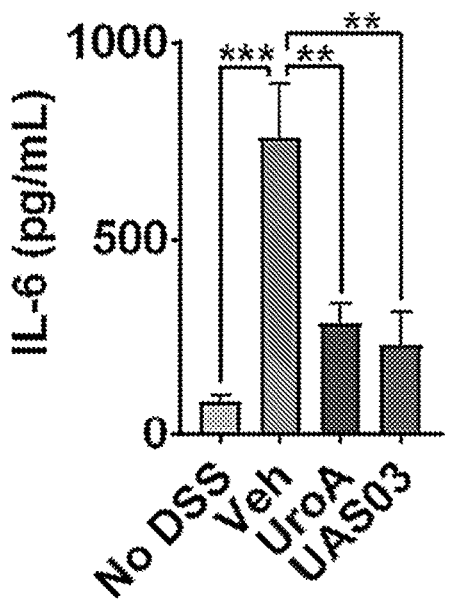
Figure 5:
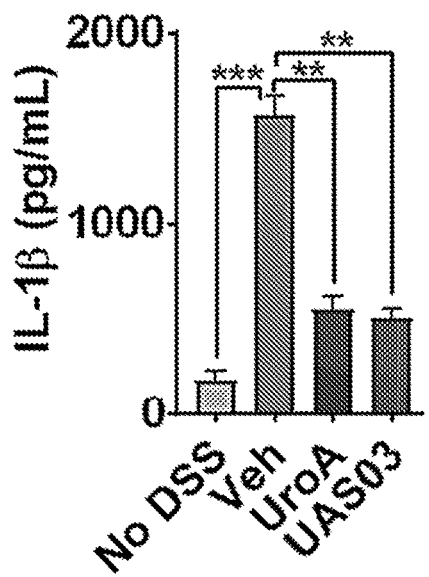
Figure 5:
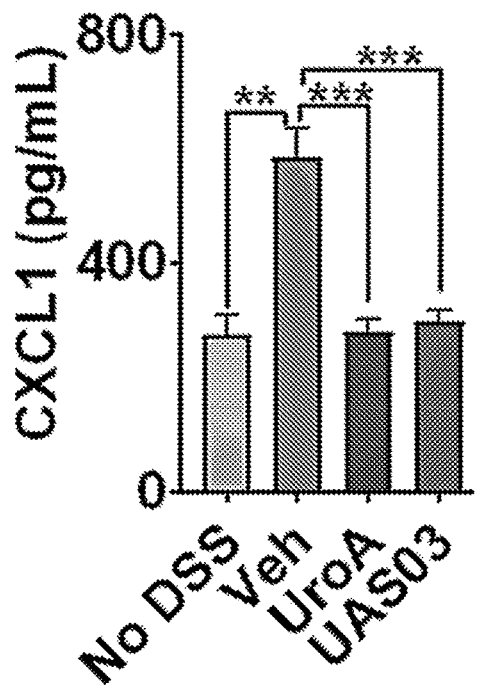
Figure 5:
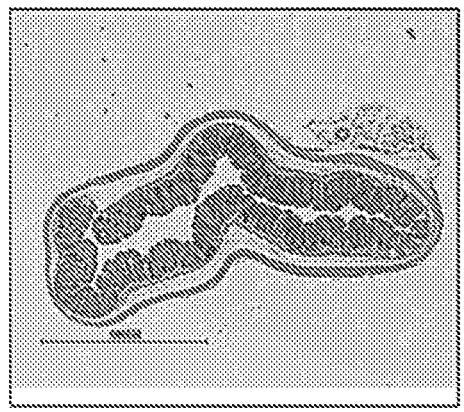
Figure 5:
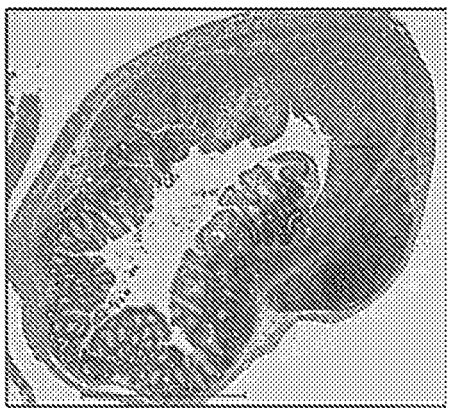
Figure 5:
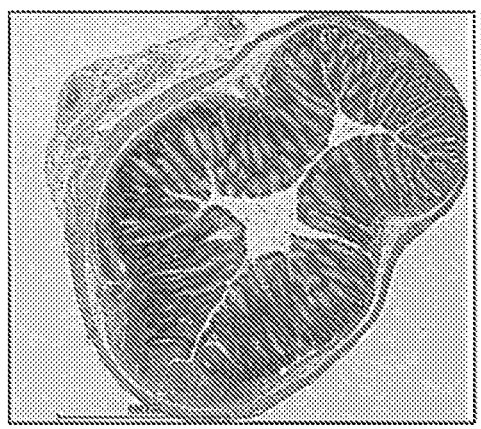
Figure 5:
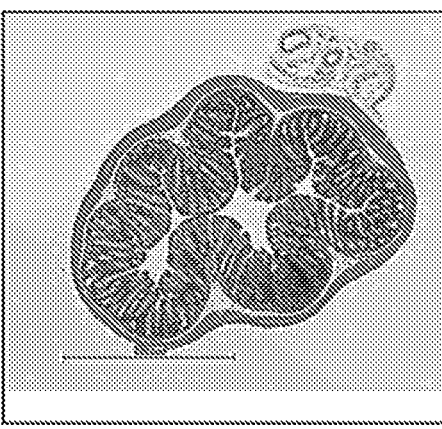
Figure 6:
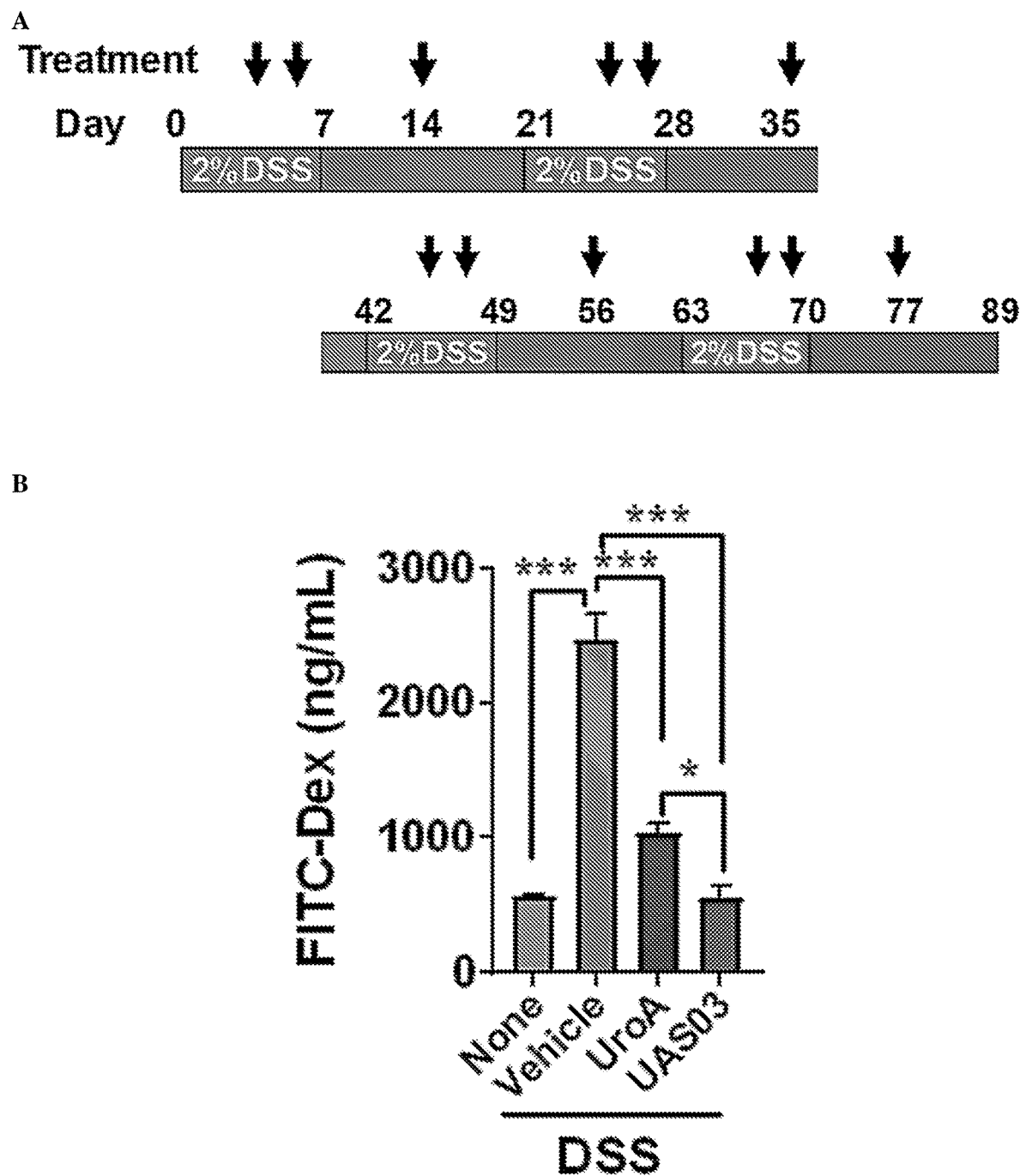
FIG. 6: Treatment with UroA/UAS03 mitigate DSS-induced chronic colitis. (A) C57BL/6 mice (7-8 week age old) were treated with four cycles of DSS (2%) with 7 days/cycle with an interval of 14 days with regular water. Control group of mice (n=5) received the regular water without DSS. UroA/UAS03 (20 mg/kg/day/body weight) that was resuspended in 0.25% sodium carboxymethylcellulose (CMC) solution (n=9) or vehicle (CMC) (n=9) was administered on $4^{th}$ and $6^{th}$ day of each DSS cycle and one treatment while on regular water. n=5/control; n=9/veh and UroA; n=8/UAS03 group) Mice were euthanized at day 89 and the colitis phenotype was characterized. (B) Intestinal permeability using FITC-dextran was evaluated. (C) Representative colon images (D) colon lengths, (E) ratios of colon weight/length are shown. (F) Serum levels of IL-6, IL-10 and TNF-α were measured using ELISA methods. (G) MPO levels were determined in colon tissues. (H) Cldn4 expression in the colons of these mice (n=3) was measured by immunoblots. Statistics performed using unpaired t-test using Graphpad Prism software. Error bars, ±SEM *$p<0.001$; $p<0.01$ *$p<0.05$.
Figure 6:
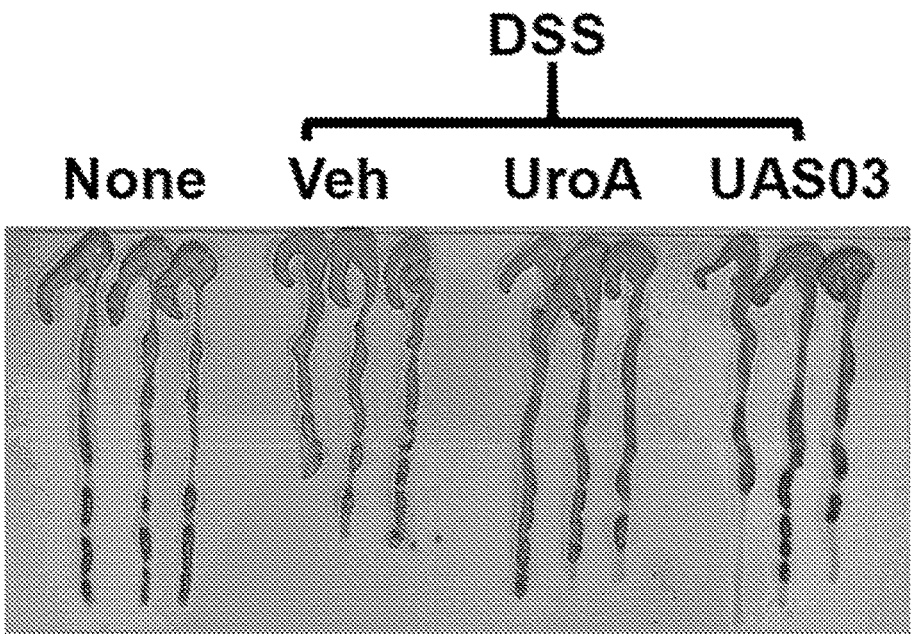
Figure 6:
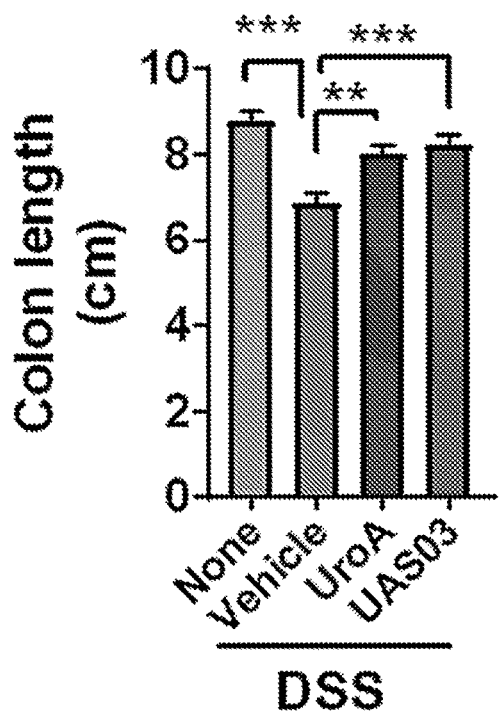
Figure 6:
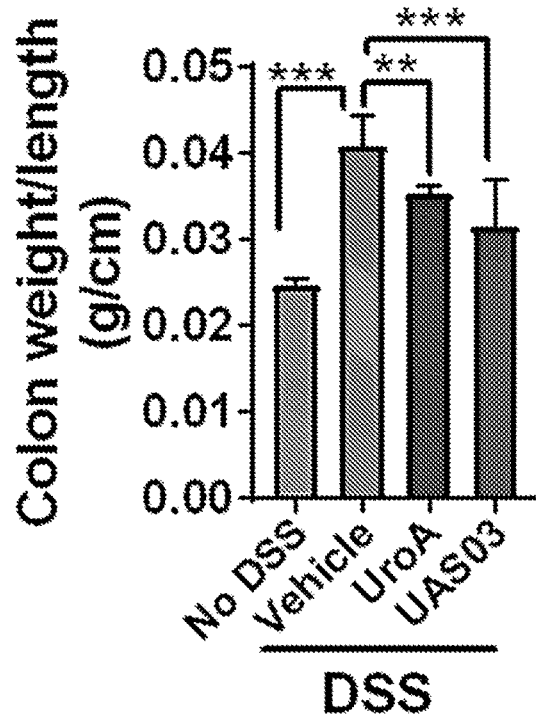
Figure 6:
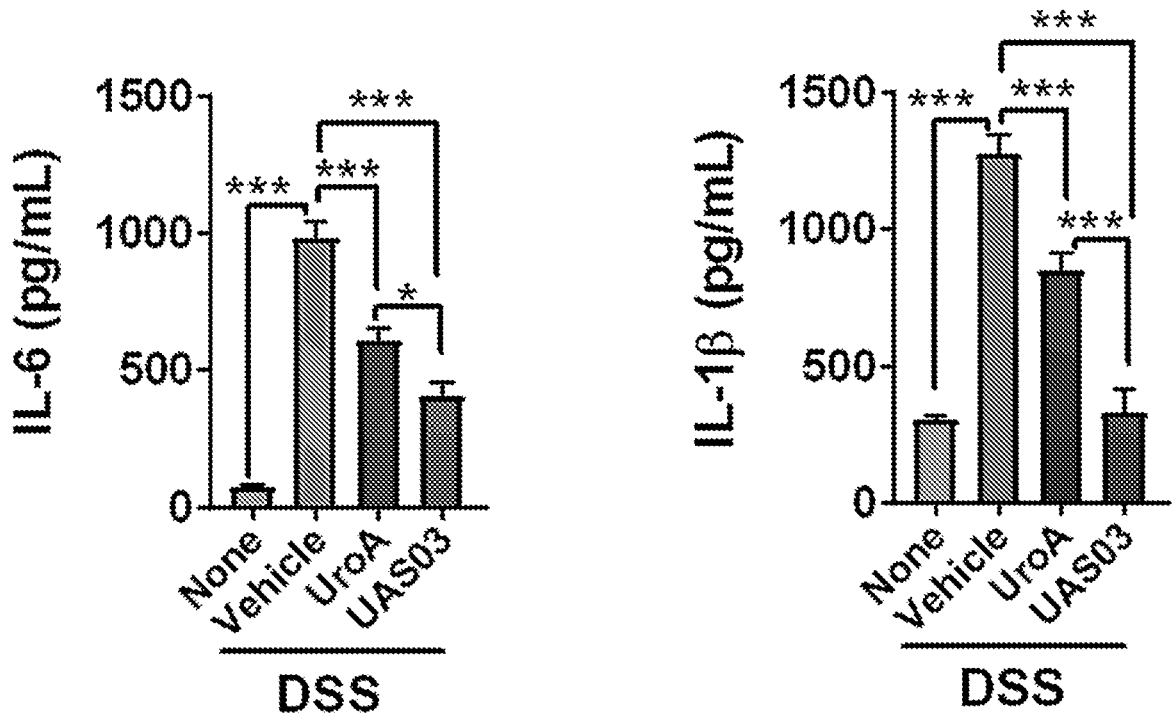
Figure 6:
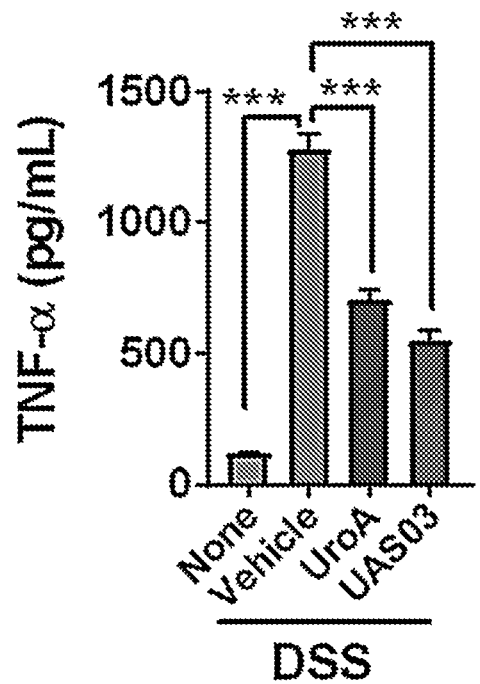
Figure 6:
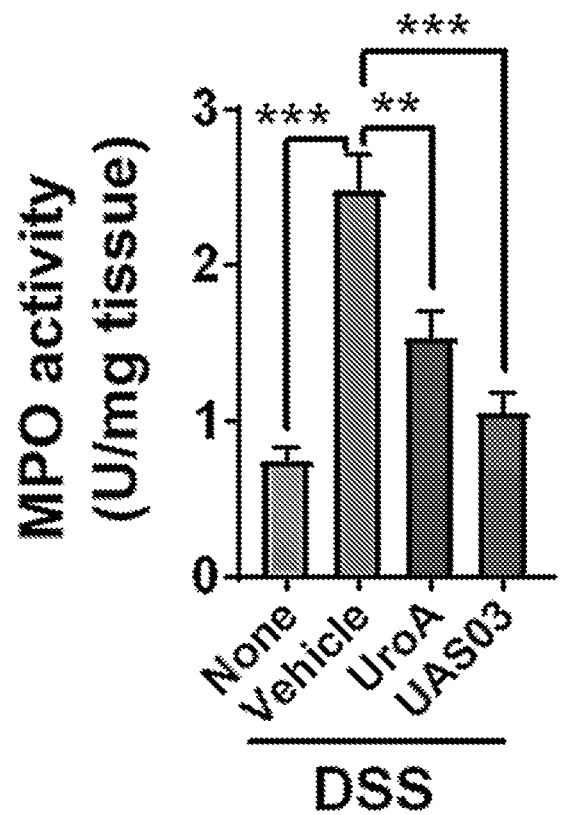
Figure 6:
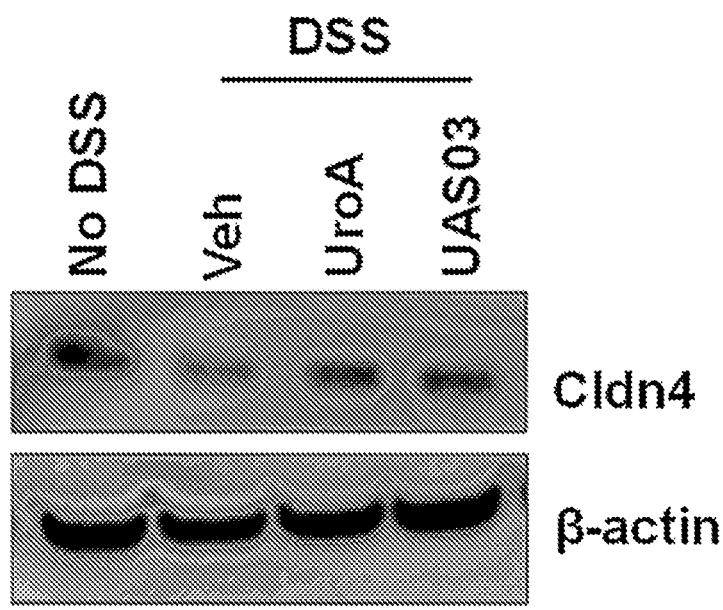

Our extensive studies in colitis models revealed that treatment with UroA/UAS03 enhanced tight junction proteins, decreased gut permeability, and reduced local and systemic inflammation leading to attenuation of colitis (FIG. 4-8). Even a single dose of UroA/UAS03 exhibited therapeutic efficacies against TNBS-induced colitis. Prophylactic benefits of UroA/UAS03 on gut barrier function and prevention of colitis development was observed (FIG. 5). The mice pre-treated with UroA/UAS03 prior to TNBS administration reduced gut permeability (FIG. 5E), which is consistent with increased expression of tight junction proteins. Despite not receiving further treatments post-TNBS administration, these mice were protected from disease development suggesting prophylactic effects of these compounds through enhanced barrier function. Moreover, UroA/UAS03 supplementing daily for 7 days induced expression of AhR, Nrf2 and Cldn4 in the colons of wild type mice without observable toxicity (FIGS. 3T, FIG. 1J-K, FIG. 3O-S, and FIG. 4R-S) suggesting potential translational applications for these compounds. Further, treatment with UroA/UAS03 also mitigated both chronic and acute DSS-induced colitis indicating model independent beneficial activities of these metabolites FIG. 6 and FIG. 5I-M). UroA/UAS03 are low affinity non-toxic AhR agonists like BNF that suppressed the pathogenesis of DSS-induced colitis.

We observed increased basal level of inflammatory mediators in Nrf2'-mice compared to wild type mice as well as in Nrf2$^{-/-}$ BMDM. Further, addition of LPS upregulated IL-6 in Nrf2$^{-/-}$ BMDM compared to wild type BMDM as well as in TNBS-induced colitis model. UroA/UAS03 failed to repair TNBS-induced barrier dysfunction and colitis in Nrf2$^{-/-}$ mice (FIG. 7).

The role of AhR in UroA/UAS03 mediated upregulation of tight junction proteins was demonstrated using AhR siRNA, colon explants from AhR$^{-/-}$ mice as well as in vivo treatments in AhR$^{-/-}$ mice. Additionally, UroA/UAS03 did not appear to mitigate TNBS-induced colitis in mice lacking AhR (FIG. 8). UAS03 seems to have some protective role against rapid body weight loss in AhR$^{-/-}$ mice that are treated with TNBS. It did not appear to protect against other parameters such as shortening colon lengths, increased permeability and increased inflammatory mediators.

The current studies highlight a role for AhR-Nrf2 in protecting from barrier dysfunction. It is possible that UroA/UAS03 are exerting colitis protective activities by two-pronged mechanism of action. These compounds appear to act on immune cells (e.g., macrophages) to prevent LPS/bacterial induced inflammation as well as exhibit anti-oxidative activities through AhR-Nrf2 pathways. These metabolites have direct impact on gut epithelium and gut barrier function by upregulating tight junction proteins. Enhanced barrier function reduces the bacterial leakage in the gut leading to reduction in systemic inflammation. In addition to anti-inflammatory and barrier protective activities, UroA/UAS03 may reduce IBD through regulating mitochondrial dysfunction.

The current study summarizes UroA and UAS03 with activities in mitigating IBDs by enhancing gut barrier function and reducing inflammation. Existing IBD treatments include utilizing anti-TNF-α antibodies to reduce inflammation; here we suggest that enhancing gut barrier functions in addition to inhibiting inflammation might provide better therapeutic options for control of IBDs.

Example Set C

UroA reduces the LPS and EtOH induced TNF-α in human primary monocytes. Peripheral blood monocytes from chronic alcoholism patients produce increased spontaneous inflammatory mediators such as TNF-α, IL-6, IL-10 and IL-12. To mimic this condition, healthy peripheral blood monocytes were exposed for one week and tested whether UroA/UAS03 reduce the LPS-induced TNF-α. Our studies suggest that UroA reduced TNF-α in chronically EtOH exposed human monocytes (FIG. 11) acknowledging its beneficial anti-inflammatory activities in ex vivo human primary cultures.

UroA/UAS03 upregulate TJ proteins and protect against LPS induced damage: TJ proteins such as Cldn4, ZO-1, Ocln play a role in maintaining the gut epithelial integrity and protect the gut from external insults such as LPS. We investigated UroA/UAS03 effects on TJ protein regulation in colon epithelial cells, HT-29 and Caco2 cells. In a series of experiments both in vivo and in vitro, we demonstrated that treatment with UroA/UAS03 upregulate TJ proteins and enhance gut barrier function. ALD is associated with disrupted TJs, increased permeability, inflammation and endotoxemia. Ocln is a tight junction protein expressed in intestinal epithelium and plays a role in maintenance of gut barrier function. We examined whether UroA/UAS03 can protect LPS (endotoxin) depletion of Ocln in colon epithelial cells. As shown in FIG. 12, treatment with LPS decreased levels of Ocln (FIG. 12A) and UroA/UAS03 protected from depletion of Ocln in colon epithelial cells (FIG. 12B). Next, we tested whether UroA exhibits protection against alcohol mediated epithelial cell damage. For this purpose, we have utilized Caco-2 monolayer cells on transwell membranes and performed transepithelial electrical resistance (TEER) and FITC-dextran permeability assays.

UroA upregulate TJ proteins and protect against EtOH induced damage. Next, we tested whether UroA exhibits protection against alcohol mediated epithelial cell damage. For this purpose, we utilized Caco-2 monolayer cells on transwell membranes and performed transepithelial electrical resistance (TEER) and FITC-dextran permeability assays. As shown in FIG. 13, EtOH induced damage in monolayered Caco2 cells and induce leakage in a time dependent manner (FIG. 13A). Among urolithins, UroA is a better compound to protect against EtOH-induced permeability (FIG. 13B) and reduces in a dose dependent manner (FIG. 13C). UroA protects against EtOH or LPS or HMGB1 induced epithelial permeability: Endotoxemia and gut barrier dysfunction are associated with pathogenesis of ALD. Gut barrier dysfunction leads to elevated intestinal permeability thus increasing circulating levels of endotoxins. Endotoxins such as LPS (representative for PAMP) and HMGB1 (representative for DAMP) induce several inflammatory cytokines, chemokines and ROS leading to further enhancement of systemic inflammation to promote pathogenesis of ALD. Our in vitro studies (FIG. 13D) suggest that HMGB1 or LPS increased gut epithelial permeability and treatment with UroA protected from EtOH or LPS or HMGB1 induced permeability. UroA also protects even at higher dose of EtOH (400 mM) induced permeability (FIG. 13E) and enhanced TEER values (FIG. 13F). Treatment with UroA protects against EtOH induced damage of tight junction proteins as evidenced from Western blots (FIG. 13G) and confocal images of stained TJ proteins, ZO-1 and Ocln (FIG. 13H).

We tested whether UAS03 could protect against higher dose of EtOH (350 mM) induced barrier dysfunction in Caco2 monolayer cells. As shown in FIG. 14, UAS03 and UroA protected against EtOH induced barrier dysfunction as evident increased TEER (FIG. 14A) and decreased permeability (FIG. 14B) corroborating with increased TJ protein, Ocln (FIG. 14C).

Treatment with UroA mitigates acute and chronic alcohol liver disease. To examine therapeutic efficacies of UroA in ALD, we adopted acute mouse model as developed by Gao B group (NIAAA) (BERTOLA et al., (2013) "Mouse model of chronic and binge ethanol feeding (the NIAAA model)" Nat Protoc. Vol. 8, No. 3, pp. 627-637). We tested therapeutic efficacies of UroA in this model. As shown in FIG. 15, UroA reduced alcohol-induced (acute model, FIG. 15A) permeability (FITC-dextran leakage, levels of fecal albumin—FIG. 15B-C), both systemic inflammation (Serum IL-6, TNF-α, IL-1β, endotoxins-FIG. 15D-G), circulating serum ALT, AST levels (FIG. 15H-I). UroA treatment also reduced TG accumulation in liver (FIG. 15J). UroA also protects against TJ protein (ZO-1) disruption at intestines (FIG. 16).

UroA protects against chronic low dose alcohol induced gut barrier dysfunction and inflammation. C57BL/6 mice (n=5 per group) were treated with EtOH (3 g/kg) twice daily orally for 5 days. UroA (20 mg/kg) was given orally 2 h prior to EtOH treatment. We evaluated gut permeability and inflammation parameters both in serum and liver (FIG. 17).

Treatment with UAS03 ameliorates chronic ALD: Since UAS03 showed higher efficacy in reducing inflammation and permeability, an experiment in the chronic ALD mouse model was performed only with UAS03 as a proof of principle (FIG. 18). Male C57BL/6N (10 week age old) were purchased from Jackson Laboratory and were acclimatized with pair fed liquid diet (Lieber DeCarli) for 1 week. After acclimatization, animals were fed with pair fed (n=5 mice/group) and alcohol diet (n=10 mice/group). Briefly, mice were fed with diet containing 17% of energy as protein, 40% as corn oil, 7.5% as carbohydrate, and 35.5% as either alcohol (5% v/w, alcohol-fed, AF) or isocaloric maltose dextrin (pair-fed, PF). Before mice went on to 5% alcohol diet, alcohol concentration was ramped from 1.6% (3 days) to 3.6% (3 days) and finally 5% for next 4 weeks. UAS03 group animals received UAS03 orally (20 mg/kg/day) on every other day after start of alcohol diet (FIG. 18A). We used 0.25% sodium carboxymethyl cellulose (CMC) as vehicle treatment. The mice were euthanized after 4 weeks and measured colon lengths (FIG. 18B-C), in vivo gut permeability (FITC-dextran assay), serum ALT, AST, endotoxin, IL-6 and TNF-α (FIG. 18E). Analysis of liver histopathology suggested that UAS03 reduced liver fat deposition supporting liver TG levels and steatosis (FIG. 18F). Levels of IL-6, TNF-α, MPO and triglycerides (TGs) in liver tissues suggest that treatment with UAS03 down regulated liver inflammation and TG levels (FIG. 18G) in these mice. UAS03 protected from deterioration of Ocln in the gut (FIG. 18H) supporting decreased intestinal permeability in UAS03 treatment group in ALD mice.

AhR has a role for UroA mediated protection in ALD model: To address the role of AhR expression for UroA mediated activities, we performed acute ALD models in C57BL/6J mice and AhR$^{-/-}$ mice. In this experiment, mice (WT, AhR$^{-/-}$ mice (n=4/group)) were treated with half the dose of EtOH (2.5 g/kg) at 0, 12 and 24 h followed by oral treatment Veh (0.25% CMC) or UroA (20 mg/kg) at 2, 14 and 26 h. As shown in FIG. 19, these mice tolerated the EtOH at low doses and UroA treatment did not appear to rescue EtOH-induced gut leakage (fecal albumin levels), serum endotoxins, TNF-α, ALT as well as liver ALT levels. UroA down regulated TG levels in AhR$^{-/-}$ mice suggesting AhR independent activities of lipid metabolism.

UroA treatment protects against EtOH-induced colon epithelial junction proteins: Colon epithelial cells (T84 cells) were treated with Vehicle (0.05% DMSO) or UroA (50 μM) for 1 h followed by EtOH (40 mM) for 6 h. The membrane and cytosolic fractions were isolated and evaluated for tight junction (TJ) and adherins junction (AJ) and desmosomes. It is evident from FIG. 20 that UroA protected from EtOH-induced internalization of membrane junction proteins to cytosol. (i.e., EtOH treatment alone has more cytosolic protein and EtOH+UroA has more membrane fraction) (FIG. 20).

UroA protects against TNF-α and IFN-γ induced permeability in CaCo-2 cells: Monolayer CaCo2 cells on transwell membrane wells were treated with TNF-α (10 ng/ml) and IFN-γ(10 ng/ml) in the presence or absence of UroA (50 μM) for 48 h. The TEER values and FITC-dextran permeability were measured as described by SINGH et al (2019) "Enhancement of the gut barrier integrity by a microbial metabolite through the Nrf2 pathway" Nat Commun., Vol. 10, No. 1, Article 89 (18 pages); (FIG. 21).

Example Set D

UAS03 (Ether) attenuates septic mortality. $C_{57}B6/J$ mice were injected with lipopolysaccharide intra-peritoneally at a septic dose of 20 mg/kg. The treated animals received either Urolithin-A or UAS03 (Ether) at 20 mg/kg intraperitoneal injection. Untreated septic animals showed 100% mortality within 50 hours. Urolithin A treated animals showed 20% survival, while UAS03 (Ether) treated animals showed 90% long term survival (FIG. 22).

Preventive and therapeutic effect of UAS03 (Ether) in septic animals. Animals were injected with LPS intraperitoneally at 20 mg/kg dose to induce sepsis. For Ether+LPS group animals were given UAS03 (20 mg/kg; intraperitoneal) 1 hour prior LPS injection. LPS+Ether group received UAS03 1 hour post LPS injection. Septic untreated animals showed 100% mortality within 50 hours; animals pretreated with UAS03 showed 70% survival; while the therapeutic group showed 100% survival (FIG. 23).

UAS03 attenuates Scleroderma associated vascular permeability in Snail transgenic mice. Calorimetric quantification of Evan's blue dye extracted from back skin using UV spectrophotometer. Vehicle treated Snail animals showed 3-fold more dye than the control animals. Animals treated with UAS03 show more than 3-fold reduction in the dye leakage (FIG. 24). This indicates that UAS03 has the ability to reduce endothelial vascular permeability.

Expression for fibrosis associated genes in the back skin of the Snail transgenic mice. The mRNA levels of the Collagen 1 were measured in back skin using RT-qPCR. Snail vehicle showed increased expression in both males and females of the vehicle treated group compared to control animal. The expression in UAS03 treated group, in both males and females, were reduced. The levels were separately assessed in males and females in vehicle and drug treated animals (FIG. 25). This data indicates that UAS03 has the ability to reduce fibrosis.

UAS03 shows autophagy induction. Autophagy induction after compound treatment for 2 hours is assessed by the presence of red and green punctate inside the cells. The HeLa cells were transfected with RFP-GFP-LC3 plasmid 48 hours prior to drug treatments. After drug treatment for 2 hours the cells are fixed and imaged. LC3 is a protein that is expressed on autophagosomes and is seen as green puncta. When the autophagosome and lysosome fuse to form autolysosomes, the acidic pH inside of it causes degradation of GFP protein and only red puncta are visible (FIG. 26). This data indicates that UroA and UAS03 have the ability to induce autophagy.

Example Set E

We synthesized several compounds and tested their anti-inflammatory activities and inhibitory activities of Monoamine oxidase A (MAO A) and Monoamine oxidase B (MAO B) in a dose dependent manner.

Screening for anti-inflammatory activities: Mouse bone marrow derived macrophages (BMDM) were plated in 96 wells plate for ELISA. To evaluate the anti-inflammatory properties, BMDMs were stimulated with *E. coli*-derived lipopolysaccharides (LPS; 055:B5; Sigma) at 50 ng/mL concentration for six hours alone or in combination with compounds at indicated concentrations in quadruplicates. For cytokine production via ELISA, the supernatant was collected and centrifuged at 12,000 rpm for 10 min at 4° C. to pellet down any cell and cytokines were quantified using IL-6 and TNF-α specific ELISA kit (Biolegend) following manufacturer's instruction. LPS induced IL-6 or TNF-α considered as 100%.

Anti-inflammatory activities (FIGS. 27-30): Inflammation is an underlying cause and promotion of several diseases including but not limited to inflammatory bowel diseases, alcoholic liver diseases, various types of cancers, arthritis, cardio vascular diseases, neurological disorders, sepsis, kidney, lung related and ageing related diseases. Here, we screened for anti-inflammatory activities of these analogues. We identified several compounds in this series displayed anti-inflammatory activities and blocked LPS-induced IL-6 and TNF-α in mouse bone marrow derived macrophages. For ease of presentation, we considered LPS induced IL-6 or TNF-α as 100%. We found UAS03, PKL 3, PKL4 and PKL 17 compared UroA (parent compound) to be effective anti-inflammatory compounds.

In summary, we synthesized and identified several anti-inflammatory compounds as potential therapeutics for numerous disorders involving inflammation.

Monoamine oxidase A (MAO A) and Monoamine oxidase B (MAO B) inhibitory activities of compounds: Assay: Briefly, 5 μg of MAO-A and MAO-B was incubated with 160 and 16 μM of MAO substrates, respectively. The enzyme assay was performed in presence of capsule compounds in a 96-well white plate. The control reaction contains equal amount of MAO buffer with the same percentage of solvent. The reaction plate was incubated at 37° C. for 60 min. After the incubation period, the reaction was stopped with addition of luciferin detection reagent. deprenyl were used as positive control for MAO-A and MAO-B, respectively. The luminescence produced was measured with multimode microplate reader, and it is directly proportional to MAO activity.

Inhibitors of MAO A and MAO B considered for treating Alzhiemer's and Parkinson's diseases. We tested several compounds utilizing pure MAO A and MAO B enzymes. We found several compounds inhibited the activities of MAO A and MAO B enzymes. FIG. 31 shows the primary screen of these compounds at 100 μM dose.

Next, we selected potential candidate compounds (PKL3, 4, 5, 12, 13, 14, 15, 16 along with UroA, B, C) and performed dose dependent (0.1, 1, 10 μM) inhibitory activities against MAO A and MAO B enzymes (FIG. 32).

FIG. 33 shows the screening of anti-inflammatory activities. Mouse bone marrow derived macrophages (BMDMs) were stimulated with LPS (50 ng/ml) with or without compounds for 6 hours. IL-6 and TNF-α levels in supernatants were measured using standard ELISA methods. Results are representative of three independent experiments with triplicates for each concentration.

FIG. 34 shows the activity of MAO enzymes in the presence of various compounds. FIG. 35 shows compounds tested against MAO-A and MAO-B activities and identified IC50 and Ki values.

Compounds Enhance Endothelial Barrier Function and Protect from Endothelial Barrier Dysfunction: Human studies show that even light alcohol consumption can impair the endothelial barrier function. Acute intoxication of alcohol can induce microvasculature leakage as well as direct exposure to endothelium leads to disruption of endothelial integrity. Increased levels of circulating endotoxin levels (e.g., LPS) and inflammatory mediators (e.g., IL-6 and TNF-α) are known to damage endothelial barrier leading to vascular leakage and enhance the systemic and tissue inflammation in ALDs. In addition, increased endothelial permeability enhances the extravasation of immune cells into liver leading to increased inflammation. To examine the effect of UroA/UAS03 on endothelial cell permeability, we utilized in vivo Evans Blue permeability assay. Briefly, C57BL/6 mice (n=4/group) were given LPS (100 μg) i.p. followed by treatment with UAS03 or UroA (20 mg/kg) after 1 h and 18 h. Evans blue (i.v.) was given to mice (24 h post LPS treatment) and 30 min later mice were euthanized and the Evans Blue from lung and liver tissues was extracted using formamide. The levels of Evans Blue was determined by OD at 620 nm. Mice treated with UroA or UAS03 reduced tissue accumulation of Evans Blue indicating protection from LPS-induced leakage (FIG. 36A). UroA/UAS03 treatment also reduced LPS-induced TNF-α levels in serum and Bronchoalveolar lavage (BAL) fluid (FIG. 36B). To evaluate direct impact of UroA or UAS03 on endothelial barrier function, we used in vivo Miles assay to test blood vessel permeability. We used vascular endothelial growth factor (VEGF) as vasodilator. In this assay, C57BL/6 mice (n=3 per group) were given vehicle or UroA or UAS03 (20 mg/kg; oral gavage). After 3 h, Evans blue (100 μL of 1% solution) was administered i.v. followed by intra-dermal administration of VEGF (2.5 ng/mouse) or PBS (control). After 30 min, mice were euthanized and the levels of Evans Blue in skin tissue surrounding the injection site was extracted and estimated as described previously (FIG. 36C). The results indicate that treatment with UroA/UAS03 protected from endothelial barrier leakage induced by VEGF (decreased Evans Blue levels), whereas vehicle treatment induced vascular leakage as evident from increased Evans Blue (FIG. 36C). To understand molecular mechanisms of UroA/UAS03 mediated endothelial barrier function, we tested the effects of these compounds in Human Umbilical Vein Endothelial Cells (HUVECs). Endotoxins or inflammatory mediators are responsible for decreasing the cell-cell and cell-matrix adhesion leading to increased barrier gaps and permeability. The VE-Cadherin (CDH5), an adherins junction (AJ) protein, can maintain the integrity of endothelial junctions through homotypic interactions with adjacent cell. As shown in FIG. 36D-E, UroA or UAS03 increased the expression of CDH5 suggesting that these metabolites potentially enhancing endothelial barrier integrity through upregulation of AJs. Moreover, results from in vitro permeability assays (albumin bound Evans Blue) also suggested that UroA/UAS03 reduced LPS (100 ng/ml) induced barrier permeability in HUVECs (FIG. 36F).

Compounds chemosensitize the chemoresistance cancers: We examined the effects of UroA and UAS03 on chemotherapeutic efficacy of 5-florouracil (5FU-5-Fluoro-1H,3H-pyrimidine-2,4-dione). Our data suggested that combination of 5FU with UroA or UAS03 reduced cell viability of 5FU resistant (5FUR) colon cancer cell lines with combination index (CI) less than 1 suggesting their synergism. UAS03 is more effective in chemo sensitization (with 32 fold higher) of 5FU treatment. Treatment with UroA decreased drug efflux activities of P-glycoprotein (P-gp), breast cancer resistance protein (BCRP) and enhanced the expression of E-cadherin in colon cancer cell lines providing potential mechanisms of action for chemosensitization. UAS03 is potent chemosensitizing adjuvant: One problem in cancer therapies is the chemoresistance to drug treatments. We investigated UroA and other compounds in chemosensitizing the colon cancer cells to 5FU treatment. The results from proliferation assay of representative colon cancer cell line (SW480) are shown in FIG. 37. Treatment with UroA or UAS03 show a minimal effect on cell proliferation. Treatment with 5FU reduced cell viability to 63%, 90% at 25 µM and 3.12 µM, respectively. Addition of UroA or UAS03 to the 5FU treatment reduced cell viability when compared to 5FU treatment alone (FIG. 37A) (increased the inhibition, FIG. 37B). UroA with 5FU (3.12 NM) reduced cell viability from 90% to 69%, whereas UAS03 reduced to 40%, which represent approximately 6 fold increase in the inhibition of cell proliferation even at 3.12 µM of 5FU. The highest concentration that we tested 100 µM for 5FU could only inhibit maximum of up to 60% cancer cell growth. Whereas in combination with UAS03, we inhibited up to 60% even at 3.12 µM of 5FU concentration reaching to plateau indicating high potency of the compound (more than 32 fold less than 5FU drug concentration to reach the similar effect). The Chou-Talalay combination index (CI) values (<1 indicates synergy) derived from isobolograms (FIG. 37C) are <0.5 suggesting their synergism in anti-proliferative activities. UroA also reduced colon cancer cell colony formation as evident from clonogenic assay (FIG. 37D). We have also observed similar trends with these compounds in other colon cancer cell lines (HT-29, HCT-116, Col205) (data not shown). UroA and UAS03 in combination with 5FU in parental and 5FU-resistant (5FUR) cell lines enhanced the sensitivity to 5FU treatment in 5FUR cell with CI values <1 suggesting their synergism (data not shown). We examined, whether combination therapy of UroA with 5FU blocks cell migration and cell growth utilizing standard wound healing assay. As shown FIG. 38, UroA in combination with 5FU inhibited cell growth and migration of colonic cancer cells into scratch (right corner image) compared to individual compounds.

UroA/UAS03 reduce drug transporters: One of the mechanisms by which cancer cells acquire chemoresistant phenotype is by the induction of ATP-binding cassette (ABC) drug efflux transporter proteins, BCRP and P-gycoprotein (P-gp). Therefore, blocking its activity and/or down-regulating the expression of BCRP, P-gp could reverse the effect and sensitize the cancer cells. We demonstrated that UroA reduced the BCRP activity (data not shown). Rh123 efflux assay (FIG. 39), UroA (50 µM) blocked efflux of Rh123 (retained Rh123 in cells).

UroA/UAS03 treatment reduce epithelial-mesenchymal transitions (EMT) signature in 5FU resistant (5FU R) colon cancer cells: We examined EMT markers in 5FU sensitive (parent) and 5FU resistant (5FUR) HCT116 colon cancer cell lines. As shown FIG. 40, 5FUR cells displayed decreased expression of ZO1, E-cadherin as well as increased expression of β-catenin and Snail compared to parent cell lines. The reciprocal expression of these molecules are hallmarks of EMT signature. Next, we examined whether treatment with UroA/UAS03 can reverse these patterns in 5FUR cells. It is evident from FIG. 41 that treatment with UroA/UAS03 upregulated ZO-1, E-Cadherin, and down regulated Snail and β-catenin even in the presence of 5FU. Overall, these results suggest that UroA/UAS03 can reverse the EMT signature patterns in 5FUR colon cancer cells in addition to enhanced anti-proliferative activities. One of the mechanisms by which cancer cells acquire chemoresistant phenotype is by the induction of drug transporters such as Multidrug resistance-associated protein 2 (MRP2), ATP-binding cassette (ABC) drug efflux transporter proteins, BCRP and P-gycoprotein (P-gp).

5FU-R colon cancer cells express higher levels of MRP2 (FIG. 42) and treatment with UroA/UAS03 reduce the expression of these transporters (FIG. 43). This could result in increase in intracellular drug concentration leading to increase in cell death/decreased proliferation of drug resistant cancer cells upon treatment with 5FU and UroA/UAS03.

These compounds can be also used for other types of cancers in combination with chemotherapeutic drugs that are chemoresistance to chemotherapeutic drugs. Additionally, using these compounds potentially help in lowering the dose of drugs to obtain similar effects without major side effects due to higher doses.

Example Set F

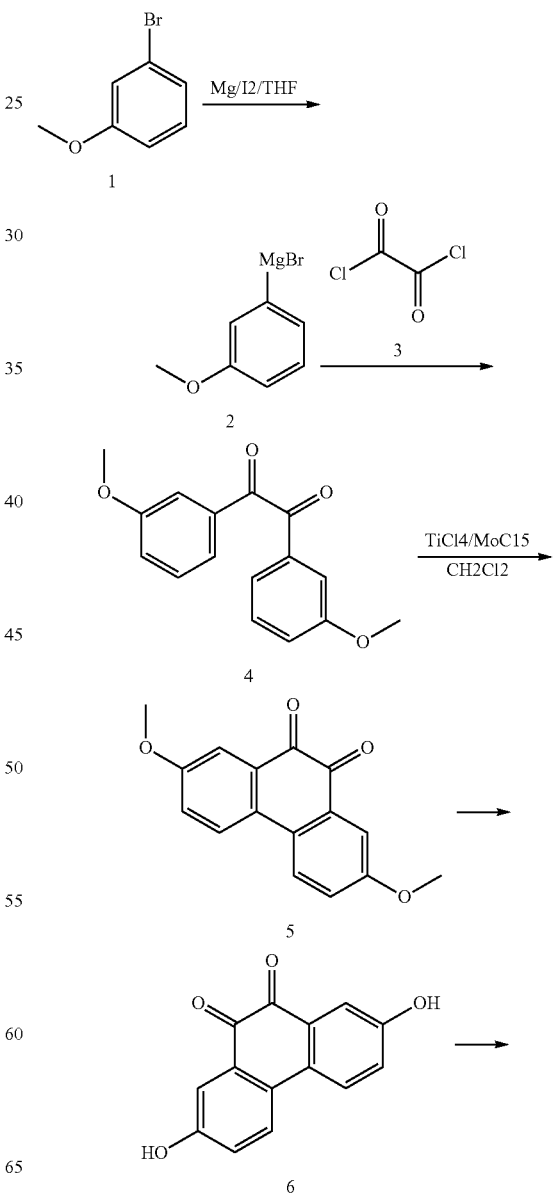

Scheme F1

-continued

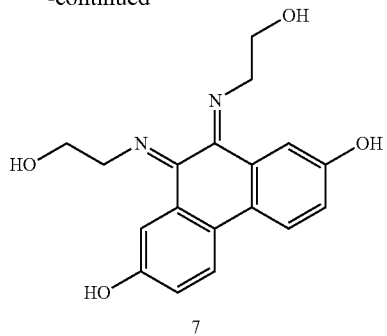

7

1. Synthesis of (3-methoxyphenyl)magnesium bromide (2)

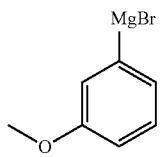

To a stirred solution of catalytic amount of I$_2$ (Iodine), magnesium 2 g (83.36 mmols) in 100 ml of anhydrous THF under nitrogen in 100 ml 2neck RB flask with water cooled condenser. To this added 1-bromo-3-methoxybenzene 15.50 g (83.36 mmols) drop wise over a period of 10 mins. After complete addition of bromo compound stirred it at room temperature for 10 mins. after some time the solvent will start to reflux, this will indicate the generation of Grignard reagent. If the more heat is evolved just cool using Ice, otherwise the solvent will reflux some time then stop slowly, finally we can observe the ash colour Grignard reagent inside the RB flask. This generated Grignard we can use directly to next step.

2. Synthesis of 1,2-bis(3-methoxyphenyl)ethane-1,2-dione (3)

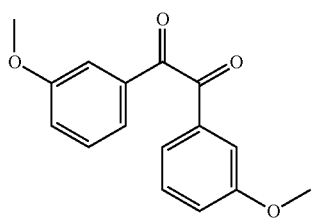 [SMILES: COc1cccc(C(=O)C(=O)c2cccc(OC)c2)c1]

To a stirred solution of previously prepared (3-methoxyphenyl)magnesium bromide in 50 ml anhydrous THF, to this added Copper bromide 10.24 g (71.42 mmols), lithium bromide 6.2 g (71.42 mmols), cool the reaction mixture at −78° C., using dry ice acetone mixture. Once the temperature reached −78° C. slowly added oxalyl chloride 4.53 g (35.71 mmols), allow the reaction stir at room temperature overnight. Completion of reaction was monitored by TLC, once the reaction is complete cool the reaction to 0° C. and quench with aqueous saturated ammonium chloride. The THF solvent was evaporated under reduced pressure dilute the reaction mixture with ethylacetate, wash the organic layer with brine, water and dried under anhydrous sodium sulphate, evaporate under reduced pressure to get 5 g of 1,2-bis(3-methoxyphenyl)ethane-1,2-dione (26%).

Mass; m/z: (M+H)=271.2

1H-NMR (DMSO-d6, 600 MHz): δ 7.60-7.52 (2H, m), 7.45-7.41 (2H, m), 7.39-7.37 (4H, m), 3.84 (6H, s); 13C-NMR (DMSO-d6, 150 MHz): 194.89, 160.27, 134.01, 131.22, 123.33, 122.40, 113.13, 56.00.

3. Synthesis of 2,7-dimethoxyphenanthrene-9,10-dione (5)

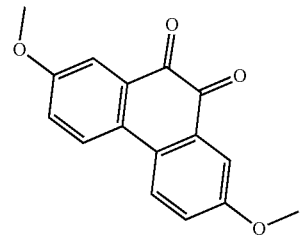 [SMILES: COc1ccc2c(c1)C(=O)C(=O)c1cc(OC)ccc1-2]

To a stirred solution of 1,2-bis(3-methoxyphenyl)ethane-1,2-dione 5 g (18.51 mmols) in 200 ml of dry Dichloromethane. Cool the reaction mixture to 0° C., to this added Ti(IV)chloride 3.51 g (18.51 mmols), Molybdenum(V)chloride 5.05 g (18.51 mmols), allow the reaction mixture to stir at room temperature over night. Completion of reaction was monitored by TLC. Cool the reaction mixture to 0° C., quench with methanol slowly, the reaction mixture was passed through celite, and evaporate under reduced pressure to get crude 2,7-dimethoxyphenanthrene-9,10-dione. The crude product was purified by column chromatography using hexane and ethylaceate as a eluent to get pure 3 g of 2,7-dimethoxyphenanthrene-9,10-dione (61%).

Mass; m/z: (M+H)=269.2

1H-NMR (DMSO-d6, 600 MHz): δ 8.09-8.08 (2H, m), 7.42 (2H, s), 7.31-7.29 (2H, m), 3.86 (6H, s); 13C-NMR (DMSO-d6, 150 MHz): 179.41, 159.61, 131.92, 129.34, 126.32, 122.80, 112.67, 56.04.

4. Synthesis of 2,7-dihydroxyphenanthrene-9,10-dione (6)

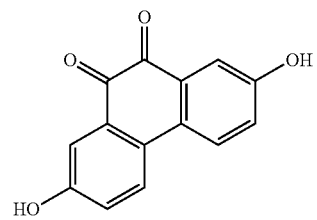 [SMILES: O=C1C(=O)c2cc(O)ccc2-c2ccc(O)cc21]

To a stirred solution of 2,7-dimethoxyphenanthrene-9,10-dione 2 g (7.46 mmol) in 100 ml of chlorobenzene, to this added anhydrous aluminum chloride 5.97 g (44.77 mmols). The reaction mixture was reflux at 135° C. Completion of reaction mixture was monitored by TLC. The reaction mixture was poured to crushed Ice, extract with ethyl acetate, wash the organic layer with brine, water, dried with anhydrous sodium sulphate and evaporate under reduced pressure to get crude 2,7-dimethoxyphenanthrene-9,10-dione. The crude product was purified by column chromatography using hexane and ethylacetate as a eluent to get pure 1.2 g of 2,7-dimethoxyphenanthrene-9,10-dione (67%).

Mass; m/z: (M−H)=239.2

1H-NMR (DMSO-d6, 600 MHz): δ 10.05 (2H, s), 7.92-7.90 (2H, m), 7.30 (2H, s), 7.11-7.09 (2H, m); 13C-NMR (DMSO-d6, 150 MHz): 179.93, 157.73, 131.64, 128.28, 125.98, 123.62, 114.97.

5. Synthesis of (9E,10E)-9,10-bis((2-hydroxyethyl)imino)-9,10-dihydrophenanthrene-2,7-diol (7)

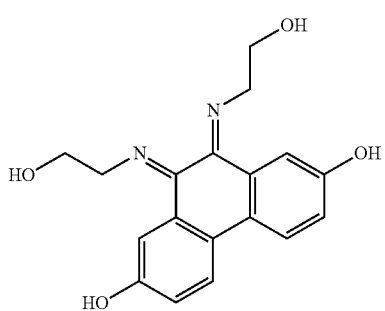 [SMILES: OCC/N=C1/C(=N/CCO)c2cc(O)ccc2-c2ccc(O)cc21]

To a stirred solution of 2,7-dimethoxyphenanthrene-9,10-dione 0.5 g (2.08 mmols) in 50 ml of ethanol. to this added catalytic amount of acetic acid, ethanol amine 0.317 g, (5.20 mmols). The reaction mixture was refluxed at 110° C. overnight. The completion of reaction was monitored by TLC. The reaction mixture was evaporate under reduced pressure, dilute the reaction mixture with ethyl acetate, wash the ethyl acetate layer with brine, water and dried with anhydrous sodium sulphate and evaporate to get crude (9E,10E)-9,10-bis((2-hydroxyethyl)imino)-9,10-dihydrophenanthrene-2,7-diol. The crude product was purified with column chromatography using Chloroform and methanol as a eluent to get pure 0.25 g of (9E,10E)-9,10-bis((2-hydroxyethyl)imino)-9,10-dihydrophenanthrene-2,7-diol (36.2%).

Mass; m/z: (M−H)=325.2

1H-NMR (DMSO-d6, 600 MHz): 9.99 (2H, s), 7.90-7.88 (2H, m), 7.40 (2H, s), 7.09-7.06 (2H, m), 5.58-5.57 (2H, m), 4.27-4.25 (4H, m), 3.48-3.46 (4H, m); 13C-NMR (DMSO-d6, 150 MHz): 157.72, 155.57, 132.98, 127.00, 126.95, 119.14, 115.03, 65.02, 55.36.

6. Synthesis of (E)-2,7-dihydroxy-10-((2-hydroxyethyl)imino)phenanthren-9(10H)-one

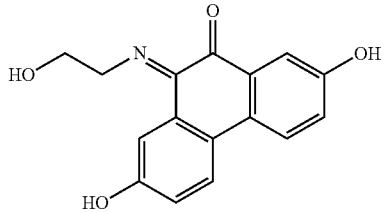 [SMILES: O=C1/C(=N/CCO)c2cc(O)ccc2-c2ccc(O)cc21]

To a stirred solution of 2,7-dimethoxyphenanthrene-9,10-dione 0.5 g (2.08 mmols) in 50 ml of ethanol. to this added catalytic amount of acetic acid, ethanol amine 0.152 g, (2.5 mmols). The reaction mixture was refluxed at 110° C. overnight. The completion of reaction was monitored by TLC. The reaction mixture was evaporate under reduced pressure, dilute the reaction mixture with ethyl acetate, wash the ethyl acetate layer with brine, water and dried with anhydrous sodium sulphate and evaporate to get crude (E)-2,7-dihydroxy-10-((2-hydroxyethyl)imino)phenanthren-9(10H)-one. The crude product was purified with column chromatography using Chloroform and methanol as a eluent to get pure 0.15 g of (E)-2,7-dihydroxy-10-((2-hydroxyethyl)imino)phenanthren-9(10H)-one (26%).

Mass; m/z: (M+H)=284.2

1H-NMR (DMSO-d6, 600 MHz): 9.51 (1H, s), 9.45 (1H, s), 8.39-8.28 (2H, m), 7.20 (1H, s), 7.11 (1H, s), 6.99-6.97 (1H, m), 6.86-6.84 (1H, s), 5.58-5.57 (2H, m), 4.27-4.25 (4H, m), 3.48-3.46 (4H, m); 13C-NMR (DMSO-d6, 150 MHz): 157.72, 155.57, 132.98, 127.00, 126.95, 119.14, 115.03, 65.02, 55.36.

7. Synthesis of 2,2'-((1E,1'E)-(2,7-dihydroxyphenanthrene-9,10-diylidene)bis(azanylylidene))bis(propane-1,3-diol)

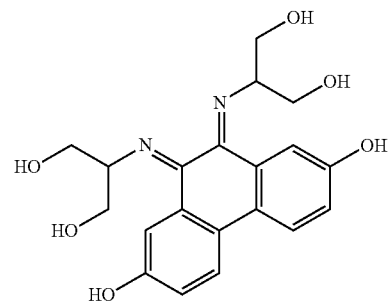 [SMILES: OCC(CO)/N=C1/C(=N/C(CO)CO)c2cc(O)ccc2-c2ccc(O)cc21]

1H-NMR (DMSO-d6, 800 MHz): 9.50 (1H, s), 9.44 (1H, s), 8.34-8.29 (2H, m), 7.78 (1H, m), 7.23 (1H, s), 6.99 (1H, s), 6.85-6.84 (1H, s), 4.60-4.58 (8H, m), 3.76-3.75 (2H, m).

8. Synthesis of (E)-10-((1,3-dihydroxypropan-2-yl)imino)-2,7-dihydroxyphenanthren-9(10H)-one

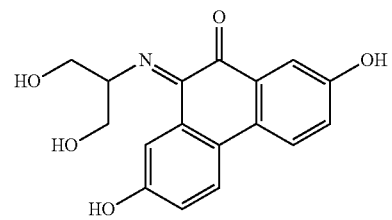 [SMILES: O=C1/C(=N/C(CO)CO)c2cc(O)ccc2-c2ccc(O)cc21]

1H-NMR (DMSO-d6, 800 MHz): 9.50 (1H, s), 9.44 (1H, s), 8.34-8.29 (2H, m), 7.78 (1H, m), 7.23 (1H, s), 6.99 (1H, s), 6.85-6.84 (1H, s), 4.60-4.58 (8H, m), 3.76-3.75 (2H, m); 13C-NMR (DMSO-d6, 200 MHz): 157.72, 155.57, 132.98, 127.00, 126.95, 119.14, 115.03, 65.02, 55.36.

9. Synthesis of 2,2'-((1E)-(2,7-dihydroxyphenanthrene-9,10-diylidene)bis(azanylylidene))bis(2-(hydroxymethyl)propane-1,3-diol)

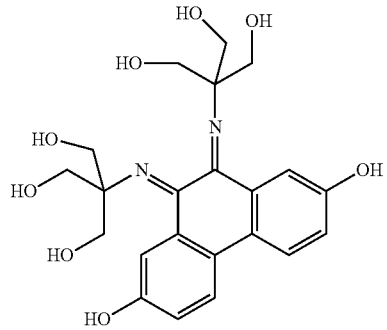 [SMILES: OCC(CO)(CO)N=C1/C(=N/C(CO)(CO)CO)c2cc(O)ccc2-c2ccc(O)cc21]

Mass; m/z: (M−H)=445.2
1H-NMR (DMSO-d6, 800 MHz): 9.50 (1H, s), 9.44 (1H, s), 8.37-8.36 (2H, m), 7.98 (2H, s), 6.99-6.86 (2H, s), 4.73 (6H, m), 3.52-3.51 (12H, m); 13C-NMR (DMSO-d6, 200 MHz): 157.72, 155.57, 137.25, 132.98, 128.00, 126.15, 118.14, 116.03, 64.02, 59.36.

10. Synthesis of (E)-10-((1,3-dihydroxy-2-(hydroxymethyl)propan-2-yl)imino)-2,7-dihydroxyphenanthren-9(10H)-one

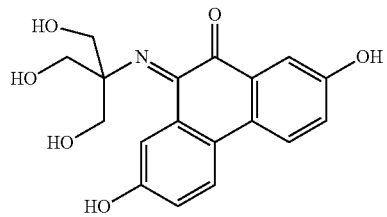 [SMILES: O=C1/C(=N/C(CO)(CO)CO)c2cc(O)ccc2-c2ccc(O)cc21]

Mass; m/z: (M−H)=342.2
1H-NMR (DMSO-d6, 800 MHz): 9.77 (1H, s), 9.71 (1H, s), 7.94-7.91 (2H, m), 7.65 (1H, s), 7.11 (1H, s), 7.02-7.01 (1H, m), 6.91-6.89 (1H, m), 5.09-5.07 (3H, m), 3.82-3.81 (6H, m); 13C-NMR (DMSO-d6, 200 MHz): 167.33, 157.01, 155.42, 133.52, 132.76, 129.80, 127.04, 122.20, 121.06, 118.16, 115.54, 109.44, 65.10, 59.34.

11. Synthesis of 9,10-diimino-9,10-dihydrophenanthrene-2,7-diol

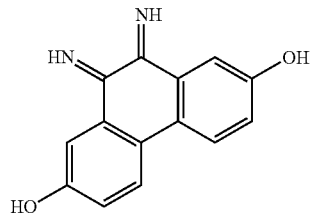 [SMILES: N=C1C(=N)c2cc(O)ccc2-c2ccc(O)cc21]

Mass; m/z: (M+H)=239.2
1H-NMR (DMSO-d6, 600 MHz): 9.96 (2H, s), 8.99 (2H, s), 8.10-8.08 (2H, m) 7.95 (2H, s), 7.57 (2H, s), 7.09-7.07 (2H, m); 13C-NMR (DMSO-d6, 150 MHz): 162.77, 158.42, 157.19, 126.99, 126.77, 125.91, 120.77, 112.17.

12. Synthesis of dibenzo[f,h]quinoxaline-6,11-diol

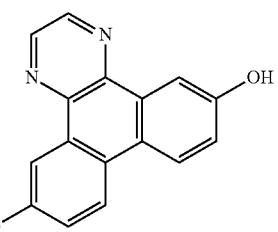

Mass; m/z: (M−H)=261.2
1H-NMR (DMSO-d6, 600 MHz): 9.95 (2H, s), 8.99 (2H, s), 8.52-8.50 (2H, m) 8.42-8.41 (2H, s), 7.28-7.26 (2H, m); 13C-NMR (DMSO-d6, 150 MHz): 156.74, 144.41, 140.96, 129.94, 124.76, 124.50.

13. Synthesis of 2-bromo-6H-benzo[c]chromene-3,8-diol

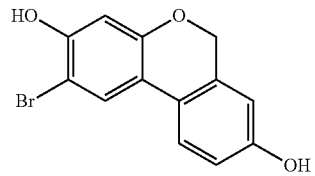 [SMILES: Oc1ccc2c(c1)COc1cc(O)c(Br)cc1-2]

1H-NMR (DMSO-d6, 600 MHz): 10.27 (1H, s), 9.58 (1H, s), 7.79 (1H, s), 7.55-7.53 (1H, m), 6.75-6.73 (1H, m), 6.62-6.61 (1H, m), 6.53 (1H, s), 4.99 (2H, s); 13C-NMR (DMSO-d6, 150 MHz): 158.74, 153.41, 126.56, 123.32, 115.86, 111.88, 105.11, 68.25.

Example Set G

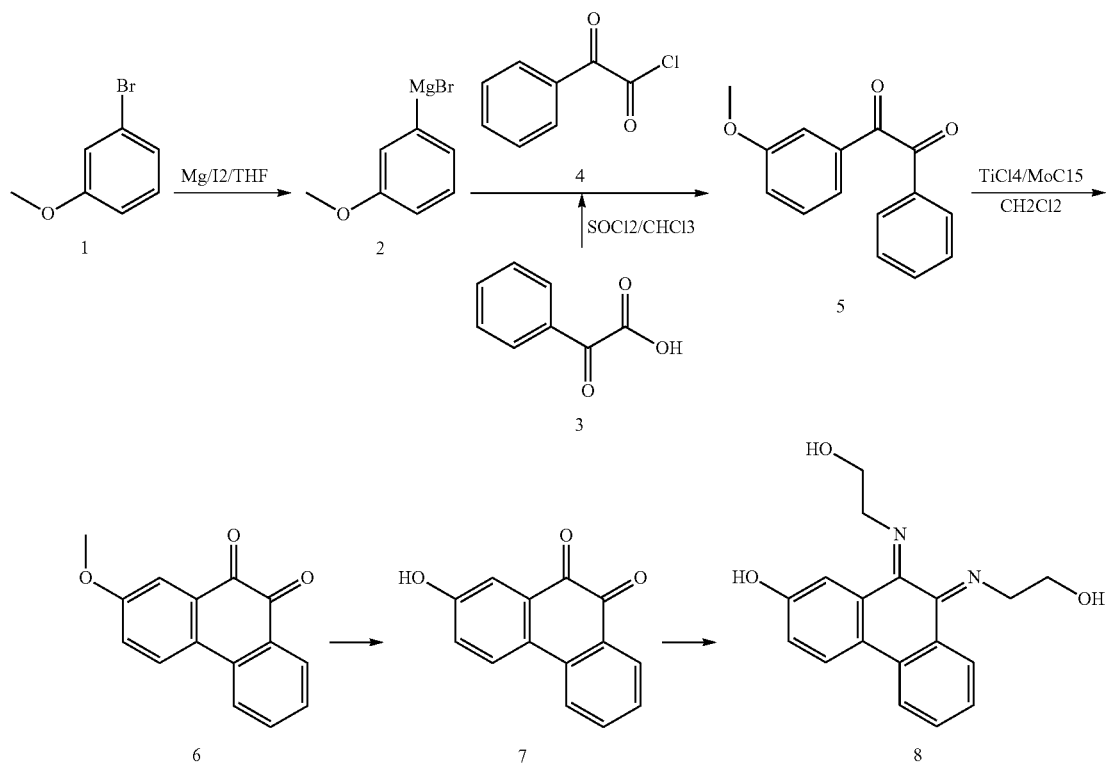

Scheme G1

1. Synthesis of 1-(3-methoxyphenyl)-2-phenylethane-1,2-dione

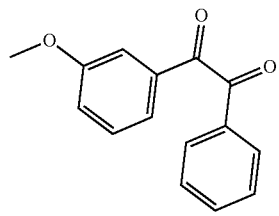 [SMILES: COc1cccc(C(=O)C(=O)c2ccccc2)c1]

Mass; m/z: (M+H)=241.2

1H-NMR (DMSO-d6, 800 MHz): δ 7.93-7.91 (2H, m), 7.80-7.79 (1H, m), 7.64-7.62 (2H, m), 7.54-7.52 (1H, m), 7.46 (1H, s), 7.43-7.39 (2H, m), 3.85 (6H, s); 13C-NMR (DMSO-d6, 200 MHz): 195.10, 160.27, 136.01, 134.01, 132.69, 131.23, 130.06, 129.97, 123.36, 122.42, 113.10, 56.00.

3. Synthesis of 2-methoxyphenanthrene-9,10-dione

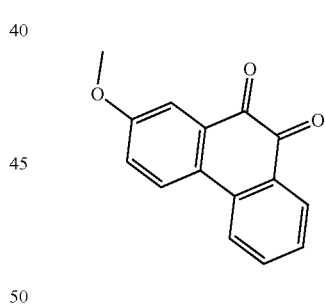

Mass; m/z: (M+H)=239.2

1H-NMR (DMSO-d6, 600 MHz): δ 8.12-8.08 (1H, m), 7.83-7.81 (2H, m), 7.61-7.57 (2H, m), 7.36-7.34 (2H, m), 3.85 (3H, s); 13C-NMR (DMSO-d6, 150 MHz): 179.41, 159.61, 131.92, 129.34, 126.32, 122.80, 112.67, 56.04.

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

What is claimed is:

1. A pharmaceutical composition comprising a compound selected from

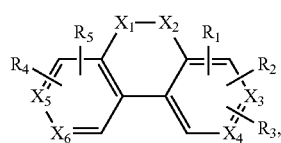

salts of formula (I), optical isomers of formula (I), geometric isomers of formula (I), salts of isomers of formula (I),

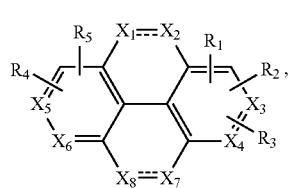

salts of formula (II), optical isomers of formula (II), geometric isomers of formula (II), salts of isomers of formula (II),

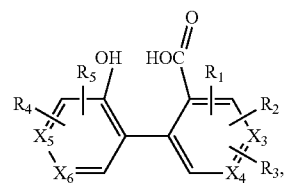

salts of formula (III), optical isomers of formula (III), geometric isomers of formula (III), and salts of isomers of formula (III), wherein the bond between $X_1$ and $X_2$ is a single bond or a double bond;

the bond between $X_7$ and $X_8$ is a single bond or a double bond;

$X_1$, $X_2$, $X_7$, and $X_8$ are the same or different and each can be independently selected from CH, $CH_2$, O, S, C—$NH_2$, C—N=$CH_2$, C(H)($NH_2$), C=O, C=N—$NH_2$, C=NH, C=N— cycloalkyl, C=N—S(O) H, C=NC(EtOH)$_3$, C=NCH(EtOH)$_2$, C=NEtOH, C($CH_3$)(OH), N, NH, C— halogen, C(H)(halogen), C-(halogen)$_2$, C-cycloalkyl, C-heterocyclyl, C-aryl, C-heteroaryl, C(H)(cycloalkyl), C(H)(heterocyclyl), C(H)(aryl), or C(H)(heteroaryl), which CH, $CH_2$, C—$NH_2$, C—N=$CH_2$, C(H)($NH_2$), C=N—$NH_2$, C=NH, C=N-cycloalkyl, C=N—S(O) H, C=NC (EtOH)$_3$, C=NCH(EtOH)$_2$, C=NEtOH, C($CH_3$) (OH), C(H)(halogen), C-cycloalkyl, C-heterocyclyl, C-aryl, C-heteroaryl, C(H)(cycloalkyl), C(H)(heterocyclyl), C(H)(aryl), or C(H)(heteroaryl), are optionally substituted with one or more of halogen, hydroxy (—OH), methanoyl (—COH), —$COCH_3$, carboxy (—$CO_2H$), ethynyl (—CCH), cyano (—CN), sulfo (—$SO_3H$), methyl, ethyl, perfluorinated methyl, or perfluorinated ethyl;

$X_1$ and $X_2$ are optionally further cyclized to form a 5 or 6 membered cycloalkyl, 5 or 6 membered heterocyclyl, 5 or 6 membered aryl, or 5 or 6 membered heteroaryl, which 5 or 6 membered cycloalkyl, 5 or 6 membered heterocyclyl, 5 or 6 membered aryl, or 5 or 6 membered heteroaryl are optionally substituted with one or more of halogen, hydroxy (—OH), methanoyl (—COH), —$COCH_3$, carboxy (—$CO_2H$), ethynyl (—CCH), cyano (—CN), sulfo (—$SO_3H$), methyl, ethyl, perfluorinated methyl, or perfluorinated ethyl;

$X_7$ and $X_8$ are optionally further cyclized to form a 5 or 6 membered cycloalkyl, 5 or 6 membered heterocyclyl, 5 or 6 membered aryl, or 5 or 6 membered heteroaryl, which 5 or 6 membered cycloalkyl, 5 or 6 membered heterocyclyl, 5 or 6 membered aryl, or 5 or 6 membered heteroaryl are optionally substituted with one or more of halogen, hydroxy (—OH), methanoyl (—COH), —COCH₃, carboxy (—CO₂H), ethynyl (—CCH), cyano (—CN), sulfo (—SO₃H), methyl, ethyl, perfluorinated methyl, or perfluorinated ethyl;

$R_1$, $R_2$, $R_3$, $R_4$, and $R_5$ are the same or different and each is independently selected from H, OH, halogen, methanoyl (—COH), —OCF₃, —COCH₃, carbonyl, carboxy (—CO₂H), ethynyl (—CCH), cyano (—CN), amine, —NO₂, sulfo (—SO₃H), $C_1$-$C_4$ alkyl, $C_2$-$C_4$ alkenyl, $C_2$-$C_4$ alkynyl, $C_1$-$C_3$ alkoxy, methyl, ethyl, perfluorinated methyl, perfluorinated ethyl, cycloalkyl, or heterocyclyl, which H, OH, methanoyl (—COH), —COCH₃, carbonyl, carboxy (—CO₂H), ethynyl (—CCH), sulfo (—SO₃H), $C_1$-$C_4$ alkyl, $C_2$-$C_4$ alkenyl, $C_2$-$C_4$ alkynyl, $C_1$-$C_3$ alkoxy, methyl, ethyl, cycloalkyl, or heterocyclyl are optionally substituted with one or more of halogen, hydroxy (—OH), methanoyl (—COH), —COCH₃, carboxy (—CO₂H), ethynyl (—CCH), cyano (—CN), sulfo (—SO₃H), methyl, ethyl, perfluorinated methyl, or perfluorinated ethyl;

$X_3$, $X_4$, $X_5$, and $X_6$ are the same or different and each is independently selected from CH or N, which CH is optionally substituted with one or more of halogen, hydroxy (—OH), methanoyl (—COH), —COCH₃, carboxy (—CO₂H), ethynyl (—CCH), cyano (—CN), sulfo (—SO₃H), methyl, ethyl, perfluorinated methyl, or perfluorinated ethyl, and with the proviso that $X_1$ and $X_2$ do not form —O—(CO)— or —(CO)—O— and with the proviso that the compound is not

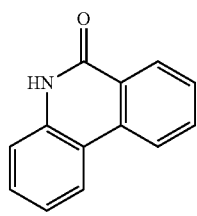 [SMILES: O=c1[nH]c2ccccc2c2ccccc12]

or

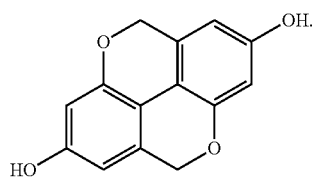 [SMILES: Oc1cc2c3c(c1)OCc1cc(O)cc(c1-3)OC2]

2. The pharmaceutical composition of claim 1, wherein $X_1$, $X_2$, $X_7$, and $X_8$ are the same or different and each can be independently selected from CH₂, O, C(H)(NH₂), C=O, C=N—NH₂, C=NH, C=N-cycloalkyl, C=N-adamantane, C=NC(EtOH)₃, C=NCH(EtOH)₂, C=NEtOH, C(CH₃)(OH), or C(H)(cycloalkyl).

3. The pharmaceutical composition of claim 1, wherein $X_1$ and $X_2$ are the same, $X_7$ and $X_8$ is the same, $X_1$ and $X_7$ is the same, $X_2$ and $X_8$ is the same, or a combination thereof.

4. The pharmaceutical composition of claim 1, wherein $X_3$, $X_4$, $X_5$, and $X_6$ are the same or different and each is independently selected from CH or N.

5. The pharmaceutical composition of claim 1, wherein $R_1$, $R_2$, $R_3$, $R_4$, and $R_5$ are the same or different and each is independently selected from H, OH, halogen, methanoyl (—COH), —OCF₃, —COCH₃, carbonyl, carboxy (—CO₂H), cyano (—CN), amine, —NO₂, methoxy, ethoxy, methyl, ethyl, perfluorinated methyl, perfluorinated ethyl, cycloalkyl, bicycloalkyl, heterocyclyl, or imidazolyl.

6. The pharmaceutical composition of claim 1, wherein the compound is selected from Formula (IA)

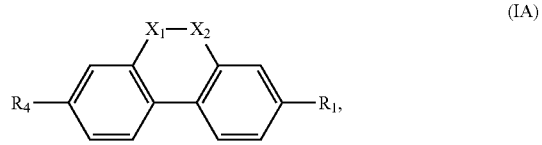

(IA)

salts of formula (IA), optical isomers of formula (IA), geometric isomers of formula (IA), and salts of isomers of formula (IA).

7. The pharmaceutical composition of claim 1, wherein $X_1$ and $X_2$ are the same or different and each is independently selected from CH₂, O, C(H)(NH₂), C=O, C=N—NH₂, C=NH, C=N-cycloalkyl, C=NC(EtOH)₃, C=NCH(EtOH)₂, C=NEtOH, C(CH₃)(OH), or C(H)(cycloalkyl), which CH₂, C(H)(NH₂), C=N—NH₂, C=NH, C=N-cycloalkyl, C=NC(EtOH)₃, C=NCH(EtOH)₂, C=NEtOH, C(CH₃)(OH), or C(H)(cycloalkyl), are optionally substituted with one or more of halogen, hydroxy (—OH), methanoyl (—COH), —COCH₃, carboxy (—CO₂H), ethynyl (—CCH), cyano (—CN), sulfo (—SO₃H), methyl, ethyl, perfluorinated methyl, or perfluorinated ethyl.

8. The pharmaceutical composition of claim 1, wherein $X_1$ and $X_2$ are the same or different and each is independently selected from CH₂, O, C=O, C=NH, C—N—cycloalkyl, C=NC(EtOH)₃, C=NCH(EtOH)₂, C=NEtOH, C(CH₃)(OH), or C(H)(cycloalkyl).

9. The pharmaceutical composition of claim 1, wherein $R_1$ and $R_2$ are the same or different and each is independently selected from H, OH, halogen, methanoyl (—COH), —OCF₃, —COCH₃, carbonyl, carboxy (—CO₂H), ethynyl (—CCH), cyano (—CN), amine, —NO₂, sulfo (—SO₃H), $C_1$-$C_4$ alkyl, $C_2$-$C_4$ alkenyl, $C_2$-$C_4$ alkynyl, $C_1$-$C_3$ alkoxy, methyl, ethyl, perfluorinated methyl, perfluorinated ethyl, which H, OH, methanoyl (—COH), —COCH₃, carbonyl, carboxy (—CO₂H), ethynyl (—CCH), sulfo (—SO₃H), $C_1$-$C_4$ alkyl, $C_2$-$C_4$ alkenyl, $C_2$-$C_4$ alkynyl, $C_1$-$C_3$ alkoxy, methyl, or ethyl, are optionally substituted with one or more of halogen, hydroxy (—OH), methanoyl (—COH), —COCH₃, carboxy (—CO₂H), ethynyl (—CCH), cyano (—CN), sulfo (—SO₃H), methyl, ethyl, perfluorinated methyl, or perfluorinated ethyl.

10. The pharmaceutical composition of claim 1, wherein $R_1$ and $R_2$ are the same or different and each is independently selected from H, OH, halogen, methanoyl (—COH), —OCF₃, —COCH₃, carbonyl, carboxy (—CO₂H), cyano (—CN), amine, —NO₂, methoxy, ethoxy, methyl, ethyl, perfluorinated methyl, or perfluorinated ethyl.

11. The pharmaceutical composition of claim 1, wherein one or more of the following compounds

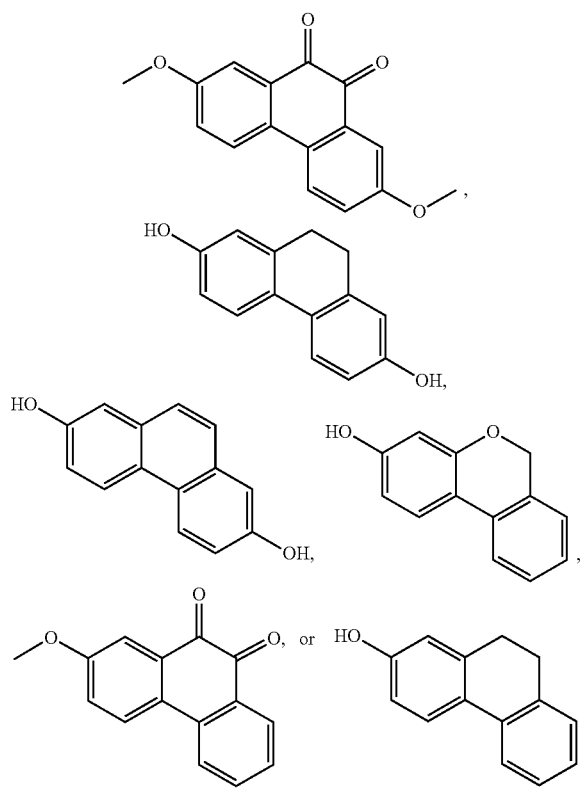

are excluded.

12. The pharmaceutical composition of claim 1, wherein the compound is selected from

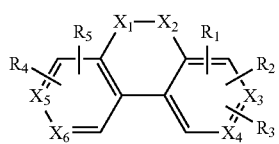

salts of formula (I), optical isomers of formula (I), geometric isomers of formula (I), and salts of isomers of formula (I), wherein
$X_1$ is O;
$X_2$ is $CH_2$; and
$X_3$, $X_4$, $X_5$, and $X_6$ are the same and are CH.

13. The pharmaceutical composition of claim 1, further comprising a formulary ingredient, an adjuvant, or a carrier.

14. A method for treating an animal for a disease, comprising one or more administrations of one or more pharmaceutical compositions of claim 1, wherein the compositions may be the same or different if there is more than one administration, and wherein the method is for treating alcoholic liver disease (ALD), non-alcoholic steatohepatitis (NASH), intestinal permeability, leaky gut, metal induced gut leakiness, stress induced gut leakiness, radiation induced gut permeability, colitis, local inflammation, inflammation in the brain, inflammation in the mouth, inflammation in the esophagus, inflammation in the stomach, inflammation in the small intestine, systemic inflammation, inflammatory bowel disease, ulcerative colitis, Crohn's disease, infection-induced inflammatory disease, sepsis, sepsis-induced kidney injury, sepsis-induced lung injury, scleroderma, vasculitis, drug-induced vasculitis, neuroinflammatory disorders, Parkinson's Disease, anxiety, depression, metabolic stress, cardiovascular disease, sarcopenia, muscle degenerative disease, Duchenne muscular dystrophy, nonalcoholic fatty liver disease, drug-induced liver injury, alpha-antitrypsin deficiency, ischemia/reperfusion injury, obesity, metabolic syndrome, type II diabetes mellitus, hyperlipidemia, osteoarthritis, amyotrophic lateral sclerosis (ALS), colon cancer, cognitive disorder, stress, mood disorder, or fibrosis.

15. The method of claim 14, wherein the method is for treating alcoholic liver disease (ALD), intestinal permeability, leaky gut, metal induced gut leakiness, stress induced gut leakiness, radiation induced gut permeability, colitis, local inflammation, inflammation in the brain, inflammation in the mouth, inflammation in the esophagus, inflammation in the stomach, inflammation in the small intestine, systemic inflammation, inflammatory bowel disease, sepsis, sepsis-induced kidney injury, sepsis-induced lung injury, scleroderma, vasculitis, drug-induced vasculitis, colon cancer, or fibrosis.

16. A method of inducing the expression of tight junction proteins in a tissue, comprising administering an effective amount of the compound of the pharmaceutical composition of claim 1 to a subject in need.

17. The method of claim 16, wherein the subject exhibits symptoms of gastrointestinal permeability or inflammation, and the composition is administered to the small and/or large intestine.

18. The method of claim 17, wherein the subject has an inflammatory bowel disease.

19. The method of claim 18, wherein the inflammatory bowel disease is Crohn's disease or ulcerative colitis.

* * * * *